US012807956B2

(12) United States Patent
Schaeper et al.

(10) Patent No.: US 12,807,956 B2
(45) Date of Patent: Nov. 24, 2026

(54) NUCLEIC ACIDS FOR INHIBITING EXPRESSION OF CNNM4 IN A CELL

(71) Applicant: ASOCIACIÓN CENTRO DE INVESTIGACIÓN COOPERATIVA EN BIOCIENCIAS-CIC bioGUNE, Derio (ES)

(72) Inventors: Ute Schaeper, Berlin (DE); Sibylle Dames, Berlin (DE); Steffen Schubert, Berlin (DE); Alfonso Martínez De La Cruz, Derio (ES); Jorge Simón Espinosa, Derio (ES); Irene Gonzalez Recio, Derio (ES); María Luz Martínez Chantar, Derio (ES)

(73) Assignee: ASOCIACIÓN CENTRO DE INVESTIGACIÓN COOPERATIVA EN BIOCIENCIAS-CIC bioGUNE, Vizcaya (ES)

( * ) Notice: Subject to any disclaimer, the term of this patent is extended or adjusted under 35 U.S.C. 154(b) by 829 days.

(21) Appl. No.: 17/999,956

(22) PCT Filed: May 26, 2021

(86) PCT No.: PCT/EP2021/064077
§ 371 (c)(1),
(2) Date: Nov. 28, 2022

(87) PCT Pub. No.: WO2021/239825
PCT Pub. Date: Dec. 2, 2021

(65) Prior Publication Data

US 2023/0265438 A1 Aug. 24, 2023
US 2024/0229041 A2 Jul. 11, 2024

(30) Foreign Application Priority Data

May 27, 2020 (EP) .................................... 20382449
Oct. 30, 2020 (EP) .................................... 20382947

(51) Int. Cl.
*C12N 15/113* (2010.01)
*A61K 31/713* (2006.01)
*A61K 47/54* (2017.01)
*A61K 48/00* (2006.01)
*A61P 1/16* (2006.01)

(52) U.S. Cl.
CPC ........ *C12N 15/1138* (2013.01); *A61K 31/713* (2013.01); *A61K 47/549* (2017.08); *A61P 1/16* (2018.01)

(58) Field of Classification Search
None
See application file for complete search history.

(56) References Cited

U.S. PATENT DOCUMENTS

2018/0170946 A1 6/2018 Lazo et al.

FOREIGN PATENT DOCUMENTS

WO WO 2017174657 A1 10/2017
WO WO 2018185253 A1 10/2018
WO WO 2020109316 A1 6/2020

OTHER PUBLICATIONS

Parmar et al., J. Med. Chem., 2018, 61: 734-744.*
Ito et al., FEBS Lett., 2005, 579: 5988-5995.*
Elbashir et al., EMBO J., 2001, 20: 6877-6888.*
Funato et al., J. Clin. Invest,. 2014, 124: 5398-5410.*
Daouti, et al., A Selective Phosphatase of Regenerating Liver Phosphatase Inhibitor Suppresses Tumor Cell Anchorage Independent Growth by a Novel Mechanism Involving p130cas Cleavage, Cancer Research, Feb. 15, 2008, pp. 1162-1169.
Jarald et al., Nucleic acid drugs: a novel approach, African Journal of Biotechnology, vol. 3(12), Dec. 2004, pp. 662-666.
Park et al., Discovery of novel PRL-3 inhibitors based on the structure-based virtual screening, Bioorganic & Medicinal Chemistry Letters, 2008, vol. 18, Issue 7, pp. 2250-2255.
Wei et al., Targeting phosphatases of regenerating liver (PRLs) in cancer, Pharmacology & Therapeutics, Oct. 2018, vol. 190, pp. 128-138.
Baaij et al., Magnesium in man: implications for health and disease. Physiol Rev. Jan. 2015;95(1):1-46.
Barbagallo et al., Serum ionized magnesium in diabetic older persons. Metabolism. Apr. 2014;63(4):502-9.
Elbashir et al., Duplexes of 21-nucleotide RNAs mediate RNA interference in cultured mammalian cells. Nature. May 24, 2001;411(6836):494-8.
Fernandez-Alvarez et al., TRAIL-producing NK cells contribute to liver injury and related fibrogenesis in the context of GNMT deficiency. Lab Invest. Feb. 2015;95(2):223-36.
Fire et al., Potent and specific genetic interference by double-stranded RNA in Caenorhabditis elegans. Nature. Feb. 19, 1998;391(6669):806-11.
Folch et al., A simple method for the isolation and purification of total lipides from animal tissues. J Biol Chem. May 1957;226(1):497-509.
Funato et al., Membrane protein CNNM4-dependent Mg2+ efflux suppresses tumor progression. J Clin Invest. Dec. 2014;124(12):5398-410.
Funato et al., Molecular function and biological importance of CNNM family Mg2+ transporters. J Biochem. Mar. 1, 2019;165(3):219-225.
Grynkiewicz et al., A new generation of Ca2+ indicators with greatly improved fluorescence properties. J Biol Chem. Mar. 25, 1985;260(6):3440-50.
Jahnen-Dechent et al., Magnesium basics. Clin Kidney J. Feb. 2012;5(Suppl 1):13-i14.

(Continued)

*Primary Examiner* — Ileana Popa
(74) *Attorney, Agent, or Firm* — Casimir Jones, S.C.; Tristan A. Fuierer

(57) ABSTRACT

The invention relates to nucleic acid products that interfere with or inhibit CNNM4 (Cyclin M4) gene expression. It further relates to therapeutic uses of CNNM4 inhibition for the treatment of diseases, such as liver diseases including non-alcoholic fatty liver disease (NAFLD), non-alcoholic steatohepatitis (NASH), liver steatosis, liver fibrosis, liver cirrhosis, liver cancer and other diseases associated with magnesium dysregulation.

21 Claims, 24 Drawing Sheets

Specification includes a Sequence Listing.

(56) References Cited

OTHER PUBLICATIONS

Ozcan et al., Endoplasmic reticulum stress links obesity, insulin action, and type 2 diabetes. Science. Oct. 15, 2004;306(5695):457-61.
Povsic et al., A Structured Literature Review of the Epidemiology and Disease Burden of Non-Alcoholic Steatohepatitis (NASH). Adv Ther. Jul. 2019;36(7):1574-1594.
Ruiz et al., Quantification in the subnanomolar range of phospholipids and neutral lipids by monodimensional thin-layer chromatography and image analysis. J Lipid Res. Jul. 1997;38(7):1482-9.
Simón et al., Magnesium accumulation upon cyclin M4 silencing activates microsomal triglyceride transfer protein improving NASH. J Hepatol. Jul. 2021;75(1):34-45.
Wagner et al., Hepatocellular carcinoma in GNMT-/- mice. Toxicol Appl Pharmacol. Jun. 1, 2009;237(2):246; author reply 247.
Watts et al., Silencing disease genes in the laboratory and the clinic. J Pathol. Jan. 2012;226(2):365-79.
Weingärtner et al., Less Is More: Novel Hepatocyte-Targeted siRNA Conjugates for Treatment of Liver-Related Disorders. Mol Ther Nucleic Acids. Sep. 4, 2020;21:242-250.
Yamazaki et al., Basolateral Mg2+ extrusion via CNNM4 mediates transcellular Mg2+ transport across epithelia: a mouse model. PLoS Genet. 2013;9(12):e1003983. 14 pages.
Younossi et al., Global epidemiology of nonalcoholic fatty liver disease-Meta-analytic assessment of prevalence, incidence, and outcomes. Hepatology. Jul. 2016;64(1):73-84.

* cited by examiner

A
Relative lipid accumulation (Fold)
0
1
2
3
4
5
6
Healthy + siRNAØ
NASH + siRNAØ
NASH + siRNA CNNM4
*

B
Relative mitochondrial ROS (Fold)
0,0
0,5
1,0
1,5
Healthy + siRNA Ø
NASH + siRNA Ø
NASH + siRNA CNNM4
**

C
% TUNEL positive cells
0
20
40
60
80
Healthy + siRNAØ
DILI + siRNAØ
DILI + siRNA CNNM4
***

GalNAc($Ac_3$)-$C_4H_8$-COOH (2)

DMT-Serinol(H)-OH (1)

(4)

DMT-Serinol(GalNAc) (3)

(DMT-Serinol(GalNAc)-CEP (5)

DMT-Serinol(GalNAc)-succinate (6)

DMT-Serinol(GalNAc)-succinyl lcaa CPG (7)

NUCLEIC ACIDS FOR INHIBITING EXPRESSION OF CNNM4 IN A CELL

CROSS-REFERENCE TO RELATED APPLICATIONS

This application is filed under the provisions of 35 U.S.C. § 371 and claims the priority of International Patent Application No. PCT/EP2021/064077 filed on 26 May 2021 entitled "NUCLEIC ACIDS FOR INHIBITING EXPRESSION OF CNNM4 IN A CELL" in the name of Ute SCHAEPER, et al., which claims priority to European Patent Application No. 20382449.5, filed on 27 May 2020, and European Patent Application No. 20382947.8, filed on 30 Oct. 2020, all of which are hereby incorporated by reference herein in their entirety.

FIELD OF THE INVENTION

The invention relates to nucleic acid products that interfere with or inhibit CNNM4 (Cyclin M4) gene expression. It further relates to therapeutic uses of CNNM4 inhibition for the treatment of diseases, among others, of liver diseases such as non-alcoholic fatty liver disease (NAFLD), non-alcoholic steatohepatitis (NASH), liver steatosis, liver fibrosis, liver cirrhosis, liver cancer and other diseases associated with magnesium dysregulation.

BACKGROUND

Double-stranded RNAs (dsRNA) able to bind through complementary base pairing to expressed mRNAs have been shown to block gene expression (Fire et al., 1998, Nature. 1998 Feb. 19; 391(6669):806-11 and Elbashir et al., 2001, Nature. 2001 May 24; 411(6836):494-8) by a mechanism that has been termed "RNA interference (RNAi)". Short dsRNAs direct gene specific, post transcriptional silencing in many organisms, including vertebrates, and have become a useful tool for studying gene function. RNAi is mediated by the RNA induced silencing complex (RISC), a sequence specific, multi component nuclease that degrades messenger RNAs having sufficient complementary or homology to the silencing trigger loaded into the RISC complex. Interfering RNAs such as siRNAs, antisense RNAs, and micro RNAs, are oligonucleotides that prevent the formation of proteins by gene silencing, i.e., inhibiting gene translation of the protein through degradation of mRNA molecules. Gene silencing agents are becoming increasingly important for therapeutic applications in medicine.

According to Watts and Corey in the Journal of Pathology (2012; Vol 226, p 365-379), there are algorithms that can be used to design nucleic acid silencing triggers, but all of these have severe limitations. It may take various experimental methods to identify potent siRNAs, as algorithms do not take into account factors such as tertiary structure of the target mRNA or the involvement of RNA binding proteins. Therefore, the discovery of a potent nucleic acid silencing trigger with minimal off-target effects is a complex process. For the pharmaceutical development of these highly charged molecules, it is necessary that they can be synthesised economically, distributed to target tissues, enter cells and function within acceptable limits of toxicity.

Chronic liver diseases comprise a group of hepatic pathologies of different aetiologies. Non-alcoholic fatty liver disease (NAFLD) has an incidence of 20-30% in the global population (Younossi et al, Hepatology 64, 73-84 (2016)) and includes a spectrum of hepatic disorders. It can progress from simple steatosis, the accumulation of lipid in the liver, to non-alcoholic steatohepatitis (NASH), which is characterized by steatosis with inflammation and occasional fibrosis. While steatosis is considered to be a relatively benign and reversible condition, there is a risk of progression to NASH, which is a chronic, progressive disease characterized by fatty liver and liver cell injury that can develop into fibrosis, cirrhosis and hepatocellular carcinoma (HCC) (Povsic et al., Adv. Ther. 36, 1574-1594 (2019)). About 20% of patients with NASH develop cirrhosis, an irreversible pathology characterized by extracellular matrix deposition that causes liver dysfunction. About a quarter of patients with liver fibrosis develop HCC, which is the most frequent form of liver cancer and the fifth cause of mortality and morbidity in the world (Younossi et al., Clin. Gastroenterol. Hepatol. 4, 748-755 (2018)). Very few patients are eligible for currently available therapeutic intervention when diagnosed, and survival rates are poor, with on average of only 6-20 months survival after diagnosis. There is therefore a clear unmet need for treatment of these and similar chronic diseases.

The liver can also suffer from acute damages. This organ plays a central role in drug metabolism and clearance and drug-induced liver injury (DILI) can result from drug overdose. DILI is the main cause of acute liver failure and transplantation in the USA and most of Europe. About 30,000 patients per year develop acetaminophen (APAP)-induced liver injury and 29% of them undergo liver transplantation. Currently, the standard therapy for DILI is treatment with N-acetylcysteine. This treatment however only rarely leads to successful rescue of the liver, meaning that new therapies are needed.

Magnesium in its $Mg^{2+}$ ionic form is the most abundant divalent cation in the cell and it is required as a cofactor for about 300 enzymatic reactions (Baaij et al., Physiol. Rev. 1920, 1-46 (2015)). Several proteins participate in this process allowing the flux of the cation across cell membranes (Jahnen-Dechent Clin. Kidney J. 5, i3-i14 (2012); Funato and Miki, J. Biochem. 165(3):219-225 (2019)). Magnesium homeostasis is maintained by a balance between renal reabsorption and urinary excretion, together with adequate daily intake. Magnesium dysregulation is present in several comorbidities of NAFLD such as insulin resistance and diabetes, cardiovascular complications and obesity (Özcan et al., Science (80). 306, 457 LP-461 (2004)). Furthermore, deficiencies in $Mg^{2+}$ are also related to triggering of the inflammatory response, mitochondrial dysfunction and decrease of anti-oxidant system activity (Barbagallo et al. Metabolism. 63, 502-509 (2014)). Cyclin M (CNNM) proteins play a key role in the transport of magnesium ions through cell membranes in different organs (Funato and Miki 2019). The inventors have surprisingly found that CNNM4 is overexpressed in the liver of patients with liver diseases such as NASH, cirrhosis and hepatocellular carcinoma (HCC) as well as in preclinical models for NASH, drug induced liver injury (DILI) and HCC. It may thereby cause magnesium perturbation and contribute to the cause and progression of diseases associated with a dysregulation of this cation, such as many types of liver diseases. The inventors have also found that CNNM4 inhibition in the liver reduces lipid content in preclinical models of NAFLD and can thereby be beneficial in the treatment of NAFLD. The effect is likely achieved at least in part by restoration of $Mg^{2+}$ homeostasis in the liver. Reducing the expression of CNNM4 is therefore a promising new therapeutic strategy for treating pathologies related to the liver, and especially those associated with magnesium perturbation such as NAFLD, liver fibrosis, HCC and metabolic syndrome.

Current treatments for NAFLD focus on changing unhealthy life-style habits of patients, such as by encouraging them to take up exercise programmes and to reduce their weight. However, long-term compliance by patients is often problematic. There is therefore a need for pharmacological interventions for effective treatment of such diseases and other liver diseases.

Renal or kidney fibrosis results from an excessive accumulation of extracellular matrix (ECM), which occurs in almost every kind of chronic liver disease. The pathogenesis is a progressive process that leads to end-stage renal failure, a devastating disorder that requires dialysis or kidney transplantation. The inventors have also found CNNM4 overexpression in renal fibrosis animal models. Renal fibrosis may therefore be treated in part by inhibiting CNNM4 in the liver and/or in the kidneys.

The inventors have surprisingly also observed CNNM4 overexpression in lung cancer, and CNNM4 inhibition may be a new way of treating such a cancer.

In summary, the inventors have surprisingly found that CNNM4 is overexpressed in a group of different pathologies, both in human samples and in animal models. These pathologies comprise liver diseases such as NAFLD, cirrhosis and HCC, or acute liver pathologies such as DILI. CNNM4 overexpression has also been observed in kidney and lung diseases. Many of these diseases are highly prevalent but lack an effective treatment. The inventors propose using CNNM4 inhibition by RNA interference as a new way of treating these diseases and provide CNNM4 siRNAs for use in such treatments.

SUMMARY OF THE INVENTION

One aspect of the invention is a double-stranded nucleic acid for inhibiting expression of CNNM4, wherein the nucleic acid comprises a first strand and a second strand, wherein the first strand sequence comprises a sequence of at least 15 nucleotides differing by no more than 3 nucleotides from any one of the sequences selected from SEQ ID NO: 243, 267, 277, 279, 287, 317, 319, 325, 333, 345, 347, 349, 361, 367, 369, 371, 377, 401, 411, 413, 415, 420, 421, 524, 526, 528, 530, 532, 534, 536, 538, 540, 542, 544, 546, 548, 549, 550, 551 and 552.

One aspect relates to a double-stranded nucleic acid that is capable of inhibiting expression of CNNM4, preferably in a cell, for use as a medicament or in associated diagnostic or therapeutic methods, wherein the nucleic acid preferably comprises or consists of a first strand and a second strand and preferably wherein the first strand comprises a sequence sufficiently complementary to a CNNM4 mRNA so as to mediate RNA interference.

One aspect relates to a composition comprising a nucleic acid as disclosed herein and a solvent (preferably water) and/or a delivery vehicle and/or a physiologically acceptable excipient and/or a carrier and/or a salt and/or a diluent and/or a buffer and/or a preservative.

One aspect relates to a composition comprising a nucleic acid as disclosed herein and a further therapeutic agent selected from e.g., an oligonucleotide, a small molecule, a monoclonal antibody, a polyclonal antibody and a peptide.

One aspect relates to a nucleic acid or a composition comprising it as disclosed herein for use as a medicament or in associated methods.

One aspect relates to a nucleic acid or a composition comprising it as disclosed herein for use in the prevention, decrease of the risk of suffering from, or treatment of a disease, disorder or syndrome.

One aspect relates to the use of a nucleic acid or a composition comprising it as disclosed herein in the prevention, decrease of the risk of suffering from, or treatment of a disease, disorder or syndrome, wherein the disease, disorder or syndrome is preferably NASH.

One aspect relates to a method of preventing, decreasing the risk of suffering from, or treating a disease, disorder or syndrome comprising administering a pharmaceutically effective dose or amount of a nucleic acid or composition comprising it as disclosed herein to an individual in need of treatment, preferably wherein the nucleic acid or composition is administered to the subject subcutaneously, intravenously or by oral, rectal, pulmonary, intramuscular or intraperitoneal administration.

DETAILED DESCRIPTION OF THE INVENTION

The present invention relates to a nucleic acid which is double-stranded and which comprises a sequence homologous to and/or complementary to a portion of an expressed RNA transcript of CNNM4, and compositions thereof. These nucleic acids, or conjugates or compositions thereof, may be used in the treatment and prevention of a variety of diseases, disorders and syndromes in which reduced expression of the CNNM4 gene product is desirable.

A first aspect of the invention is a double-stranded nucleic acid for inhibiting expression of CNNM4, preferably in a cell, wherein the nucleic acid comprises a first strand and a second strand, wherein the first strand sequence comprises a sequence of at least 15 nucleotides differing by no more than 3 nucleotides from any one of the sequences selected from SEQ ID NO: 243, 267, 277, 279, 287, 317, 319, 325, 333, 345, 347, 349, 361, 367, 369, 371, 377, 401, 411, 413, 415, 420, 421, 524, 526, 528, 530, 532, 534, 536, 538, 540, 542, 544, 546, 548, 549, 550, 551 and 552. These nucleic acids among others have the advantage of being active in various species that are relevant for pre-clinical and clinical development and/or of having few relevant off-target effects. Having few relevant off-target effects means that a nucleic acid specifically inhibits the intended target and does not significantly inhibit other genes or inhibits only one or few other genes at a therapeutically acceptable level.

Preferably, the first strand sequence comprises a sequence of at least 16, more preferably at least 17, yet more preferably at least 18 and most preferably all 19 nucleotides differing by no more than 3 nucleotides, preferably by no more than 2 nucleotides, more preferably by no more than 1 nucleotide, and most preferably not differing by any nucleotide from any one of the sequences selected from SEQ ID NO: 243, 267, 277, 279, 287, 317, 319, 325, 333, 345, 347, 349, 361, 367, 369, 371, 377, 401, 411, 413, 415, 420, 421, 524, 526, 528, 530, 532, 534, 536, 538, 540, 542, 544, 546, 548, 549, 550, 551 and 552.

Preferably, the first strand sequence of the nucleic acid consists of one of the sequences selected from SEQ ID NOs: 243, 267, 277, 279, 287, 317, 319, 325, 333, 345, 347, 349, 361, 367, 369, 371, 377, 401, 411, 413, 415, 420, 421, 524, 526, 528, 530, 532, 534, 536, 538, 540, 542, 544, 546, 548, 549, 550, 551 and 552. The sequence may however be modified by a number of nucleic acid modifications that do not change the identity of the nucleotide. For example, modifications of the backbone or sugar residues of the nucleic acid do not change the identity of the nucleotide because the base itself remains the same as in the reference sequence.

A nucleic acid that comprises a sequence according to a reference sequence herein means that the nucleic acid comprises a sequence of contiguous nucleotides in the order as defined in the reference sequence.

When reference is made herein to a reference sequence comprising or consisting of a number of nucleotides that are not shown to be modified in that sequence, the same reference also encompasses the same nucleotide sequence in which one, several, such as two, three, four, five, six, seven or more, including all, nucleotides are modified by modifications such as 2'-OMe, 2'-F, are linked to a ligand, or a linker, have a 3' end or 5' end modification or any other modification. It also encompasses sequences in which two or more nucleotides are linked to each other by the natural phosphodiester linkage or by any other linkage such as a phosphorothioate or a phosphorodithioate linkage.

A double-stranded nucleic acid is a nucleic acid in which the first strand and the second strand hybridise to each other over at least part of their lengths and are therefore capable of forming a duplex region under physiological conditions, such as in PBS at 37° C. at a concentration of 1 μM of each strand. The first and second strand are preferably able to hybridise to each other and therefore to form a duplex region over a region of at least 15 nucleotides, preferably 16, 17, 18 or 19 nucleotides. This duplex region comprises nucleotide base parings between the two strands, preferably based on Watson-Crick base pairing and/or wobble base pairing (such as GU base pairing). All the nucleotides of the two strands within a duplex region do not have to base pair to each other to form a duplex region. A certain number of mismatches, deletions or insertions between the nucleotide sequences of the two strands are acceptable. Overhangs on either end of the first or second strand or unpaired nucleotides at either end of the double-stranded nucleic acid are also possible. The double-stranded nucleic acid is preferably a stable double-stranded nucleic acid under physiological conditions, and preferably has a melting temperature (Tm) of 45° C. or more, preferably 50° C. or more, and more preferably 55° C. or more for example in PBS at a concentration of 1 μM of each strand.

A stable double-stranded nucleic acid under physiological conditions is a double-stranded nucleic acid that has a Tm of 45° C. or more, preferably 50° C. or more, and more preferably 55° C. or more, for example in PBS at a concentration of 1 μM of each strand.

The first strand and the second strand are preferably capable of forming a duplex region (i.e., are complementary to each other) over i) at least a portion of their lengths, preferably over at least 15 nucleotides of both of their lengths, ii) over the entire length of the first strand, iii) over the entire length of the second strand or iv) over the entire length of both the first and the second strand. Strands being complementary to each other over a certain length means that the strands are able to base pair to each other, either via Watson-Crick or wobble base pairing, over that length. Each nucleotide of the length does not necessarily have to be able to base pair with its counterpart in the other strand over the entire given length as long as a stable double-stranded nucleotide under physiological conditions can be formed. It is however, preferred, in certain embodiments, if each nucleotide of the length can base pair with its counterpart in the other strand over the entire given length.

A certain number of mismatches, deletions or insertions between the first strand and the target sequence, or between the first strand and the second strand can be tolerated in the context of the siRNA and even have the potential in certain cases to increase RNA interference (e.g., inhibition) activity.

The inhibition activity of the nucleic acids according to the present invention relies on the formation of a duplex region between all or a portion of the first strand and a portion of a target nucleic acid. The portion of the target nucleic acid that forms a duplex region with the first strand, defined as beginning with the first base pair formed between the first strand and the target sequence and ending with the last base pair formed between the first strand and the target sequence, inclusive, is the target nucleic acid sequence or simply, target sequence. The duplex region formed between the first strand and the second strand need not be the same as the duplex region formed between the first strand and the target sequence. That is, the second strand may have a sequence different from the target sequence; however, the first strand must be able to form a duplex structure with both the second strand and the target sequence, at least under physiological conditions.

The complementarity between the first strand and the target sequence may be perfect (i.e., 100% identity with no nucleotide mismatches or insertions or deletions in the first strand as compared to the target sequence).

The complementarity between the first strand and the target sequence may not be perfect. The complementarity may be from about 70% to about 100%. More specifically, the complementarity may be at least 70%, 80%, 85%, 90% or 95% and intermediate values.

The identity between the first strand and the complementary sequence of the target sequence may range from about 75% to about 100%. More specifically, the complementarity may be at least 75%, 80%, 85%, 90% or 95% and intermediate values, provided a nucleic acid is capable of reducing or inhibiting the expression of CNNM4.

A nucleic acid having less than 100% complementarity between the first strand and the target sequence may be able to reduce the expression of CNNM4 to the same level as a nucleic acid having perfect complementarity between the first strand and target sequence. Alternatively, it may be able to reduce expression of CNNM4 to a level that is 15%, 20%, 25%, 30%, 35%, 40%, 45%, 50%, 55%, 60%, 65%, 70%, 75%, 80%, 85%, 90%, 95%, 98%, 99% or 100% of the level of reduction achieved by the nucleic acid with perfect complementarity.

In one aspect, a nucleic acid of the present disclosure is a nucleic acid wherein (a) the first strand sequence comprises a sequence differing by no more than 3 nucleotides from any one of the first strand sequences of Table 1 and optionally wherein the second strand sequence comprises a sequence differing by no more than 3 nucleotides from the second strand sequence in the same line of the table;

(b) the first strand sequence comprises a sequence differing by no more than 2 nucleotides from any one of the first strand sequences of Table 1 and optionally wherein the second strand sequence comprises a sequence differing by no more than 2 nucleotides from the second strand sequence in the same line of the table;

(c) the first strand sequence comprises a sequence differing by no more than 1 nucleotide from any one of the first strand sequences of Table 1 and optionally wherein the second strand sequence comprises a sequence differing by no more than 1 nucleotide from the second strand sequence in the same line of the table;

(d) the first strand sequence comprises a sequence corresponding to nucleotides 2 to 17 from the 5' end of any one of the first strand sequences of Table 1 and optionally wherein the second strand sequence comprises a sequence corresponding to nucleotides 2 to 17 from the 5' end of the second strand sequence in the same line of the table;

(e) the first strand sequence comprises a sequence corresponding to nucleotides 2 to 18 from the 5' end of any one of the first strand sequences of Table 1 and optionally wherein the second strand sequence comprises a sequence corresponding to nucleotides 2 to 18 from the 5' end of the second strand sequence in the same line of the table;

(f) the first strand sequence comprises a sequence corresponding to nucleotides 2 to 19 from the 5' end of any one of the first strand sequences of Table 1 and optionally wherein the second strand sequence comprises a sequence corresponding to nucleotides 2 to 19 from the 5' end of the second strand sequence in the same line of the table;

(g) the first strand sequence comprises a sequence corresponding to nucleotides 2 to 19 from the 5' end of any one of the first strand sequences of Table 1 and optionally wherein the second strand sequence comprises a sequence corresponding to nucleotides 1 to 18 from the 5' end of the second strand sequence in the same line of the table;

(h) the first strand sequence comprises a sequence of any one of the first strand sequences of Table 1 and optionally wherein the second strand sequence comprises a sequence of the second strand sequence in the same line of the table; or (i) the first strand sequence consists of any one of the first strand sequences of Table 1 and optionally wherein the second strand sequence consists of the sequence of the second strand sequence in the same line of the table;

wherein Table 1 is:

TABLE 1

| First strand sequence (SEQ ID NO:) | Second strand sequence (SEQ ID NO:) |
|---|---|
| 239 | 240 or 374 |
| 241 | 242 or 376 |
| 243 | 244 or 378 |
| 245 | 246 or 379 |
| 247 | 248 or 380 |
| 249 | 250 or 386 |
| 251 | 252 |
| 253 | 254 or 388 |
| 255 | 256 or 390 |
| 257 | 258 or 392 |
| 259 | 260 or 394 |
| 261 | 262 or 396 |
| 263 | 264 or 398 |
| 265 | 266 or 400 |
| 267 | 268 or 402 |
| 269 | 270 or 404 |
| 271 | 272 or 406 |
| 273 | 274 or 408 |
| 275 | 276 or 410 |
| 277 | 278 or 412 |
| 279 | 280 or 414 |
| 281 | 282 or 416 |
| 283 | 284 |
| 285 | 286 |
| 287 | 288 |
| 289 | 290 |
| 291 | 292 |
| 293 | 294 |
| 295 | 296 |
| 297 | 298 |
| 299 | 300 |

TABLE 1-continued

| First strand sequence (SEQ ID NO:) | Second strand sequence (SEQ ID NO:) |
|---|---|
| 301 | 302 |
| 303 | 304 |
| 305 | 306 |
| 307 | 308 |
| 309 | 310 |
| 311 | 312 |
| 313 | 314 |
| 315 | 316 |
| 317 | 318 |
| 319 | 320 |
| 321 | 322 |
| 323 | 324 |
| 325 | 326 |
| 327 | 328 |
| 329 | 330 |
| 331 | 332 |
| 333 | 334 |
| 335 | 336 |
| 337 | 338 |
| 339 | 340 |
| 341 | 342 |
| 342 | 344 |
| 345 | 346 |
| 347 | 348 |
| 349 | 350 |
| 351 | 352 |
| 353 | 354 |
| 355 | 356 |
| 357 | 358 |
| 359 | 360 |
| 361 | 362 |
| 363 | 364 |
| 365 | 366 |
| 367 | 368 |
| 369 | 370 |
| 371 | 372 |
| 373 | 240 or 374 |
| 375 | 242 or 376 |
| 377 | 244 or 378 |
| 379 | 246 or 380 |
| 381 | 248 or 382 |
| 383 | 384 |
| 385 | 250 or 386 |
| 387 | 254 or 388 |
| 389 | 256 or 390 |
| 391 | 258 or 392 |
| 393 | 260 or 394 |
| 395 | 262 or 396 |
| 397 | 264 or 398 |
| 399 | 266 or 400 |
| 401 | 268 or 402 |
| 403 | 270 or 404 |
| 405 | 272 or 406 |
| 407 | 274 or 408 |
| 409 | 276 or 410 |
| 411 | 278 or 412 |
| 413 | 280 or 414 |
| 415 | 282 or 416 |
| 417 | 318 |
| 418 | 320 |
| 419 | 346 |
| 420 | 362 |
| 421 | 370 |
| 434 | 435 |
| 436 | 437 |
| 438 | 439 |
| 440 | 441 |
| 442 | 443 |
| 444 | 445 |
| 446 | 447 |
| 448 | 449 |
| 524 | 525 |
| 526 | 527 |
| 528 or 548 | 529 |
| 530 | 531 |
| 532 or 549 | 533 |
| 534 | 535 |

TABLE 1-continued

| First strand sequence (SEQ ID NO:) | Second strand sequence (SEQ ID NO:) |
|---|---|
| 536 | 537 |
| 538 | 539 |
| 540 or 550 | 541 |
| 542 or 551 | 543 |
| 544 | 545 |
| 546 or 552 | 547 |

In one aspect, the nucleic acid is a nucleic acid wherein:

(a) the first strand sequence comprises the sequence of SEQ ID NO 325 and optionally wherein the second strand sequence comprises the sequence of SEQ ID NO: 326; or (b) the first strand sequence comprises the sequence of SEQ ID NO 371 and optionally wherein the second strand sequence comprises the sequence of SEQ ID NO: 372; or (c) the first strand sequence comprises the sequence of SEQ ID NO 411 and optionally wherein the second strand sequence comprises the sequence of SEQ ID NO: 278 or 412; or (d) the first strand sequence comprises the sequence of SEQ ID NO 413 and optionally wherein the second strand sequence comprises the sequence of SEQ ID NO: 280 or 414; or (e) the first strand sequence comprises the sequence of SEQ ID NO 420 and optionally wherein the second strand sequence comprises the sequence of SEQ ID NO: 362; or (f) the first strand sequence comprises the sequence of SEQ ID NO 421 and optionally wherein the second strand sequence comprises the sequence of SEQ ID NO: 370; or (g) the first strand sequence consists of SEQ ID NO: 371 and optionally wherein the second strand sequence consists of SEQ ID NO: 372; or (h) the first strand sequence consists of SEQ ID NO: 411 and optionally wherein the second strand sequence consists of SEQ ID NO: 278 or 412; or (i) the first strand sequence consists of SEQ ID NO: 413 and optionally wherein the second strand sequence consists of SEQ ID NO: 280 or 414; or (j) the first strand sequence consists of SEQ ID NO: 420 and optionally wherein the second strand sequence consists of SEQ ID NO: 362; or (k) the first strand sequence consists of SEQ ID NO: 421 and optionally wherein the second strand sequence consists of SEQ ID NO: 370; or (l) the first strand sequence consists of SEQ ID NO: 548 and optionally wherein the second strand sequence consists of SEQ ID NO: 529; or (m) the first strand sequence consists of SEQ ID NO: 549 and optionally wherein the second strand sequence consists of SEQ ID NO: 533; or (n) the first strand sequence consists of SEQ ID NO: 550 and optionally wherein the second strand sequence consists of SEQ ID NO: 541; or (o) the first strand sequence consists of SEQ ID NO: 551 and optionally wherein the second strand sequence consists of SEQ ID NO: 543; or (p) the first strand sequence consists of SEQ ID NO: 548 and optionally wherein the second strand sequence consists of SEQ ID NO: 547.

In one aspect, if the 5'-most nucleotide of the first strand is a nucleotide other than A or U, this nucleotide is replaced by an A or U. Preferably, if the 5'-most nucleotide of the first strand is a nucleotide other than U, this nucleotide is replaced by U, and more preferably by U with a 5' vinylphosphonate.

In one aspect, there is a mismatch between the first nucleotide at the 5' end of the first strand and the corresponding nucleotide (the nucleotide with which it would form a base pair if there was no mismatch) in the second strand. For example, the 5' nucleotide of the first strand may be a U and the corresponding nucleotide in the second strand may be any nucleotide other than an A. In this case, the two nucleotides are unable to form a classical Watson-Crick base pair and there is a mismatch between the two nucleotides.

When a nucleic acid of the invention does not comprise the entire sequence of a reference first strand and/or second strand sequence, as for example given in Table 1, or one or both strands differ from the corresponding reference sequence by one, two or three nucleotides, this nucleic acid preferably retains at least 30%, more preferably at least 50%, more preferably at least 70%, more preferably at least 80%, even more preferably at least 90%, yet more preferably at least 95% and most preferably at least 100% of the CNNM4 inhibition activity compared to the inhibition activity of the corresponding nucleic acid that comprises the entire first strand and second strand reference sequences in a comparable experiment.

In one aspect, the nucleic acid is a nucleic acid wherein the first strand sequence comprises, or preferably consists of, the sequence of SEQ ID NO: 325 and optionally wherein the second strand sequence comprises, or consists of, a sequence of at least 15, preferably at least 16, more preferably at least 17, yet more preferably at least 18 and most preferably all nucleotides of the sequence of SEQ ID NO: 326; or wherein the first strand sequence comprises, or preferably consists of, the sequence of SEQ ID NO: 371 and optionally wherein the second strand sequence comprises, or consists of, a sequence of at least 15, preferably at least 16, more preferably at least 17, yet more preferably at least 18 and most preferably all nucleotides of the sequence of SEQ ID NO: 372; or wherein the first strand sequence comprises, or preferably consists of, the sequence of SEQ ID NO: 411 and optionally wherein the second strand sequence comprises, or consists of, a sequence of at least 15, preferably at least 16, more preferably at least 17, yet more preferably at least 18 and most preferably all nucleotides of the sequence of SEQ ID NO: 478 or 412; or wherein the first strand sequence comprises, or preferably consists of, the sequence of SEQ ID NO: 412 and optionally wherein the second strand sequence comprises, or consists of, a sequence of at least 15, preferably at least 16, more preferably at least 17, yet more preferably at least 18 and most preferably all nucleotides of the sequence of SEQ ID NO:

280 or 414; or wherein the first strand sequence comprises, or preferably consists of, the sequence of SEQ ID NO: 420 and optionally wherein the second strand sequence comprises, or consists of, a sequence of at least 15, preferably at least 16, more preferably at least 17, yet more preferably at least 18 and most preferably all nucleotides of the sequence of SEQ ID NO: 362; or wherein the first strand sequence comprises, or preferably consists of, the sequence of SEQ ID NO: 421 and optionally wherein the second strand sequence comprises, or consists of, a sequence of at least 15, preferably at least 16, more preferably at least 17, yet more preferably at least 18 and most preferably all nucleotides of the sequence of SEQ ID NO: 370; or wherein the first strand sequence comprises, or preferably consists of, the sequence of SEQ ID NO: 548 and optionally wherein the second strand sequence comprises, or consists of, a sequence of at least 15, preferably at least 16, more preferably at least 17, yet more preferably at least 18 and most preferably all nucleotides of the sequence of SEQ ID NO: 529; or wherein the first strand sequence comprises, or preferably consists of, the sequence of SEQ ID NO: 549 and optionally wherein the second strand sequence comprises, or consists of, a sequence of at least 15, preferably at least 16, more preferably at least 17, yet more preferably at least 18 and most preferably all nucleotides of the sequence of SEQ ID NO: 533; or wherein the first strand sequence comprises, or preferably consists of, the sequence of SEQ ID NO: 550 and optionally wherein the second strand sequence comprises, or consists of, a sequence of at least 15, preferably at least 16, more preferably at least 17, yet more preferably at least 18 and most preferably all nucleotides of the sequence of SEQ ID NO: 541; or wherein the first strand sequence comprises, or preferably consists of, the sequence of SEQ ID NO: 551 and optionally wherein the second strand sequence comprises, or consists of, a sequence of at least 15, preferably at least 16, more preferably at least 17, yet more preferably at least 18 and most preferably all nucleotides of the sequence of SEQ ID NO: 543; or wherein the first strand sequence comprises, or preferably consists of, the sequence of SEQ ID NO: 552 and optionally wherein the second strand sequence comprises, or consists of, a sequence of at least 15, preferably at least 16, more preferably at least 17, yet more preferably at least 18 and most preferably all nucleotides of the sequence of SEQ ID NO: 547.

In one aspect, the nucleic acid is a double-stranded nucleic acid for inhibiting expression of CNNM4, preferably in a cell, wherein the nucleic acid comprises a first nucleic acid strand and a second nucleic acid strand, wherein the first strand is capable of hybridising under physiological conditions to a nucleic acid of a sequence selected from SEQ ID NO: 240, 242, 244, 250, 252, 254, 256, 258, 260, 262, 264, 266, 268, 270, 272, 274, 276, 278, 280, 282, 284, 286, 288, 290, 292, 294, 296, 298, 300, 302, 304, 306, 308, 310, 312, 314, 316, 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378, 380, 382, 384, 386, 388, 390, 392, 394, 396, 398, 400, 402, 404, 406, 408, 410, 412, 414, 416, 423, 425, 427, 429, 431, 433, 435, 437, 439, 441, 443, 445, 447, 449, 525, 527, 529, 531, 533, 535, 537, 539, 541, 543, 545 and 547; and wherein the second strand is capable of hybridising under physiological conditions to the first strand to form a duplex region.

Nucleic acids that are capable of hybridising under physiological conditions are nucleic acids that are capable of forming base pairs, preferably Watson-Crick or wobble base-pairs, between at least a portion of the opposed nucleotides in the strands so as to form at least a duplex region. Such a double-stranded nucleic acid is preferably a stable double-stranded nucleic acid under physiological conditions (for example in PBS at 37° C. at a concentration of 1 μM of each strand), meaning that under such conditions, the two strands stay hybridised to each other. The Tm of the double-stranded nucleotide is preferably 45° C. or more, preferably 50° C. or more and more preferably 55° C. or more.

One aspect of the present invention relates to a nucleic acid for inhibiting expression of CNNM4, preferably in a cell, wherein the nucleic acid comprises a first sequence of at least 15, preferably at least 16, more preferably at least 17, yet more preferably at least 18 and most preferably all nucleotides differing by no more than 3 nucleotides, preferably no more than 2 nucleotides, more preferably no more than 1 nucleotide and most preferably not differing by any nucleotide from any of the sequences of Table 4, the first sequence being able to hybridise to a CNNM4 gene transcript (such as an mRNA) under physiological conditions. Preferably, the nucleic acid further comprises a second sequence of at least 15, preferably at least 16, more preferably at least 17, yet more preferably at least 18 and most preferably all nucleotides differing by no more than 3 nucleotides, preferably no more than 2 nucleotides, more preferably no more than 1 nucleotide and most preferably not differing by any nucleotide from any of the sequences of Table 4, wherein the second sequence is able to hybridise to the first sequence under physiological conditions and preferably wherein the nucleic acid is an siRNA that is capable of inhibiting CNNM4 expression via the RNAi pathway.

One aspect relates to any double-stranded nucleic acid as disclosed in Table 2, preferably for inhibiting expression of CNNM4, provided that the double-stranded nucleic acid is capable of inhibiting expression of CNNM4. These nucleic acids are all siRNAs with various nucleotide modifications. Some of them are conjugates comprising GalNAc moieties that can be specifically targeted to cells with GalNAc receptors, such as hepatocytes.

One aspect relates to a double-stranded nucleic acid that is capable of inhibiting expression of CNNM4, preferably in a cell, for use as a medicament or in associated diagnostic or therapeutic methods, wherein the nucleic acid preferably comprises or consists of a first strand and a second strand and preferably wherein the first strand comprises a sequence sufficiently complementary to a CNNM4 mRNA so as to mediate RNA interference.

The nucleic acids described herein may be capable of inhibiting the expression of CNNM4, preferably in a cell. The nucleic acids may be capable of inhibiting CNNM4 expression completely, resulting in 0% remaining expression upon treatment with the nucleic acids. The nucleic acids may be capable of partially inhibiting CNNM4 expression. Partial inhibition means that CNNM4 expression is decreased by 15%, 20%, 30%, 40%, 50%, 60%, 70%, 75%, 80%, 85%, 90%, 95% or more, or intermediate values, as compared to the absence of a nucleic acid of the invention under comparable conditions. The level of inhibition may be measured by comparing a treated sample with an untreated sample or with a sample treated with a control such as for example a siRNA that does not target CNNM4. Inhibition may be measured by measuring CNNM4 mRNA and/or protein levels or levels of a biomarker or indicator that correlates with CNNM4 presence or activity. It may be measured in cells that may have been treated in vitro with a nucleic acid described herein. Alternatively, or in addition, inhibition may be measured in cells, such as hepatocytes, or tissue, such as liver tissue, or an organ, such as the liver, or in a body fluid such as blood, serum, lymph or in any other body part or fluid that has been taken from a subject previously treated with a nucleic acid disclosed herein. Preferably, inhibition of CNNM4 expression is determined by comparing the CNNM4 mRNA level measured in CNNM4-expressing cells after 24 or 48 hours in vitro treatment with a double-stranded RNA disclosed herein under ideal conditions (see the examples for appropriate concentrations and conditions) to the CNNM4 mRNA level measured in control cells that were untreated or mock treated or treated with a control double-stranded RNA under the same or at least comparable conditions.

One aspect of the present invention relates to a nucleic acid, wherein the first strand and the second strand are present on a single strand of a nucleic acid that loops around so that the first strand and the second strand are able to hybridise to each other and to thereby form a double-stranded nucleic acid with a duplex region.

Preferably, the first strand and the second strand of the nucleic acid are separate strands. The two separate strands are preferably each 17-25 nucleotides in length, more preferably 18-25 nucleotides in length. The two strands may be of the same or different lengths. The first strand may be 17-25 nucleotides in length, preferably it may be 18-24 nucleotides in length, it may be 18, 19, 20, 21, 22, 23 or 24 nucleotides in length. Most preferably, the first strand is 19 nucleotides in length. The second strand may independently be 17-25 nucleotides in length, preferably it may be 18-24 nucleotides in length, it may be 18, 19, 20, 21, 22, 23 or 24 nucleotides in length. More preferably, the second strand is 18 or 19 or 20 nucleotides in length, and most preferably it is 19 nucleotides in length.

Preferably, the first strand and the second strand of the nucleic acid form a duplex region of 17-25 nucleotides in length. More preferably, the duplex region is 18-24 nucleotides in length. The duplex region may be 17, 18, 19, 20, 21, 22, 23, 24 or 25 nucleotides in length. In the most preferred embodiment, the duplex region is 18 or 19 nucleotides in length. The duplex region is defined here as the region between and including the 5'-most nucleotide of the first strand that is base paired to a nucleotide of the second strand to the 3'-most nucleotide of the first strand that is base paired to a nucleotide of the second strand. The duplex region may comprise nucleotides in either or both strands that are not base-paired to a nucleotide in the other strand. It may comprise one, two, three or four such nucleotides on the first strand and/or on the second strand. However, preferably, the duplex region consists of 17-25 consecutive nucleotide base pairs. That is to say that it preferably comprises 17-25 consecutive nucleotides on both of the strands that all base pair to a nucleotide in the other strand. More preferably, the duplex region consists of 18 or 19 consecutive nucleotide base pairs, most preferably 18.

In each of the embodiments disclosed herein, the nucleic acid may be blunt ended at both ends; have an overhang at one end and a blunt end at the other end; or have an overhang at both ends.

The nucleic acid may have an overhang at one end and a blunt end at the other end. The nucleic acid may have an overhang at both ends. The nucleic acid may be blunt ended at both ends. The nucleic acid may be blunt ended at the end with the 5' end of the first strand and the 3' end of the second strand or at the 3' end of the first strand and the 5' end of the second strand.

The nucleic acid may comprise an overhang at a 3' or 5' end. The nucleic acid may have a 3' overhang on the first strand. The nucleic acid may have a 3' overhang on the second strand. The nucleic acid may have a 5' overhang on the first strand. The nucleic acid may have a 5' overhang on the second strand. The nucleic acid may have an overhang at both the 5' end and 3' end of the first strand. The nucleic acid may have an overhang at both the 5' end and 3' end of the second strand. The nucleic acid may have a 5' overhang on the first strand and a 3' overhang on the second strand. The nucleic acid may have a 3' overhang on the first strand and a 5' overhang on the second strand. The nucleic acid may have a 3' overhang on the first strand and a 3' overhang on the second strand. The nucleic acid may have a 5' overhang on the first strand and a 5' overhang on the second strand.

An overhang at the 3' end or 5' end of the second strand or the first strand may consist of 1, 2, 3, 4 and 5 nucleotides in length. Optionally, an overhang may consist of 1 or 2 nucleotides, which may or may not be modified.

In one embodiment, the 5' end of the first strand is a single-stranded overhang of one, two or three nucleotides, preferably of one nucleotide.

Preferably, the nucleic acid is an siRNA. siRNAs are short interfering or short silencing RNAs that are able to inhibit the expression of a target gene through the RNA interference (RNAi) pathway. Inhibition occurs through targeted degradation of mRNA transcripts of the target gene after transcription. The siRNA forms part of the RISC complex. The RISC complex specifically targets the target RNA by sequence complementarity of the first (antisense) strand with the target sequence.

Preferably, the nucleic acid is capable of inhibiting CNNM4. The inhibition is preferably mediated by the RNA interference (RNAi) mechanism. Preferably, the nucleic acid mediates RNA interference (i.e., it is capable of inhibiting its target) with an efficacy of at least 50% inhibition, more preferably at least 70%, more preferably at least 80%, even more preferably at least 90%, yet more preferably at least 95% and most preferably 100% inhibition. The inhibition efficacy is preferably measured by comparing the CNNM4 mRNA level in cells, such as hepatocytes, treated with a CNNM4-specific siRNA to the CNNM4 mRNA level in cells treated with a control in a comparable experiment. The control can be a treatment with a non-CNNM4 targeting siRNA or without a siRNA. The nucleic acid, or at least the first strand of the nucleic acid, is therefore preferably able to be incorporated into the RISC complex. As a result, the nucleic acid, or at least the first strand of the nucleic acid, is therefore able to guide the RISC complex to a specific target RNA with which the nucleic acid, or at least the first strand of the nucleic acid, is at least partially complementary. The RISC complex then specifically cleaves this target RNA and as a result leads to inhibition of the expression of the gene from which the RNA stems.

Nucleic Acid Modifications

Nucleic acids discussed herein include unmodified RNA as well as RNA which has been modified, e.g., to improve efficacy or stability. Unmodified RNA refers to a molecule in which the components of the nucleic acid, namely sugars, bases, and phosphate moieties, are the same or essentially the same as those which occur in nature, for example as occur naturally in the human body. The term “modified nucleotide” as used herein refers to a nucleotide in which one or more of the components of the nucleotide, namely the sugar, base, and phosphate moiety, is/are different from those which occur in nature. The term “modified nucleotide” also refers in certain cases to molecules that are not nucleotides in the strict sense of the term because they lack, or have a substitute of, an essential component of a nucleotide, such as the sugar, base or phosphate moiety. A nucleic acid comprising such modified nucleotides is still to be understood as being a nucleic acid, even if one or more of the nucleotides of the nucleic acid has been replaced by a modified nucleotide that lacks, or has a substitution of, an essential component of a nucleotide.

Modifications of the nucleic acid of the present invention generally provide a powerful tool in overcoming potential limitations including, but not limited to, in vitro and in vivo stability and bioavailability inherent to native RNA molecules. The nucleic acids according to the invention may be modified by chemical modifications. Modified nucleic acids can also minimise the possibility of inducing interferon activity in humans. Modifications can further enhance the functional delivery of a nucleic acid to a target cell. The modified nucleic acids of the present invention may comprise one or more chemically modified ribonucleotides of either or both of the first strand or the second strand. A ribonucleotide may comprise a chemical modification of the base, sugar or phosphate moieties. The ribonucleic acid may be modified by substitution with or insertion of analogues of nucleic acids or bases.

Throughout the description of the invention, “same or common modification” means the same modification to any nucleotide, be that A, G, C or U modified with a group such as a methyl group (2'-OMe) or a fluoro group (2'-F). For example, 2'-F-dU, 2'-F-dA, 2'-F-dC, 2'-F-dG are all considered to be the same or common modification, as are 2'-OMe-rU, 2'-OMe-rA; 2'-OMe-rC; 2'-OMe-rG. In contrast, a 2'-F modification is a different modification compared to a 2'-OMe modification.

Preferably, at least one nucleotide of the first and/or second strand of the nucleic acid is a modified nucleotide, preferably a non-naturally occurring nucleotide such as preferably a 2'-F modified nucleotide.

A modified nucleotide can be a nucleotide with a modification of the sugar group. The 2' hydroxyl group (OH) can be modified or replaced with a number of different “oxy” or “deoxy” substituents.

Examples of “oxy”-2' hydroxyl group modifications include alkoxy or aryloxy (OR, e.g., R=H, alkyl (such as methyl), cycloalkyl, aryl, aralkyl, heteroaryl or sugar); polyethyleneglycols (PEG), $O(CH_2CH_2O)_nCH_2CH_2OR$; “locked” nucleic acids (LNA) in which the 2' hydroxyl is connected, e.g., by a methylene bridge, to the 4' carbon of the same ribose sugar; O-AMINE (AMINE=$NH_2$, alkylamino, dialkylamino, heterocyclyl, arylamino, diaryl amino, heteroaryl amino, or diheteroaryl amino, ethylene diamine, or polyamino) and aminoalkoxy, $O(CH_2)n$AMINE, (e.g., AMINE=$NH_2$, alkylamino, dialkylamino, heterocyclyl, arylamino, diaryl amino, heteroaryl amino, or diheteroaryl amino, ethylene diamine, or polyamino).

“Deoxy” modifications include hydrogen, halogen, amino (e.g., $NH_2$, alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$, alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Other substituents of certain embodiments include 2'-methoxyethyl, 2'-$OCH_3$, 2'-O-allyl, 2'-C-allyl, and 2'-fluoro.

The sugar group can also contain one or more carbons that possess the opposite stereochemical configuration than that of the corresponding carbon in ribose. Thus, a modified nucleotide may contain a sugar such as arabinose.

Modified nucleotides can also include “abasic” sugars, which lack a nucleobase at C-1'. These abasic sugars can further contain modifications at one or more of the constituent sugar atoms.

The 2' modifications may be used in combination with one or more phosphate internucleoside linker modifications (e.g., phosphorothioate or phosphorodithioate).

One or more nucleotides of a nucleic acid of the present invention may be modified. The nucleic acid may comprise at least one modified nucleotide. The modified nucleotide may be in the first strand. The modified nucleotide may be in the second strand. The modified nucleotide may be in the duplex region. The modified nucleotide may be outside the duplex region, i.e., in a single-stranded region. The modified nucleotide may be on the first strand and may be outside the duplex region. The modified nucleotide may be on the second strand and may be outside the duplex region. The 3'-terminal nucleotide of the first strand may be a modified nucleotide. The 3'-terminal nucleotide of the second strand may be a modified nucleotide. The 5'-terminal nucleotide of the first strand may be a modified nucleotide. The 5'-terminal nucleotide of the second strand may be a modified nucleotide.

A nucleic acid of the invention may have 1 modified nucleotide or a nucleic acid of the invention may have about 2-4 modified nucleotides, or a nucleic acid may have about 4-6 modified nucleotides, about 6-8 modified nucleotides, about 8-10 modified nucleotides, about 10-12 modified nucleotides, about 12-14 modified nucleotides, about 14-16 modified nucleotides about 16-18 modified nucleotides, about 18-20 modified nucleotides, about 20-22 modified nucleotides, about 22-24 modified nucleotides, about 24-26 modified nucleotides or about 26-28 modified nucleotides. In each case the nucleic acid comprising said modified nucleotides retains at least 50% of its activity as compared to the same nucleic acid but without said modified nucleotides or vice versa. The nucleic acid may retain 55%, 60%, 65%, 70%, 75%, 80%, 85%, 90%, 95% or 100% and intermediate values of its activity as compared to the same nucleic acid but without said modified nucleotides, or may have more than 100% of the activity of the same nucleic acid without said modified nucleotides.

The modified nucleotide may be a purine or a pyrimidine. At least half of the purines may be modified. At least half of the pyrimidines may be modified. All of the purines may be modified. All of the pyrimidines may be modified. The modified nucleotides may be selected from the group consisting of a 3' terminal deoxy thymine (dT) nucleotide, a 2'-O-methyl (2'-OMe) modified nucleotide, a 2' modified nucleotide, a 2' deoxy modified nucleotide, a locked nucleotide, an abasic nucleotide, a 2' amino modified nucleotide, a 2' alkyl modified nucleotide, a 2'-deoxy-2'-fluoro (2'-F) modified nucleotide, a morpholino nucleotide, a phosphoramidate, a non-natural base comprising nucleotide, a nucleotide comprising a 5'-phosphorothioate group, a nucleotide comprising a 5' phosphate or 5' phosphate mimic and a terminal nucleotide linked to a cholesteryl derivative or a dodecanoic acid bisdecylamide group.

The nucleic acid may comprise a nucleotide comprising a modified base, wherein the base is selected from 2-aminoadenosine, 2,6-diaminopurine, inosine, pyridin-4-one, pyridin-2-one, phenyl, pseudouracil, 2,4,6-trimethoxy benzene, 3-methyl uracil, dihydrouridine, naphthyl, aminophenyl, 5-alkylcytidine (e.g., 5-methylcytidine), 5-alkyluridine (e.g., ribothymidine), 5-halouridine (e.g., 5-bromouridine), 6-azapyrimidine, 6-alkylpyrimidine (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, beta-D-mannosylqueosine, uridine-5-oxyacetic acid and 2-thiocytidine.

Many of the modifications described herein and that occur within a nucleic acid will be repeated within a polynucleotide molecule, such as a modification of a base, or a phosphate moiety, or a non-linking O of a phosphate moiety.

In some cases, the modification will occur at all of the possible positions/nucleotides in the polynucleotide but in many cases it will not. A modification may only occur at a 3' or 5' terminal position, may only occur in a terminal region, such as at a position on a terminal nucleotide or in the last 2, 3, 4, 5, or 10 nucleotides of a strand. A modification may occur in a double-strand region, a single-strand region, or in both. A modification may occur only in the double-strand region of a nucleic acid of the invention or may only occur in a single-strand region of a nucleic acid of the invention. A phosphorothioate or phosphorodithioate modification at a non-linking O position may only occur at one or both termini, may only occur in a terminal region, e.g., at a position on a terminal nucleotide or in the last 2, 3, 4 or 5 nucleotides of a strand, or may occur in duplex and/or in single-strand regions, particularly at termini. The 5' end and/or 3' end may be phosphorylated.

Stability of a nucleic acid of the invention may be increased by including particular bases in overhangs, or by including modified nucleotides, in single-strand overhangs, e.g., in a 5' or 3' overhang, or in both. Purine nucleotides may be included in overhangs. All or some of the bases in a 3' or 5' overhang may be modified. Modifications can include the use of modifications at the 2' OH group of the ribose sugar, the use of deoxyribonucleotides, instead of ribonucleotides, and modifications in the phosphate group, such as phosphorothioate or phosphorodithioate modifications. Overhangs need not be homologous with the target sequence.

Nucleases can hydrolyse nucleic acid phosphodiester bonds. However, chemical modifications to nucleic acids can confer improved properties, and, can render oligoribonucleotides more stable to nucleases.

Modified nucleic acids, as used herein, can include one or more of:

(i) alteration, e.g., replacement, of one or both of the non-linking phosphate oxygens and/or of one or more of the linking phosphate oxygens (referred to as linking even if at the 5' and 3' terminus of the nucleic acid of the invention);
(ii) alteration, e.g., replacement, of a constituent of the ribose sugar, e.g., of the 2' hydroxyl on the ribose sugar;
(iii) replacement of the phosphate moiety with “dephospho” linkers;
(iv) modification or replacement of a naturally occurring base;
(v) replacement or modification of the ribose-phosphate backbone; and
(vi) modification of the 3' end or 5' end of the first strand and/or the second strand, e.g., removal, modification or replacement of a terminal phosphate group or conjugation of a moiety, e.g., a fluorescently labelled moiety, to either the 3' or 5' end of one or both strands.

The terms replacement, modification and alteration indicate a difference from a naturally occurring molecule.

Specific modifications are discussed in more detail below.

The nucleic acid may comprise one or more nucleotides on the second and/or first strands that are modified. Alternating nucleotides may be modified, to form modified nucleotides.

Alternating as described herein means to occur one after another in a regular way. In other words, alternating means to occur in turn repeatedly. For example, if one nucleotide is modified, the next contiguous nucleotide is not modified and the following contiguous nucleotide is modified and so on. One nucleotide may be modified with a first modification, the next contiguous nucleotide may be modified with a second modification and the following contiguous nucleotide is modified with the first modification and so on, where the first and second modifications are different.

Some representative modified nucleic acid sequences of the present invention are shown in the examples. These examples are meant to be representative and not limiting.

In one aspect of the nucleic acid, at least nucleotides 2 and 14 of the first strand are modified, preferably by a first common modification, the nucleotides being numbered consecutively starting with nucleotide number 1 at the 5' end of the first strand. The first modification is preferably 2'-F.

In one aspect, at least one, several or preferably all the even-numbered nucleotides of the first strand are modified, preferably by a first common modification, the nucleotides being numbered consecutively starting with nucleotide number 1 at the 5' end of the first strand. The first modification is preferably 2'-F.

In one aspect, at least one, several or preferably all the odd-numbered nucleotides of the first strand are modified, the nucleotides being numbered consecutively starting with nucleotide number 1 at the 5' end of the first strand. Preferably, they are modified by a second modification. This second modification is preferably different from the first modification if the nucleic acid also comprises a first modification, for example of nucleotides 2 and 14 or of all the even-numbered nucleotides of the first strand. The first modification is preferably any 2' ribose modification that is of the same size or smaller in volume than a 2'-OH group, or a locked nucleic acid (LNA), or an unlocked nucleic acid (UNA), or a 2'-Fluoroarabino Nucleic Acid (FANA) modification. A 2' ribose modification that is of the same size or smaller in volume than a 2'-OH group can for example be a 2'-F, 2'-H, 2'-halo, or 2'—$NH_2$. The second modification is preferably any 2' ribose modification that is larger in volume than a 2'-OH group. A 2' ribose modification that is larger in volume than a 2'-OH group can for example be a 2'-OMe, 2'-O-MOE (2'-O-methoxyethyl), 2'-O-allyl or 2'-O-alkyl, with the proviso that the nucleic is capable of reducing the expression of the target gene to at least the same extent as the same nucleic acid without the modification(s) under comparable conditions. The first modification is preferably 2'-F and/or the second modification is preferably 2'-OMe.

In the context of this disclosure, the size or volume of a substituent, such as a 2' ribose modification, is preferably measured as the van der Waals volume.

In one aspect, at least one, several or preferably all the nucleotides of the second strand in a position corresponding to an even-numbered nucleotide of the first strand are modified, preferably by a third modification. Preferably in the same nucleic acid nucleotides 2 and 14 or all the even numbered nucleotides of the first strand are modified with a first modification. In addition, or alternatively, the odd-numbered nucleotides of the first strand are modified with a second modification. Preferably, the third modification is different from the first modification and/or the third modification is the same as the second modification. The first modification is preferably any 2' ribose modification that is of the same size or smaller in volume than a 2'-OH group, or a locked nucleic acid (LNA), or an unlocked nucleic acid (UNA), or a 2'-Fluoroarabino Nucleic Acid (FANA) modification. A 2' ribose modification that is of the same size or smaller in volume than a 2'-OH group can for example be a 2'-F, 2'-H, 2'-halo, or 2'-$NH_2$. The second and/or third modification is preferably any 2' ribose modification that is larger in volume than a 2'-OH group. A 2' ribose modification that is larger in volume than a 2'-OH group can for example be a 2'-OMe, 2'-O-MOE (2'-O-methoxyethyl), 2'-O-allyl or 2'-O-alkyl, with the proviso that the nucleic is capable of reducing the expression of the target gene to at least the same extent as the same nucleic acid without the modification(s) under comparable conditions. The first modification is preferably 2'-F and/or the second and/or third modification is/are preferably 2'-OMe. The nucleotides on the first strand are numbered consecutively starting with nucleotide number 1 at the 5' end of the first strand.

A nucleotide of the second strand that is in a position corresponding, for example, to an even-numbered nucleotide of the first strand is a nucleotide of the second strand that is base-paired to an even-numbered nucleotide of the first strand.

In one aspect, at least one, several or preferably all the nucleotides of the second strand in a position corresponding to an odd-numbered nucleotide of the first strand are modified, preferably by a fourth modification. Preferably in the same nucleic acid nucleotides 2 and 14 or all the even numbered nucleotides of the first strand are modified with a first modification. In addition, or alternatively, the odd-numbered nucleotides of the first strand are modified with a second modification. In addition, or alternatively, all the nucleotides of the second strand in a position corresponding to an even-numbered nucleotide of the first strand are modified with a third modification. The fourth modification is preferably different from the second modification and preferably different from the third modification and the fourth modification is preferably the same as the first modification. The first and/or fourth modification is preferably any 2' ribose modification that is of the same size or smaller in volume than a 2'-OH group, or a locked nucleic acid (LNA), or an unlocked nucleic acid (UNA), or a 2'-Fluoroarabino Nucleic Acid (FANA) modification. A 2' ribose modification that is of the same size or smaller in volume than a 2'-OH group can for example be a 2'-F, 2'-H, 2'-halo, or 2'—$NH_2$. The second and/or third modification is preferably any 2' ribose modification that is larger in volume than a 2'-OH group. A 2' ribose modification that is larger in volume than a 2'-OH group can for example be a 2'-OMe, 2'-O-MOE (2'-O-methoxyethyl), 2'-O-allyl or 2'-O-alkyl, with the proviso that the nucleic is capable of reducing the expression of the target gene to at least the same extent as the same nucleic acid without the modification(s) under comparable conditions. The first and/or the fourth modification is/are preferably a 2'-OMe modification and/or the second and/or third modification is/are preferably a 2'-F modification. The nucleotides on the first strand are numbered consecutively starting with nucleotide number 1 at the 5' end of the first strand.

In one aspect of the nucleic acid, the nucleotide/nucleotides of the second strand in a position corresponding to nucleotide 11 or nucleotide 13 or nucleotides 11 and 13 or nucleotides 11-13 of the first strand is/are modified by a fourth modification. Preferably, all the nucleotides of the second strand other than the nucleotide/nucleotides in a position corresponding to nucleotide 11 or nucleotide 13 or nucleotides 11 and 13 or nucleotides 11-13 of the first strand is/are modified by a third modification. Preferably in the same nucleic acid nucleotides 2 and 14 or all the even numbered nucleotides of the first strand are modified with a first modification. In addition, or alternatively, the odd-numbered nucleotides of the first strand are modified with a second modification. The fourth modification is preferably different from the second modification and preferably different from the third modification and the fourth modification is preferably the same as the first modification. The first and/or fourth modification is preferably any 2' ribose modification that is of the same size or smaller in volume than a 2'-OH group, or a locked nucleic acid (LNA), or an unlocked nucleic acid (UNA), or a 2'-Fluoroarabino Nucleic Acid (FANA) modification. A 2' ribose modification that is of the same size or smaller in volume than a 2'-OH group can for example be a 2'-F, 2'-H, 2'-halo, or 2'—$NH_2$. The second and/or third modification is preferably any 2' ribose modification that is larger in volume than a 2'-OH group. A 2' ribose modification that is larger in volume than a 2'-OH group can for example be a 2'-OMe, 2'-O-MOE (2'-O-methoxyethyl), 2'-O-allyl or 2'-O-alkyl, with the proviso that the nucleic is capable of reducing the expression of the target gene to at least the same extent as the same nucleic acid without the modification(s) under comparable conditions. The first and/or the fourth modification is/are preferably a 2'-OMe modification and/or the second and/or third modification is/are preferably a 2'-F modification. The nucleotides on the first strand are numbered consecutively starting with nucleotide number 1 at the 5' end of the first strand.

In one aspect of the nucleic acid, all the even-numbered nucleotides of the first strand are modified by a first modification, all the odd-numbered nucleotides of the first strand are modified by a second modification, all the nucleotides of the second strand in a position corresponding to an even-numbered nucleotide of the first strand are modified by a third modification, all the nucleotides of the second strand in a position corresponding to an odd-numbered nucleotide of the first strand are modified by a fourth modification, wherein the first and/or fourth modification is/are 2'-F and/or the second and/or third modification is/are 2'-OMe.

In one aspect of the nucleic acid, all the even-numbered nucleotides of the first strand are modified by a first modification, all the odd-numbered nucleotides of the first strand are modified by a second modification, all the nucleotides of the second strand in positions corresponding to nucleotides 11-13 of the first strand are modified by a fourth modification, all the nucleotides of the second strand other than the nucleotides corresponding to nucleotides 11-13 of the first strand are modified by a third modification, wherein the first and fourth modification are 2'-F and the second and third modification are 2'-OMe. In one embodiment in this aspect, the 3' terminal nucleotide of the second strand is an inverted RNA nucleotide (i.e., the nucleotide is linked to the 3' end of the strand through its 3' carbon, rather than through its 5' carbon as would normally be the case). When the 3' terminal nucleotide of the second strand is an inverted RNA nucleotide, the inverted RNA nucleotide is preferably an unmodified nucleotide in the sense that it does not comprise any modifications compared to the natural nucleotide counterpart. Specifically, the inverted RNA nucleotide is preferably a 2'-OH nucleotide. Preferably, in this aspect when the 3' terminal nucleotide of the second strand is an inverted RNA nucleotide, the nucleic acid is blunt-ended at least at the end that comprises the 5' end of the first strand.

One aspect of the present invention is a nucleic acid as disclosed herein for inhibiting expression of the CNNM4 gene, preferably in a cell, wherein said first strand includes modified nucleotides or unmodified nucleotides at a plurality of positions in order to facilitate processing of the nucleic acid by RISC.

In one aspect, "facilitate processing by RISC" means that the nucleic acid can be processed by RISC, for example any modification present will permit the nucleic acid to be processed by RISC and preferably, will be beneficial to processing by RISC, suitably such that siRNA activity can take place.

One aspect is a nucleic acid as disclosed herein, wherein the nucleotides at positions 2 and 14 from the 5' end of the first strand are not modified with a 2'-OMe modification, and the nucleotide/nucleotides on the second strand which corresponds to position 11 or position 13 or positions 11 and 13 or positions 11, 12 and 13 of the first strand is/are not modified with a 2'-OMe modification (in other words, they are naturally occurring nucleotides or are modified with a modification other than 2'-OMe).

In one aspect, the nucleotide on the second strand which corresponds to position 13 of the first strand is the nucleotide that forms a base pair with position 13 (from the 5' end) of the first strand.

In one aspect, the nucleotide on the second strand which corresponds to position 11 of the first strand is the nucleotide that forms a base pair with position 11 (from the 5' end) of the first strand.

In one aspect, the nucleotide on the second strand which corresponds to position 12 of the first strand is the nucleotide that forms a base pair with position 12 (from the 5' end) of the first strand.

For example, in a 19-mer nucleic acid which is double-stranded and blunt ended, position 13 (from the 5' end) of the first strand would pair with position 7 (from the 5' end) of the second strand. Position 11 (from the 5' end) of the first strand would pair with position 9 (from the 5' end) of the second strand. This nomenclature may be applied to other positions of the second strand.

In one aspect, in the case of a partially complementary first and second strand, the nucleotide on the second strand that "corresponds to" a position on the first strand may not necessarily form a base pair if that position is the position in which there is a mismatch, but the principle of the nomenclature still applies.

One aspect is a nucleic acid as disclosed herein, wherein the nucleotides at positions 2 and 14 from the 5' end of the first strand are not modified with a 2'-OMe modification, and the nucleotides on the second strand which correspond to position 11, or 13, or 11 and 13, or 11-13 of the first strand are modified with a 2'-F modification.

One aspect is a nucleic acid as disclosed herein, wherein the nucleotides at positions 2 and 14 from the 5' end of the first strand are modified with a 2'-F modification, and the nucleotides on the second strand which correspond to position 11, or 13, or 11 and 13, or 11-13 of the first strand are not modified with a 2'-OMe modification.

One aspect is a nucleic acid as disclosed herein, wherein the nucleotides at positions 2 and 14 from the 5' end of the first strand are modified with a 2'-F modification, and the nucleotides on the second strand which correspond to position 11, or 13, or 11 and 13, or 11-13 of the first strand are modified with a 2'-F modification.

One aspect is a nucleic acid as disclosed herein wherein greater than 50% of the nucleotides of the first and/or second strand comprise a 2'-OMe modification, such as greater than 55%, 60%, 65%, 70%, 75%, 80%, or 85%, or more, of the first and/or second strand comprise a 2'-OMe modification.

One aspect is a nucleic acid as disclosed herein wherein greater than 50% of the nucleotides of the first and/or second strand comprise a naturally occurring RNA modification, such as wherein greater than 55%, 60%, 65%, 70%, 75%, 80%, or 85% or more of the first and/or second strands comprise such a modification. Suitable naturally occurring modifications include, as well as 2'-OMe, other 2' sugar modifications, in particular a 2'-H modification resulting in a DNA nucleotide.

One aspect is a nucleic acid as disclosed herein comprising no more than 20%, such as no more than 15% such as no more than 10%, of nucleotides which have 2' modifications that are not 2'-OMe modifications on the first and/or second strand.

One aspect is a nucleic acid as disclosed herein, wherein the number of nucleotides in the first and/or second strand with a 2'-modification that is not a 2'-OMe modification is no more than 7, more preferably no more than 5, and most preferably no more than 3.

One aspect is a nucleic acid as disclosed herein comprising no more than 20%, (such as no more than 15% or no more than 10%) of 2'-F modifications on the first and/or second strand.

One aspect is a nucleic acid as disclosed herein, wherein the number of nucleotides in the first and/or second strand with a 2'-F modification is no more than 7, more preferably no more than 5, and most preferably no more than 3.

One aspect is a nucleic acid as disclosed herein, wherein all nucleotides are modified with a 2'-OMe modification except positions 2 and 14 from the 5' end of the first strand and the nucleotides on the second strand which correspond to position 11, or 13, or 11 and 13, or 11-13 of the first strand. Preferably the nucleotides that are not modified with 2'-OMe are modified with fluoro at the 2' position (2'-F modification).

Preferred is a nucleic acid as disclosed herein wherein all nucleotides of the nucleic acid are modified at the 2' position of the sugar. Preferably these nucleotides are modified with a 2'-F modification where the modification is not a 2'-OMe modification.

In one aspect the nucleic acid is modified on the first strand with alternating 2'-OMe modifications and 2-F modifications, and positions 2 and 14 (starting from the 5' end) are modified with 2'-F. Preferably the second strand is modified with 2'-F modifications at nucleotides on the second strand which correspond to position 11, or 13, or 11 and 13, or 11-13 of the first strand. Preferably the second strand is modified with 2'-F modifications at positions 11-13 counting from the 3' end starting at the first position of the complementary (double-stranded) region, and the remaining modifications are naturally occurring modifications, preferably 2'-OMe. The complementary region at least in this case starts at the first position of the second strand that has a corresponding nucleotide in the first strand, regardless of whether the two nucleotides are able to base pair to each other.

In one aspect of the nucleic acid, each of the nucleotides of the first strand and of the second strand is a modified nucleotide.

Unless specifically stated otherwise, herein the nucleotides of the first strand are numbered contiguously starting with nucleotide number 1 at the 5' end of the first strand. Nucleotides of the second strand are numbered contiguously starting with nucleotide number 1 at the 3' end of the second strand.

An "odd numbered" nucleotide is a nucleotide numbered with an odd number in a strand in which the nucleotides are numbered contiguously starting either from the indicated end or from the 5' end of the strand if the end from which the nucleotides are numbered is not indicated. An "even numbered" nucleotide is a nucleotide numbered with an even number in a strand in which the nucleotides are numbered contiguously starting either from the indicated end or from the 5' end of the strand if the end from which the nucleotides are numbered is not indicated.

One or more nucleotides on the first and/or second strand may be modified, to form modified nucleotides. One or more of the odd-numbered nucleotides of the first strand may be modified. One or more of the even-numbered nucleotides of the first strand may be modified by at least a second modification, wherein the at least second modification is different from the modification on the one or more odd nucleotides. At least one of the one or more modified even numbered-nucleotides may be adjacent to at least one of the one or more modified odd-numbered nucleotides.

A plurality of odd-numbered nucleotides in the first strand may be modified in the nucleic acid of the invention. A plurality of even-numbered nucleotides in the first strand may be modified by a second modification. The first strand may comprise adjacent nucleotides that are modified by a common modification. The first strand may also comprise adjacent nucleotides that are modified by a second different modification (i.e., the first strand may comprise nucleotides that are adjacent to each other and modified by a first modification as well as other nucleotides that are adjacent to each other and modified by a second modification that is different to the first modification).

One or more of the odd-numbered nucleotides of the second strand (wherein the nucleotides are numbered contiguously starting with nucleotide number 1 at the 3' end of the second strand) may be modified by a modification that is different to the modification of the odd-numbered nucleotides on the first strand (wherein the nucleotides are numbered contiguously starting with nucleotide number 1 at the 5' end of the first strand) and/or one or more of the even-numbered nucleotides of the second strand may be modified by the same modification of the odd-numbered nucleotides of the first strand. At least one of the one or more modified even-numbered nucleotides of the second strand may be adjacent to the one or more modified odd-numbered nucleotides. A plurality of odd-numbered nucleotides of the second strand may be modified by a common modification and/or a plurality of even-numbered nucleotides may be modified by the same modification that is present on the first stand odd-numbered nucleotides. A plurality of odd-numbered nucleotides on the second strand may be modified by a modification that is different from the modification of the first strand odd-numbered nucleotides.

The second strand may comprise adjacent nucleotides that are modified by a common modification, which may be a modification that is different from the modification of the odd-numbered nucleotides of the first strand.

In the nucleic acid of the invention, each of the odd-numbered nucleotides in the first strand and each of the even-numbered nucleotides in the second strand may be modified with a common modification and, each of the even-numbered nucleotides may be modified in the first strand with a different modification and each of the odd-numbered nucleotides may be modified in the second strand with the different modification.

The nucleic acid of the invention may have the modified nucleotides of the first strand shifted by at least one nucleotide relative to the unmodified or differently modified nucleotides of the second strand.

One or more or each of the odd numbered-nucleotides may be modified in the first strand and one or more or each of the even-numbered nucleotides may be modified in the second strand. One or more or each of the alternating nucleotides on either or both strands may be modified by a second modification. One or more or each of the even-numbered nucleotides may be modified in the first strand and one or more or each of the even-numbered nucleotides may be modified in the second strand. One or more or each of the alternating nucleotides on either or both strands may be modified by a second modification. One or more or each of the odd-numbered nucleotides may be modified in the first strand and one or more of the odd-numbered nucleotides may be modified in the second strand by a common modification. One or more or each of the alternating nucleotides on either or both strands may be modified by a second modification. One or more or each of the even-numbered nucleotides may be modified in the first strand and one or more or each of the odd-numbered nucleotides may be modified in the second strand by a common modification. One or more or each of the alternating nucleotides on either or both strands may be modified by a second modification.

The nucleic acid of the invention may comprise single- or double-stranded constructs that comprise at least two regions of alternating modifications in one or both of the strands. These alternating regions can comprise up to about 12 nucleotides but preferably comprise from about 3 to about 10 nucleotides. The regions of alternating nucleotides may be located at the termini of one or both strands of the nucleic acid of the invention. The nucleic acid may comprise from 4 to about 10 nucleotides of alternating nucleotides at each of the termini (3' and 5') and these regions may be separated by from about 5 to about 12 contiguous unmodified or differently or commonly modified nucleotides.

The odd numbered nucleotides of the first strand may be modified and the even numbered nucleotides may be modified with a second modification. The second strand may comprise adjacent nucleotides that are modified with a common modification, which may be the same as the modification of the odd-numbered nucleotides of the first strand. One or more nucleotides of the second strand may also be modified with the second modification. One or more nucleotides with the second modification may be adjacent to each other and to nucleotides having a modification that is the same as the modification of the odd-numbered nucleotides of the first strand. The first strand may also comprise phosphorothioate linkages between the two nucleotides at the 3' end and at the 5' end or a phosphorodithioate linkage between the two nucleotides at the 3' end. The second strand may comprise a phosphorothioate or phosphorodithioate linkage between the two nucleotides at the 5' end. The second strand may also be conjugated to a ligand at the 5' end.

The nucleic acid of the invention may comprise a first strand comprising adjacent nucleotides that are modified with a common modification. One or more such nucleotides may be adjacent to one or more nucleotides which may be modified with a second modification. One or more nucleotides with the second modification may be adjacent. The second strand may comprise adjacent nucleotides that are modified with a common modification, which may be the same as one of the modifications of one or more nucleotides of the first strand. One or more nucleotides of the second strand may also be modified with the second modification. One or more nucleotides with the second modification may be adjacent. The first strand may also comprise phosphorothioate linkages between the two nucleotides at the 3' end and at the 5' end or a phosphorodithioate linkage between the two nucleotides at the 3' end. The second strand may comprise a phosphorothioate or phosphorodithioate linkage between the two nucleotides at the 3' end. The second strand may also be conjugated to a ligand at the 5' end.

The nucleotides numbered from 5' to 3' on the first strand and 3' to 5' on the second strand, 1, 3, 5, 7, 9, 11, 13, 15, 17, 19, 21, 23 and 25 may be modified by a modification on the first strand. The nucleotides numbered 2, 4, 6, 8, 10, 12, 14, 16, 18, 20, 22 and 24 may be modified by a second modification on the first strand. The nucleotides numbered 1, 3, 5, 7, 9, 11, 13, 15, 17, 19, 21, 23 may be modified by a modification on the second strand. The nucleotides numbered 2, 4, 6, 8, 10, 12, 14, 16, 18, 20, 22 and 24 may be modified by a second modification on the second strand. Nucleotides are numbered for the sake of the nucleic acid of the present invention from 5' to 3' on the first strand and 3' to 5' on the second strand.

The nucleotides numbered 2, 4, 6, 8, 10, 12, 14, 16, 18, 20, 22 and 24 may be modified by a modification on the first strand. The nucleotides numbered 1, 3, 5, 7, 9, 11, 13, 15, 17, 19, 21, 23 may be modified by a second modification on the first strand. The nucleotides numbered 1, 3, 5, 7, 9, 11, 13, 15, 17, 19, 21, 23 may be modified by a modification on the second strand. The nucleotides numbered 2, 4, 6, 8, 10, 12, 14, 16, 18, 20, 22 and 24 may be modified by a second modification on the second strand.

Clearly, if the first and/or the second strand are shorter than 25 nucleotides in length, such as 19 nucleotides in length, there are no nucleotides numbered 20, 21, 22, 23, 24 and 25 to be modified. The skilled person understands the description above to apply to shorter strands, accordingly.

One or more modified nucleotides on the first strand may be paired with modified nucleotides on the second strand having a common modification. One or more modified nucleotides on the first strand may be paired with modified nucleotides on the second strand having a different modification. One or more modified nucleotides on the first strand may be paired with unmodified nucleotides on the second strand. One or more modified nucleotides on the second strand may be paired with unmodified nucleotides on the first strand. In other words, the alternating nucleotides can be aligned on the two strands such as, for example, all the modifications in the alternating regions of the second strand are paired with identical modifications in the first strand or alternatively the modifications can be offset by one nucleotide with the common modifications in the alternating regions of one strand pairing with dissimilar modifications (i.e. a second or further modification) in the other strand. Another option is to have dissimilar modifications in each of the strands.

The modifications on the first strand may be shifted by one nucleotide relative to the modified nucleotides on the second strand, such that common modified nucleotides are not paired with each other.

The modification and/or modifications may each and individually be selected from the group consisting of 3' terminal deoxy thymine, 2'-OMe, a 2' deoxy modification, a 2' amino modification, a 2' alkyl modification, a morpholino modification, a phosphoramidate modification, 5'-phosphorothioate group modification, a 5' phosphate or 5' phosphate mimic modification and a cholesteryl derivative or a dodecanoic acid bisdecylamide group modification and/or the modified nucleotide may be any one of a locked nucleotide, an abasic nucleotide or a non-natural base comprising nucleotide.

At least one modification may be 2'-OMe and/or at least one modification may be 2'-F. Further modifications as described herein may be present on the first and/or second strand.

The nucleic acid of the invention may comprise an inverted RNA nucleotide at one or several of the strand ends. Such inverted nucleotides provide stability to the nucleic acid. Preferably, the nucleic acid comprises at least an inverted nucleotide at the 3' end of the first and/or the second strand and/or at the 5' end of the second strand. More preferably, the nucleic acid comprises an inverted nucleotide at the 3' end of the second strand. Most preferably, the nucleic acid comprises an inverted RNA nucleotide at the 3' end of the second strand and this nucleotide is preferably an inverted A. An inverted nucleotide is a nucleotide that is linked to the 3' end of a nucleic acid through its 3' carbon, rather than its 5' carbon as would normally be the case or is linked to the 5' end of a nucleic acid through its 5' carbon, rather than its 3' carbon as would normally be the case. The inverted nucleotide is preferably present at an end of a strand not as an overhang but opposite a corresponding nucleotide in the other strand. Accordingly, the nucleic acid is preferably blunt-ended at the end that comprises the inverted RNA nucleotide. An inverted RNA nucleotide being present at the end of a strand preferably means that the last nucleotide at this end of the strand is the inverted RNA nucleotide. A nucleic acid with such a nucleotide is stable and easy to synthesise. The inverted RNA nucleotide is preferably an unmodified nucleotide in the sense that it does not comprise any modifications compared to the natural nucleotide counterpart. Specifically, the inverted RNA nucleotide is preferably a 2'-OH nucleotide.

Nucleic acids of the invention may comprise one or more nucleotides modified at the 2' position with a 2'-H, and therefore having a DNA nucleotide within the nucleic acid. Nucleic acids of the invention may comprise DNA nucleotides at positions 2 and/or 14 of the first strand counting from the 5' end of the first strand. Nucleic acids may comprise DNA nucleotides on the second strand which correspond to position 11, or 13, or 11 and 13, or 11-13 of the first strand.

In one aspect there is no more than one DNA nucleotide per nucleic acid of the invention.

Nucleic acids of the invention may comprise one or more LNA nucleotides. Nucleic acids of the invention may comprise LNA nucleotides at positions 2 and/or 14 of the first strand counting from the 5' end of the first strand. Nucleic acids may comprise LNA on the second strand which correspond to position 11, or 13, or 11 and 13, or 11-13 of the first strand.

Some representative modified nucleic acid sequences of the present invention are shown in the examples. These examples are meant to be representative and not limiting.

Preferably, the nucleic acid may comprise a first modification and a second or further modification which are each and individually selected from the group comprising 2'-OMe modification and 2'-F modification. The nucleic acid may comprise a modification that is 2'-OMe that may be a first modification, and a second modification that is 2'-F. The nucleic acid of the invention may also include a phosphorothioate or phosphorodithioate modification and/or a deoxy modification which may be present in or between the terminal 2 or 3 nucleotides of each or any end of each or both strands.

In one aspect of the nucleic acid, at least one nucleotide of the first and/or second strand is a modified nucleotide, wherein if the first strand comprises at least one modified nucleotide:

(i) at least one or both of the nucleotides 2 and 14 of the first strand is/are modified by a first modification; and/or (ii) at least one, several, or all the even-numbered nucleotides of the first strand is/are modified by a first modification; and/or (iii) at least one, several, or all the odd-numbered nucleotides of the first strand is/are modified by a second modification; and/or wherein if the second strand comprises at least one modified nucleotide:

(iv) at least one, several, or all the nucleotides of the second strand in a position corresponding to an even-numbered nucleotide of the first strand is/are modified by a third modification; and/or (v) at least one, several, or all the nucleotides of the second strand in a position corresponding to an odd-numbered nucleotide of the first strand is/are modified by a fourth modification; and/or (vi) at least one, several, or all the nucleotides of the second strand in a position corresponding to nucleotide 11 or nucleotide 13 or nucleotides 11 and 13 or nucleotides 11-13 of the first strand is/are modified by a fourth modification; and/or (vii) at least one, several, or all the nucleotides of the second strand in a position other than the position corresponding to nucleotide 11 or nucleotide 13 or nucleotides 11 and 13 or nucleotides 11-13 of the first strand is/are modified by a third modification;

wherein the nucleotides on the first strand are numbered consecutively starting with nucleotide number 1 at the 5' end of the first strand;

wherein the modifications are preferably at least one of the following:

(a) the first modification is preferably different from the second and from the third modification;

(b) the first modification is preferably the same as the fourth modification;

(c) the second and the third modification are preferably the same modification;

(d) the first modification is preferably a 2'-F modification;

(e) the second modification is preferably a 2'-OMe modification;

(f) the third modification is preferably a 2'-OMe modification; and/or (g) the fourth modification is preferably a 2'-F modification; and wherein optionally the nucleic acid is conjugated to a ligand.

One aspect is a double-stranded nucleic acid for inhibiting expression of CNNM4, preferably in a cell, wherein the nucleic acid comprises a first strand and a second strand, wherein the first strand sequence comprises a sequence of at least 15 nucleotides differing by no more than 3 nucleotides from any one of the sequences selected from SEQ ID NO: 243, 267, 277, 279, 287, 317, 319, 325, 333, 345, 347, 349, 361, 367, 369, 371, 377, 401, 411, 413, 415, 420, 421, 524, 526, 528, 530, 532, 534, 536, 538, 540, 542, 544, 546, 548, 549, 550, 551 and 552, wherein all the even-numbered nucleotides of the first strand are modified by a first modification, all the odd-numbered nucleotides of the first strand are modified by a second modification, all the nucleotides of the second strand in a position corresponding to an even-numbered nucleotide of the first strand are modified by a third modification, all the nucleotides of the second strand in a position corresponding to an odd-numbered nucleotide of the first strand are modified by a fourth modification, wherein the first and fourth modification are 2'-F and the second and third modification are 2'-OMe.

One aspect is a double-stranded nucleic acid for inhibiting expression of CNNM4, preferably in a cell, wherein the nucleic acid comprises a first strand and a second strand, wherein the first strand sequence comprises a sequence of at least 15 nucleotides differing by no more than 3 nucleotides from any one of the sequences selected from SEQ ID NO: 243, 267, 277, 279, 287, 317, 319, 325, 333, 345, 347, 349, 361, 367, 369, 371, 377, 401, 411, 413, 415, 420, 421, 524, 526, 528, 530, 532, 534, 536, 538, 540, 542, 544, 546, 548, 549, 550, 551 and 552, wherein all the even-numbered nucleotides of the first strand are modified by a first modification, all the odd-numbered nucleotides of the first strand are modified by a second modification, all the nucleotides of the second strand in positions corresponding to nucleotides 11-13 of the first strand are modified by a fourth modification, all the nucleotides of the second strand other than the nucleotides corresponding to nucleotides 11-13 of the first strand are modified by a third modification, wherein the first and fourth modification are 2'-F and the second and third modification are 2'-OMe.

The 3' and 5' ends of an oligonucleotide can be modified. Such modifications can be at the 3' end or the 5' end or both ends of the molecule. They can include modification or replacement of an entire terminal phosphate or of one or more of the atoms of the phosphate group. For example, the 3' and 5' ends of an oligonucleotide can be conjugated to other functional molecular entities such as labelling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5' O, N, S or C group of the sugar. Alternatively, the linker can connect to or replace the terminal atom of a nucleotide surrogate (e.g., PNAs). These spacers or linkers can include e.g., $—(CH_2)_n—$, $—(CH_2)_nN—$, $—(CH_2)_nO—$, $—(CH_2)_nS—$, $—(CH_2CH_2O)_nCH_2CH_2O—$ (e.g., n=3 or 6), abasic sugars, amide, carboxy, amine, oxyamine, oxyimine, thioether, disulfide, thiourea, sulfonamide, or morpholino, or biotin and fluorescein reagents. The 3' end can be an —OH group.

Other examples of terminal modifications include dyes, intercalating agents (e.g., acridines), cross-linkers (e.g., psoralene, mitomycin C), porphyrins (TPPC4, texaphyrin, Sapphyrin), polycyclic aromatic hydrocarbons (e.g., phenazine, dihydrophenazine), artificial endonucleases, EDTA, lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles).

Terminal modifications can also be useful for monitoring distribution, and in such cases the groups to be added may include fluorophores, e.g., fluorescein or an Alexa dye. Terminal modifications can also be useful for enhancing uptake, useful modifications for this include cholesterol. Terminal modifications can also be useful for cross-linking an RNA agent to another moiety.

Terminal modifications can be added for a number of reasons, including to modulate activity or to modulate resistance to degradation. Terminal modifications useful for modulating activity include modification of the 5' end with phosphate or phosphate analogues. Nucleic acids of the invention, on the first or second strand, may be 5' phosphorylated or include a phosphoryl analogue at the 5' prime terminus. 5'-phosphate modifications include those which are compatible with RISC mediated gene silencing. Suitable modifications include: 5'-monophosphate ($(HO)_2(O)P$—O-5'); 5'-diphosphate ($(HO)_2(O)P$—O—P(HO)(O)—O-5'); 5'-triphosphate ($(HO)_2(O)P$—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; $(HO)_2(S)P$—O-5'); 5'-monodithiophosphate (phosphorodithioate; (HO)(HS)(S)P—O-5'), 5'-phosphorothiolate ($(HO)_2(O)P$—S-5'); any additional combination of oxygen/sulfur replaced monophosphate, diphosphate and triphosphates (e.g., 5'-alpha-thiotriphosphate, 5'-gamma-thiotriphosphate, etc.), 5'-phosphoramidates ($(HO)_2(O)P$—NH-5', $(HO)(NH_2)(O)P$—O-5'), 5' alkylphosphonates (alkyl=methyl, ethyl, isopropyl, propyl, etc., e.g. RP(OH)(O)—O-5'- (wherein R is an alkyl), $(OH)_2(O)P$-5'-$CH_2$—), 5' vinylphosphonate, 5'-alkyletherphosphonates (alkylether=methoxymethyl ($MeOCH_2$—), ethoxymethyl, etc., e.g. RP(OH)(O)—O-5'- (wherein R is an alkylether)).

Certain moieties may be linked to the 5' terminus of the first strand or the second strand. These include abasic ribose moiety, abasic deoxyribose moiety, modifications abasic ribose and abasic deoxyribose moieties including 2'-O alkyl modifications; inverted abasic ribose and abasic deoxyribose moieties and modifications thereof, C6-imino-Pi; a mirror nucleotide including L-DNA and L-RNA; 5'OMe nucleotide; and nucleotide analogues including 4',5'-methylene nucleotide; 1-(3-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non-bridging methylphosphonate and 5'-mercapto moieties.

In each sequence described herein, a C-terminal "—OH" moiety may be substituted for a C-terminal "—$NH_2$" moiety, and vice-versa.

The invention also provides a nucleic acid according to any aspect of the invention described herein, wherein the first strand has a terminal 5' (E)-vinylphosphonate nucleotide at its 5' end. This terminal 5' (E)-vinylphosphonate nucleotide is preferably linked to the second nucleotide in the first strand by a phosphodiester linkage.

The first strand of the nucleic acid may comprise formula (I):

$$(vp)\text{-}N_{(po)}[N_{(po)}]_n\text{-} \qquad (I)$$

where '(vp)-' is the 5' (E)-vinylphosphonate, 'N' is a nucleotide, 'po' is a phosphodiester linkage, and n is from 1 to (the total number of nucleotides in the first strand—2), preferably wherein n is from 1 to (the total number of nucleotides in the first strand—3), more preferably wherein n is from 1 to (the total number of nucleotides in the first strand—4).

Preferably, the terminal 5' (E)-vinylphosphonate nucleotide is an RNA nucleotide, preferably a (vp)-U.

A terminal 5' (E)-vinylphosphonate nucleotide is a nucleotide wherein the natural phosphate group at the 5'-end has been replaced with a E-vinylphosphonate, in which the bridging 5'-oxygen atom of the terminal nucleotide of the 5' phosphorylated strand is replaced with a methynyl (—CH=) group:

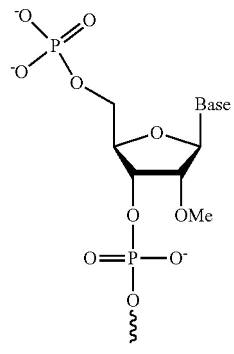

Nucleotides with a natural phosphate at the 5'-end

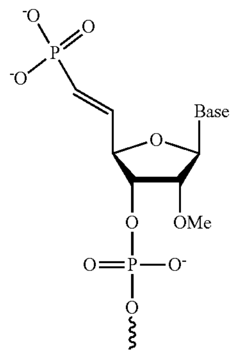

Nucleotide with a E-vinylphosphonate at the 5'-end

A 5' (E)-vinylphosphonate is a 5' phosphate mimic. A biological mimic is a molecule that is capable of carrying out the same function as and is structurally very similar to the original molecule that is being mimicked. In the context of the present invention, 5' (E)-vinylphosphonate mimics the function of a normal 5' phosphate, e.g. enabling efficient RISC loading. In addition, because of its slightly altered structure, 5' (E) vinylphosphonate is capable of stabilizing the 5'-end nucleotide by protecting it from dephosphorylation by enzymes such as phosphatases.

In one aspect, the first strand has a terminal 5' (E)-vinylphosphonate nucleotide at its 5' end, the terminal 5' (E)-vinylphosphonate nucleotide is linked to the second nucleotide in the first strand by a phosphodiester linkage and the first strand comprises a) more than 1 phosphodiester linkage; b) phosphodiester linkages between at least the terminal three 5' nucleotides and/or c) phosphodiester linkages between at least the terminal four 5' nucleotides.

In one aspect, the first strand and/or the second strand of the nucleic acid comprises at least one phosphorothioate (ps) and/or at least one phosphorodithioate (ps2) linkage between two nucleotides.

In one aspect, the first strand and/or the second strand of the nucleic acid comprises more than one phosphorothioate and/or more than one phosphorodithioate linkage.

In one aspect, the first strand and/or the second strand of the nucleic acid comprises a phosphorothioate or phosphorodithioate linkage between the terminal two 3' nucleotides or phosphorothioate or phosphorodithioate linkages between the terminal three 3' nucleotides.

Preferably, the linkages between the other nucleotides in the first strand and/or the second strand are phosphodiester linkages.

In one aspect, the first strand and/or the second strand of the nucleic acid comprises a phosphorothioate linkage between the terminal two 5' nucleotides or a phosphorothioate linkages between the terminal three 5' nucleotides.

In one aspect, the nucleic acid of the present invention comprises one or more phosphorothioate or phosphorodithioate modifications on one or more of the terminal ends of the first and/or the second strand. Optionally, each or either end of the first strand may comprise one or two or three phosphorothioate or phosphorodithioate modified nucleotides (internucleoside linkage). Optionally, each or either end of the second strand may comprise one or two or three phosphorothioate or phosphorodithioate modified nucleotides (internucleoside linkage).

In one aspect, the nucleic acid comprises a phosphorothioate linkage between the terminal two or three 3' nucleotides and/or 5' nucleotides of the first and/or the second strand. Preferably, the nucleic acid comprises a phosphorothioate linkage between each of the terminal three 3' nucleotides and the terminal three 5' nucleotides of the first strand and of the second strand. Preferably, all remaining linkages between nucleotides of the first and/or of the second strand are phosphodiester linkages.

In one aspect, the nucleic acid comprises a phosphorodithioate linkage between each of the two, three or four terminal nucleotides at the 3' end of the first strand and/or comprises a phosphorodithioate linkage between each of the two, three or four terminal nucleotides at the 3' end of the second strand and/or a phosphorodithioate linkage between each of the two, three or four terminal nucleotides at the 5' end of the second strand and comprises a linkage other than a phosphorodithioate linkage between the two, three or four terminal nucleotides at the 5' end of the first strand.

In one aspect, the nucleic acid comprises a phosphorothioate linkage between the terminal three 3' nucleotides and the terminal three 5' nucleotides of the first strand and of the second strand. Preferably, all remaining linkages between nucleotides of the first and/or of the second strand are phosphodiester linkages.

In one aspect, the nucleic acid:

(i) has a phosphorothioate linkage between the terminal three 3' nucleotides and the terminal three 5' nucleotides of the first strand;

(ii) is conjugated to a triantennary ligand either on the 3' end nucleotide or on the 5' end nucleotide of the second strand;

(iii) has a phosphorothioate linkage between the terminal three nucleotides of the second strand at the end opposite to the one conjugated to the triantennary ligand; and (iv) optionally all remaining linkages between nucleotides of the first and/or of the second strand are phosphodiester linkages.

In one aspect, the nucleic acid:

(i) has a terminal 5' (E)-vinylphosphonate nucleotide at the 5' end of the first strand;

(ii) has a phosphorothioate linkage between the terminal three 3' nucleotides on the first and second strand and between the terminal three 5' nucleotides on the second strand or it has a phosphorodithioate linkage between the terminal two 3' nucleotides on the first and second strand and between the terminal two 5' nucleotides on the second strand; and (iii) optionally all remaining linkages between nucleotides of the first and/or of the second strand are phosphodiester linkages.

The use of a phosphorodithioate linkage in the nucleic acid of the invention reduces the variation in the stereochemistry of a population of nucleic acid molecules compared to molecules comprising a phosphorothioate in that same position. Phosphorothioate linkages introduce chiral centres and it is difficult to control which non-linking oxygen is substituted for sulphur. The use of a phosphorodithioate ensures that no chiral centre exists in that linkage and thus reduces or eliminates any variation in the population of nucleic acid molecules, depending on the number of phosphorodithioate and phosphorothioate linkages used in the nucleic acid molecule.

In one aspect, the nucleic acid comprises a phosphorodithioate linkage between the two terminal nucleotides at the 3' end of the first strand and a phosphorodithioate linkage between the two terminal nucleotides at the 3' end of the second strand and a phosphorodithioate linkage between the two terminal nucleotides at the 5' end of the second strand and comprises a linkage other than a phosphorodithioate linkage between the two, three or four terminal nucleotides at the 5' end of the first strand. Preferably, the first strand has a terminal 5' (E)-vinylphosphonate nucleotide at its 5' end. This terminal 5' (E)-vinylphosphonate nucleotide is preferably linked to the second nucleotide in the first strand by a phosphodiester linkage. Preferably, all the linkages between the nucleotides of both strands other than the linkage between the two terminal nucleotides at the 3' end of the first strand and the linkages between the two terminal nucleotides at the 3' end and at the 5' end of the second strand are phosphodiester linkages.

In one aspect, the nucleic acid comprises a phosphorothioate linkage between each of the three terminal 3' nucleotides and/or between each of the three terminal 5' nucleotides on the first strand, and/or between each of the three terminal 3' nucleotides and/or between each of the three terminal 5' nucleotides of the second strand when there is no phosphorodithioate linkage present at that end. No phosphorodithioate linkage being present at an end means that the linkage between the two terminal nucleotides, or preferably between the three terminal nucleotides of the nucleic acid end in question are linkages other than phosphorodithioate linkages.

In one aspect, all the linkages of the nucleic acid between the nucleotides of both strands other than the linkage between the two terminal nucleotides at the 3' end of the first strand and the linkages between the two terminal nucleotides at the 3' end and at the 5' end of the second strand are phosphodiester linkages.

Other phosphate linkage modifications are possible.

The phosphate linker can also be modified by replacement of a linking oxygen with nitrogen (bridged phosphoroamidates), sulfur (bridged phosphorothioates) and carbon (bridged methylenephosphonates). The replacement can occur at a terminal oxygen. Replacement of the non-linking oxygens with nitrogen is possible.

The phosphate groups can also individually be replaced by non-phosphorus containing connectors.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. In certain embodiments, replacements may include the methylenecarbonylamino and methylenemethylimino groups.

The phosphate linker and ribose sugar may be replaced by nuclease resistant nucleotides. Examples include the morpholino, cyclobutyl, pyrrolidine and peptide nucleic acid (PNA) nucleoside surrogates. In certain embodiments, PNA surrogates may be used.

In one aspect, the nucleic acid, which is preferably an siRNA that inhibits expression of CNNM4, preferably via RNAi, and preferably in a cell, comprises one or more or all of:

(i) a modified nucleotide;

(ii) a modified nucleotide other than a 2'-OMe modified nucleotide at positions 2 and 14 from the 5' end of the first strand, preferably a 2'-F modified nucleotide;

(iii) each of the odd-numbered nucleotides of the first strand as numbered starting from one at the 5' end of the first strand are 2'-OMe modified nucleotides;

(iv) each of the even-numbered nucleotides of the first strand as numbered starting from one at the 5' end of the first strand are 2'-F modified nucleotides;

(v) the second strand nucleotide corresponding to position 11 and/or 13 or 11-13 of the first strand is modified by a modification other than a 2'-OMe modification, preferably wherein one or both or all of these positions comprise a 2'-F modification;

(vi) an inverted nucleotide, preferably a 3'-3' linkage at the 3' end of the second strand;

(vii) one or more phosphorothioate linkages;

(viii) one or more phosphorodithioate linkages; and/or (ix) the first strand has a terminal 5' (E)-vinylphosphonate nucleotide at its 5' end, in which case the terminal 5' (E)-vinylphosphonate nucleotide is preferably a uridine and is preferably linked to the second nucleotide in the first strand by a phosphodiester linkage.

All the features of the nucleic acids can be combined with all other aspects of the invention disclosed herein.

Ligands

The nucleic acids of the invention may be conjugated to a ligand. Efficient delivery of oligonucleotides, in particular double-stranded nucleic acids of the invention, to cells in vivo is important and requires specific targeting and substantial protection from the extracellular environment, particularly serum proteins. One method of achieving specific targeting is to conjugate a ligand to the nucleic acid. In some embodiments, the ligand helps in targeting the nucleic acid to a target cell which has a cell surface receptor that binds to and internalizes the conjugated ligand. In such embodiments, there is a need to conjugate appropriate ligands for the desired receptor molecules in order for the conjugated molecules to be taken up by the target cells by mechanisms such as different receptor-mediated endocytosis pathways or functionally analogous processes. In other embodiments, a ligand which can mediate internalization of the nucleic acid into a target cell by mechanisms other than receptor mediated endocytosis may alternatively be conjugated to a nucleic acid of the invention for cell or tissue specific targeting.

One example of a conjugate that mediates receptor mediated endocytosis is the asialoglycoprotein receptor complex (ASGP-R) which has high affinity to the GalNAc moiety described herein. The ASGP-R complex is composed of varying ratios of multimers of membrane ASGR1 and ASGR2 receptors, which are highly abundant on hepatocytes. One of the first disclosures of the use of triantennary cluster glycosides as conjugated ligands was in U.S. Pat. No. 5,885,968. Conjugates having three GalNAc ligands and comprising phosphate groups are known and are described in Dubber et al. (Bioconjug. Chem. 2003 January-February; 14(1):239-46.). The ASGP-R complex shows a 50-fold higher affinity for N-Acetyl-D-Galactosamine (GalNAc) than D-Gal.

The ASGP-R complex recognizes specifically terminal ß-galactosyl subunits of glycosylated proteins or other oligosaccharides (Weigel, P. H. et. al., Biochim. Biophys. Acta. 2002 Sep. 19; 1572(2-3):341-63) and can be used for delivering a drug to the liver's hepatocytes expressing the receptor complex by covalent coupling of galactose or galactosamine to the drug substance (Ishibashi, S.; et. al., J Biol. Chem. 1994 Nov. 11; 269(45):27803-6). Furthermore, the binding affinity can be significantly increased by the multi-valency effect, which is achieved by the repetition of the targeting moiety (Biessen E A, et al., J Med Chem. 1995 Apr. 28; 38(9): 1538-46).

The ASGP-R complex is a mediator for an active uptake of terminal β-galactosyl containing glycoproteins to the cell's endosomes. Thus, the ASGPR is highly suitable for targeted delivery of drug candidates conjugated to such ligands like, e.g., nucleic acids into receptor-expressing cells (Akinc et al., Mol Ther. 2010 July; 18(7): 1357-64).

More generally the ligand can comprise a saccharide that is selected to have an affinity for at least one type of receptor on a target cell. In particular, the receptor is on the surface of a mammalian liver cell, for example, the hepatic asialoglycoprotein receptor complex described before (ASGP-R).

The saccharide may be selected from N-acetyl galactosamine, mannose, galactose, glucose, glucosamine and fucose. The saccharide may be N-acetyl galactosamine (GalNAc).

A ligand for use in the present invention may therefore comprise (i) one or more N-acetyl galactosamine (GalNAc) moieties and derivatives thereof, and (ii) a linker, wherein the linker conjugates the GalNAc moieties to a nucleic acid as defined in any preceding aspects. The linker may be a monovalent structure or bivalent or trivalent or tetravalent branched structure. The nucleotides may be modified as defined herein.

The ligand may therefore comprise GalNAc.

In one aspect, the nucleic acid is conjugated to a ligand comprising a compound of formula (II):

$$[S—X^1—P—X^2]_3\text{-}A\text{-}X^3— \qquad \text{(II)}$$

wherein:

S represents a saccharide, preferably wherein the saccharide is N-acetyl galactosamine;

$X^1$ represents $C_3$-$C_6$ alkylene or $(—CH_2—CH_2—O)_m(—CH_2)_2—$ wherein m is 1, 2, or 3;

P is a phosphate or modified phosphate, preferably a thiophosphate;

$X^2$ is alkylene or an alkylene ether of the formula $(—CH_2)_n—O—CH_2—$ where n=1-6;

A is a branching unit;

$X^3$ represents a bridging unit;

wherein a nucleic acid according to the present invention is conjugated to $X^3$ via a phosphate or modified phosphate, preferably a thiophosphate.

In formula (II), the branching unit "A" preferably branches into three in order to accommodate three saccharide ligands. The branching unit is preferably covalently attached to the remaining tethered portions of the ligand and the nucleic acid. The branching unit may comprise a branched aliphatic group comprising groups selected from alkyl, amide, disulphide, polyethylene glycol, ether, thioether and hydroxyamino groups. The branching unit may comprise groups selected from alkyl and ether groups.

The branching unit A may have a structure selected from:

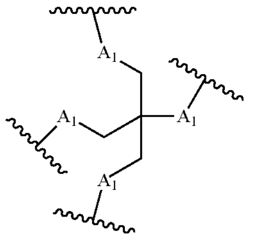

and

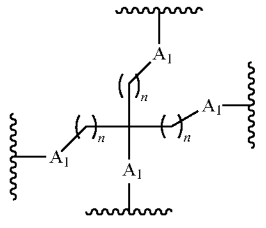

wherein each $A_1$ independently represents O, S, C═O or NH; and each n independently represents an integer from 1 to 20.

The branching unit may have a structure selected from:

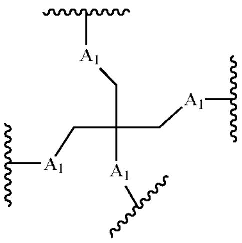;
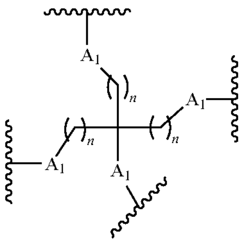
and

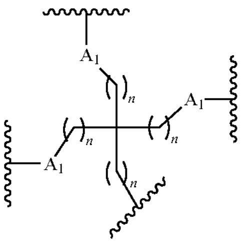

wherein each $A_1$ independently represents O, S, C═O or NH; and each n independently represents an integer from 1 to 20.

The branching unit may have a structure selected from:

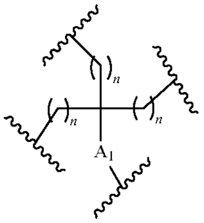
and
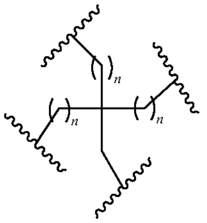

wherein $A_1$ is O, S, C═O or NH; and each n independently represents an integer from 1 to 20.

The branching unit may have the structure:

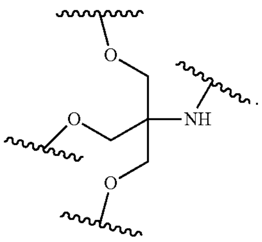 [SMILES: *NC(CO*)(CO*)CO*]

The branching unit may have the structure:

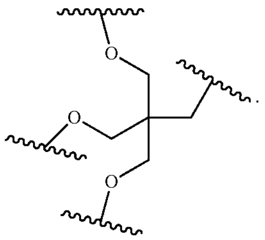 [SMILES: *CC(CO*)(CO*)CO*]

The branching unit may have the structure:

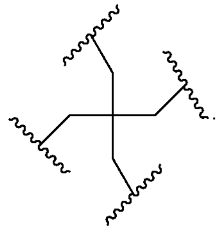 [SMILES: *CC(C*)(C*)C*]

Alternatively, the branching unit A may have a structure selected from:

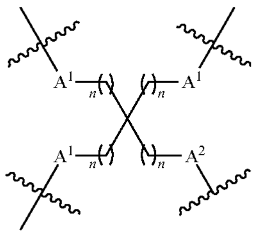

$A^1 = O, NR^1, C(R^1)_2$
$A^2 = NR^2$
n = 1 to 4

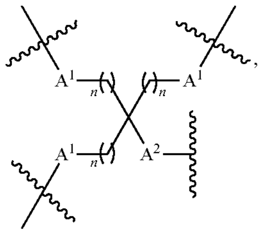

$A^1 = O, NR^1, C(R^1)_2$
$A^2 = NR^2$
n = 1 to 4 wherein:

R1 is hydrogen or C1-C10 alkylene;

and R2 is C1-C10 alkylene.

Optionally, the branching unit consists of only a carbon atom.

The "$X^3$" portion is a bridging unit. The bridging unit is linear and is covalently bound to the branching unit and the nucleic acid.

$X^3$ may be selected from —$C_1$-$C_{20}$ alkylene-, —$C_2$-$C_{20}$ alkenylene-, an alkylene ether of formula —($C_1$-$C_{20}$ alkylene)-O—($C_1$-$C_{20}$ alkylene)-, —C(O)—$C_1$-$C_{20}$ alkylene-, —$C_0$-$C_4$ alkylene(Cy)$C_0$-$C_4$ alkylene- wherein Cy represents a substituted or unsubstituted 5 or 6 membered cycloalkylene, arylene, heterocyclylene or heteroarylene ring, —$C_1$-$C_4$ alkylene-NHC(O)—$C_1$-$C_4$ alkylene-, —$C_1$-$C_4$ alkylene-C(O)NH—$C_1$-$C_4$ alkylene-, —$C_1$-$C_4$ alkylene-SC(O)—$C_1$-$C_4$ alkylene-, —$C_1$-$C_4$ alkylene-C(O)S—$C_1$-$C_4$ alkylene-, —$C_1$-$C_4$ alkylene-OC(O)—$C_1$-$C_4$ alkylene-, —$C_1$-$C_4$ alkylene-C(O)O—$C_1$-$C_4$ alkylene-, and —$C_1$-$C_6$ alkylene-S—S—$C_1$-$C_6$ alkylene-.

$X^3$ may be an alkylene ether of formula —($C_1$-$C_{20}$ alkylene)-O—($C_1$-$C_{20}$ alkylene)-. $X^3$ may be an alkylene ether of formula —($C_1$-$C_{20}$ alkylene)-O—($C_4$-$C_{20}$ alkylene)-, wherein said ($C_4$-$C_{20}$ alkylene) is linked to Z. $X^3$ may be selected from the group consisting of —$CH_2$—O—$C_3H_6$—, —$CH_2$—O—$C_4H_8$—, —$CH_2$—O—$C_6H_{12}$— and —$CH_2$—O—$C_8H_{16}$—, especially —$CH_2$—O—$C_4H_8$—, —$CH_2$—O—$C_6H_{12}$— and —$CH_2$—O—$C_8H_{16}$—, wherein in each case the —$CH_2$— group is linked to A.

In one aspect, the nucleic acid is conjugated to a ligand comprising a compound of formula (III):

$$[S—X^1—P—X^2]_3\text{-}A\text{-}X^3— \quad (III)$$

wherein:

S represents a saccharide, preferably GalNAc;

$X^1$ represents $C_3$-$C_6$ alkylene or (—$CH_2$—$CH_2$—O)$_m$(—$CH_2$)$_2$— wherein m is 1, 2, or 3;

P is a phosphate or modified phosphate, preferably a thiophosphate;

$X^2$ is $C_1$-$C_8$ alkylene;

A is a branching unit selected from:

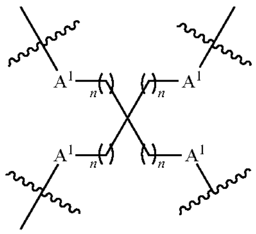

$A^1$ = O, NH
n = 1 to 4

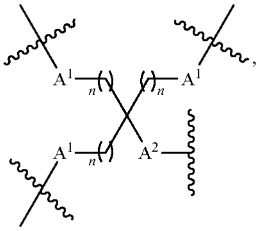

$A^1$ = O, NH
$A^2$ = NH, $CH_2$, O
n = 1 to 4

$X^3$ is a bridging unit;

wherein a nucleic acid according to the present invention is conjugated to $X^3$ via a phosphate or a modified phosphate, preferably a thiophosphate.

The branching unit A may have the structure:

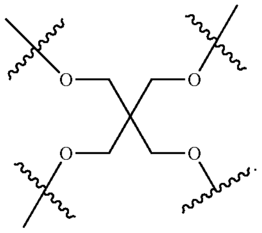 [SMILES: *OCC(CO*)(CO*)CO*]

The branching unit A may have the structure:

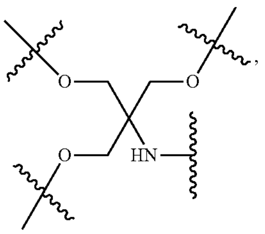

wherein $X^3$ is attached to the nitrogen atom.

$X^3$ may be $C_1$-$C_{20}$ alkylene. Preferably, $X^3$ is selected from the group consisting of —$C_3H_6$, —$C_4H_8$—, —$C_6H_{12}$— and —$C_8H_{16}$—, especially —$C_4H_8$—, —$C_6H_{12}$— and —$C_8H_{16}$—.

In one aspect, the nucleic acid is conjugated to a ligand comprising a compound of formula (IV):

$$[S—X^1—P—X^2]_3\text{-}A\text{-}X^3— \quad (IV)$$

wherein:

S represents a saccharide, preferably GalNAc;

$X^1$ represents $C_3$-$C_6$ alkylene or (—$CH_2$—$CH_2$—O)$_m$(—$CH_2$)$_2$— wherein m is 1, 2, or 3;

P is a phosphate or modified phosphate, preferably a thiophosphate;

$X^2$ is an alkylene ether of formula —$C_3H_6$—O—$CH_2$—;

A is a branching unit;

$X^3$ is an alkylene ether of formula selected from the group consisting of —$CH_2$—O—$CH_2$—, —$CH_2$—O—$C_2H_4$—, —$CH_2$—O—$C_3H_6$—, —$CH_2$—O—$C_4H_8$—, —$CH_2$—O—$C_5H_{10}$—, —$CH_2$—O—$C_6H_{12}$—, —$CH_2$—O—$C_7H_{14}$—, and —$CH_2$—O—$C_8H_{16}$—, wherein in each case the —$CH_2$— group is linked to A, and wherein $X^3$ is conjugated to a nucleic acid according to the present invention by a phosphate or modified phosphate, preferably a thiophosphate.

The branching unit may comprise carbon. Preferably, the branching unit is a carbon.

$X^3$ may be selected from the group consisting of —$CH_2$—O—$C_4H_8$—, —$CH_2$—O—$C_5H_{10}$—, —$CH_2$—O—$C_6H_{12}$—, —$CH_2$—O—$C_7H_{14}$—, and —$CH_2$—O—$C_8H_{16}$—. Preferably, $X^3$ is selected from the group consisting of —$CH_2$—O—$C_4H_8$—, —$CH_2$—O—$C_6H_{12}$— and —$CH_2$—O—$C_8H_{16}$.

$X^1$ may be (—$CH_2$—$CH_2$—O)(—$CH_2$)$_2$—. $X^1$ may be (—$CH_2$—$CH_2$—O)$_2$(—$CH_2$)$_2$—. $X^1$ may be (—$CH_2$—$CH_2$—O)$_3$(—$CH_2$)$_2$—. Preferably, $X^1$ is (—$CH_2$—$CH_2$—O)$_2$(—$CH_2$)$_2$—. Alternatively, $X^1$ represents $C_3$-$C_6$ alkylene. $X^1$ may be propylene. $X^1$ may be butylene. $X^1$ may be pentylene. $X^1$ may be hexylene. Preferably the alkyl is a linear alkylene. In particular, $X^1$ may be butylene.

$X^2$ represents an alkylene ether of formula $—C_3H_6—O—CH_2—$ i.e. $C_3$ alkoxy methylene, or $—CH_2CH_2CH_2OCH_2—$.

For any of the above aspects, when P represents a modified phosphate group, P can be represented by:

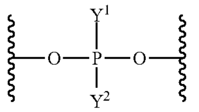

wherein $Y^1$ and $Y^2$ each independently represent =O, =S, —O, —OH, —SH, $—BH_3$, $—OCH_2CO_2$, $—OCH_2CO_2R^x$, $—OCH_2C(S)OR^x$, and $—OR^x$, wherein $R^x$ represents $C_1$-$C_6$ alkyl and wherein

 indicates attachment to the remainder of the compound.

By modified phosphate it is meant a phosphate group wherein one or more of the non-linking oxygens is replaced. Examples of modified phosphate groups include phosphorothioate, phosphorodithioates, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulphur. One, each or both non-linking oxygens in the phosphate group can be independently any one of S, Se, B, C, H, N, or OR (R is alkyl or aryl).

The phosphate can also be modified by replacement of a linking oxygen with nitrogen (bridged phosphoroamidates), sulfur (bridged phosphorothioates) and carbon (bridged methylenephosphonates). The replacement can occur at a terminal oxygen. Replacement of the non-linking oxygens with nitrogen is possible.

For example, $Y^1$ may represent —OH and $Y^2$ may represent =O or =S; or $Y^1$ may represent —O— and $Y^2$ may represent =O or =S;

$Y^1$ may represent =O and $Y^2$ may represent $—CH_3$, —SH, $—OR^x$, or $—BH_3$ $Y^1$ may represent =S and $Y^2$ may represent $—CH_3$, $OR^x$ or —SH.

It will be understood by the skilled person that in certain instances there will be delocalisation between $Y^1$ and $Y^2$.

Preferably, the modified phosphate group is a thiophosphate group. Thiophosphate groups include bithiophosphate (i.e. where $Y^1$ represents =S and $Y^2$ represents $—S^-$) and monothiophosphate (i.e. where $Y^1$ represents $—O^-$ and $Y^2$ represents =S, or where $Y^1$ represents =O and $Y^2$ represents $—S^-$). Preferably, P is a monothiophosphate. The inventors have found that conjugates having thiophosphate groups in replacement of phosphate groups have improved potency and duration of action in vivo.

P may also be an ethylphosphate (i.e. where $Y^1$ represents =O and $Y^2$ represents $OCH_2CH_3$).

The saccharide may be selected to have an affinity for at least one type of receptor on a target cell. In particular, the receptor is on the surface of a mammalian liver cell, for example, the hepatic asialoglycoprotein receptor complex (ASGP-R).

For any of the above or below aspects, the saccharide may be selected from N-acetyl with one or more of galactosamine, mannose, galactose, glucose, glucosamine and fructose. Typically a ligand to be used in the present invention may include N-acetyl galactosamine (GalNAc). Preferably the compounds of the invention may have 3 ligands, which will each preferably include N-acetyl galactosamine.

"GalNAc" refers to 2-(Acetylamino)-2-deoxy-D-galactopyranose, commonly referred to in the literature as N-acetyl galactosamine. Reference to "GalNAc" or "N-acetyl galactosamine" includes both the β-form: 2-(Acetylamino)-2-deoxy-β-D-galactopyranose and the α-form: 2-(Acetylamino)-2-deoxy-α-D-galactopyranose. In certain embodiments, both the β-form: 2-(Acetylamino)-2-deoxy-β-D-galactopyranose and α-form: 2-(Acetylamino)-2-deoxy-α-D-galactopyranose may be used interchangeably. Preferably, the compounds of the invention comprise the β-form, 2-(Acetylamino)-2-deoxy-β-D-galactopyranose.

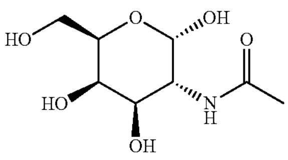

2-(Acetylamino)-2-deoxy-D-galactopyranose

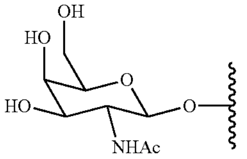 [SMILES: *OC1OC(CO)C(O)C(O)C1NC(C)=O]

2-(Acetylamino)-2-deoxy-β-D-galactopyranose

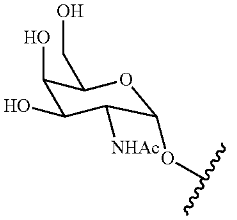 [SMILES: *OC1OC(CO)C(O)C(O)C1NC(C)=O]

2-(Acetylamino)-2-deoxy-α-D-galactopyranose

In one aspect, the nucleic acid is a conjugated nucleic acid, wherein the nucleic acid is conjugated to a triantennary ligand with one of the following structures:

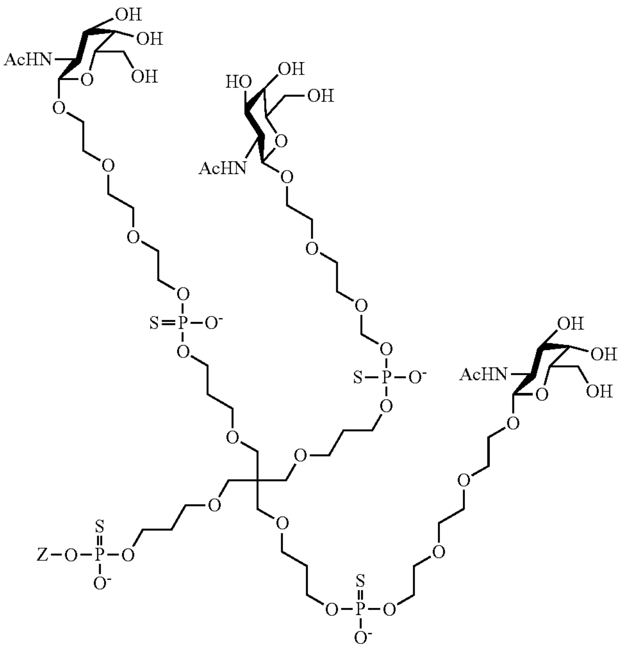
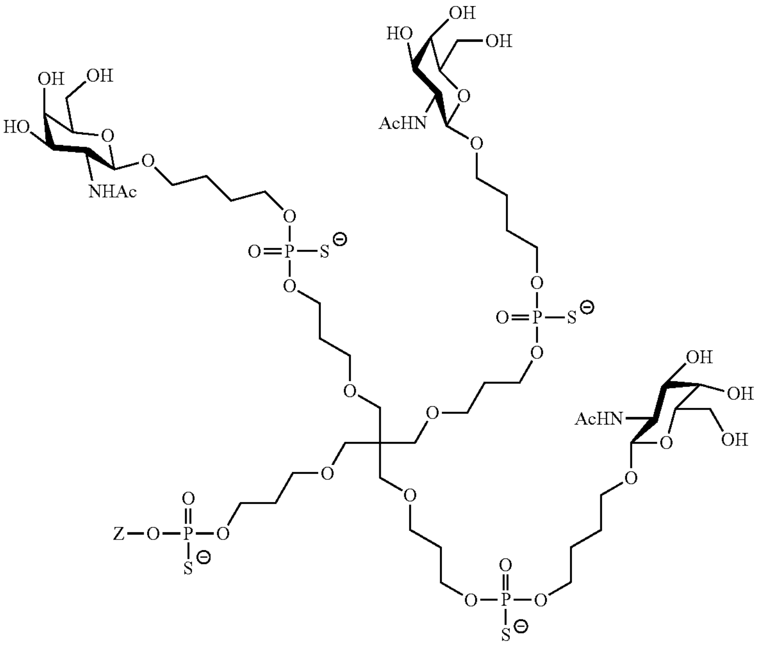

-continued
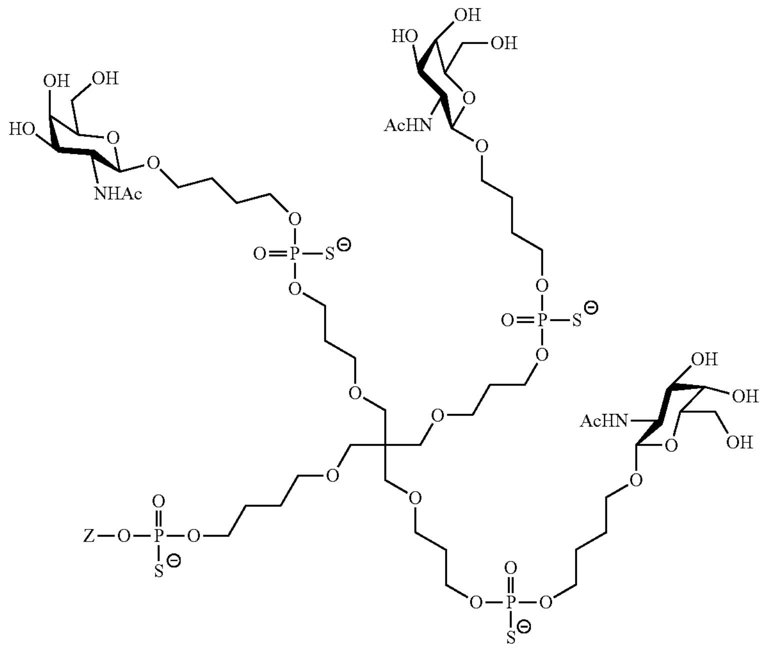
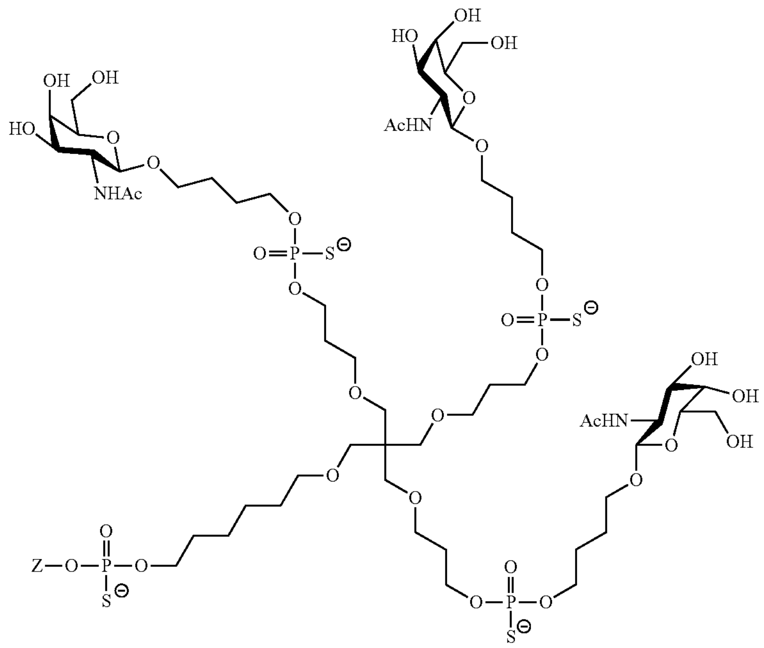

-continued
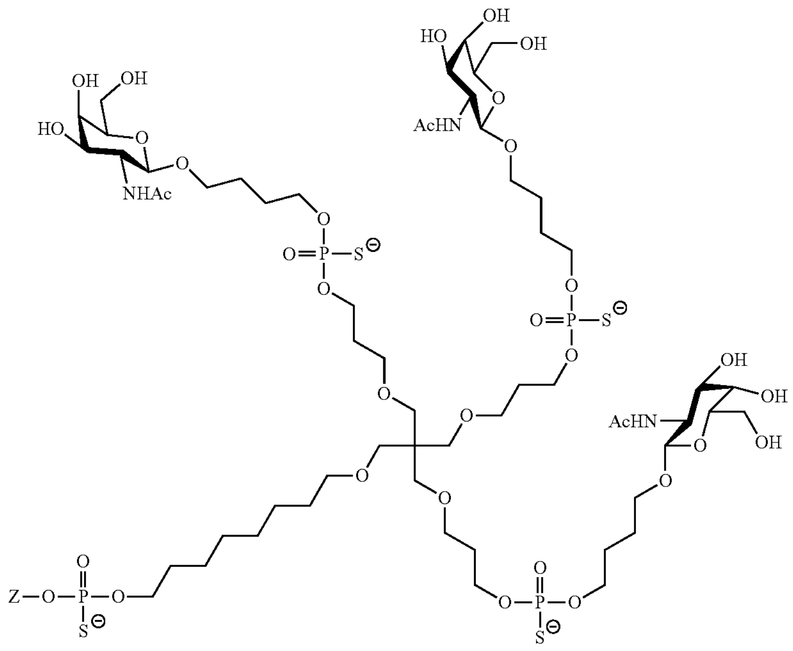
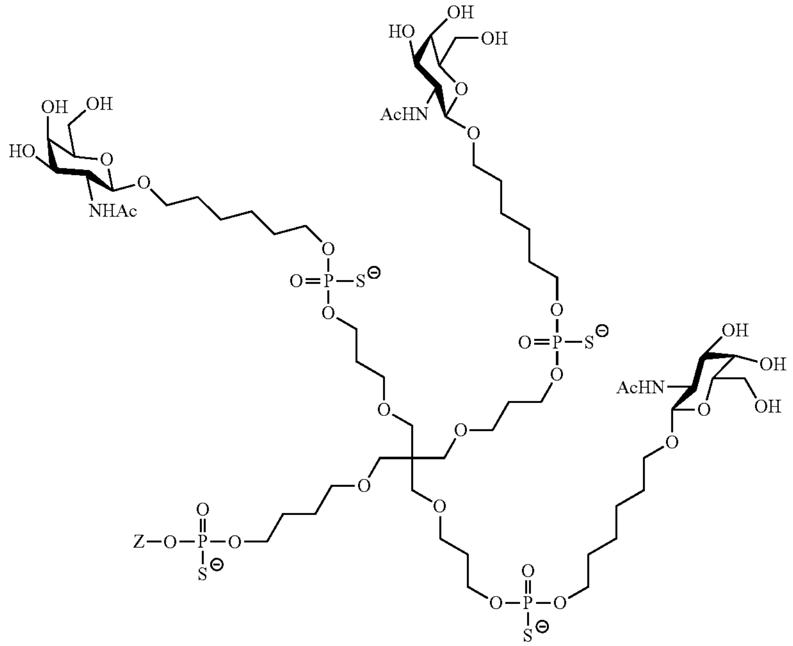

-continued
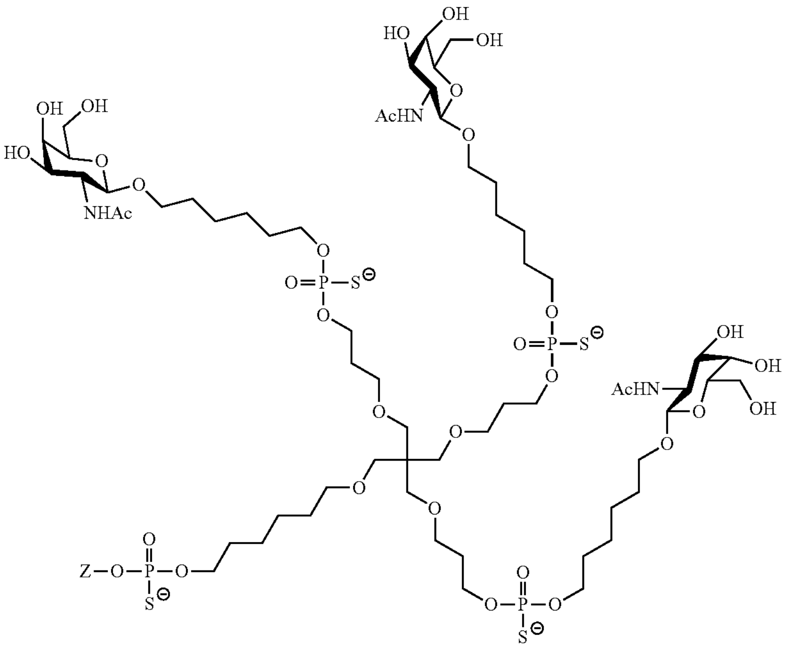
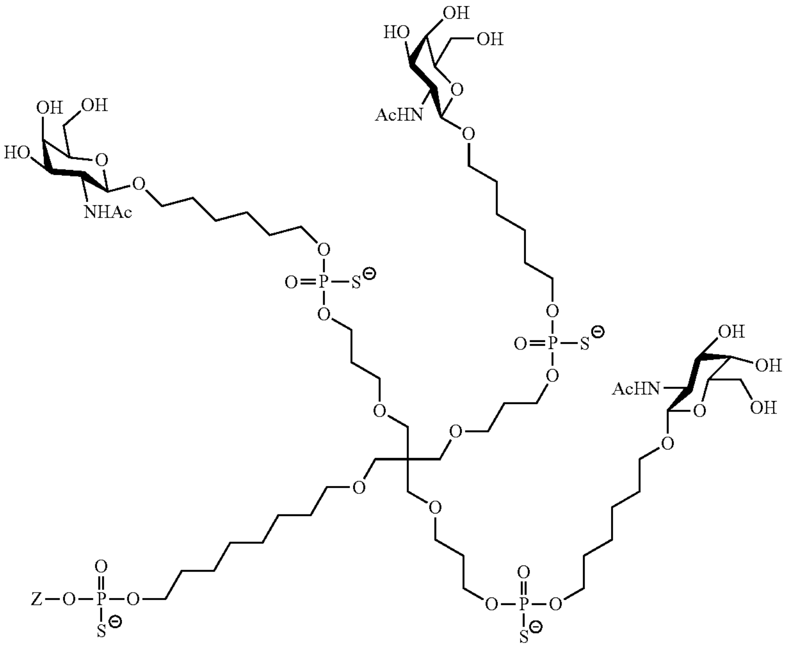

-continued
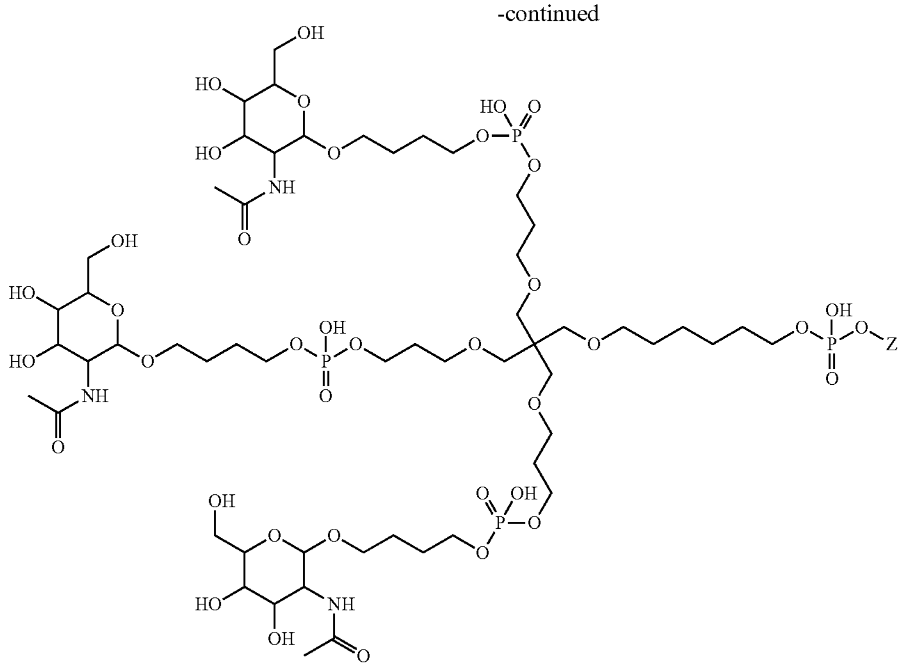
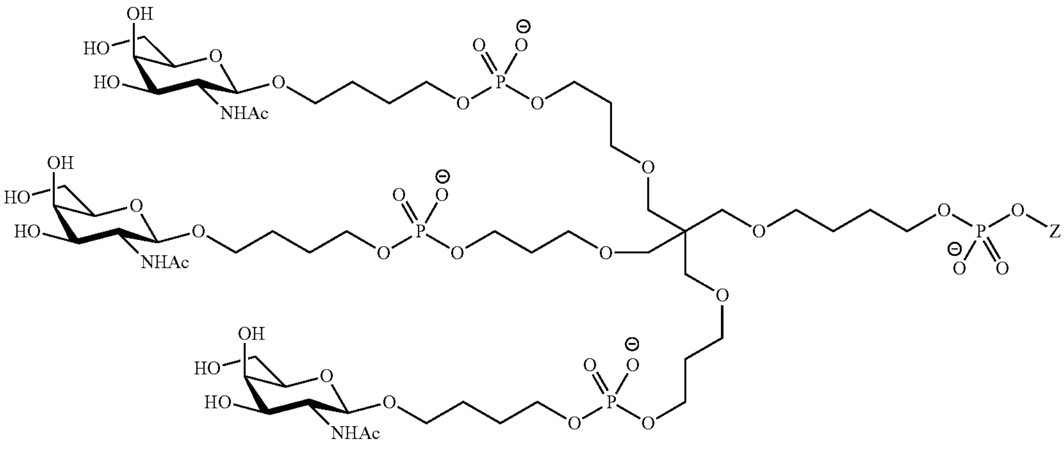
wherein Z is any nucleic acid as defined herein.

Preferably, the nucleic acid is a conjugated nucleic acid, wherein the nucleic acid is conjugated to a triantennary ligand with the following structures:

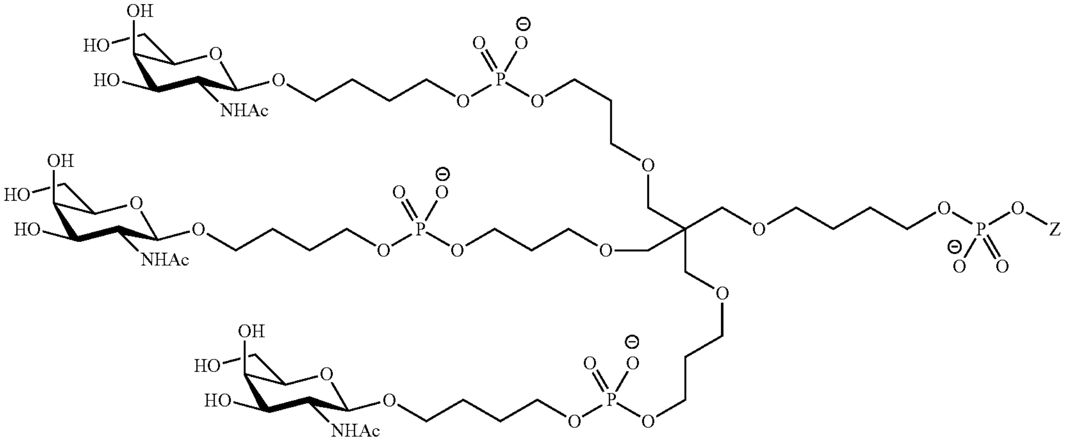

wherein Z is any nucleic acid as defined herein.

A ligand of formula (II), (III) or (IV) or any one of the triantennary ligands disclosed herein can be attached at the 3'-end of the first (antisense) strand and/or at any of the 3' and/or 5' end of the second (sense) strand. The nucleic acid can comprise more than one ligand of formula (II), (III) or (IV) or any one of the triantennary ligands disclosed herein. However, a single ligand of formula (II), (III) or (IV) or any one of the triantennary ligands disclosed herein is preferred because a single such ligand is sufficient for efficient targeting of the nucleic acid to the target cells. Preferably in that case, at least the last two, preferably at least the last three and more preferably at least the last four nucleotides at the end of the nucleic acid to which the ligand is attached are linked by a phosphodiester linkage.

Preferably, the 5'-end of the first (antisense) strand is not attached to a ligand of formula (II), (III) or (IV) or any one of the triantennary ligands disclosed herein, since a ligand in this position can potentially interfere with the biological activity of the nucleic acid.

A nucleic acid with a single ligand of formula (II), (III) or (IV) or any one of the triantennary ligands disclosed herein at the 5' end of a strand is easier and therefore cheaper to synthesise than the same nucleic acid with the same ligand at the 3' end. Preferably therefore, a single ligand of any of formulae (II), (III) or (IV) or any one of the triantennary ligands disclosed herein is covalently attached to (conjugated with) the 5' end of the second strand of the nucleic acid.

In one aspect, the first strand of the nucleic acid is a compound of formula (V):

(V)

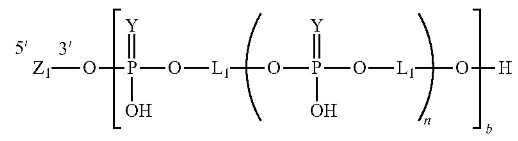

wherein b is preferably 0 or 1; and the second strand is a compound of formula (VI):

(VI)

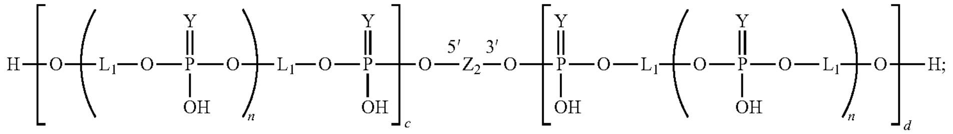

wherein:

c and d are independently preferably 0 or 1;

$Z_1$ and $Z_2$ are respectively the first and second strand of the nucleic acid;

Y is independently O or S;

n is independently 0, 1, 2 or 3; and $L_1$ is a linker to which a ligand is attached, wherein $L_1$ is the same or different in formulae (V) and (VI), and is the same or different within formulae (V) and (VI) when $L_1$ is present more than once within the same formula, wherein $L_1$ is preferably of formula (VII);

and wherein b+c+d is preferably 2 or 3.

Preferably, $L_1$ in formulae (V) and (VI) is of formula (VII):

(VII)

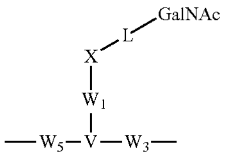

wherein:

L is selected from the group comprising, or preferably consisting of:

—$(CH_2)$—C(O)—, wherein r=2-12;

—$(CH_2$—$CH_2$—$O)_s$—$CH_2$—C(O)—, wherein s=1-5;

—$(CH_2)_t$—CO—NH—$(CH_2)$+—NH—C(O)—, wherein t is independently 1-5;

—$(CH_2)_u$—CO—NH—$(CH_2)_u$—C(O)—, wherein u is independently 1-5; and

—$(CH_2)_v$—NH—C(O)—, wherein v is 2-12; and wherein the terminal C(O), if present, is attached to X of formula (VII), or if X is absent, to $W_1$ of formula (VII), or if $W_1$ is absent, to V of formula (VII);

$W_1$, $W_3$ and $W_5$ are individually absent or selected from the group comprising, or preferably consisting of:

-continued

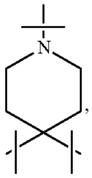,
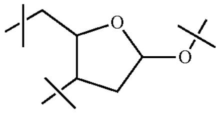
or
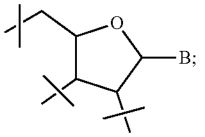

wherein B, if present, is a modified or natural nucleobase.

In one aspect, the first strand is a compound of formula (VIII)

(VIII)

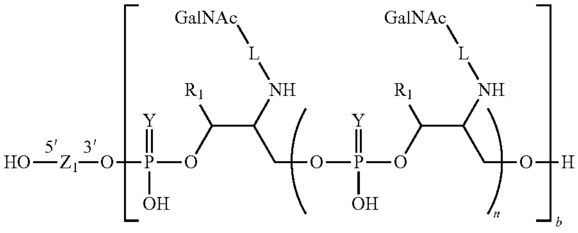

wherein b is preferably 0 or 1; and the second strand is a compound of formula (IX):

(IX)

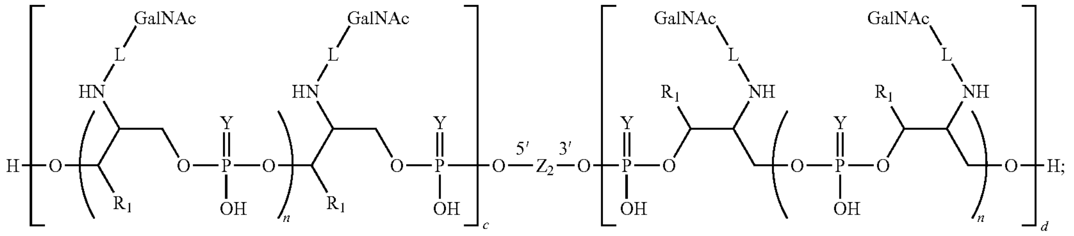

—$(CH_2)_r$, wherein r=1-7;

—$(CH_2)_s$—O—$(CH_2)_s$—, wherein s is independently 0-5;

—$(CH_2)_t$—S—$(CH_2)_r$, wherein t is independently 0-5;

X is absent or is selected from the group comprising, or preferably consisting of: NH, $NCH_3$ or $NC_2H_5$;

V is selected from the group comprising, or preferably consisting of:

CH, N, 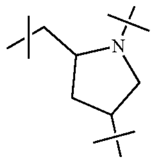, 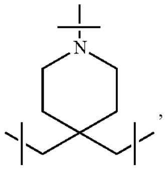, wherein c and d are independently preferably 0 or 1;

wherein:

$Z_1$ and $Z_2$ are respectively the first and second strand of the nucleic acid;

Y is independently O or S;

$R_1$ is H or methyl;

n is independently preferably 0, 1, 2 or 3; and

L is the same or different in formulae (VIII) and (IX), and is the same or different within formulae (VIII) and (IX) when L is present more than once within the same formula, and is selected from the group comprising, or preferably consisting of:

—$(CH_2)$—C(O)—, wherein r=2-12;

—$(CH_2$—$CH_2$—$O)_s$—$CH_2$—C(O)—, wherein s=1-5;

—$(CH_2)_t$—CO—NH—$(CH_2)$+—NH—C(O)—, wherein t is independently 1-5;

—$(CH_2)_u$—CO—NH—$(CH_2)_u$—C(O)—, wherein u is independently 1-5; and

—$(CH_2)_v$—NH—C(O)—, wherein v is 2-12; and wherein the terminal C(O), if present, is attached to the NH group (of the linker, not of the targeting ligand); and wherein b+c+d is preferably 2 or 3.

In one aspect, the first strand of the nucleic acid is a compound of formula (X):

(X)

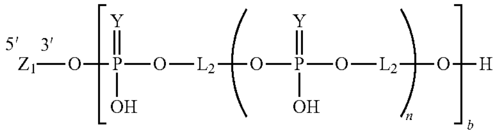

wherein b is preferably 0 or 1; and the second strand is a compound of formula (XI):

(XI)

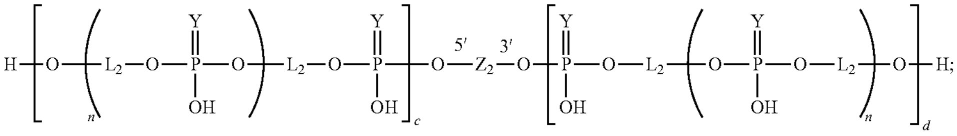

wherein:

c and d are independently preferably 0 or 1;

$Z_1$ and $Z_2$ are respectively the first and second RNA strand of the nucleic;

Y is independently O or S;

n is independently preferably 0, 1, 2 or 3; and $L_2$ is the same or different in formulae (X) and (XI) and is the same or different in moieties bracketed by b, c and d, and is selected from the group comprising, or preferably consisting of:

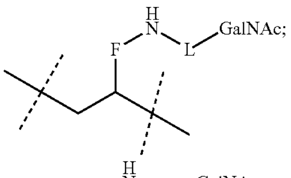

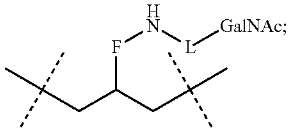

and

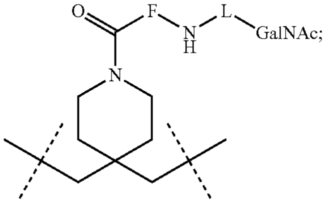

or n is 0 and $L_2$ is:

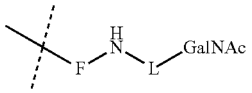

and the terminal OH group is absent such that the following moiety is formed:

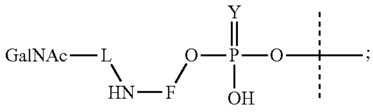

wherein:

F is a saturated branched or unbranched (such as unbranched) $C_{1-8}$alkyl (e.g. $C_{1-6}$alkyl) chain wherein one of the carbon atoms is optionally replaced with an oxygen atom provided that said oxygen atom is separated from another heteroatom (e.g. an O or N atom) by at least 2 carbon atoms;

L is the same or different in formulae (X) and (XI) and is selected from the group comprising, or preferably consisting of:

$-(CH_2)-C(O)-$, wherein r=2-12;

$-(CH_2-CH_2-O)_s-CH_2-C(O)-$, wherein s=1-5;

$-(CH_2)_t-CO-NH-(CH_2)_t-NH-C(O)-$, wherein t is independently 1-5;

$-(CH_2)_u-CO-NH-(CH_2)_u-C(O)-$, wherein u is independently 1-5; and $-(CH_2)_v-NH-C(O)-$, wherein v is 2-12; and wherein the terminal C(O), if present, is attached to the NH group (of the linker, not of the targeting ligand);

and wherein b+c+d is preferably 2 or 3.

In one aspect, b is 0, c is 1 and d is 1; b is 1, c is 0 and d is 1; b is 1, cis 1 and d is 0; or b is 1, c is 1 and d is 1 in any of the nucleic acids of formulae (V) and (VI) or (VIII) and (IX) or (X) and (XI). Preferably, b is 0, c is 1 and d is 1; b is 1, c is 0 and d is 1; or bis 1, c is 1 and d is 1. Most preferably, b is 0, c is 1 and dis 1.

In one aspect, Y is O in any of the nucleic acids of formulae (V) and (VI) or (VIII) and (IX) or (X) and (XI). In another aspect, Y is S. In a preferred aspect, Y is independently selected from O or S in the different positions in the formulae.

In one aspect, $R_1$ is H or methyl in any of the nucleic acids of formulae (VIII) and (IX). In one aspect, $R_1$ is H. In another aspect, $R_1$ is methyl.

In one aspect, n is 0, 1, 2 or 3 in any of the nucleic acids of formulae (V) and (VI) or (VIII) and (IX) or (X) and (XI). Preferably, n is 0.

Examples of F moieties in any of the nucleic acids of formulae (X) and (XI) include $(CH_2)_{1-6}$ e.g. $(CH_2)_{14}$ e.g. $CH_2$, $(CH_2)_4$, $(CH_2)_5$ or $(CH_2)_6$, or $CH_2O(CH_2)_{2-3}$, e.g. $CH_2O(CH_2)CH_3$.

In one aspect, $L_2$ in formulae (X) and (XI) is:

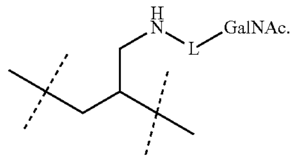

In one aspect, $L_2$ is:

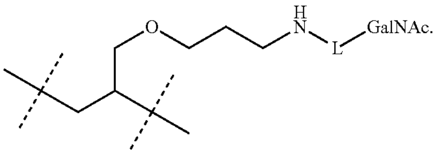

In one aspect, $L_2$ is:

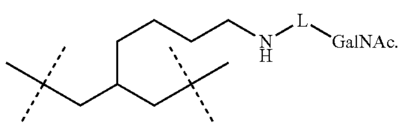

In one aspect, $L_2$ is:

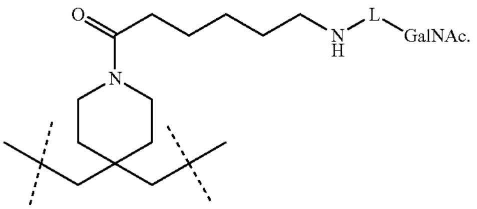

In one aspect, n is 0 and $L_2$ is:

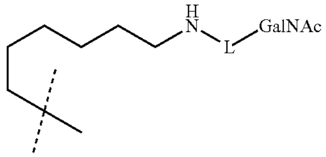

and the terminal OH group is absent such that the following moiety is formed:

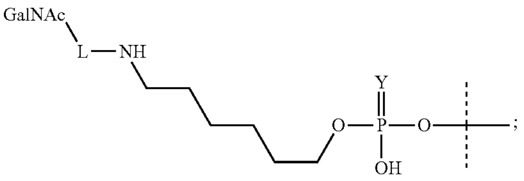

wherein Y is O or S.

In one aspect, L in the nucleic acids of formulae (V) and (VI) or (VIII) and (IX) or (X) and (XI), is selected from the group comprising, or preferably consisting of:

$—(CH_2)—C(O)—$, wherein r=2-12;

$—(CH_2—CH_2—O)_s—CH_2—C(O)—$, wherein s=1-5;

$—(CH_2)_t—CO—NH—(CH_2)_t—NH—C(O)—$, wherein t is independently 1-5;

$—(CH_2)_u—CO—NH—(CH_2)_u—C(O)—$, wherein u is independently 1-5; and $—(CH_2)_v—NH—C(O)—$, wherein v is 2-12;

wherein the terminal C(O) is attached to the NH group.

Preferably, L is $—(CH_2)_r—C(O)—$, wherein r=2-12, more preferably r=2-6 even more preferably, r=4 or 6 e.g. 4.

Preferably, L is:

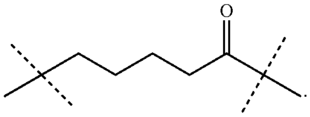

Within the moiety bracketed by b, c and d, $L_2$ in the nucleic acids of formulae (X) and (XI) is typically the same. Between moieties bracketed by b, c and d, $L_2$ may be the same or different. In an embodiment, $L_2$ in the moiety bracketed by c is the same as the $L_2$ in the moiety bracketed by d. In an embodiment, $L_2$ in the moiety bracketed by c is not the same as $L_2$ in the moiety bracketed by d. In an embodiment, the $L_2$ in the moieties bracketed by b, c and d is the same, for example when the linker moiety is a serinol-derived linker moiety.

Serinol derived linker moieties may be based on serinol in any stereochemistry i.e. derived from L-serine isomer, D-serine isomer, a racemic serine or other combination of isomers. In a preferred aspect of the invention, the serinol-GalNAc moiety (SerGN) has the following stereochemistry:

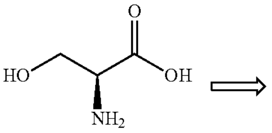

L-Serine

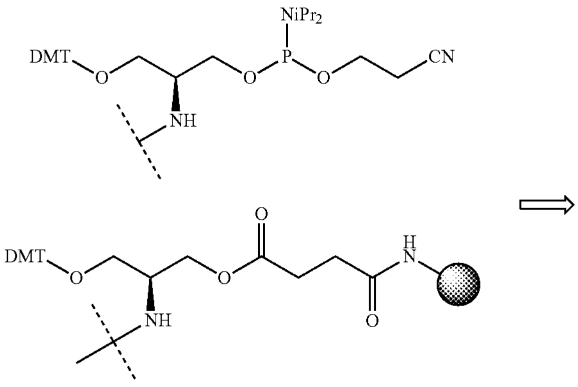

(S)-Serinol building blocks

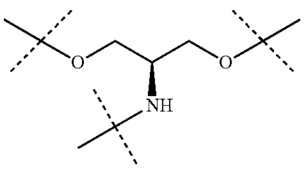

Serinol derived linker moieties i.e. is based on an (S)-serinol-amidite or (S)-serinol succinate solid supported building block derived from L-serine isomer.

In a preferred aspect, the first strand of the nucleic acid is a compound of formula (VIII) and the second strand of the nucleic acid is a compound of formula (IX), wherein:

b is 0;

c and d are 1, n is 0, $Z_1$ and $Z_2$ are respectively the first and second strand of the nucleic acid, Y is S, $R_1$ is H, and L is $—(CH_2)_4—C(O)—$, wherein the terminal C(O) of L is attached to the N atom of the linker (ie not a possible N atom of a targeting ligand).

In another preferred aspect, the first strand of the nucleic acid is a compound of formula (V) and the second strand of the nucleic acid is a compound of formula (VI), wherein:

b is 0, c and d are 1, n is 0, $Z_1$ and $Z_2$ are respectively the first and second strand of the nucleic acid, Y is S, $L_1$ is of formula (VII), wherein:

$W_1$ is $—CH_2—O—(CH_2)_3—$, $W_3$ is $—CH_2—$, $W_5$ is absent,

V is CH,

X is NH, and

L is $—(CH_2)_4—C(O)—$ wherein the terminal C(O) of L is attached to the N atom of X in formula (VII).

In another preferred aspect, the first strand of the nucleic acid is a compound of formula (V) and the second strand of the nucleic acid is a compound of formula (VI), wherein:

b is 0, c and d are 1, n is 0, $Z_1$ and $Z_2$ are respectively the first and second strand of the nucleic acid, Y is S, $L_1$ is of formula (VII), wherein:

$W_1$, $W_3$ and $W_5$ are absent,

V is

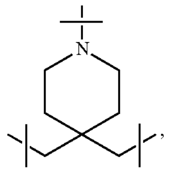

X is absent, and

L is $—(CH_2)_4—C(O)—NH—(CH_2)_5—C(O)—$, wherein the terminal C(O) of L is attached to the N atom of V in formula (VII).

In one aspect, the nucleic acid is conjugated to a triantennary ligand with the following structure:

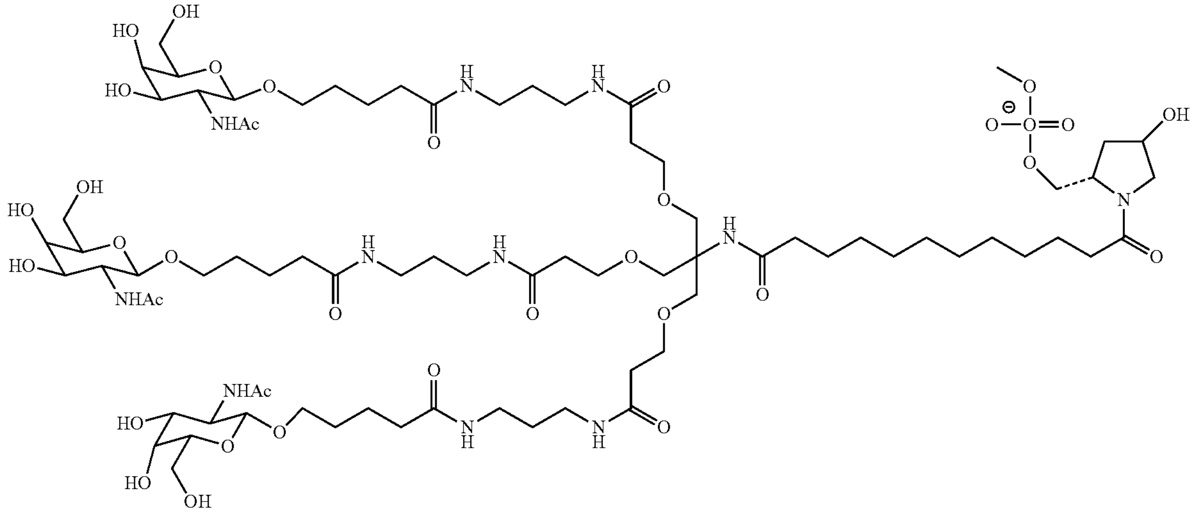

wherein the nucleic acid is conjugated to the ligand via the phosphate group of the ligand a) to the last nucleotide at the 5' end of the second strand; b) to the last nucleotide at the 3' end of the second strand; or c) to the last nucleotide at the 3' end of the first strand.

In one aspect of the nucleic acid, the cells that are targeted by the nucleic acid with a ligand are hepatocytes.

In any one of the above ligands where GalNAc is present, the GalNAc may be substituted for any other targeting ligand, such as those mentioned herein, in particular mannose, galactose, glucose, glucosamine and fucose.

A particularly preferred embodiment is a nucleic acid wherein the first strand comprises or consists of SEQ ID NO: 237 and the second strand optionally comprises or consists of SEQ ID NO: 156. This nucleic acid can be further conjugated to a ligand, preferably at the 5' end of the second (sense) strand. Even more preferred is a nucleic acid wherein the first strand comprises or consists of SEQ ID NO: 237 and the second strand optionally comprises or consists of SEQ ID NO: 238. Most preferred in this embodiment is a siRNA that consists of SEQ ID NO: 237 and SEQ ID NO: 238. One aspect of the invention is EU414.

An alternative particularly preferred embodiment is a nucleic acid wherein the first strand comprises or consists of SEQ ID NO: 237 and the second strand optionally comprises or consists of SEQ ID NO: 553. This nucleic acid can be further conjugated to a ligand, preferably at the 5' end of the second (sense) strand. Even more preferred is a nucleic acid wherein the first strand comprises or consists of SEQ ID NO: 237 and the second strand optionally comprises or consists of SEQ ID NO: 460. Most preferred in this embodiment is a siRNA that consists of SEQ ID NO: 237 and SEQ ID NO: 460. One aspect of the invention is EU420.

An alternative particularly preferred embodiment is a nucleic acid wherein the first strand comprises or consists of SEQ ID NO: 461 and the second strand optionally comprises or consists of SEQ ID NO: 554. This nucleic acid can be further conjugated to a ligand, preferably at the 5' end of the second (sense) strand. Even more preferred is a nucleic acid wherein the first strand comprises or consists of SEQ ID NO: 461 and the second strand optionally comprises or consists of SEQ ID NO: 462. Most preferred in this embodiment is a siRNA that consists of SEQ ID NO: 461 and SEQ ID NO: 462. One aspect of the invention is EU422.

In one aspect, the nucleic acid is conjugated to a ligand that comprises a lipid, and more preferably, a ligand that comprises a cholesterol.

Compositions, Uses and Methods

The present invention also provides compositions comprising a nucleic acid of the invention. The nucleic acids and compositions may be used as medicaments or as diagnostic agents, alone or in combination with other agents. For example, one or more nucleic acid(s) of the invention can be combined with a delivery vehicle (e.g., liposomes) and/or excipients, such as carriers, diluents. Other agents such as preservatives and stabilizers can also be added. Pharmaceutically acceptable salts or solvates of any of the nucleic acids of the invention are likewise within the scope of the present invention. Methods for the delivery of nucleic acids are known in the art and within the knowledge of the person skilled in the art.

Compositions disclosed herein are particularly pharmaceutical compositions. Such compositions are suitable for administration to a subject.

In one aspect, the composition comprises a nucleic acid disclosed herein, or a pharmaceutically acceptable salt or solvate thereof, and a solvent and/or a delivery vehicle and/or a physiologically acceptable excipient and/or a carrier and/or a salt and/or a diluent and/or a buffer and/or a preservative.

Pharmaceutically acceptable carriers or diluents include those used in formulations suitable for oral, rectal, nasal or parenteral (including subcutaneous, intramuscular, intravenous, intradermal, and transdermal) administration. The formulations may conveniently be presented in unit dosage form and may be prepared by any of the methods well known in the art of pharmacy. Subcutaneous or transdermal modes of administration may be particularly suitable for the compounds described herein.

The therapeutically effective amount of a nucleic acid of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person.

Nucleic acids of the present invention, or salts thereof, may be formulated as pharmaceutical compositions prepared for storage or administration, which typically comprise a therapeutically effective amount of a nucleic acid of the invention, or a salt thereof, in a pharmaceutically acceptable carrier.

The nucleic acid or conjugated nucleic acid of the present invention can also be administered in combination with other therapeutic compounds, either administrated separately or simultaneously, e.g., as a combined unit dose. The invention also includes a composition comprising one or more nucleic acids according to the present invention in a physiologically/pharmaceutically acceptable excipient, such as a stabilizer, preservative, diluent, buffer, and the like.

In one aspect, the composition comprises a nucleic acid disclosed herein and a further therapeutic agent selected from the group comprising an oligonucleotide, a small molecule, a monoclonal antibody, a polyclonal antibody and a peptide. In one embodiment, the further therapeutic agent is an inhibitor of CNNM4. In a preferred embodiment, the further therapeutic agent is the small molecule 7-amino-2-phenyl-5H-thieno[3,2-c]pyridin-4-one (PubChem CID 91383855) or the rhodanine derivative 2-[5-(4-Oxo-2-thioxo-thiazolidin-5-ylidenemethyl)-furan-2-yl]-benzoic acid as described in Park, H., et al. 2008. Bioorg Med Chem Lett. 18(7):2250-5 (Chemspider ID 1014170).

In certain embodiments, two or more nucleic acids of the invention with different sequences may be administered simultaneously or sequentially.

In another aspect, the present invention provides a composition, e.g., a pharmaceutical composition, comprising one or a combination of different nucleic acids of the invention and at least one pharmaceutically acceptable carrier.

Dosage levels for the medicament and compositions of the invention can be determined by those skilled in the art by experimentation. In one aspect, a unit dose may contain between about 0.01 mg/kg and about 100 mg/kg body weight of nucleic acid or conjugated nucleic acid. Alternatively, the dose can be from 10 mg/kg to 25 mg/kg body weight, or 1 mg/kg to 10 mg/kg body weight, or 0.05 mg/kg to 5 mg/kg body weight, or 0.1 mg/kg to 5 mg/kg body weight, or 0.1 mg/kg to 1 mg/kg body weight, or 0.1 mg/kg to 0.5 mg/kg body weight, or 0.5 mg/kg to 1 mg/kg body weight. Alternatively, the dose can be from about 0.5 mg/kg to about 10 mg/kg body weight, or about 0.6 mg/kg to about 8 mg/kg body weight, or about 0.7 mg/kg to about 7 mg/kg body weight, or about 0.8 mg/kg to about 6 mg/kg body weight, or about 0.9 mg/kg to about 5.5 mg/kg body weight, or about 1 mg/kg to about 5 mg/kg body weight, or about 1 mg/kg body weight, or about 3 mg/kg body weight, or about 1 mg/kg body weight, or about 3 mg/kg body weight, or about 5 mg/kg body weight, wherein "about" is a deviation of up to 30%, preferably up to 20%, more preferably up to 10%, yet more preferably up to 5% and most preferably 0% from the indicated value. Dosage levels may also be calculated via other parameters such as, e.g., body surface area.

The dosage and frequency of administration may vary depending on whether the treatment is therapeutic or prophylactic (e.g., preventative), and may be adjusted during the course of treatment. In certain prophylactic applications, a relatively low dosage is administered at relatively infrequent intervals over a relatively long period of time. Some subjects may continue to receive treatment over their lifetime. In certain therapeutic applications, a relatively high dosage at relatively short intervals is sometimes required until progression of the disease is reduced or until the patient shows partial or complete amelioration of symptoms of disease. Thereafter, the patient may be switched to a suitable prophylactic dosing regimen.

Actual dosage levels of a nucleic acid of the invention alone or in combination with one or more other active ingredients in the pharmaceutical compositions of the present invention may be varied so as to obtain an amount of the active ingredient which is effective to achieve the desired therapeutic response for a particular patient, composition, and mode of administration, without causing deleterious side effects to the subject or patient. A selected dosage level will depend upon a variety of factors, such as pharmacokinetic factors, including the activity of the particular nucleic acid or composition employed, the route of administration, the time of administration, the rate of excretion of the particular nucleic acid being employed, the duration of the treatment, other drugs, compounds and/or materials used in combination with the particular compositions employed, the age, sex, weight, condition, general health and prior medical history of the subject or patient being treated, and similar factors well known in the medical arts.

The pharmaceutical composition may be a sterile injectable aqueous suspension or solution, or in a lyophilised form.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. Compositions may be formulated for any suitable route and means of administration.

The pharmaceutical compositions and medicaments of the present invention may be administered to a mammalian subject in a pharmaceutically effective dose. The mammal may be selected from a human, a non-human primate, a simian or prosimian, a dog, a cat, a horse, cattle, a pig, a goat, a sheep, a mouse, a rat, a hamster, a hedgehog and a guinea pig, or other species of relevance. On this basis, "CNNM4" as used herein denotes nucleic acid or protein in any of the above-mentioned species, if expressed therein naturally or artificially, but preferably this wording denotes human nucleic acids or proteins.

Pharmaceutical compositions of the invention may be administered alone or in combination with one or more other therapeutic or diagnostic agents. A combination therapy may include a nucleic acid of the present invention combined with at least one other therapeutic agent selected based on the particular patient, disease or condition to be treated. Examples of other such agents include, inter alia, a therapeutically active small molecule or polypeptide, a single chain antibody, a classical antibody or fragment thereof, or a nucleic acid molecule which modulates gene expression of one or more additional genes, and similar modulating therapeutics which may complement or otherwise be beneficial in a therapeutic or prophylactic treatment regimen.

Pharmaceutical compositions are typically sterile and stable under the conditions of manufacture and storage. The composition may be formulated as a solution, microemulsion, liposome, or other ordered structure suitable to high drug concentration. The carrier may be a solvent or dispersion medium containing, for example, water, alcohol such as ethanol, polyol (e.g., glycerol, propylene glycol, and liquid polyethylene glycol), or any suitable mixtures. The proper fluidity may be maintained, for example, by the use of a coating such as lecithin, by the maintenance of the required particle size in the case of dispersion and by use of surfactants according to formulation chemistry well known in the art. In certain embodiments, isotonic agents, e.g., sugars, polyalcohols such as mannitol, sorbitol, or sodium chloride may be desirable in the composition. Prolonged absorption of injectable compositions may be brought about by including in the composition an agent that delays absorption for example, monostearate salts and gelatine.

One aspect of the invention is a nucleic acid or a composition disclosed herein for use as a medicament. The nucleic acid or composition is preferably for use in the prevention, decrease of the risk of suffering from, or treatment of a disease, disorder or syndrome.

The present invention provides a nucleic acid for use, alone or in combination with one or more additional therapeutic agents in a pharmaceutical composition, for treatment or prophylaxis of conditions, diseases and disorders responsive to inhibition of CNNM4 expression.

One aspect of the invention is the use of a nucleic acid or a composition as disclosed herein in the prevention, decrease of the risk of suffering from, or treatment of a disease, disorder or syndrome.

One aspect of the invention is the use of a nucleic acid or a composition as disclosed herein in a method of inhibiting the expression of CNNM4 in a cell, preferably in vitro.

One aspect of the invention is a method of inhibiting the expression of CNNM4 in a cell, preferably in vitro, comprising a step of administering a nucleic acid or a composition as disclosed herein to cells, preferably in vitro.

Nucleic acids and pharmaceutical compositions of the invention may be used in the treatment of a variety of conditions, disorders or diseases. Treatment with a nucleic acid of the invention preferably leads to in vivo CNNM4 depletion, preferably in the liver and/or in blood. As such, nucleic acids of the invention, and compositions comprising them, will be useful in methods for treating a variety of pathological disorders in which inhibiting the expression of CNNM4 may be beneficial. The present invention provides methods for treating a disease, disorder or syndrome comprising the step of administering to a subject in need thereof a therapeutically effective amount of a nucleic acid of the invention.

The invention thus provides methods of treatment or prevention of a disease, disorder or syndrome, the method comprising the step of administering to a subject (e.g., a patient) in need thereof a therapeutically effective amount of a nucleic acid or pharmaceutical composition comprising a nucleic acid of the invention.

The most desirable therapeutically effective amount is an amount that will produce a desired efficacy of a particular treatment selected by one of skill in the art for a given subject in need thereof. This amount will vary depending upon a variety of factors understood by the skilled worker, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through experimentation, namely by monitoring a subject's response to administration of a compound and adjusting the dosage accordingly. See, e.g., Remington: The Science and Practice of Pharmacy 21st Ed., Univ. of Sciences in Philadelphia (USIP), Lippincott Williams & Wilkins, Philadelphia, P A, 2005.

In certain embodiments, nucleic acids and pharmaceutical compositions of the invention may be used to treat or prevent a disease, disorder or syndrome.

In certain embodiments, the present invention provides methods for treating a disease, disorder or syndrome in a mammalian subject, such as a human, the method comprising the step of administering to a subject in need thereof a therapeutically effective amount of a nucleic acid as disclosed herein.

Administration of a "therapeutically effective dosage" of a nucleic acid of the invention may result in a decrease in severity of disease symptoms, an increase in frequency and duration of disease symptom-free periods, or a prevention of impairment or disability due to the disease affliction.

Nucleic acids of the invention may be beneficial in treating or diagnosing a disease, disorder or syndrome that may be diagnosed or treated using the methods described herein. Treatment and diagnosis of other diseases, disorders or syndromes are also considered to fall within the scope of the present invention.

One aspect of the invention is a method of preventing, decreasing the risk of suffering from, or treating a disease, disorder or syndrome comprising administering a pharmaceutically effective dose or amount a nucleic acid or a composition disclosed herein to an individual in need of treatment, preferably wherein the nucleic acid or composition is administered to the subject subcutaneously, intravenously or by oral, rectal, pulmonary, intramuscular or intraperitoneal administration. Preferably, it is administered subcutaneously.

The disease, disorder or syndrome to be prevented, or treated with a nucleic acid or composition disclosed herein is preferably a disease, disorder or syndrome associated with magnesium dysregulation, preferably hypomagnesemia in the liver.

The disease, disorder or syndrome to be prevented or treated with a nucleic acid or composition disclosed herein is preferably associated with magnesium dysregulation, such as hypomagnesemia in the liver and/or it is associated with aberrant expression and/or over-expression or ectopic expression or localisation or accumulation of CNNM4. The disease, disorder or syndrome to be prevented or treated can have genetic causes or can be acquired.

The disease, disorder or syndrome to be prevented or treated with a nucleic acid or composition disclosed herein is:

a) selected from a liver disease, a kidney disease or a lung disease, preferably a liver disease;

b) selected from non-alcoholic steatohepatitis (NASH), liver cirrhosis, hepatocellular carcinoma (HCC), drug-induced liver injury (DILI), non-alcoholic fatty liver disease (NAFLD), fatty liver, liver cancer, liver fibrosis, veno-occlusive liver disease, hepatic sinusoidal obstruction syndrome (SOS), steatosis, Budd-Chiari syndrome, viral hepatitis B, viral hepatitis C, alcoholic hepatitis, hepatic ischemia reperfusion injury, primary biliary cirrhosis (PBC), a chronic liver disease, an acute liver disease, liver damage, a non-proliferative liver disease, cholangiocarcinoma (bile duct cancer), a disease associated with hypomagnesemia in the liver, magnesium dysregulation, kidney fibrosis, acute kidney injury (AKI), chronic kidney disease, kidney nephritis, kidney nephrosis, lung cancer, lung adenocarcinoma (LUAD), lung fibrosis, metabolic syndrome, a cardiovascular disease or complication, obesity, insulin resistance, diabetes, acetaminophen (APAP)-induced liver injury, inflammatory response, mitochondrial dysfunction, a decrease of anti-oxidant system activity, a non-proliferative disease, arteriosclerosis or any combination thereof;

c) a liver disease selected from non-alcoholic steatohepatitis (NASH), liver cirrhosis, hepatocellular carcinoma (HCC), drug-induced liver injury (DILI), non-alcoholic fatty liver disease (NAFLD), fatty liver, liver cancer, liver fibrosis, veno-occlusive liver disease, hepatic sinusoidal obstruction syndrome (SOS), steatosis, Budd-Chiari syndrome, viral hepatitis B, viral hepatitis C, alcoholic hepatitis, hepatic ischemia reperfusion injury, primary biliary cirrhosis (PBC), a chronic liver disease, an acute liver disease, liver damage, a non-proliferative liver disease cholangiocarcinoma (bile duct cancer), a disease associated with hypomagnesemia in the liver, preferably the liver disease is non-alcoholic steatohepatitis (NASH);

d) a liver disease selected from non-alcoholic steatohepatitis (NASH), liver cirrhosis, hepatocellular carcinoma (HCC), drug-induced liver injury (DILI), non-alcoholic fatty liver disease (NAFLD) and fatty liver;

e) a liver disease selected from non-alcoholic steatohepatitis (NASH), liver cirrhosis, liver fibrosis, veno-occlusive liver disease, drug-induced liver injury (DILI), hepatocellular carcinoma (HCC) and Budd-Chiari syndrome and hepatitis;

f) a liver disease selected from non-alcoholic steatohepatitis (NASH), liver cirrhosis, liver fibrosis, drug-induced liver injury (DILI) and hepatocellular carcinoma (HCC);

g) a liver disease selected from non-alcoholic steatohepatitis (NASH), drug-induced liver injury (DILI) and liver cirrhosis;

h) non-alcoholic fatty liver disease (NAFLD);

i) non-alcoholic steatohepatitis (NASH);

j) drug-induced liver injury (DILI);

k) a kidney disease, preferably selected from kidney fibrosis, acute kidney injury (AKI), a chronic kidney disease, kidney nephritis and kidney nephrosis, and most preferably the kidney disease is kidney fibrosis; and/or l) a lung disease, preferably selected from lung cancer, lung adenocarcinoma (LUAD) and liver fibrosis, and most preferably the lung disease is lung adenocarcinoma (LUAD).

Liver cancer is preferably hepatocellular carcinoma (HCC) or cholangiocarcinoma (bile duct cancer).

In one embodiment, nucleic acids or compositions of the invention are for use or are used in a method of treatment to:

a) increase the $Mg^{2+}$ level in the liver of a subject;

b) reduce the $Mg^{2+}$ level in the plasma or serum of a subject;

c) restore $Mg^{2+}$ homeostasis in the liver of a subject;

d) reduce the lipid content in the liver of a subject;

e) reduce inflammation by reactive oxygen species (ROS), preferably in the liver of a subject;

f) reduce the reactive oxygen species (ROS) level, preferably in the liver of a subject;

g) reduce inflammation, preferably in the liver of a subject; and/or h) reduce fibrosis, preferably in the liver of a subject.

Preferably, the use of a nucleic acid or composition disclosed herein increases the $Mg^{2+}$ level in the liver of a subject treated with the nucleic acid or composition to the corresponding level expected in a healthy subject. Alternatively, it increases the $Mg^{2+}$ level in the liver of the subject treated with the nucleic acid or composition such that the difference between the $Mg^{2+}$ level in the liver of the subject before treatment and the corresponding level expected in a healthy subject is at least temporarily reduced by 10%, 20%, 30%, 40%, 50%, 60%, 70%, 80%, 90% or 95%.

Preferably, the use of a nucleic acid or composition disclosed herein reduces the $Mg^{2+}$ level in the plasma or serum of a subject treated with the nucleic acid or composition to the corresponding level expected in a healthy subject. Alternatively, it reduces the $Mg^{2+}$ level in the plasma or serum of the subject treated with the nucleic acid or composition such that the difference between the $Mg^{2+}$ level in the plasma or serum of the subject before treatment and the corresponding level expected in a healthy subject is at least temporarily reduced by 10%, 20%, 30%, 40%, 50%, 60%, 70%, 80%, 90% or 95%.

Preferably, the use of a nucleic acid or composition disclosed herein reduces the lipid content in the liver of a subject treated with the nucleic acid or composition to the corresponding level expected in a healthy subject. Alternatively, it reduces the lipid content in the liver of the subject treated with the nucleic acid or composition such that the difference between the lipid content in the liver of the subject before treatment and the corresponding level expected in a healthy subject is at least temporarily reduced by 10%, 20%, 30%, 40%, 50%, 60%, 70%, 80%, 90% or 95%.

Preferably, the use of a nucleic acid or composition disclosed herein reduces inflammation by reactive oxygen species (ROS) in the liver of a subject treated with the nucleic acid or composition to the corresponding level expected in a healthy subject. Alternatively, it reduces the inflammation by reactive oxygen species (ROS) in the liver of the subject treated with the nucleic acid or composition such that the difference between the inflammation by reactive oxygen species (ROS) in the liver of the subject before treatment and the corresponding level expected in a healthy subject is at least temporarily reduced by 10%, 20%, 30%, 40%, 50%, 60%, 70%, 80%, 90% or 95%.

Preferably, the use of a nucleic acid or composition disclosed herein reduces reactive oxygen species (ROS) level in the liver of a subject treated with the nucleic acid or composition to the corresponding level expected in a healthy subject. Alternatively, it reduces the reactive oxygen species (ROS) level in the liver of a subject treated with the nucleic acid or composition to a level such that the difference between the reactive oxygen species (ROS) level in the liver of the subject before treatment and the corresponding value expected in a healthy subject is at least temporarily reduced by 10%, 20%, 30%, 40%, 50%, 60%, 70%, 80%, 90% or 95%.

Preferably, the use of a nucleic acid or composition disclosed herein reduces inflammation in the liver of a subject treated with the nucleic acid or composition to the corresponding level expected in a healthy subject. Alternatively, it reduces the inflammation in the liver of the subject treated with the nucleic acid or composition such that the difference between the inflammation in the liver of the subject before treatment and the corresponding level expected in a healthy subject is at least temporarily reduced by 10%, 20%, 30%, 40%, 50%, 60%, 70%, 80%, 90% or 95%.

Preferably, the use of a nucleic acid or composition disclosed herein reduces fibrosis in the liver of a subject treated with the nucleic acid or composition to the corresponding level expected in a healthy subject. Alternatively, it reduces the fibrosis in the liver of the subject treated with the nucleic acid or composition such that the difference between the fibrosis in the liver of the subject before treatment and the corresponding level expected in a healthy subject is at least temporarily reduced by 10%, 20%, 30%, 40%, 50%, 60%, 70%, 80%, 90% or 95%. Fibrosis in the liver of a subject can be measured for example by measuring the level of alpha smooth muscle actin ($\alpha$SMA) or collagen deposition in the liver of the subject.

It is evident that an appropriate dosage regimen of a nucleic acid or composition is necessary to achieve these outcomes. The skilled person will be able to determine the dosage regimen necessary to achieve these outcomes.

Liver diseases in general, but particularly liver diseases caused by drugs (drug-induced liver injury or DILI), manifest themselves clinically with a variety of symptoms which as such are not particular informative. Non-limiting examples of symptoms include: loss of appetite, exhaustion, giddiness, weight loss, nausea, vomiting, fever, pain in the upper right abdominal region, arthralgias, myalgias, itching, rashes, discoloration of excretions may be mentioned, yellowing of the eyes and of the skin.

As an expert in the field knows, the presence of active liver disease is often detected by the existence of elevated enzyme levels in the blood. Specifically, blood levels of ALT (alanine aminotransferase) and AST (aspartate aminotransferase) above clinically accepted normal ranges are known to be indicative of on-going liver damage. Routine monitoring of liver disease patients for blood levels of ALT and AST is used clinically to measure progress of the liver disease while on medical treatment. Reduction of elevated ALT and AST to within the accepted normal range is taken as clinical evidence reflecting a reduction in the severity of the patient on-going liver damage. In a particular embodiment, the liver disease is caused by any kind of liver damage.

A nucleic acid or compositions disclosed herein may be for use in a regimen comprising treatments once or twice weekly, every week, every two weeks, every three weeks, every four weeks, every five weeks, every six weeks, every seven weeks, every eight weeks, every nine weeks, every ten weeks, every eleven weeks, every twelve weeks, every three months, every four months, every five months, every six months or in regimens with varying dosing frequency such as combinations of the before-mentioned intervals. The nucleic acid or composition may be for use subcutaneously, intravenously or using any other application routes such as oral, rectal, pulmonary, or intraperitoneal. Preferably, it is for use subcutaneously.

An exemplary treatment regime is administration once every two weeks, once every three weeks, once every four weeks, once a month, once every two or three months or once every four, five or six or more months. Dosages may be selected and readjusted by the skilled health care professional as required to maximize therapeutic benefit for a particular subject, e.g., patient. The nucleic acids will typically be administered on multiple occasions. Intervals between single dosages can be, for example, 2-5 days, weekly, bi-weekly, monthly, every two or three months, every four or five months, every six months, or yearly. Intervals between administrations can also be irregular, based on nucleic acid target gene product levels for example in the blood or liver of the subject or patient.

In cells and/or subjects treated with or receiving a nucleic acid or composition as disclosed herein, the CNNM4 expression may be inhibited compared to untreated cells and/or subjects by a range from 15% up to 100% but at least about 30%, 35%, 40%, 45%, 50%, 55%, 60%, 65%, 70%, 75%, 80%, 85%, 90%, 95%, 98%, or 100% or intermediate values. The level of inhibition may allow treatment of a disease associated with CNNM4 expression or overexpression or hypomagnesemia, preferably in the liver, or may serve to further investigate the functions and physiological roles of CNNM4 gene products. The level of inhibition is preferably measured in the liver or in the blood or in the kidneys, preferably in the liver, of the subject treated with the nucleic acid or composition.

One aspect is the use of a nucleic acid or composition as disclosed herein in the manufacture of a medicament for treating a disease, disorder or syndromes, such as those as listed above or additional pathologies associated with elevated levels of CNNM4, preferably in the liver or in the kidneys, or hypomagnesemia, preferably in the liver, or additional therapeutic approaches where inhibition of CNNM4 expression is desired. A medicament is a pharmaceutical composition.

Each of the nucleic acids of the invention and pharmaceutically acceptable salts and solvates thereof constitutes an individual embodiment of the invention.

Also included in the invention is a method of treating or preventing a disease, disorder or syndrome, such as those listed above, comprising administration of a composition comprising a nucleic acid or composition as described herein, to an individual in need of treatment (to improve such pathologies). The nucleic acid or composition may be administered in a regimen comprising treatments twice every week, once every week, every two weeks, every three weeks, every four weeks, every five weeks, every six weeks, every seven weeks, or every eight to twelve or more weeks or in regimens with varying dosing frequency such as combinations of the before-mentioned intervals. The nucleic acid or conjugated nucleic acid may be for use subcutaneously or intravenously or other application routes such as oral, rectal or intraperitoneal.

A nucleic acid of the invention may be administered by any appropriate administration pathway known in the art, including but not limited to aerosol, enteral, nasal, ophthalmic, oral, parenteral, rectal, vaginal, or transdermal (e.g., topical administration of a cream, gel or ointment, or by means of a transdermal patch). "Parenteral administration" is typically associated with injection at or in communication with the intended site of action, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal administration.

The use of a chemical modification pattern of the nucleic acids confers nuclease stability in serum and makes for example subcutaneous application route feasible.

Solutions or suspensions used for intradermal or subcutaneous application typically include one or more of: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and/or tonicity adjusting agents such as, e.g., sodium chloride or dextrose. The pH can be adjusted with acids or bases, such as hydrochloric acid or sodium hydroxide, or buffers with citrate, phosphate, acetate and the like. Such preparations may be enclosed in ampoules, disposable syringes or multiple dose vials made of glass or plastic.

Sterile injectable solutions may be prepared by incorporating a nucleic acid in the required amount in an appropriate solvent with one or a combination of ingredients described above, as required, followed by sterilization microfiltration. Dispersions may be prepared by incorporating the active compound into a sterile vehicle that contains a dispersion medium and optionally other ingredients, such as those described above. In the case of sterile powders for the preparation of sterile injectable solutions, the methods of preparation are vacuum drying and freeze-drying (lyophilization) that yield a powder of the active ingredient in addition to any additional desired ingredient from a sterile-filtered solution thereof.

When a therapeutically effective amount of a nucleic acid of the invention is administered by, e.g., intravenous, cutaneous or subcutaneous injection, the nucleic acid will be in the form of a pyrogen-free, parenterally acceptable aqueous solution. Methods for preparing parenterally acceptable solutions, taking into consideration appropriate pH, isotonicity, stability, and the like, are within the skill in the art. A preferred pharmaceutical composition for intravenous, cutaneous, or subcutaneous injection will contain, in addition to a nucleic acid, an isotonic vehicle such as sodium chloride injection, Ringer's injection, dextrose injection, dextrose and sodium chloride injection, lactated Ringer's injection, or other vehicle as known in the art. A pharmaceutical composition of the present invention may also contain stabilizers, preservatives, buffers, antioxidants, or other additives well known to those of skill in the art.

The amount of nucleic acid which can be combined with a carrier material to produce a single dosage form will vary depending on a variety of factors, including the subject being treated, and the particular mode of administration. In general, it will be an amount of the composition that produces an appropriate therapeutic effect under the particular circumstances. Generally, out of one hundred percent, this amount will range from about 0.01% to about 99% of nucleic acid, from about 0.1% to about 70%, or from about 1% to about 30% of nucleic acid in combination with a pharmaceutically acceptable carrier.

The nucleic acid may be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Dosage regimens may be adjusted to provide the optimum desired response (e.g., a therapeutic response). For example, a dose may be administered, several divided doses may be administered over time, or the dose may be proportionally reduced or increased as indicated by the particular circumstances of the therapeutic situation, on a case by case basis. It is especially advantageous to formulate parenteral compositions in dosage unit forms for ease of administration and uniformity of dosage when administered to the subject or patient. As used herein, a dosage unit form refers to physically discrete units suitable as unitary dosages for the subjects to be treated; each unit containing a predetermined quantity of active compound calculated to produce a desired therapeutic effect. The specification for the dosage unit forms of the invention depend on the specific characteristics of the active compound and the particular therapeutic effect(s) to be achieved and the treatment and sensitivity of any individual patient.

The nucleic acid or composition of the present invention can be produced using routine methods in the art including chemical synthesis, such as solid phase chemical synthesis.

Nucleic acids or compositions of the invention may be administered with one or more of a variety of medical devices known in the art. For example, in one embodiment, a nucleic acid of the invention may be administered with a needleless hypodermic injection device. Examples of well-known implants and modules useful in the present invention are in the art, including e.g., implantable micro-infusion pumps for controlled rate delivery; devices for administering through the skin; infusion pumps for delivery at a precise infusion rate; variable flow implantable infusion devices for continuous drug delivery; and osmotic drug delivery systems. These and other such implants, delivery systems, and modules are known to those skilled in the art.

In certain embodiments, the nucleic acid or composition of the invention may be formulated to ensure a desired distribution in vivo. To target a therapeutic compound or composition of the invention to a particular in vivo location, they can be formulated, for example, in liposomes which may comprise one or more moieties that are selectively transported into specific cells or organs, thus enhancing targeted drug delivery.

The invention is characterized by high specificity at the molecular and tissue-directed delivery level. The sequences of the nucleic acids of the invention are highly specific for their target, meaning that they do not inhibit the expression of genes that they are not designed to target or only minimally inhibit the expression of genes that they are not designed to target and/or only inhibit the expression of a low number of genes that they are not designed to target. A further level of specificity is achieved when nucleic acids are linked to a ligand that is specifically recognised and internalised by a particular cell type. This is for example the case when a nucleic acid is linked to a ligand comprising GalNAc moieties, which are specifically recognised and internalised by hepatocytes. This leads to the nucleic acid inhibiting the expression of their target only in the cells that are targeted by the ligand to which they are linked. These two levels of specificity potentially confer a better safety profile than the currently available treatments. In certain embodiments, the present invention thus provides nucleic acids of the invention linked to a ligand comprising one or more GalNAc moieties, or comprising one or more other moieties that confer cell-type or tissue-specific internalisation of the nucleic acid thereby conferring additional specificity of target gene knockdown by RNA interference.

The nucleic acid as described herein may be formulated with a lipid in the form of a liposome. Such a formulation may be described in the art as a lipoplex. The composition with a lipid/liposome may be used to assist with delivery of the nucleic acid of the invention to the target cells. The lipid delivery system herein described may be used as an alternative to a conjugated ligand. The modifications herein described may be present when using the nucleic acid of the invention with a lipid delivery system or with a ligand conjugate delivery system.

Such a lipoplex may comprise a lipid composition comprising:

i) a cationic lipid, or a pharmaceutically acceptable salt thereof;

ii) a steroid;

iii) a phosphatidylethanolamine phospholipid; and/or iv) a PEGylated lipid.

The cationic lipid may be an amino cationic lipid.

The content of the cationic lipid component may be from about 55 mol % to about 65 mol % of the overall lipid content of the composition. In particular, the cationic lipid component is about 59 mol % of the overall lipid content of the composition.

The compositions can further comprise a steroid. The steroid may be cholesterol. The content of the steroid may be from about 26 mol % to about 35 mol % of the overall lipid content of the lipid composition. More particularly, the content of steroid may be about 30 mol % of the overall lipid content of the lipid composition.

The phosphatidylethanolamine phospholipid may be selected from the group consisting of 1,2-diphytanoyl-sn-glycero-3-phosphoethanolamine (DPhyPE), 1,2-dioleoyl-sn-glycero-3-phosphoethanolamine (DOPE), 1,2-distearoyl-sn-glycero-3-phosphoethanolamine (DSPE), 1,2-Dilauroyl-sn-glycero-3-phosphoethanolamine (DLPE), 1,2-Dimyristoyl-sn-glycero-3-phosphoethanolamine (DMPE), 1,2-Dipalmitoyl-sn-glycero-3-phosphoethanolamine (DPPE), 1,2-Dilinoleoyl-sn-glycero-3-phosphoethanolamine (DLoPE), 1-Palmitoyl-2-oleoyl-sn-glycero-3-phosphoethanolamine (POPE), 1,2-Dierucoyl-sn-glycero-3-phosphoethanolamine (DEPE), 1,2-Disqualeoyl-sn-glycero-3-phosphoethanolamine (DSQPE) and 1-Stearoyl-2-linoleoyl-sn-glycero-3-phosphoethanolamine (SLPE). The content of the phospholipid may be about 10 mol % of the overall lipid content of the composition.

The PEGylated lipid may be selected from the group consisting of 1,2-dimyristoyl-sn-glycerol, methoxypolyethylene glycol (DMG-PEG) and C16-Ceramide-PEG. The content of the PEGylated lipid may be about 1 to 5 mol % of the overall lipid content of the composition.

The content of the cationic lipid component in the composition may be from about 55 mol % to about 65 mol % of the overall lipid content of the lipid composition, preferably about 59 mol % of the overall lipid content of the lipid composition.

The composition may have a molar ratio of the components of i):ii):iii):iv) selected from 55:34:10:1; 56:33:10:1; 57:32:10:1; 58:31:10:1; 59:30:10:1; 60:29:10:1; 61:28:10:1; 62:27:10:1; 63:26:10:1; 64:25:10:1; and 65:24:10:1.

Neutral liposome compositions may be formed from, for example, dimyristoyl phosphatidylcholine (DMPC) or dipalmitoyl phosphatidylcholine (DPPC). Anionic liposome compositions may be formed from dimyristoyl phosphatidylglycerol, while anionic fusogenic liposomes may be formed primarily from dioleoyl phosphatidylethanolamine (DOPE). Another type of liposomal composition may be formed from phosphatidylcholine (PC) such as, for example, soybean PC, and egg PC. Another type is formed from mixtures of phospholipid and/or phosphatidylcholine and/or cholesterol.

A positively charged synthetic cationic lipid, N-[1-(2,3-dioleyloxy)propyl]-N,N, N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells. DOTMA analogues can also be used to form liposomes.

Derivatives and analogues of lipids described herein may also be used to form liposomes.

A liposome containing a nucleic acid can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The nucleic acid preparation is then added to the micelles that include the lipid component. The cationic groups on the lipid interact with the nucleic acid and condense around the nucleic acid to form a liposome. After condensation, the detergent is removed, e.g., by dialysis, to yield a liposomal preparation of nucleic acid.

If necessary, a carrier compound that assists in condensation can be added during the condensation reaction, e.g., by controlled addition. For example, the carrier compound can be a polymer other than a nucleic acid (e.g., spermine or spermidine). pH can also be adjusted to favour condensation.

Nucleic acid formulations of the present invention may include a surfactant. In one embodiment, the nucleic acid is formulated as an emulsion that includes a surfactant.

A surfactant that is not ionized is a non-ionic surfactant. Examples include non-ionic esters, such as ethylene glycol esters, propylene glycol esters, glyceryl esters etc., nonionic alkanolamides, and ethers such as fatty alcohol ethoxylates, propoxylated alcohols, and ethoxylated/propoxylated block polymers.

A surfactant that carries a negative charge when dissolved or dispersed in water is an anionic surfactant. Examples include carboxylates, such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates.

A surfactant that carries a positive charge when dissolved or dispersed in water is a cationic surfactant. Examples include quaternary ammonium salts and ethoxylated amines.

A surfactant that has the ability to carry either a positive or negative charge is an amphoteric surfactant. Examples include acrylic acid derivatives, substituted alkylamides, N-alkylbetaines and phosphatides.

"Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic. A micelle may be formed by mixing an aqueous solution of the nucleic acid, an alkali metal alkyl sulphate, and at least one micelle forming compound.

Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerol, polyglycerol, lysine, polylysine, triolein, polyoxyethylene ethers and analogues thereof, polidocanol alkyl ethers and analogues thereof, chenodeoxycholate, deoxycholate, and mixtures thereof.

Phenol and/or m-cresol may be added to the mixed micellar composition to act as a stabiliser and preservative. An isotonic agent such as glycerine may as be added.

A nucleic acid preparation may be incorporated into a particle such as a microparticle. Microparticles can be produced by spray-drying, lyophilisation, evaporation, fluid bed drying, vacuum drying, or a combination of these methods.

Definitions

As used herein, the terms "inhibit", "down-regulate", or "reduce" with respect to gene expression mean that the expression of the gene, or the level of RNA molecules or equivalent RNA molecules encoding one or more proteins or protein subunits (e.g., mRNA), or the activity of one or more proteins or protein subunits, is reduced below that observed either in the absence of the nucleic acid or conjugated nucleic acid of the invention or as compared to that obtained with an siRNA molecule with no known homology to the human transcript (herein termed non-silencing control). Such control may be conjugated and modified in an analogous manner to the molecule of the invention and delivered into the target cell by the same route. The expression after treatment with the nucleic acid of the invention may be reduced to 95%, 90%, 80%, 70%, 60%, 50%, 40%, 30%, 20%, 15%, 10%, 5% or 0% or to intermediate values, or less than that observed in the absence of the nucleic acid or conjugated nucleic acid. The expression may be measured in the cells to which the nucleic acid is applied. Alternatively, especially if the nucleic acid is administered to a subject, the level can be measured in a different group of cells or in a tissue or an organ or in a body fluid such as blood or plasma. The level of inhibition is preferably measured in conditions that have been selected because they show the greatest effect of the nucleic acid on the target mRNA level in cells treated with the nucleic acid in vitro. The level of inhibition may for example be measured after 24 hours or 48 hours of treatment with a nucleic acid at a concentration of between 0.038 nM-10 μM, preferably 1 nM, 10 nM or 100 nM. These conditions may be different for different nucleic acid sequences or for different types of nucleic acids, such as for nucleic acids that are unmodified or modified or conjugated to a ligand or not. Examples of suitable conditions for determining levels of inhibition are described in the examples.

By nucleic acid it is meant a nucleic acid comprising two strands comprising nucleotides, that is able to interfere with gene expression. Inhibition may be complete or partial and results in down regulation of gene expression in a targeted manner. The nucleic acid comprises two separate polynucleotide strands; the first strand, which may also be a guide strand; and a second strand, which may also be a passenger strand. The first strand and the second strand may be part of the same polynucleotide molecule that is self-complementary which 'folds' back to form a double-stranded molecule. The nucleic acid may be an siRNA molecule.

The nucleic acid may comprise ribonucleotides, modified ribonucleotides, deoxynucleotides, deoxyribonucleotides, or nucleotide analogues non-nucleotides that are able to mimic nucleotides such that they may 'pair' with the corresponding base on the target sequence or complementary strand. The nucleic acid may further comprise a double-stranded nucleic acid portion or duplex region formed by all or a portion of the first strand (also known in the art as a guide strand) and all or a portion of the second strand (also known in the art as a passenger strand). The duplex region is defined as beginning with the first base pair formed between the first strand and the second strand and ending with the last base pair formed between the first strand and the second strand, inclusive.

By duplex region it is meant the region in two complementary or substantially complementary oligonucleotides that form base pairs with one another, either by Watson-Crick base pairing or any other manner that allows for a duplex between oligonucleotide strands that are complementary or substantially complementary. For example, an oligonucleotide strand having 21 nucleotide units can base pair with another oligonucleotide of 21 nucleotide units, yet only 19 nucleotides on each strand are complementary or substantially complementary, such that the "duplex region" consists of 19 base pairs. The remaining base pairs may exist as 5' and 3' overhangs, or as single-stranded regions. Further, within the duplex region, 100% complementarity is not required; substantial complementarity is allowable within a duplex region. Substantial complementarity refers to complementarity between the strands such that they are capable of annealing under biological conditions. Techniques to empirically determine if two strands are capable of annealing under biological conditions are well known in the art. Alternatively, two strands can be synthesised and added together under biological conditions to determine if they anneal to one another. The portion of the first strand and second strand that forms at least one duplex region may be fully complementary and is at least partially complementary to each other. Depending on the length of a nucleic acid, a perfect match in terms of base complementarity between the first strand and the second strand is not necessarily required. However, the first and second strands must be able to hybridise under physiological conditions.

As used herein, the terms "non-pairing nucleotide analogue" means a nucleotide analogue which includes a non-base pairing moiety including but not limited to: 6 des amino adenosine (Nebularine), 4-Me-indole, 3-nitropyrrole, 5-nitroindole, Ds, Pa, N3-Me ribo U, N3-Me riboT, N3-Me dC, N3-Me-dT, N1-Me-dG, N1-Me-dA, N3-ethyl-dC, and N3-Me dC. In some embodiments the non-base pairing nucleotide analogue is a ribonucleotide. In other embodiments it is a deoxyribonucleotide.

As used herein, the term, "terminal functional group" includes without limitation a halogen, alcohol, amine, carboxylic, ester, amide, aldehyde, ketone, and ether groups.

An "overhang" as used herein has its normal and customary meaning in the art, i.e. a single-stranded portion of a nucleic acid that extends beyond the terminal nucleotide of a complementary strand in a double-strand nucleic acid. The term "blunt end" includes double-stranded nucleic acid whereby both strands terminate at the same position, regardless of whether the terminal nucleotide(s) are base-paired. The terminal nucleotide of a first strand and a second strand at a blunt end may be base paired. The terminal nucleotide of a first strand and a second strand at a blunt end may not be paired. The terminal two nucleotides of a first strand and a second strand at a blunt end may be base-paired. The terminal two nucleotides of a first strand and a second strand at a blunt end may not be paired.

The term "serinol-derived linker moiety" means the linker moiety comprises the following structure:

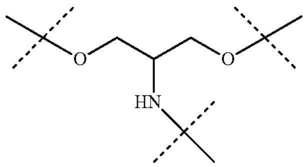

An O atom of said structure typically links to an RNA strand and the N atom typically links to the targeting ligand.

The terms "patient," "subject," and "individual" may be used interchangeably and refer to either a human or a non-human animal. These terms include mammals such as humans, primates, livestock animals (e.g., bovines, porcines), companion animals (e.g., canines, felines) and rodents (e.g., mice and rats).

As used herein, "treating" or "treatment" and grammatical variants thereof refer to an approach for obtaining beneficial or desired clinical results. The term may refer to slowing the onset or rate of development of a condition, disorder or disease, reducing or alleviating symptoms associated with it, generating a complete or partial regression of the condition, or some combination of any of the above. For the purposes of this invention, beneficial or desired clinical results include, but are not limited to, reduction or alleviation of symptoms, diminishment of extent of disease, stabilization (i.e., not worsening) of state of disease, delay or slowing of disease progression, amelioration or palliation of the disease state, and remission (whether partial or total), whether detectable or undetectable. "Treatment" can also mean prolonging survival relative to expected survival time if not receiving treatment. A subject (e.g., a human) in need of treatment may thus be a subject already afflicted with the disease or disorder in question. The term "treatment" includes inhibition or reduction of an increase in severity of a pathological state or symptoms relative to the absence of treatment, and is not necessarily meant to imply complete cessation of the relevant disease, disorder or condition.

As used herein, the terms "preventing" and grammatical variants thereof refer to an approach for preventing the development of, or altering the pathology of, a condition, disease or disorder. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g., a human) in need of prevention may thus be a subject not yet afflicted with the disease or disorder in question. The term "prevention" includes slowing the onset of disease relative to the absence of treatment, and is not necessarily meant to imply permanent prevention of the relevant disease, disorder or condition. Thus "preventing" or "prevention" of a condition may in certain contexts refer to reducing the risk of developing the condition, or preventing or delaying the development of symptoms associated with the condition.

As used herein, an "effective amount," "therapeutically effective amount" or "effective dose" is an amount of a composition (e.g., a therapeutic composition or agent) that produces at least one desired therapeutic effect in a subject, such as preventing or treating a target condition or beneficially alleviating a symptom associated with the condition.

As used herein, the term "pharmaceutically acceptable salt" refers to a salt that is not harmful to a patient or subject to which the salt in question is administered. It may be a salt chosen, e.g., among acid addition salts and basic salts. Examples of acid addition salts include chloride salts, citrate salts and acetate salts. Examples of basic salts include salts wherein the cation is selected from alkali metal cations, such as sodium or potassium ions, alkaline earth metal cations, such as calcium or magnesium ions, as well as substituted ammonium ions, such as ions of the type $N(R^1)(R^2)(R^3)(R^4)^+$, wherein $R^1$, $R^2$, $R^3$ and $R^4$ independently will typically designate hydrogen, optionally substituted C1-6-alkyl groups or optionally substituted C2-6-alkenyl groups. Examples of relevant C1-6-alkyl groups include methyl, ethyl, 1-propyl and 2-propyl groups. Examples of C2-6-alkenyl groups of possible relevance include ethenyl, 1-propenyl and 2-propenyl. Other examples of pharmaceutically acceptable salts are described in "Remington's Pharmaceutical Sciences", 17th edition, Alfonso R. Gennaro (Ed.), Mark Publishing Company, Easton, PA, USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977). A "pharmaceutically acceptable salt" retains qualitatively a desired biological activity of the parent compound without imparting any undesired effects relative to the compound. Examples of pharmaceutically acceptable salts include acid addition salts and base addition salts. Acid addition salts include salts derived from nontoxic inorganic acids, such as hydrochloric, nitric, phosphorous, phosphoric, sulfuric, hydrobromic, hydroiodic and the like, or from nontoxic organic acids such as aliphatic mono- and di-carboxylic acids, phenyl-substituted alkanoic acids, hydroxy alkanoic acids, aromatic acids, aliphatic and aromatic sulfonic acids and the like. Base addition salts include salts derived from alkaline earth metals, such as sodium, potassium, magnesium, calcium and the like, as well as from nontoxic organic amines, such as N, N'-dibenzylethylenediamine, N-methylglucamine, chloroprocaine, choline, diethanolamine, ethylenediamine, procaine and the like.

The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. Exemplary pH buffering agents include phosphate, citrate, acetate, tris/hydroxymethyl)aminomethane (TRIS), N-Tris(hydroxymethyl)methyl-3-aminopropanesulphonic acid (TAPS), ammonium bicarbonate, diethanolamine, histidine, which is a preferred buffer, arginine, lysine, or acetate or mixtures thereof. The term further encompasses any agents listed in the US Pharmacopeia for use in animals, including humans. A "pharmaceutically acceptable carrier" includes any and all physiologically acceptable, i.e., compatible, solvents, dispersion media, coatings, antimicrobial agents, isotonic and absorption delaying agents, and the like. In certain embodiments, the carrier is suitable for intravenous, intramuscular, subcutaneous, parenteral, spinal or epidermal administration (e.g., by injection or infusion). Depending on selected route of administration, the nucleic acid may be coated in a material or materials intended to protect the compound from the action of acids and other natural inactivating conditions to which the nucleic acid may be exposed when administered to a subject by a particular route of administration.

The term "solvate" in the context of the present invention refers to a complex of defined stoichiometry formed between a solute (in casu, a nucleic acid compound or pharmaceutically acceptable salt thereof according to the invention) and a solvent. The solvent in this connection may, for example, be water or another pharmaceutically acceptable, typically small-molecular organic species, such as, but not limited to, acetic acid or lactic acid. When the solvent in question is water, such a solvate is normally referred to as a hydrate.

As it is used herein, the term "CNNM4" means "Cyclin and CBS domain divalent metal cation transport mediator" (also known as Ancient Conserved Domain Protein, ACDP, Cyclin M or CNNM). CNNMs are membrane proteins encoded by four genes, CNNM1, CNNM2, CNNM3 and CNNM4 that are evolutionary expressed throughout development and in all adult tissues, except for CNNM1 which is mainly expressed in the brain. CNNMs play a key role in the transport of magnesium ions ($Mg^{2+}$) through the cell membranes in different organs (Funato et al., 2014. J Clin Invest. 124(12):5398-5410). CNNM4 corresponds to the human gene identified by ID number ENSG00000158158 in the Ensembl database (according to release 93 of July 2018). According to the Ensembl database, CNNM4 encodes at least 4 transcript or splice variants. Thus, the disclosure relates to variant CNNM4-201 (ENST00000377075.2) and to the other three variants CNNM4-204 (ENST00000496186.5), CNNM4-203 (ENST00000493384.1) and CNNM4-202 (ENST00000482716.5). CNNM4 gene encodes the protein "Metal transporter CNNM4" identified by the Uniprot Database as Q6P4Q7 (according to version 130 of Oct. 10, 2018).

As used herein, a "liver disease" is an acute or chronic damage to the liver, usually caused by infection, injury, exposure to drugs or toxic compounds, alcohol, impurities in foods, and the abnormal build-up of normal substances in the blood, an autoimmune process, or by a genetic defect (such as haemochromatosis). Sometimes the exact cause of the disease or injury may not be known. Liver disease can be classified as acute or chronic liver disease based in the duration of the disease. In acute liver diseases, such as acute hepatitis and acute liver failure (ALF), the history of the disease does not exceed six months. Liver diseases of longer duration are classified as chronic liver diseases. Non-limiting examples of common liver diseases include cirrhosis, liver fibrosis, non-alcoholic fatty liver disease (NAFLD), non-alcoholic steatohepatitis (NASH), hepatic ischemia reperfusion injury, primary biliary cirrhosis (PBC), and hepatitis, including viral and alcoholic hepatitis. Most common forms of viral hepatitis are hepatitis B and C (HBV and HCV, respectively). Chronic hepatitis may result in cirrhosis. The death of liver cells through a process known as apoptosis is common in all forms of liver diseases. Apoptosis of liver cells is linked to liver fibrosis and other liver disease.

The term "liver damage", as used herein, is used to denote any type of hepatic trauma (injury), including chronic and acute trauma as well as pathological change present in liver cell or tissue. The clinical conditions of liver damage may include, without being limited thereto, degeneration of live cells, vasculitis of liver, spotty necrosis or focal necrosis present in liver, inflammatory cell infiltration or fibroblast proliferation in liver and portal area, or hepatomegaly, and hepatocirrhosis, hepatoma resulted from severe liver damage, and the like. Liver disease results from an injury to the liver. The injury to the liver may be caused by toxins, including alcohol, some drugs, impurities in foods, the abnormal build-up of normal substances in the blood, by infection or by an autoimmune disorder. In some cases, the liver damage resulting from an injury to the liver include, but is not limited to fatty liver, cirrhosis, primary biliary cirrhosis, primary sclerosing cholangitis, and alpha1-antitrypsin deficiency. The liver damage includes, but is not limited to cirrhosis, liver fibrosis, non-alcoholic fatty liver disease (NAFLD), non-alcoholic steatohepatitis (NASH), hepatic ischemia reperfusion injury, hepatitis, including viral and alcoholic hepatitis and primary biliary cirrhosis (PBC).

As used herein, "fibrosis" is the formation of excess fibrous connective tissue in an organ or tissue in a reparative or reactive process. This can be a reactive, benign, or pathological state. In response to injury, this is called scarring, and if fibrosis arises from a single cell line, this is called a fibroma. Physiologically, fibrosis acts to deposit connective tissue, which can interfere with or totally inhibit the normal architecture and function of the underlying organ or tissue. Fibrosis can be used to describe the pathological state of excess deposition of fibrous tissue, as well as the process of connective tissue deposition in healing. Fibrosis is defined by the pathological accumulation of extracellular matrix (ECM) proteins and results in scarring and thickening of the affected tissue. It is in essence an exaggerated wound healing response which interferes with normal organ function. Fibrosis may affect any organ. In a preferred embodiment, fibrosis is liver fibrosis.

As used herein, "liver fibrosis" is the scarring process that represents the liver's response to injury. In the same way as skin and other organs heal wounds through deposition of collagen and other matrix constituents so the liver repairs injury through the deposition of new collagen. Liver fibrosis is the first stage of liver scarring. Later, if more of the liver becomes scarred, it may lead to liver cirrhosis.

As used herein, "veno-occlusive liver disease" or "hepatic sinusoidal obstruction syndrome (SOS)" is characterized by hepatomegaly, right upper quadrant pain, jaundice, and ascites, most often occurring in patients undergoing hematopoietic cell transplantation (HCT) and less commonly following the use of certain chemotherapeutic agents in non-transplant settings, ingestion of alkaloid toxins, after high dose radiation therapy, or liver transplantation. The hepatic venous outflow obstruction in SOS is due to occlusion of the terminal hepatic venules and hepatic sinusoids As used herein, "drug-induced liver injury (DILI)" means injury to the liver developed following the use of one or more drugs.

As used herein, "steatosis", also called fatty change, is the process describing the abnormal retention of lipids within a cell. It reflects an impairment of the normal processes of synthesis and elimination of triglyceride fat. Excess lipid accumulates in vesicles that displace the cytoplasm. When the vesicles are large enough to distort the nucleus, the condition is known as macrovesicular steatosis; otherwise, the condition is known as microvesicular steatosis. While not particularly detrimental to the cell in mild cases, large accumulations can disrupt cell constituents, and in severe cases the cell may even burst. The risk factors associated with steatosis are varied, and include diabetes mellitus, protein malnutrition, hypertension, cell toxins, obesity, anoxia, and sleep apnoea. As the liver is the primary organ of lipid metabolism it is most often associated with steatosis; however, it may occur in any organ, commonly the kidneys, heart, and muscle. In a preferred embodiment, the steatosis is caused in the liver.

As used herein, "non-alcoholic steatohepatitis (NASH)" is a liver syndrome. It causes liver damage that is histologically indistinguishable from alcoholic hepatitis. It can however also be present patients who do not suffer from alcohol dependence. NASH develops most often in patients with at least one of the following risk factors: obesity, dyslipidaemia, and glucose intolerance. The pathogenesis is not always well understood but seems to be linked to insulin resistance (e.g., as in obesity or metabolic syndrome). Most patients are asymptomatic. Laboratory findings include elevation in aminotransferase levels. Biopsy is required to confirm the diagnosis.

As used herein, "cirrhosis", means a late stage of progressive hepatic fibrosis characterized by distortion of the hepatic architecture and the formation of regenerative nodules. It is generally considered to be irreversible in its advanced stages, at which point the only treatment option may be liver transplantation. Reversal of cirrhosis (in its earlier stages) is possible in several forms of liver disease following treatment of the underlying cause. Patients with cirrhosis are susceptible to a variety of complications, and their life expectancy is usually short.

As used herein, "hepatocellular carcinoma (HCC)", means an aggressive tumour that often occurs in the setting of chronic liver disease and cirrhosis. It is typically diagnosed late in its course, and the median survival following diagnosis is approximately 6 to 20 months.

Although the mainstay of therapy is surgical resection, the majority of patients are not eligible because of tumour extent or underlying liver dysfunction.

As used herein, "Budd-Chiari syndrome" (BCS) is defined as hepatic venous outflow tract obstruction, independent of the level or mechanism of obstruction, provided the obstruction is not due to cardiac disease, pericardial disease, or sinusoidal obstruction syndrome (veno-occlusive disease). Primary Budd-Chiari syndrome is present when there is obstruction due to a predominantly venous process (thrombosis or phlebitis), whereas secondary Budd-Chiari is present when there is compression or invasion of the hepatic veins and/or the inferior vena cava by a lesion that originates outside of the vein (e.g., a malignancy).

As used herein, "hepatitis" means an inflammation of the liver, irrespective of the cause. Hepatitis may be caused by a number of conditions, including drug toxicity, immune diseases, and viruses. It is characterized by jaundice, liver enlargement, and fever.

As used herein, a "kidney disease" is an acute or chronic damage to the kidney. It refers to a disease occurring in kidneys due to various reasons including extrinsic factors, intrinsic factors, genetic factors, etc. Non-limiting examples of renal diseases include: nephritis, nephrosis, renal fibrosis, thin glomerular basement membrane (TGBM), minimal change disease (MCD), membranous glomerulonephritis (MGN), focal segmental glomerulosclerosis (FSGS), DM nephropathy, IgA nephropathy (IgAN), tubulointerstitial nephritis (TIN), Henoch-Schonlein Purpura (HSP) nephritis, acute tubular injury, BK virus nephropathy, acute cellular rejection, chronic antibody mediated rejection, chronic active antibody mediated rejection, chronic calcineurin inhibitor toxicity, acute kidney injury, chronic kidney disease, ischemic renal disease, glomerulonephritis, lupus nephritis, polycystic kidney disease, pyelonephritis, nephrolith, renal tuberculosis, renal tumour, chronic renal failure, end stage renal failure, sepsis, renal injury caused by hepatic injury, etc.

As used herein, "acute kidney injury (AKI)" or "acute renal failure (ARF)" is an abrupt loss of kidney function that develops within 7 days. Non-limiting causes include: damage to the kidney tissue caused by decreased kidney blood flow (kidney ischemia) from any cause (e.g., low blood pressure), exposure to substances harmful to the kidney, an inflammatory process in the kidney, or an obstruction of the urinary tract that impedes the flow of urine. AKI is diagnosed on the basis of characteristic laboratory findings, such as elevated blood urea nitrogen and creatinine, or inability of the kidneys to produce sufficient amounts of urine. AKI may lead to a number of complications, including metabolic acidosis, high potassium levels, uremia, changes in body fluid balance, and effects on other organ systems, including death. People who have experienced AKI may have an increased risk of chronic kidney disease in the future.

As used herein, "chronic kidney disease (CKD)" means a type of kidney disease in which there is gradual loss of kidney function over a period of months or years. Early on there are typically no symptoms. Later, leg swelling, feeling tired, vomiting, loss of appetite, or confusion may develop. Complications may include heart disease, high blood pressure, bone disease, or anaemia. Non-limiting causes of chronic kidney disease include diabetes, high blood pressure, glomerulonephritis, and polycystic kidney disease. Risk factors include a family history of the condition. Diagnosis is generally by blood tests to measure the glomerular filtration rate and urine tests to measure albumin. Further tests such as an ultrasound or kidney biopsy may be performed to determine the underlying cause.

As used herein, "nephritis" means an inflammation of the kidneys and may involve the glomeruli, tubules, or interstitial tissue surrounding the glomeruli and tubules. Non-limiting causes include: infections, toxins and autoimmune disorders. Nephritis includes glomerulonephritis (inflammation of the glomeruli) and interstitial nephritis or tubulo-interstitial nephritis (inflammation of the spaces between renal tubules).

As used herein, "nephrosis" means any degenerative disease of the kidney tubules. Nephrosis can be caused by kidney disease, or it may be a complication of another disorder, particularly diabetes. The diagnosis is established via urine testing for the presence of protein, blood testing for lower-than-normal levels of protein, and observation of oedema.

As used herein, a "respiratory disease" means any pathological condition affecting the organs and tissues that make gas exchange possible in higher organisms, and includes conditions of the upper respiratory tract, trachea, bronchi, bronchioles, alveoli, pleura and pleural cavity, and the nerves and muscles of breathing.

As used herein, a "lung disease" is any respiratory disease affecting the lungs. A lung disease may be an acute or chronic damage to the lung. Non-limiting examples of lung diseases include: asthma, chronic obstructive pulmonary disease, chronic or acute bronchitis, cystic fibrosis emphysema, acute respiratory distress syndrome, bacterial pneumonia, tuberculosis pulmonary embolism and lung cancer.

As used herein, "pulmonary fibrosis" means a respiratory disease in which scars are formed in the lung tissues, leading to breathing problems. Scar formation, the accumulation of excess fibrous connective tissue (the process called fibrosis), leads to thickening of the walls and causes reduced oxygen supply in the blood. As a consequence, patients may suffer from shortness of breath. Symptoms of pulmonary fibrosis include: shortness of breath, chronic dry, hacking coughing, fatigue and weakness, chest discomfort including chest pain, loss of appetite and rapid weight loss. As disclosed herein, pulmonary fibrosis may be a secondary effect of other diseases and/or of specific treatments comprising a non-invasive administration for systemic and local delivery of therapeutic agents to the lungs, such as intranasal administration and oral inhalative administration. Non-liming examples of diseases and conditions that may cause pulmonary fibrosis as a secondary effect include: inhalation of environmental and occupational pollutants, such as metals in asbestosis, silicosis and exposure to certain gases; hypersensitivity pneumonitis, most often resulting from inhaling dust contaminated with bacterial, fungal, or animal products; cigarette smoking; some connective tissue diseases such as rheumatoid arthritis, Systemic lupus erythematosus (SLE) and scleroderma, sarcoidosis and granulomatosis with polyangiitis; infections; certain medications, e.g., amiodarone, bleomycin (pingyangmycin), busulfan, methotrexate, apomorphine and nitrofurantoin; radiation therapy to the chest.

The invention will now be described with reference to the following non-limiting Figures and Examples.

EXAMPLES

Example 1

Materials and Methods

Human Samples

Figure 1:
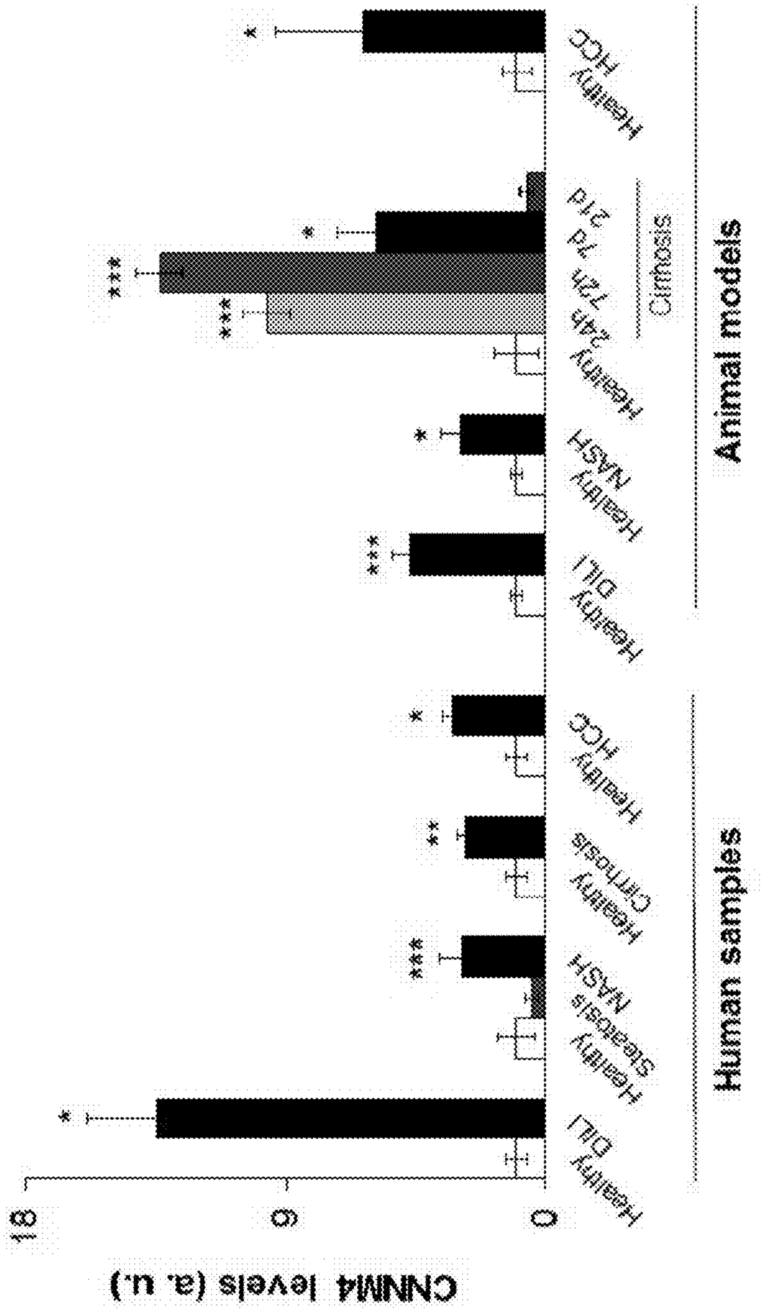
FIG. 1. CNNM4 expression in liver determined by IHC in human samples and mouse models from DILI and different pathologies of chronic liver disease. *$p<0.05$ vs Healthy; $p<0.01$ vs Healthy; *p<0,001 vs Healthy.

All the studies were performed in agreement with the Declaration of Helsinki and according to local national laws. The Human Ethics Committee of each hospital approved the study procedures and written informed consent was obtained from all patients before inclusion in the study.

Magnesium was quantified from human serum samples from a cohort of 8 healthy samples, 31 obese-diagnosed patients and 43 from a cohort of clinical trials. Patients were evaluated for non-alcoholic fatty liver disease (NAFLD) by different markers once discarded alcoholic disease and viral hepatitis infection.

Human CNNM4 expression in non-alcoholic fatty liver disease NAFLD was determined in a cohort of 42 patients: 10 healthy patients, 20 patients diagnosed with steatosis and 12 diagnosed with NAFLD. The CNNM4 levels in cirrhotic patients were determined in a cohort of 12 patients from which 5 were diagnosed as healthy and 7 as cirrhotic. 47 hepatocellular carcinoma (HCC) patients' CNNM4 levels were also determined: 6 patients were healthy and 41 patients were diagnosed HCC. CNNM4 levels were determined in a cohort of 11 drug-induced liver injury (DILI) patients and compared to 3 healthy patients. Finally, renal fibrosis 14 human samples were analysed to determine CNNM4 expression. 7 samples were healthy and another 7 have been diagnoses with renal fibrosis.

Animal Experiments

All the animal experiments were conducted in accordance with the Spanish Guide for Care and use of Laboratory animals, and with the International Care and Use Committee Standards. All procedures were approved by the CIC bioGUNE's Animal Care and Use Committee and the competent authority (Diputación de Bizkaia). Mice were housed in a temperature-controlled animal facility (AAALAC-accredited) within 12-hour light/dark cycles. G-They were fed a standard diet (Harlan Tekland) with water ad libitum.

NAFLD animal model: 0.1% methionine and choline-deficient diet (0.1% MCDD) for CNNM4 determination C57BL/6J wild-type mice were fed with a methionine (0.1%) and choline (0%) deficient diet for 4 weeks. At the end of the treatment animals were sacrificed and liver were split into several pieces for subsequent analysis including: RNA or protein extraction, formalin fixation for histology and immunohistochemistry or metabolic analysis. Blood for serum analysis was collected once a week during the treatment.

Pre-clinical study: NAFLD animal model with siRNA therapy C57BL/6J wild-type mice were fed with a methionine (0.1%) and choline (0%) deficient diet for 4 weeks. 2 weeks after the beginning of the diet mice were divided in two groups and subjected to an in vivo silencing CNNM4 or unrelated siRNA control, receiving either 200 µll of a 0.75 µg/µl solution of or CNNM4-specific in vivo siRNA (Custom Ambion, USA) or control siRNA (Sigma-Aldrich, USA) using Invivofectamine® 3.0 Reagent (Invitrogen, USA) following the manufacturer's instructions. Tail vein injection was performed twice a week until the fourth week. At the end of the treatment animals were sacrificed and liver were split into several pieces for subsequent analysis including: RNA or protein extraction, formalin fixation for histology and immunohistochemistry or metabolic analysis. Blood for serum analysis was collected once a week during the treatment.

Cirrhosis Animal Model: Bile Duct Ligation (BDL)

Adult C57BL/6J wilt-type mice were subjected to BDL as described previously (Fernández-Álvarez et al., 2015. Lab Invest. 95(2):223-36). Briefly, mice were anesthetized with 1.5% isofluorane in 02 and the abdomen was opened. The bile duct was separated from the portal vein and the hepatic artery, performing a suture around the bile duct and securing with a surgical know. Finally, the abdomen was closed and mice sacrificed at 24 h, 48 h, 72 h, 3 days and 21 days. Liver were split into several pieces for subsequent analysis including: RNA or protein extraction, formalin fixation for histology and immunohistochemistry or metabolic analysis. Blood for serum analysis was collected once a week during the treatment.

Hepatocellular Carcinoma Animal Model (HCC): GNMT−/− Mice

Adult GNMT−/− mice were grown from 7 to 9 months, when they are described to develop spontaneously HCC (Wagner et al., 2009. Toxicol Appl Pharmacol. 1; 237(2): 246; author reply 247). At that time animals were sacrificed and liver were split into several pieces for subsequent analysis including: RNA or protein extraction, formalin fixation for histology and immunohistochemistry or metabolic analysis. Blood for serum analysis was collected once a week during the treatment.

Drug Induced Liver Injury (DILI): Acetaminophen (APAP) Overdose

Adult C57BL/6J wilt-type mice were treated with 500 mg/kg of acetaminophen (APAP) to induce acute liver injury. After 48 h of treatment, mice were sacrificed and liver were split into several pieces for subsequent analysis including: RNA or protein extraction, formalin fixation for histology and immunohistochemistry or metabolic analysis. Blood for serum analysis was collected once a week during the treatment.

Isolation of Primary Hepatocytes, Culture and Treatments

Primary hepatocytes from 3-month old wild-type (C57BL/6J) mice were isolated by perfusion with collagenase Type I (Worthington, USA). Briefly, animals were anesthetized with isoflurane (1.5% isoflurane in 02). Then, the abdomen was opened and a catheter was inserted into the inferior vena cava. Liver was perfused with buffer A (1×PBS, 5 mM EGTA, 37° C. and oxygenated) and the portal vein was cut. Next, liver was perfused with buffer B (1×PBS, 1 mM CaCl2 37° C. and oxygenated) to remove EGTA, and finally perfused with buffer C (1×PBS, 2 mM CaCl2, 0.65 BSA, collagenase type 1, 37° C. and oxygenated). After buffer C perfusion, liver was separated from the resto of the body and placed into a petri dish with MEM (Gibco, USA). Gall bladder was carefully removed and, then, liver was mechanically disaggregated with forceps. The digested liver diluted in MEM was filtered through a sterile gauze and filtered liver cells were collected and washed three times (1×4' at 400 RPM and 2×5' at 500 RPM) in 10% FBS (Gibco)/1% PSG (Gibco) supplemented MEM, conserving all supernadant Kupffer and Hepatic Stellate cells isolation. After the final wash, hepatocytes contained in the pellet were resuspended in 10% FBS 1% PSG MEM for subsequently culturing.

Primary hepatocytes were seeded over previously collagen-coated culture dishes at a density of 7600 cells/mm2 in 10% FBS/1% PSG supplemented MEM and placed in an incubator at 37°C, 5% CO2-95% air. After 6 hours of attachment, culture medium and unattached hepatocytes were removed with fresh 0% FBS/1% PSG MEM for the aimed treatment.

THLE2 Cells

THLE-2 cells were purchased from ATCC (ATCC® CRL-2706™). They were maintained on Bronchial Epithelial Growth Medium (BEGM™, Lonza) supplemented with BEGM Bullet Kit™ (Lonza) and 10% FBS. They were split with 0.05% trypsin-EDTA and collected in BEGM. After centrifugation at 123 g during 5 minutes, supernatant was discarded and pellet resuspended.

Plasmid Transfection

Plasmids were transfected into primary mouse hepatocytes for overexpression using jetPRIMER (Polyplus, USA) transfection reagent following manufacturer's protocol. In a 24-well plate, 0.5 μg of plasmid were added to the jePRIMER buffer and vortexed 10 s before adding 1 μl jetPRIMER reagent. The mix was vortexed 10 s, spun down and incubated 10' at RT). Transfections were performed in cell suspension medium and transfection mix was replaced for fresh medium 6 h after transfection unless indicated.

Gene Silencing by siRNA Delivery

Cells were transfected with specific siRNAs (Hs n7o for human CNNM4 and Mm n7o for mouse CNNM4) at a final concentration of 100 nM using DharmaFECT 1 reagent (Dharmacon) following manufacturer's protocol. DharmaFECT 1 and siRNA were diluted separately in 0% FBS/1% PSG MEM for 5' at RT. Dilutions were then mixed and incubated 20' at RT. siRNA transfection mixes were then added to cell suspension medium and replaced for fresh medium after 6 h.

Gene Silencing by shRNA Delivery

Cells were transfected with a CNNM4 shRNA (SEQ ID NO: 454) by using Lipofectamine® 3000 (Thermofisher) and following the protocol according manufacturer instructions. 7.5 μl lipofectamine and the shRNA were diluted separately in 0.2 ml culture medium and incubated during 5' at room temperature. After incubation they were mixed again and incubated for 30' at room temperature before delivering to the cells.

RNA Isolation

Total RNA from whole liver or cultured cells was isolated using TRIzol reagent (Invitrogen) according to manufacturer's instruction. In case of cell mRNA extraction, 5 μg of Glycogen (Ambion, USA) were used in the RNA precipitation step to facilitate the visibility of the RNA pellet. RNA concentration was determined spectrophometrically using the Nanodrop ND-100 spectrophotometer (ThermoFisher Scientific, USA).

Retrotranscription 1-2 μg of isolated RNA were treated with DNAse I (Invitrogren) and used to synthesize cDNA by M-MLV reverse transcriptase in the presence of random primers and RNAseOUT (all from Invitrogen). Resulting cDNA was diluted 1/10 (1/20 if 2 μg were used) in RNAse free water (Sigma-Aldrich).

Real Time Quantitative PCR (RT-qPCR)

qPCRs were performed using either the ViiA 7 or the QS6 Real time PCR System with SYBR Select Master Mix (Applied Biosystems, USA). 1.5 μl of cDNA were used and including the specific primers for a total reaction volume of 6.5 μl in a 384-well plate (Applied Biosystems). All reactions were performed in triplicate. PCR conditions for the primers were optimized and 40 cycles with a melting temperature of 60° C. and 30 s per step were used. Both *Homo Sapiens* and *Mus musculus* primers were designed using the Primer 3 software via the NCBI-Nucleotide webpage (www.ncbi.nlm.nih.gov/nucleotide) and synthesized by Sigma Aldrich. After checking the specificity of the PCR products with the melting curve, data were normalized to the expression of a housekeeping gene (GAPDH, ARP).

Protein Extraction and Analysis

Extraction of total protein was performed as indicated. Cells were washed with cold PBS buffer and resuspended in 200 μl of RIPA lysis buffer (1.6 mM NaH2PO4, 8.4 mM Na2HPO4, 0.5% Azide, 0.1 M NaCl, 0.1% SDS, 0.1% Triton X-100, 5 mg/ml sodium deoxycholate). The lysis buffer was supplemented with protease and phosphatase inhibitor cocktails (Roche, Switzerland). They were centrifuged (13000 rpm, 20' at 4° C.) and the supernatand (protein extract) was quantified for total protein content by the Bradford protein assay (Bio-Rad) and determined using a Spectramax M3 spectrophotometer (Molecular Devices, USA). In the case of frozen liver tissue, approximately 50 μg of tissue was homogenized by using a Precellys 24 tissue homogenizer (Precellys, France) in 500 μl of buffer. In all cases, the lysates were centrifuged (13000 rpm, 20 min, 4° C.) and the supernatant (protein extract) was quantified for total protein content by the Bradford protein assay or by BCA protein assay (Pierce, USA) depending on the type of lysis buffer used and determined using a Spectramax M3 spectrophotometer.

Western Blotting

Protein extracts were boiled at 95° C. for 5 min in SDS-PAGE sample buffer (250 mM Tris-HCl pH 6.8, 500 mM β-mercaptoethanol, 50% glycerol, 10% SDS and bromophenol blue). An appropriate amount of protein (between 5 and 50 μg), depending on protein abundance and antibody sensitivity, were separated by sodium dodecyl sulphate-polyacrylamide gel electrophoresis (SDS-PAGE) in 3% to 15% acrylamide gels (depending on the molecular weight of the protein of interest), using a Mini-PROTEAN Electrophoresis System (Bio-Rad). Gels were transferred onto nitrocellulose membranes by electroblotting using a Mini Trans-Blot cell (Bio-Rad). Membranes were blocked with 5% nonfat milk in TBS pH 8 containing 0.1% Tween-20 (Sigma Aldrich) (TBST-0.1%), for 1 hour at RT, washed three times during 10' with TBST-0.1% and incubated overnight at 4° C. with commercial primary antibodies.

Primary antibodies and their optimal incubation conditions are detailed in Table 6. Membranes were then washed three times during 10' with TBST-0.1% and incubated for 1 hour at RT in blocking solution containing secondary antibody conjugated to horseradish-peroxidase (HRP, Table 6). Immunoreactive proteins were detected by using Western Lightning Enhanced Chemiluminescence reagent (ECL, PerkinElmer, USA) and exposed to Super Rx-N X-ray films (Fuji, Japan) in a Curix 60 Developer (AGFA, Belgium).

Sudan Red for Lipid Staining

O.C.T-included frozen liver samples were cut into 10 μm sections. Sections were washed in 60% isopropanol and then stained with fresh Sudan III (0.5% in isopropanol; Sigma Aldrich) solution for 30 min. Samples were then washed again in 60% isopropanol and then counterstained with hematoxylin and eosin. The sections were then washed with distilled water and mounted in DPX mounting medium. Images were taken with an upright light microscope (Zeiss).

ROS Determination by DHE

O.C.T-embedded 8 μm sections were incubated with MnTBAP 150 UM 1 h at RT. The samples were then incubated with dihydroethidium (DHE) 5 μM for 30 min at 37° C. and sections were mounted with Fluoromount-G (Southern Biotech, USA) containing 0.7 mg/l of DAPI to counterstain nuclei. Images were taken using an Axioimager D1 (Zeiss).

Immunohistochemistry for CNNM4 Determination

Paraffin-embedded sections (5 μm thick) were unmasked according to the primary antibody to be used and subjected to peroxide blocking (3% H2O2 in PBS, 10', RT). For stainings with mouse-hosted antibodies in mouse tissues, samples were blocked with goat anti-mouse Fab fragment (Jackson Immunoresearch, USA) (1:10, 1 h, RT) and the blocked with 5% goat serum (30', RT). Then, sections were incubated in a humid chamber with the CNNM4 primary antibody (Ab191207, Abcam) in DAKO antibody diluent (DAKO) at 1:100 followed by Envision anti rabbit (DAKO) HRP-conjugated secondary antibody incubation (30', RT). Colorimetric detection was confirmed with Vector VIP chromogen (Vector) and sections were counterstained with hematoxylin. Samples were mounted using DPX mounting medium. Images were taken with an upright light microscope (Zeiss).

Immunofluorescence for αSMA Determination

For α-SMA staining, O.C.T-embedded 10 μm sections were incubated with a 1/200 dilution in 2% BSA in 0.01% PBS-azide of the primary antibody conjugated to Cy3 (C6198, Sigma Aldrich) and mounted with Fluoromount-G (Southern Biotech) containing 0.7 mg/l of DAPI to counterstain nuclei. Images were taken using an Axioimager D1 (Zeiss).

BODIPY for Lipid Quantification in Primary Hepatocytes

Primary hepatocytes cultured in high lipid content medium (OA) or methionine/choline deficient medium (MDMC) were fixed in 4% paraformaldehyde (10', RT) in PBS and incubated with BODIPY 493/503 (Molecular Probes, Invitrogen) at 1 mg/ml (1 h, RT). BODIPY immunocytofluorescence images were taken using an Axioimager D1 (Zeiss) microscope. Quantification of lipid bodies was performed using Frida Software and represented as mean area per total number of cells.

Data Analysis

The average sum of intensities or stained area percentage of each sample were calculated using the FRIDA software (http://bui3.win.ad.jhu.edu/frida/, John Hopkins University).

Liver Lipid Quantification 30 mg of frozen liver were homogenized with 10 volumes of ice-cold PBS in a potter homogenizer. Fatty acids were measured in the homogenates using the Wako Chemicals kit (Richmond, VA) and lipids were quantified as described (Folch et al., 1957. J Biol Chem. 226(1):497-509). Briefly, lipids were extracted from 1.5 mg of protein from liver homogenates. Phosphatidylcholine (PC), phosphatidylethanolamine (PE), fatty acids (FAS) and cholesterol (Ch) were separated by thin layer chromatography (TLC) and quantified as described (Ruiz and Ochoa, 1997). Triglycerides (TGs) were measured in the lipid extract with the A. Menarini Diagnostics (Italy) kit.

Intracellular Magnesium Levels

Primary hepatocytes grown in glass coverslips were loaded with 2 μM Mag-S-Tz or 1 μM Mag-S-Tz-AM diluted REF (Gruskos et al., 2016. J. Am. Chem. Soc. 138 (44), pp 14639-14649) in 0% FBS/1% PSG medium and incubated at 37° C. and 5% CO2 during 30' or 1 h respectively. After removing the dye-containing medium, a 30' incubation in 0% FBS/1% PSG was performed. Coverslips were then washed in a 20 mM Tris-HCl, 2.4 mM CaCl2, 10 mM glucose, pH 7.4 buffer and mounted on a perfusion chamber with thermostat on a Eclipse TE 300-based microspectrofluorometer (Nikon, USA) and visualized with a 40× oil-immersion fluorescence. Intracellular Mg2+ levels were determines using the method described by Grynkiewicz (Grynkiewiz et al., 1985. J Biol Chem. 260(6):3440-50). The 340/380 nm excited light ratio was determined with a Delta system (Photon Technologies International, Princeton) and converted into $Mg^{2+}$ concentration from the standard equation:

$$[Mg^{2+}]i = \frac{(R - R_{min})}{(R_{max} - R)} \times K_d \times Q$$

Where Kd is the $Mg^{2+}$ dissociation constant of Mag-S-Tz (3.2 mM) and Mag-S-Tz-AM (8.9 mM) and Q is the ratio of the minimum/maximum fluorescence intensity at 380 nm.

Extracellular Magnesium Levels

Extracellular magnesium was quantified using the QuantiCrom™ Magnesium Assay Kit (BioAssay Systems, USA). Briefly, 5 μl of serum or culture media were mixed with 200 μl of a 1:1 mix of Reagent A and Reagent B. After 2' incubation at RT, OD was determined at 500 nm length using a Spectramax M3 spectrophotometer (Molecular Devices, USA). Then, 10 μl of EDTA were added and OD500 was determined again. Magnesium concentrations were finally calculated by comparing to the OD500 from a standard concentration (2 mg/ml).

Mitochondrial ROS Determination

Mitochondrial ROS was measured using MitoSOX™ Red reagent (Life Technologies), following manufacturer's instructions. Briefly, primary hepatocytes and hepatoma cells were incubated with MitoSOX reagent (2.5 μM, 10', 37°C in a CO2 incubator) in normal culture medium. Then, cells were washed twice with PBS and the fluorescence was measured at an excitation of 510 nm and emission of 595 nm using a spectrophotometer. Final values were normalized to total protein concentration.

Cell Death Determination by TUNEL

Cell Death was analysed by using the In situ Cell Death detection Kit (Roche) following the manufacturer's instructions as above indicated. Cells were subjected peroxide block (3% H2O2 in methanol) for 3 minutes before incubation with TUNEL diluent buffer containing FITC-conjugated primary antibody (dilution 1/50) for 1 hour at 37° C. Sections were mounted in Dako fluorescence mounting medium (Dako). Images were taken using an Axioimager D1 (Zeiss) microscope and cell viability was calculated by determining the % of TUNEL positive cells.

Results

CNNM4 Overexpression in Liver Pathologies

Figure 2:
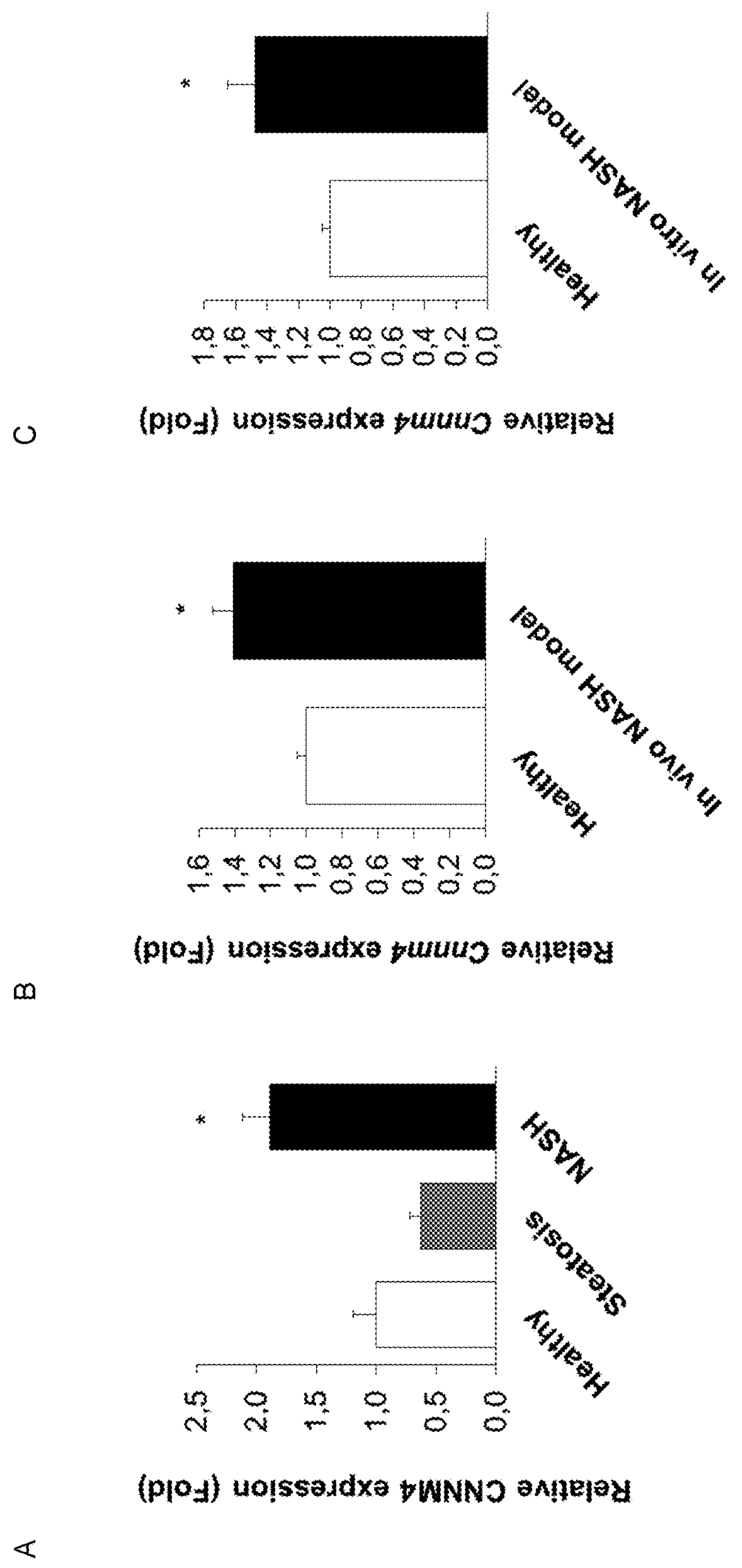
FIG. 2A. CNNM4 expression, determined by qPCR of CNNM4 mRNA levels in human liver samples from healthy subjects compared with samples from steatotic and NASH patients.
FIG. 2B. CNNM4 expression, determined by qPCR of CNNM4 mRNA levels in an in vivo mouse model.
FIG. 2C. CNNM4 expression determined by qPCR of CNNM4 mRNA levels in an in vitro mouse cell model. *$p<0.05$ vs Healthy.

Chronic liver disease includes a group of different pathologies. A method to detect CNNM4 expression by immunohistochemistry (IHC) in human liver biopsies and livers from mouse animal models has been developed. Herein CNNM4 expression has been characterized in DILI and all the stages from chronic liver disease, both in human biopsies and animal models, observing an overexpression of the protein in all the pathologies (FIG. 1). These results were confirmed by a method to detect CNNM4 expression by qPCR of CNNM4 mRNA levels in human liver samples from healthy subjects compared with samples from steatotic and NASH patients (FIG. 2A). CNNM4 expression could also be determined by qPCR of CNNM4 mRNA levels in an in vivo NASH mouse model (FIG. 2B), as well as in an in vitro NASH mouse cell model (FIG. 2C).

CNNM4 a New Target for Treating Liver Disease

Figure 3:
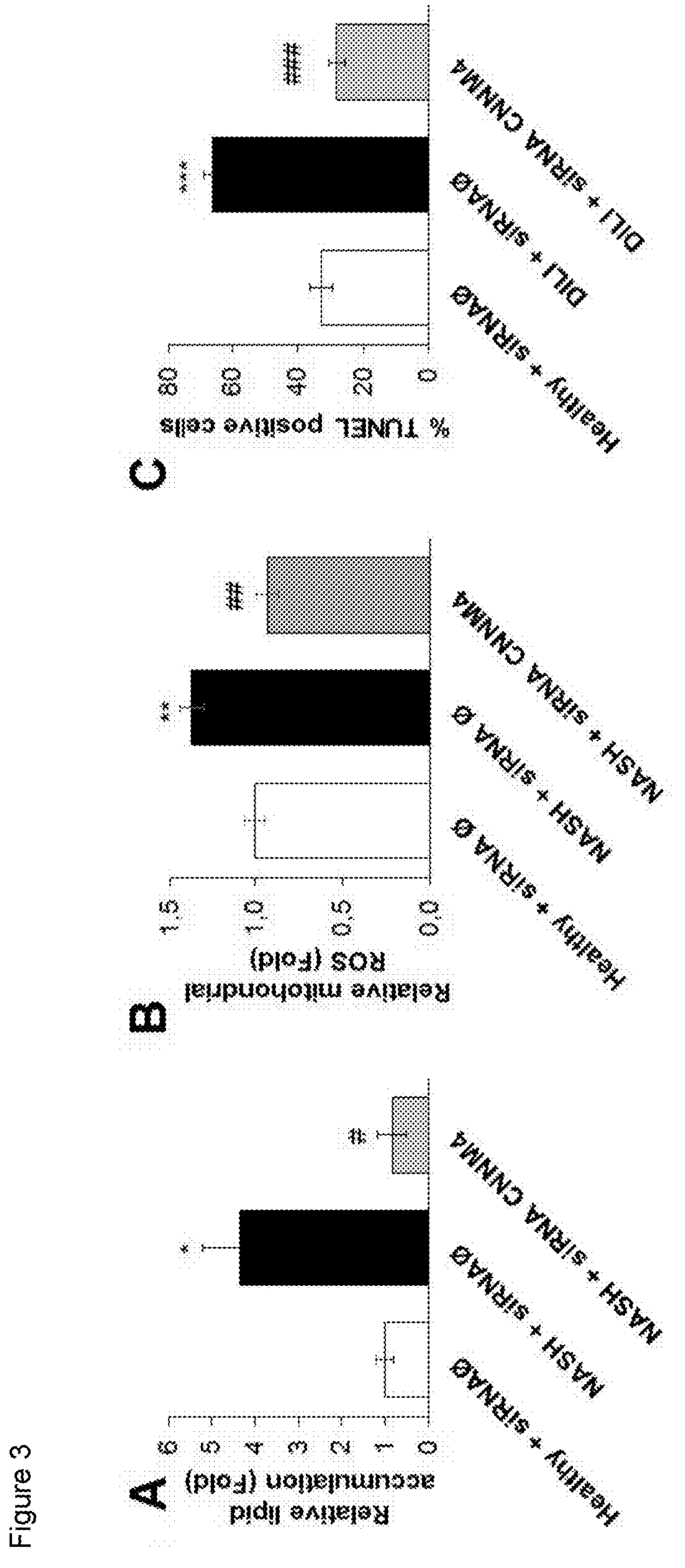
FIG. 3A. Lipid content in NASH-induced primary hepatocytes return into healthy levels when treated with siRNA CNNM4.
FIG. 3B. Inflammation induced by ROS in treated mice.
FIG. 3C. DILI-induced cell death is decreased by siRNA therapy. *$p<0.05$ vs Healthy $p<0.01$ vs Healthy; *$p<0.001$ vs Healthy; #$p<0.05$ vs NASH; ##$p<0.01$ vs NASH; ###$p<0.001$ vs DILI.
Figure 4:
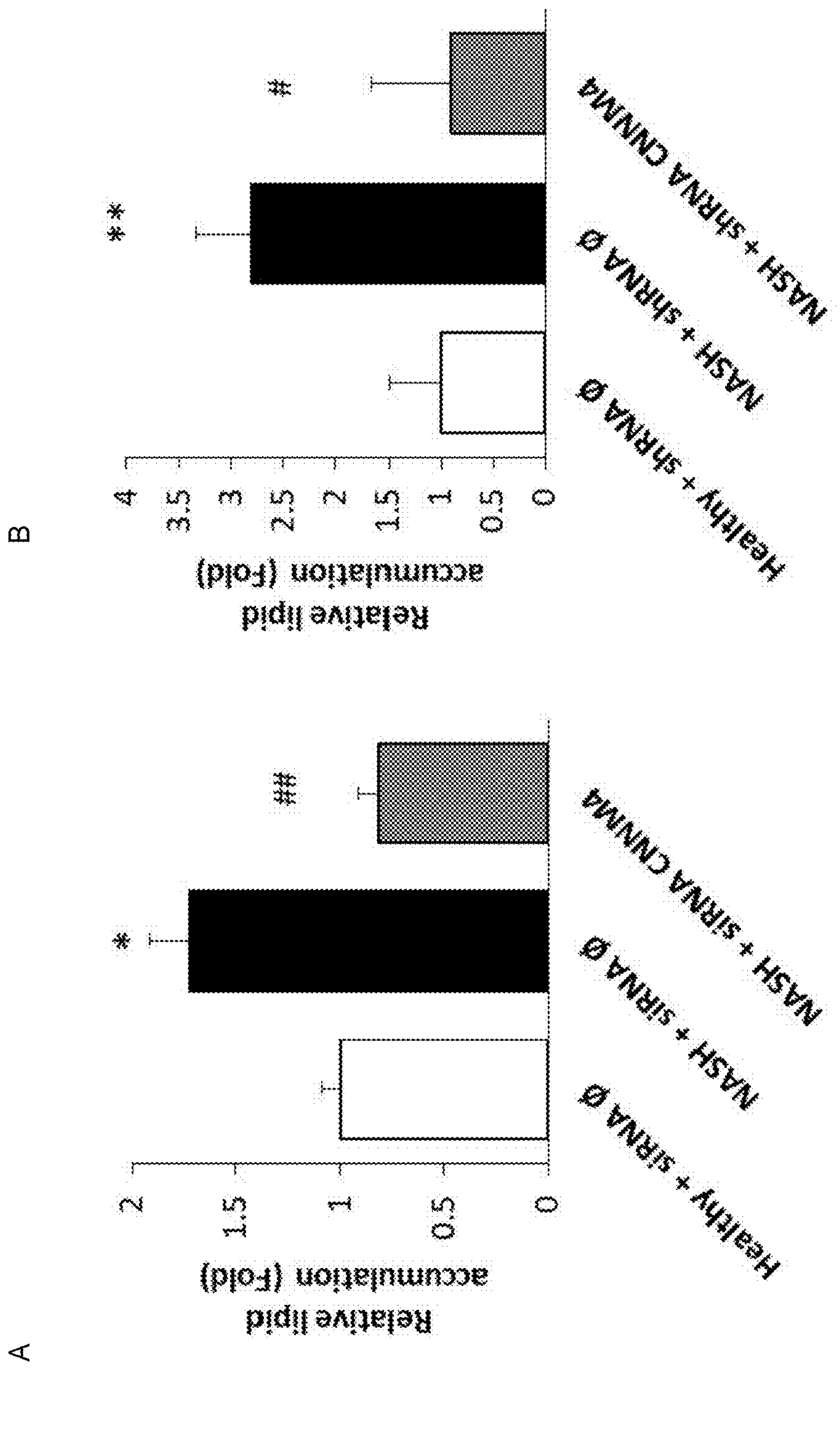
FIG. 4A. The lipid content in NASH-induced human cells returns to healthy levels when treated with CNNM4 siRNA.
FIG. 4B. The lipid content in NASH-induced human cells returns to healthy levels when treated with CNNM4 shRNA. *$p<0.05$ vs Healthy **$p<0.01$ vs Healthy; #$p<0.05$ vs NASH control; ##$p<0.01$ vs NASH control.

The overexpression observed in CNNM4 determination by IHC suggests CNNM4 as a potential target for treating liver disease, both for DILI and chronic disease. An in vitro study was performed inducing NASH in primary hepatocytes and treating them with a siRNA CNNM4 therapy. In case of NASH model-primary hepatocytes the lipid content and inflammation by reactive oxygen species (ROS) were measured, observing that both get restored in NASH hepatocytes treated with the siRNA therapy (FIGS. 3A and 3B). A further in vitro study was performed on DILI induced by acetaminophen overdose. The expected cell death in the DILI model-hepatocytes was observed, as well as restoration upon siRNA treatment (FIG. 3C). A further in vitro study was performed in which NASH was induced in human cells and these cells were then treated with a siRNA CNNM4 therapy or with a shRNA CNNM4 therapy. Relative lipid accumulation restoration was observed both in NASH-induced human cells (THLE2 cells) treated with the siRNA therapy (FIG. 4A) and in NASH-induced human cells treated with the shRNA therapy (FIG. 4B).

Specificity and Need of Targeting CNNM4

Figure 5:
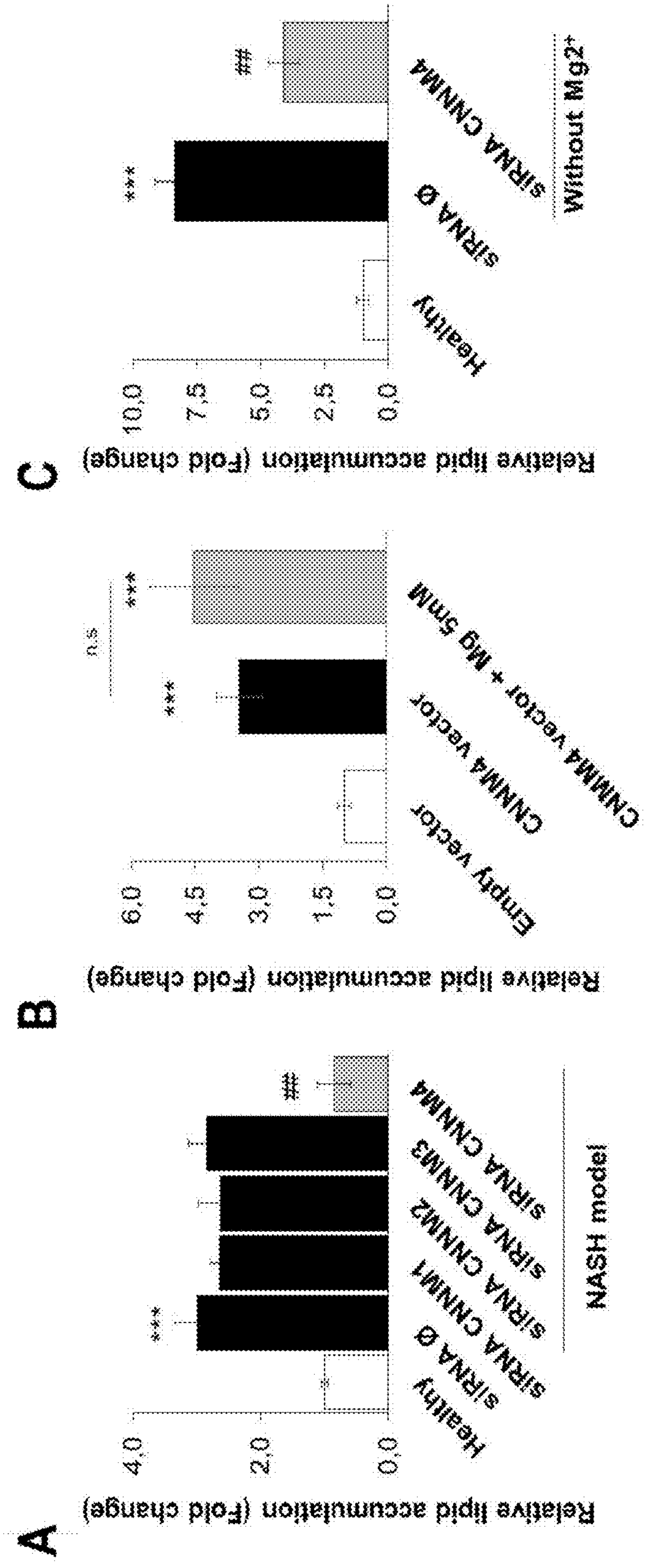
FIG. 5A. The lipid content in NASH-induced primary hepatocytes does not return to healthy levels when treated with siRNAs against CNNM1, CNNM2 or CNNM3.
FIG. 5B. Magnesium supplementation does not reduce lipid content in primary hepatocytes when CNNM4 is overexpressed.
FIG. 5C. CNNM4 siRNA treatment of primary hepatocytes reduces lipid accumulation caused by magnesium deficiency. ***$p<0.001$ vs Healthy; ##$p<0.01$ vs NASH model/Without $Mg2++$siRNA Ø.

Having observed the protective effect of siRNA CNNM4-therapies from NASH and DILI, the effect of targeted silencing the other proteins of CNNM family (CNNM1, CNNM2 and CNNM3) was determined. NASH was induced in primary hepatocytes and they were treated with siRNAs against CNNM1, CNNM2 and CNNM3. Differently than with siRNA CNNM4 therapy, silencing the other proteins of the CNNM family had no effect, indicating the specificity of a possible the treatment based only on CNNM4 and not on other CNNM family proteins (FIG. 5A). Furthermore, experiments were conducted which prove the need of a CNNM4-based treatment. In a first experiment, lipid accumulation was induced in primary hepatocytes by CNNM4 overexpression to mimic the situation observed in NASH patients and animal models. Magnesium supplementation had no effect on the level of lipid accumulation in those hepatocytes (FIG. 5B). In a second experiment, lipid accumulation was induced by magnesium deprivation in primary hepatocytes, which is leads to a similar physiological condition as CNNM4 overexpression. In this case, siRNA CNNM4 therapy reduced lipid accumulation (FIG. 5C). These last two results indicate that magnesium supplementation is not sufficient for treating NASH and that there is a need for a CNNM4-based therapy.

Preclinical Study of a siRNA CNNM4-Based Therapy

Figure 6:
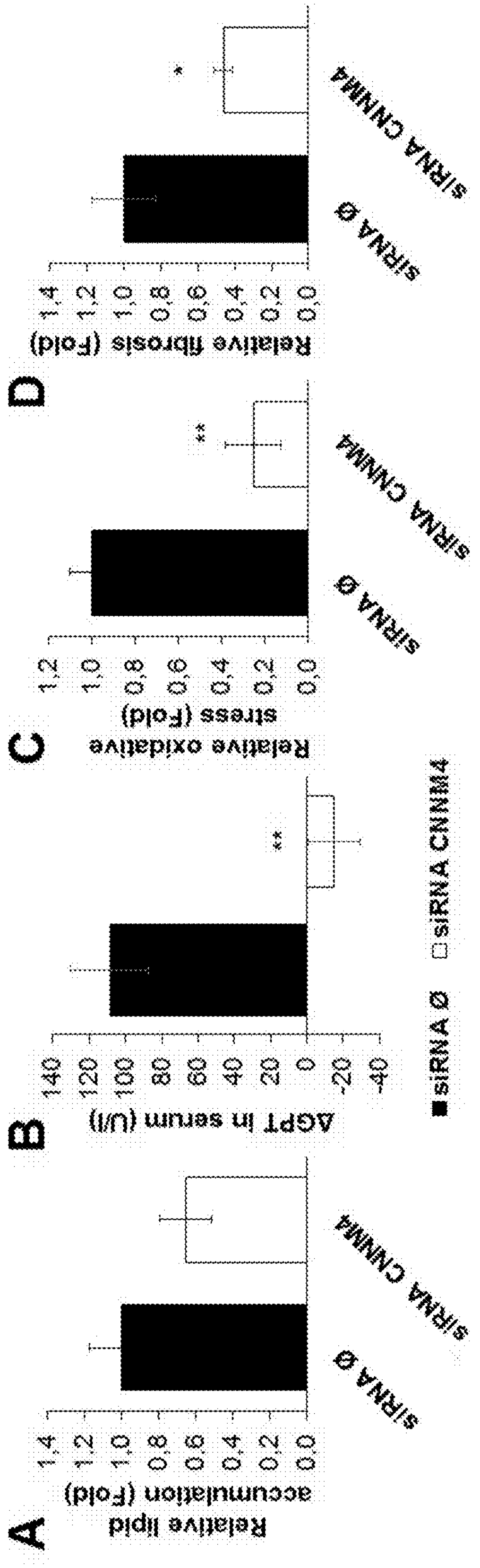
FIG. 6. Parameters analysed for observing NAFLD progression after CNNM4 siRNA therapy. A) Sudan Red as indicator of lipid content decrease, B) GPT in serum as indicator of liver damage, C) DHE as indicator of inflammation by ROS and D) αSMA as indicator of fibrosis. $^*p<0.05$ vs siRNA Ø; $^{**}p<0.01$ vs siRNA Ø.

A preclinical study in NAFLD, the first stage of chronic liver disease, was developed to test the efficacy of CNNM4 modulation not only in cells but also in animals. Mice were fed a 0.1% methionine and choline-deficient diet (0.1% MCDD) during two weeks in order for them to develop NAFLD. A subgroup was then treated with a siRNA CNNM4 therapy and another with a siCtrl RNA. Animals were sacrificed and different biomarkers were measured in order to analyse NAFLD progression. Sudan red staining was used to measure lipid accumulation (FIG. 6A). Transaminase levels in serum, which are indicative of liver damage, were also measured (FIG. 6B). DHE staining was used to quantify inflammation caused by ROS (FIG. 6C) and α-smooth-muscle actin (αSMA) levels were measured to indicate the progression of fibrosis (FIG. 6D). These results clearly indicate that siRNA CNNM4 therapy reduces NAFLD.

Pharmacological Inhibition of CNNM4

Figure 7:
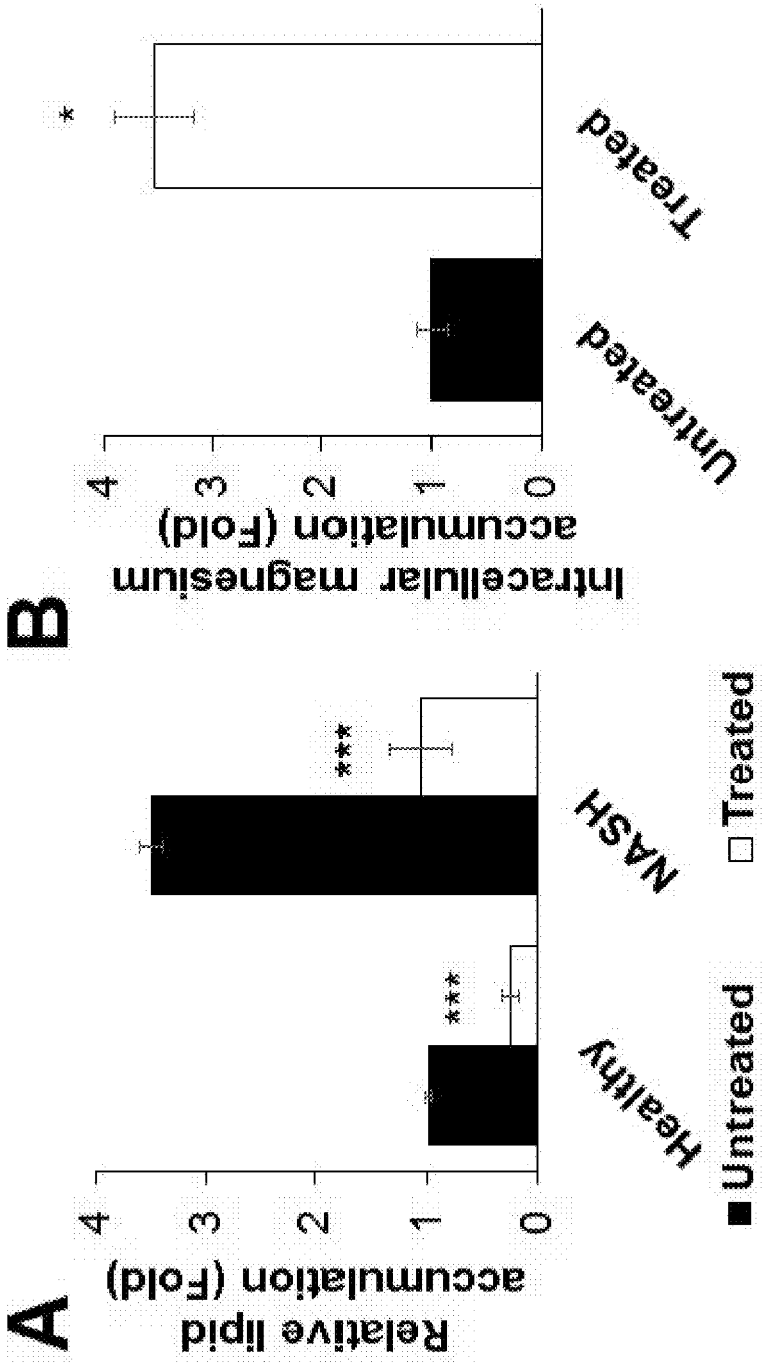
FIG. 7. Pharmacological inhibition of CNNM4 by 7-amino-2-phenyl-5H-thieno[3,2-c]pyridin-4-one. Treated hepatocytes have A) reduced lipid levels and B) an increase of intracellular magnesium levels. $^*p<0.05$ vs Untreated; $^{***}p<0.001$ vs Untreated.

In addition to siRNA therapy, CNNM4 activity can be also modulated pharmacologically. An in vitro assay was performed inducing NASH in primary hepatocytes and treating them with the compound 7-amino-2-phenyl-5H-thieno[3,2-c]pyridin-4-one. It can be observed that this pharmacological inhibition of CNNM4 has the same effect as siRNA therapy in NASH-induced hepatocytes, it decreases its lipid content (FIG. 7A) and leads them to accumulate magnesium (FIG. 7B). It is therefore expected that a combination therapy of a CNNM4 siRNA and 7-amino-2-phenyl-5H-thieno[3,2-c]pyridin-4-one or one of its derivatives with similar function could lead to a potent treatment of NASH.

CNNM4 Over-Expression in Pathologies of Different Organs

Figure 8:
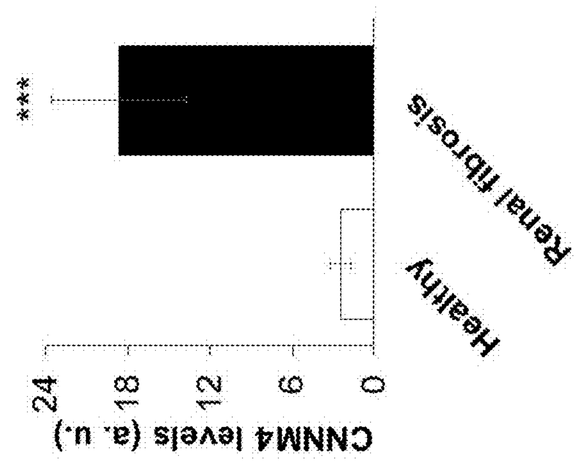
FIG. 8. CNNM4 expression determined by IHC in animal samples of renal fibrosis. $^{***}p<0.001$ vs Healthy.
Figure 9A:
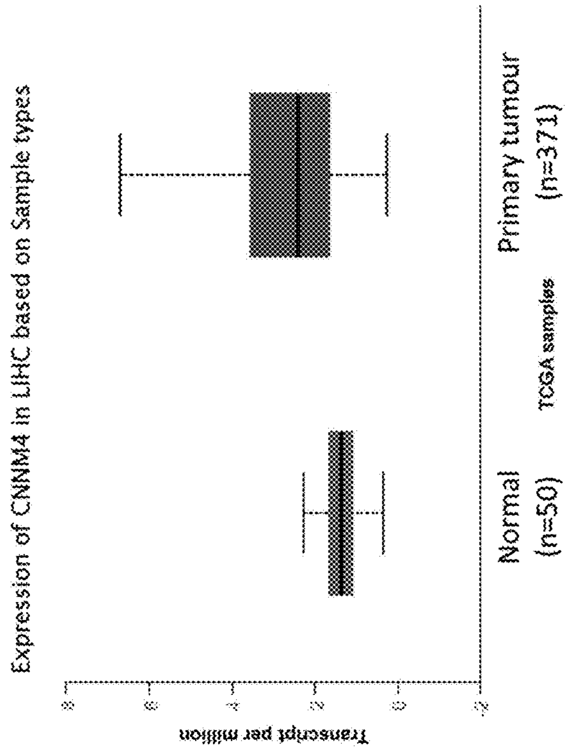
FIG. 9. A) CNNM4 expression determined in TCGA (The Cancer Genome Atlas) primary tumour samples of Liver Hepatocellular Carcinoma (HHC) compared to normal tissue. B) CNNM4 expression determined in TCGA (The Cancer Genome Atlas) primary tumour samples of lung adenocarcinoma (LUAD) compared to normal tissue.
Figure 9B:
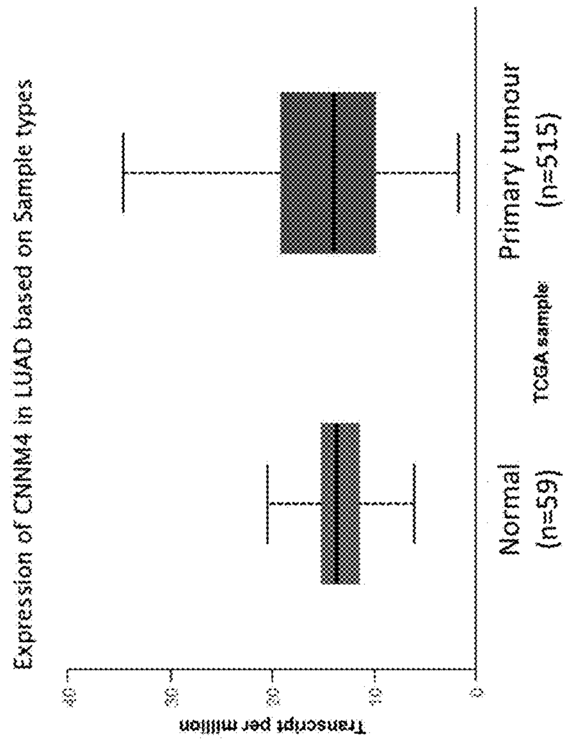

As shown in FIG. 1, CNNM4 is overexpressed in different liver pathologies, both in animal models and in human samples. However, fibrosis development occurs not only in liver but also in other organs such as the kidneys. There may be similarities in the development of fibrosis in both tissues and CNNM4 may also be deregulated in this organ. This is indeed the case. We observed a CNNM4 overexpression in a renal fibrosis mouse model, indicating that a therapy that reduces CNNM4 expression may also be effective in the treatment of kidney fibrosis (FIG. 8). In addition, an analysis of TCGA (The Cancer Genome Atlas) data show that CNNM4 is overexpressed in primary tumour samples of Liver Hepatocellular Carcinoma (HHC) and in primary tumour samples of lung adenocarcinoma (LUAD) compared to normal tissue (FIGS. 9A and 9B). Overexpression of CNNM4 has also been detected in cholangiocarcinoma (bile duct cancer). restore $Mg^{2+}$ homeostasis In summary, the presented results prove that CNNM4 is a suitable target for preventing NAFLD progression and indicates that inhibiting it could also ameliorate other liver pathologies (DILI, cirrhosis and HCC), renal fibrosis and lung cancer. CNNM4 is overexpressed in all these diseases. In addition, for DILI, the in vitro studies show a protective effect of siRNA therapy from APAP overdose. Inhibiting or silencing CNNM4, especially by siRNA therapy, is a suitable method for treating liver disease, renal fibrosis and lung cancer.

Example 2—Synthesis of Building Blocks

Figure 10:
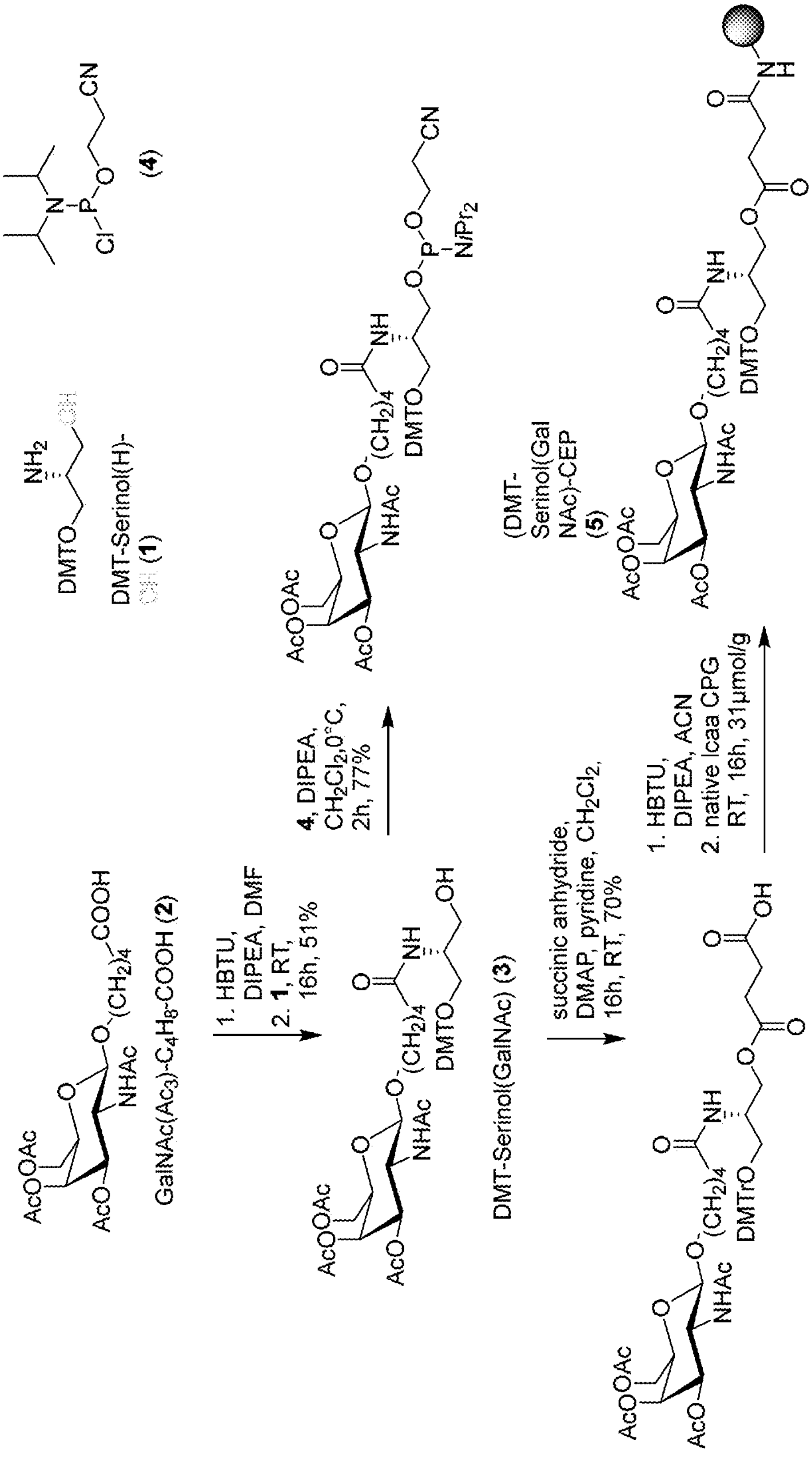
FIG. 10. Possible synthesis route to DMT-Serinol(GalNAc)-CEP and CPG.

The synthesis route for DMT-Serinol(GalNAc)-CEP and CPG as described below is outlined in FIG. 10. Starting material DMT-Serinol(H) (1) was made according to literature published methods (Hoevelmann et al. Chem. Sci., 2016, 7, 128-135) from commercially available L-Serine. GalNAc($Ac_3$)—$C_4H_8$—COOH (2) was prepared according to literature published methods (Nair et al. J. Am. Chem. Soc., 2014, 136 (49), pp 16958-1696), starting from commercially available per-acetylated galactose amine. Phosphitylation reagent 2-Cyanoethyl-N,N-diisopropylchlorophosphor-amidite (4) is commercially available. Synthesis of (vp)-mU-phos was performed as described in Prakash, Nucleic Acids Res. 2015, 43(6), 2993-3011 and Haraszti, Nucleic Acids Res. 2017, 45(13), 7581-7592. Synthesis of the phosphoramidite derivatives of ST43 (ST43-phos) as well as ST23 (ST23-phos) can be performed as described in WO2017/174657.

DMT-Serinol(GalNAc) (3)

HBTU (9.16 g, 24.14 mmol) was added to a stirring solution of GalNAc($Ac_3$)—$C_4H_8$—COOH (2) (11.4 g, 25.4 mmol) and DIPEA (8.85 ml, 50.8 mmol). After 2 minutes activation time a solution of DMT-Serinol(H) (1) (10 g, 25.4 mmol) in Acetonitrile (anhydrous) (200 ml) was added to the stirring mixture. After 1 h LCMS showed good conversion. The reaction mixture was concentrated in vacuo. The residue was dissolved up in EtOAc, washed subsequently with water (2×) and brine. The organic layer was dried over $Na_2SO4$, filtered and concentrated under reduced pressure. The residue was further purified by column chromatography (3% MeOH in $CH_2Cl_2$+1% $Et_3N$, 700 g silica). Product containing fractions were pooled, concentrated and stripped with $CH_2Cl_2$ (2×) to yield to yield 10.6 g (51%) of DMT-Serinol (GalNAc) (3) as an off-white foam.

DMT-Serinol(GalNAc)-CEP (5)

2-Cyanoethyl-N,N-diisopropylchlorophosphoramidite (4) (5.71 ml, 25.6 mmol) was added slowly to a stirring mixture of DMT-Serinol(GalNAc) (3) (15.0 g, 17.0 mmol), DIPEA (14.9 ml, 85 mmol) and 4 Å molecular sieves in Dichloromethane (dry) (150 ml) at 0° C. under argon atmosphere. The reaction mixture was stirred at 0° C. for 1 h. TLC indicated complete conversion. The reaction mixture was filtered and concentrated in vacuo to give a thick oil. The residue was dissolved in Dichloromethane and was further purified by flash chromatography (0-50% acetone in toluene 1% Et3N, 220 g silica). Product containing fractions were pooled and concentrated in vacuo. The resulting oil was stripped with MeCN (2×) to yield 13.5 g (77%) of the colorless DMT-Serinol(GalNAc)-CEP (5) foam.

DMT-Serinol(GalNAc)-succinate (6)

DMAP (1.11 g, 9.11 mmol) was added to a stirring solution of DMT-Serinol(GalNAc) (3) (7.5 g, 9.11 mmol) and succinic anhydride (4.56 g, 45.6 mmol) in a mixture of Dichloromethane (50 ml) and Pyridine (50 ml) under argon atmosphere. After 16 h of stirring the reaction mixture was concentrated in vacuo and the residue was taken up in EtOAc and washed with 5% citric acid (aq). The aqueous layer was extracted with EtOAc. The combined organic layers were washed subsequently with sat $NaHCO_3$ (aq.) and brine, dried over $Na_2SO_4$, filtered and concentrated in vacuo. Further purification was achieved by flash chromatography (0-5% MeOH in $CH_2Cl_2$+1% $Et_3N$, 120 g silica). Product containing fractions were pooled and concentrated in vacuo. The residue was stripped with MeCN (3×) to yield 5.9 g (70%) DMT-Serinol(GalNAc)-succinate (6).

DMT-Serinol(GalNAc)-succinyl-Icaa-CPG (7)

The DMT-Serinol(GalNAc)-succinate (6) (1 eq.) and HBTU (1.1 eq.) were dissolved in $CH_3CN$ (10 ml). Diisopropylethylamine (2 eq.) was added to the solution, and the mixture was swirled for 2 min followed by addition native amino-Icaa-CPG (500 A, 88 μmol/g, 1 eq.). The suspension was gently shaken at room temperature on a wrist-action shaker for 16 h, then filtered and washed with acetonitrile. The solid support was dried under reduced pressure for 2 h. The unreacted amines on the support were capped by stirring with $AC_2O$/2,6-lutidine/NMI at room temperature (2×15 min). The washing of the support was repeated as above. The solid was dried under vacuum to yield DMT-Serinol (GalNAc)-succinyl-Icaa-CPG (7) (loading: 34 μmol/g, determined by detritylation assay).

Example 3—Oligonucleotide Synthesis

Example compounds were synthesised according to methods described below and known to the person skilled in the art. Assembly of the oligonucleotide chain and linker building blocks was performed by solid phase synthesis applying phosphoramidite methodology.

Downstream cleavage, deprotection and purification followed standard procedures that are known in the art.

Oligonucleotide syntheses was performed on an AKTA oligopilot 10 using commercially available 2'O-Methyl RNA and 2' Fluoro-2' Deoxy RNA base loaded CPG solid support and phosphoramidites (all standard protection, ChemGenes, LinkTech) were used. Synthesis of DMT-(S)-Serinol(GalNAc)-succinyl Icaa CPG (7) and DMT-(S)-Serinol(GalNAc)-CEP (5) are described in example 2.

Ancillary reagents were purchased from EMP Biotech. Synthesis was performed using a 0.1 M solution of the phosphoramidite in dry acetonitrile (<20 ppm $H_2O$) and benzylthiotetrazole (BTT) was used as activator (0.3M in acetonitrile). Coupling time was 10 min. A Cap/OX/Cap or Cap/Thio/Cap cycle was applied (Cap: $Ac_2O$/NMI/Lutidine/Acetonitrile, Oxidizer: 0.05M $I_2$ in pyridine/$H_2O$). Phosphorothioates were introduced using commercially available thiolation reagent 50 mM EDITH in acetonitrile (Link technologies). DMT cleavage was achieved by treatment with 3% dichloroacetic acid in toluene. Upon completion of the programmed synthesis cycles a diethylamine (DEA) wash was performed. All oligonucleotides were synthesized in DMT-off mode.

Attachment of the Serinol(GalNAc) moiety was achieved by use of either base-loaded (S)-DMT-Serinol(GalNAc)-succinyl-Icaa-CPG (7) or a (S)-DMT-Serinol(GalNAc)-CEP (5). Tri-antennary GalNAc clusters (ST23/ST43) were introduced by successive coupling of the branching trebler amidite derivative (C6XLT-phos) followed by the GalNAc amidite (ST23-phos). Attachment of (vp)-mU moiety was achieved by use of (vp)-mU-phos in the last synthesis cycle. The (vp)-mU-phos does not provide a hydroxy group suitable for further synthesis elongation and therefore, does not possess an DMT-group. Hence coupling of (vp)-mU-phos results in synthesis termination.

For the removal of the methyl esters masking the vinylphosphonate, the CPG carrying the fully assembled oligonucleotide was dried under reduced pressure and transferred into a 20 ml PP syringe reactor for solid phase peptide synthesis equipped with a disc frit (Carl Roth GmbH). The CPG was then brought into contact with a solution of 250 μL TMSBr and 177 μL pyridine in $CH_2Cl_2$ (0.5 ml/μmol solid support bound oligonucleotide) at room temperature and the reactor was sealed with a Luer cap. The reaction vessels were slightly agitated over a period of 2×15 min, the excess reagent discarded, and the residual CPG washed 2× with 10 ml acetonitrile. Further downstream processing did not alter from any other example compound.

The single strands were cleaved off the CPG by 40% aq. methylamine treatment (90 min, RT). The resulting crude oligonucleotide was purified by ion exchange chromatography (Resource Q, 6 ml, GE Healthcare) on a AKTA Pure HPLC System using a sodium chloride gradient. Product containing fractions were pooled, desalted on a size exclusion column (Zetadex, EMP Biotech) and lyophilised until further use.

All final single-stranded products were analysed by AEX-HPLC to prove their purity. Identity of the respective single-stranded products was proved by LC-MS analysis.

Example 4—Double-Strand Formation

Individual single strands were dissolved in a concentration of 60 OD/ml in $H_2O$. Both individual oligonucleotide solutions were added together in a reaction vessel. For easier reaction monitoring a titration was performed. The first strand was added in 25% excess over the second strand as determined by UV-absorption at 260 nm. The reaction mixture was heated to 80°C for 5 min and then slowly cooled to RT. Double-strand formation was monitored by ion pairing reverse phase HPLC. From the UV-area of the residual single strand the needed amount of the second strand was calculated and added to the reaction mixture. The reaction was heated to 80° C. again and slowly cooled to RT. This procedure was repeated until less than 10% of residual single strand was detected.

Example 5

Reduction of human CNNM4 mRNA level in human HepG2 cells by transfection of CNNM4 siRNAs.

In vitro test shows reduction of CNNM4 mRNA levels in human HepG2 cells by transfection of CNNM4 siRNA molecules.

Figure 11:
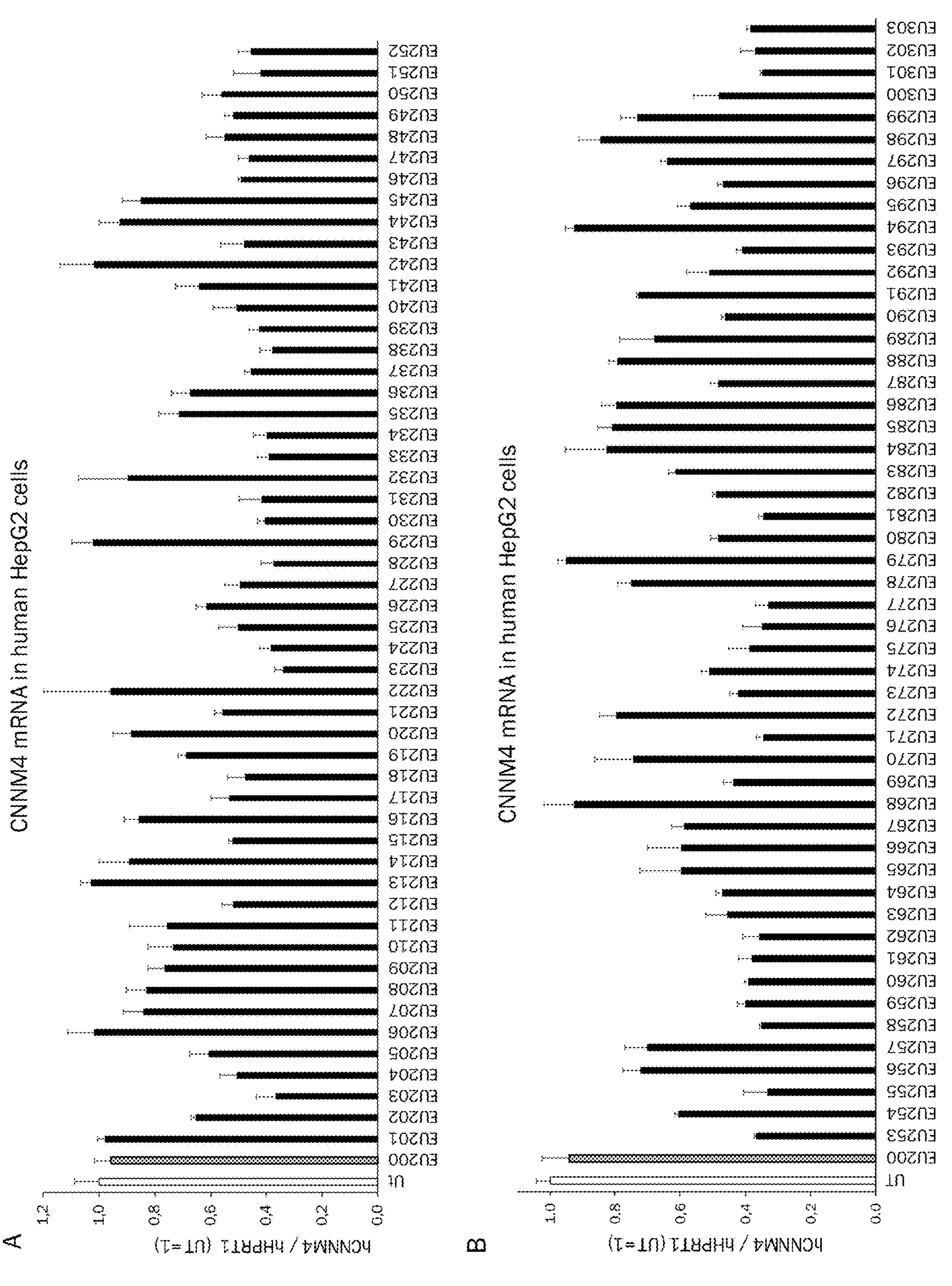
FIG. 11. Reduction of human CNNM4 mRNA level in human HepG2 cells by transfection of CNNM4 siRNAs FIG. 12. Reduction of CNNM4 mRNA level in murine Hepa 1-6 cells by transfection of CNNM4 siRNAs.

HepG2 cells were seeded in 96 well plates at a density of 40 000 cells per well with 10 nM siRNA and 0.3 μl RNAiFect added to the culture medium. The following day, cells were lysed for RNA extraction and CNNM4 and HPRT1 mRNA levels were determined by Taqman qRT-PCR. Values obtained for CNNM4 mRNA were normalized to values generated for the housekeeping gene HRPT1 and related to mean of untreated sample (ut) set at 1-fold target gene expression. Each bar represents mean+/−SD from three biological replicates. siRNA duplexes used in this study are listed in Table 2. Results are shown in FIGS. 11A and 11B.

Example 6

Reduction of CNNM4 mRNA level in murine Hepa 1-6 cells by transfection of CNNM4 siRNAs.

In vitro test shows reduction of CNNM4 mRNA levels in murine Hepa 1-6 cells by transfection of different CNNM4 siRNA molecules at a concentration of 10 nM.

Figure 12:
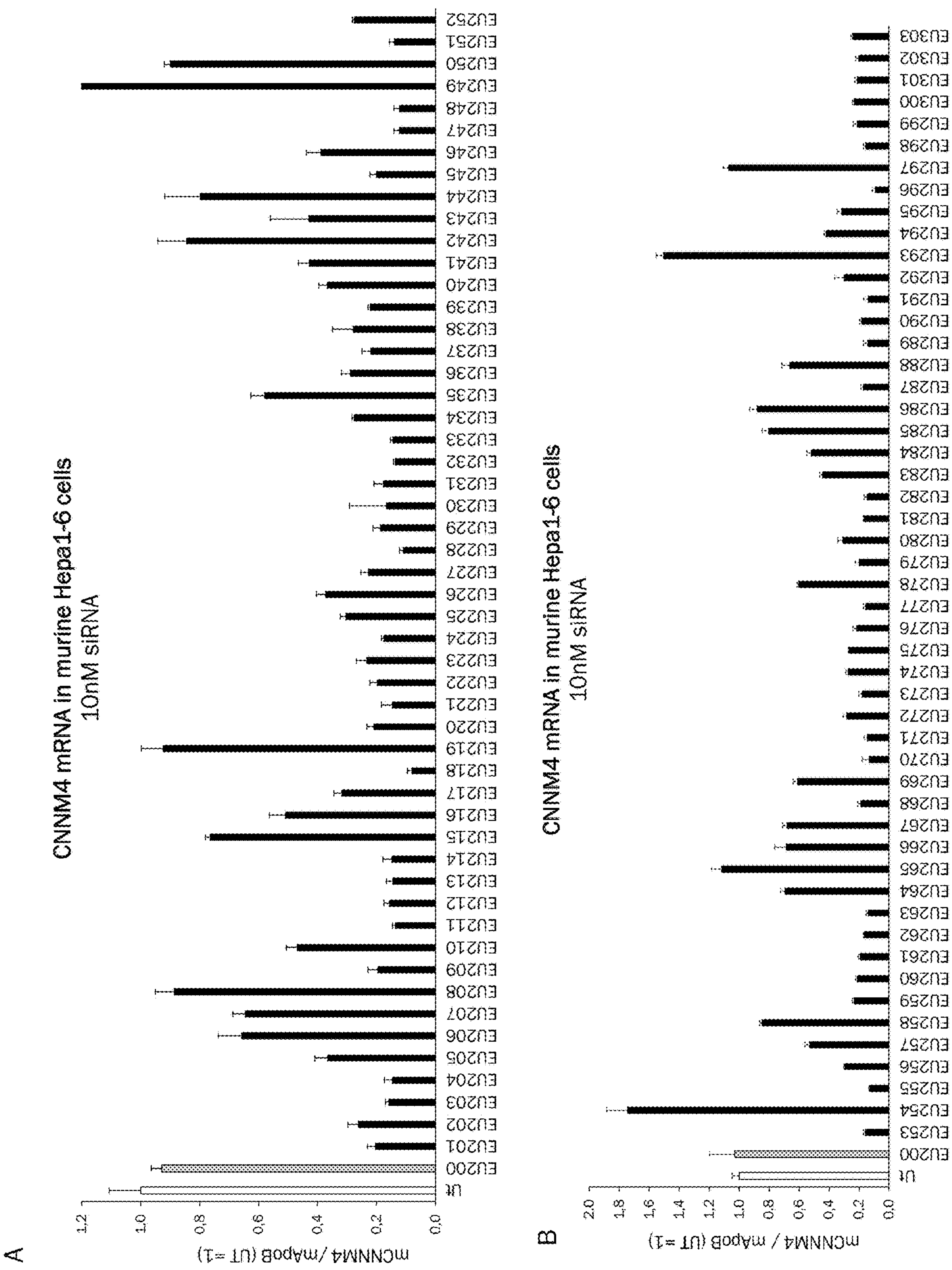
Figure 13:
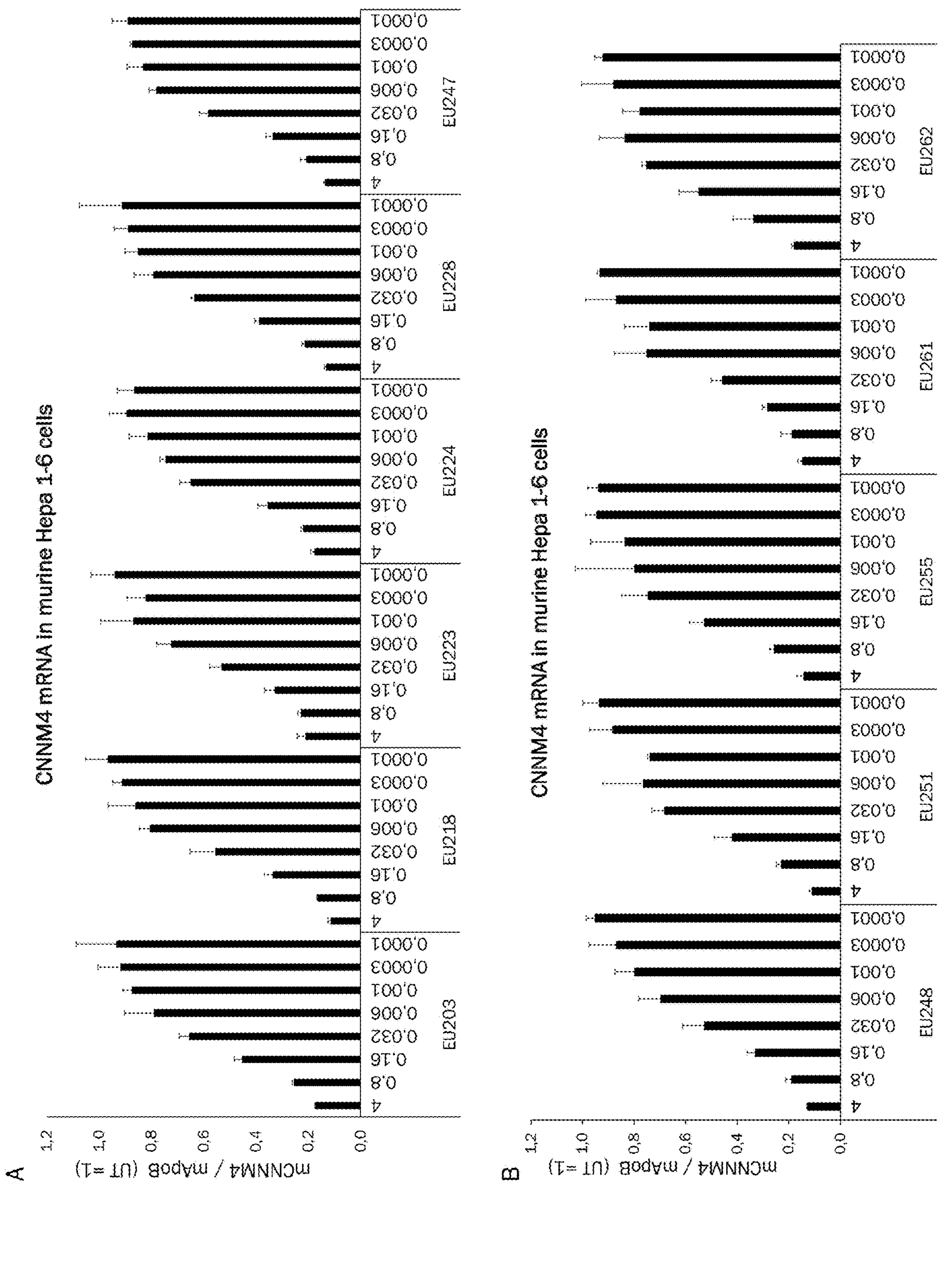
FIG. 13. Dose-dependent reduction of CNNM4 mRNA level in murine Hepa 1-6 cells by transfection of CNNM4 siRNAs FIG. 14. Inhibition of human CNNM4 gene expression in primary human hepatocytes by receptor mediated uptake of CNNM4 siRNA conjugates FIG. 15. Inhibition of mouse CNNM4 gene expression in primary mouse hepatocytes by receptor mediated uptake of CNNM4 siRNA conjugates.
Figure 13:
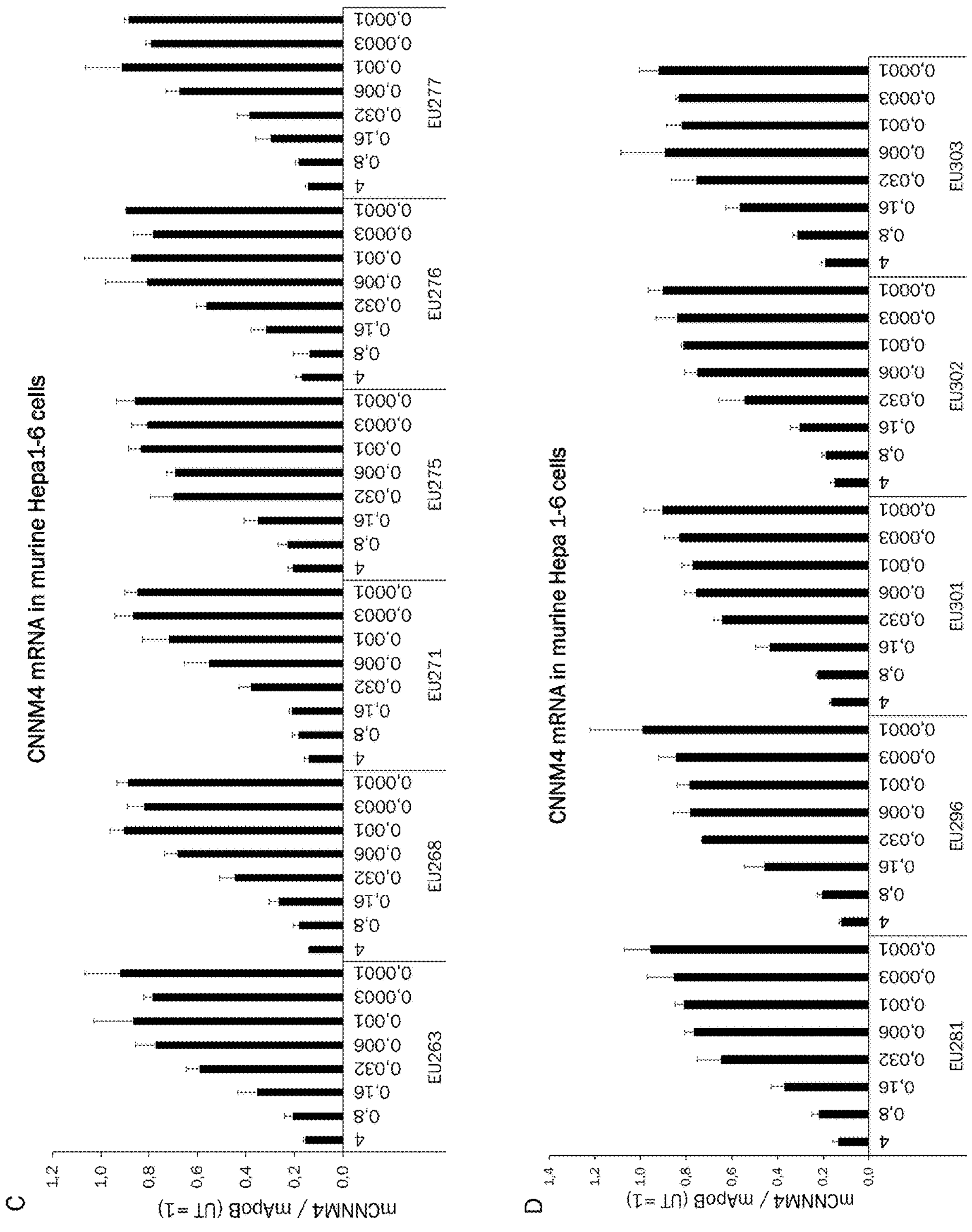

Hepa 1-6 cells were seeded in 96 well plates at a density of 12 500 cells per well in the presence of 10 nM siRNA and 0.6 μl RNAiFect added to the culture medium. The following day, cells were lysed for RNA extraction and CNNM4 and ApoB mRNA levels were determined by Taqman qRT-PCR. Values obtained for CNNM4 mRNA were normalized to values generated for the housekeeping gene ApoB and related to mean of untreated sample (ut) set at 1-fold target gene expression. Each bar represents mean+/−SD from three biological replicates. siRNA duplexes used in this study are listed in Table 2. Results are shown in FIGS. 12A and 12B.

Example 7

Dose-dependent reduction of CNNM4 mRNA level in murine Hepa 1-6 cells by transfection of CNNM4 siRNAs.

In vitro test shows reduction of CNNM4 siRNAs mRNA levels in murine Hepa 1-6 cells by transfection of different CNNM4 siRNA molecules in a dose range of 4 nM to 0.0001 nM.

Hepa 1-6 cells were seeded in 96 well plates at a density of 12 500 cells per well in the presence of 4 nM, 0.8 nM, 0.16 nM, 0.032 nM, 0.006 nM, 0.001 nM, 0.0003 nM or 0.0001 nM siRNA and 0.6 μl RNAiFect added to the culture medium. The following day, cells were lysed for RNA extraction and CNNM4 and ApoB mRNA levels were determined by Taqman qRT-PCR. Values obtained for CNNM4 mRNA were normalized to values generated for the housekeeping gene ApoB and related to mean of untreated sample (ut) set at 1-fold target gene expression. Each bar represents mean+/−SD from three biological replicates.

siRNA duplexes used in this study are listed in Table 2. Results are shown in FIGS. 13A to 13D.

Example 8

Inhibition of human CNNM4 gene expression in primary human hepatocytes by receptor mediated uptake of CNNM4 siRNA conjugates.

The example shows dose-dependent reduction of human CNNM4 mRNA levels by EU401 to EU414 in primary human hepatocytes.

Figure 14:
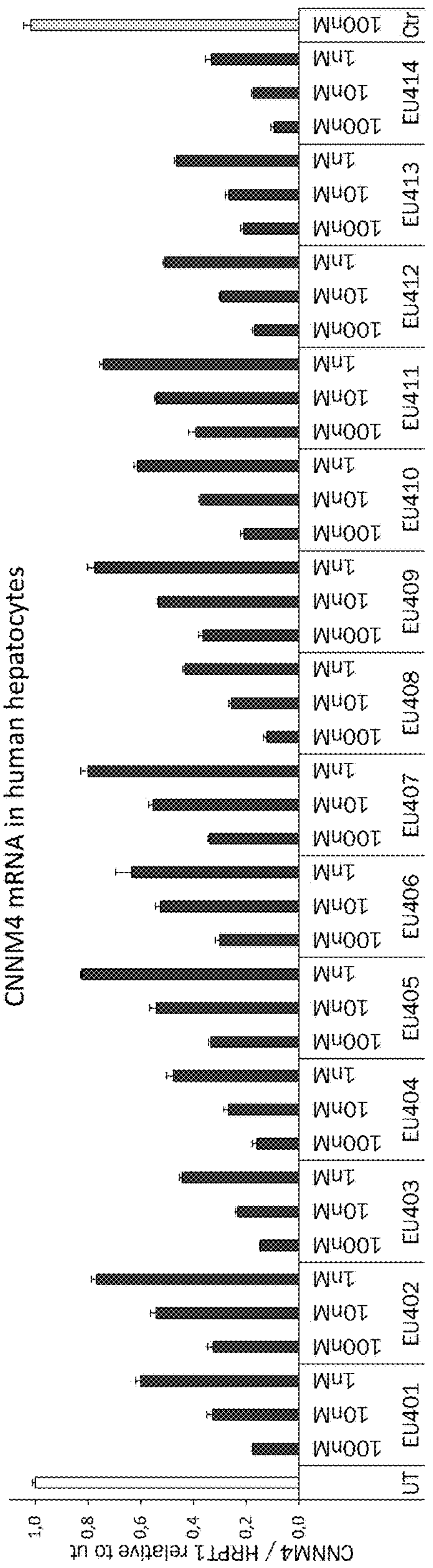

Primary human hepatocytes (Life Technologies) were seeded in a 96 well plate at a density of 35 000 cells per well in plating medium and incubated with CNNM4 siRNA conjugates EU401 to EU414, at concentrations of 100 nM, 10 nM and 1 nM as shown in FIG. 14, or they were incubated with non-targeting control conjugates (Ctr) at 100 nM (Ctr is EU400). The following day, cells were lysed for RNA extraction and CNNM4 and HPRT1 mRNA levels were determined by Taqman qRT-PCR. Values obtained for CNNM4 mRNA were normalized to values generated for the housekeeping gene HRPT1 and related to mean of untreated sample (ut) set at 1-fold target gene expression. Each bar represents mean+/−SD from three biological replicates. siRNA conjugates used in this study are listed in Table 2. Results are shown in FIG. 14.

Example 9

Inhibition of mouse CNNM4 gene expression in primary mouse hepatocytes by receptor mediated uptake of CNNM4 siRNA conjugates.

The example shows dose-dependent reduction of mouse CNNM4 mRNA levels by EU401 to 408 and by EU410 to EU414 in primary mouse hepatocytes.

Figure 15:
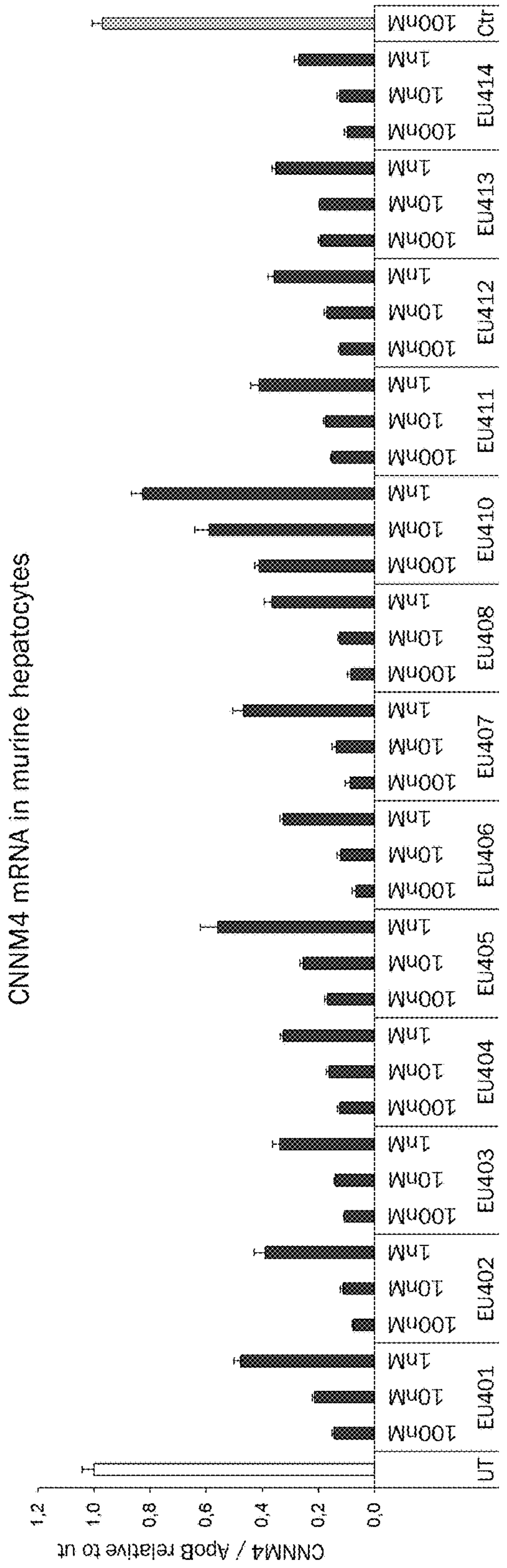

Primary mouse hepatocytes were seeded in a 96 well plate at a density of 25 000 cells per well in plating medium and incubated with CNNM4 siRNA conjugates EU401 to 408 and EU410 to EU414, at concentrations of 100 nM, 10 nM and 1 nM as shown in FIG. 15, or they were incubated with non-targeting control conjugates (Ctr) at 100 nM (Ctr is EU400). The following day, cells were lysed for RNA extraction and CNNM4 and ApoB mRNA levels were determined by Taqman qRT-PCR. Values obtained for CNNM4 mRNA were normalized to values generated for the housekeeping gene ApoB and related to mean of untreated sample (ut) set at 1-fold target gene expression. Each bar represents mean+/−SD from three biological replicates. siRNA conjugates used in this study are listed in Table 2. Results are shown in FIG. 15.

Example 10

Inhibition of human CNNM4 gene expression in primary human hepatocytes by receptor mediated uptake of CNNM4 siRNA conjugates.

The example shows dose-dependent reduction of human CNNM4 mRNA levels by EU415 to EU422 in primary human hepatocytes.

Figure 16:
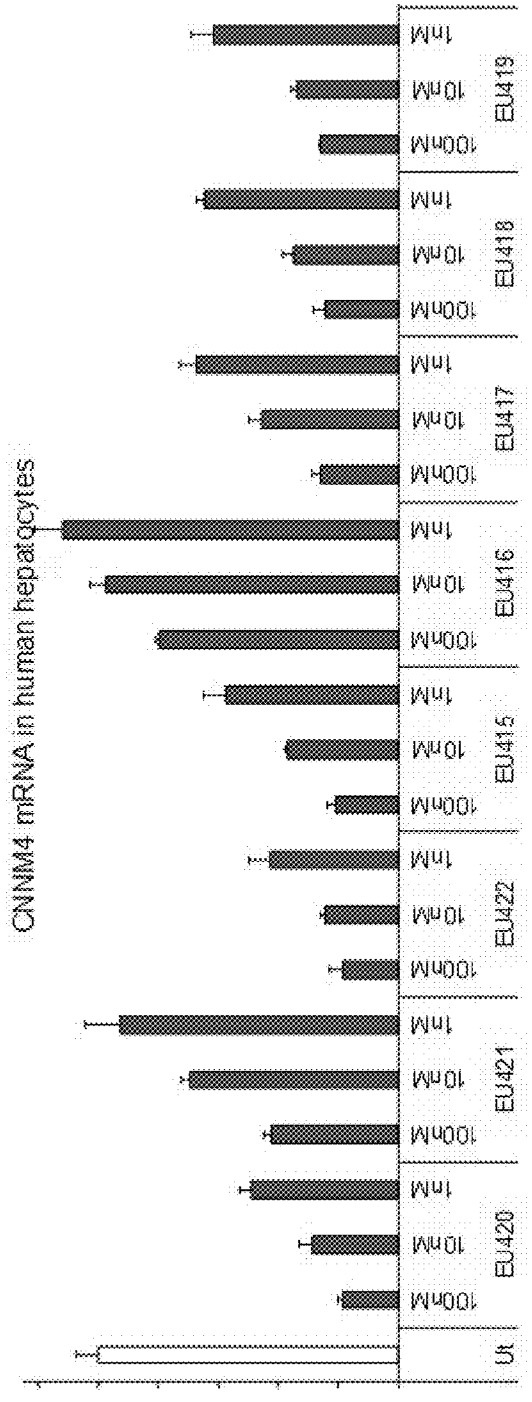
FIG. 16. Inhibition of human CNNM4 gene expression in primary human hepatocytes by receptor mediated uptake of CNNM4 siRNA conjugates.

Primary human hepatocytes (Life Technologies) were seeded in a 96-well plate at a density of 35 000 cells per well in plating medium and incubated with CNNM4 siRNA conjugates EU415 to EU422 in concentrations of 100 nM, 10 nM and 1 nM as shown in FIG. 16, or they were incubated with a non-targeting control conjugates (Ctr) at 100 nM (Ctr is EU423). The following day, cells were lysed for RNA extraction and CNNM4 and HPRT1 mRNA levels were determined by Taqman qRT-PCR. Values obtained for CNNM4 mRNA were normalized to values generated for the housekeeping gene HRPT1 and related to mean of untreated sample (ut) set at 1-fold target gene expression. Each bar represents mean+/−SD from three biological replicates. siRNA conjugates used in this study are listed in Table 2. Results are shown in FIG. 16.

Example 11

Inhibition of CNNM4 gene expression in primary murine hepatocytes by receptor mediated uptake of CNNM4 siRNA conjugates.

The example shows dose-dependent reduction of mouse CNNM4 mRNA levels by EU415 to EU424 in primary mouse hepatocytes.

Figure 17:
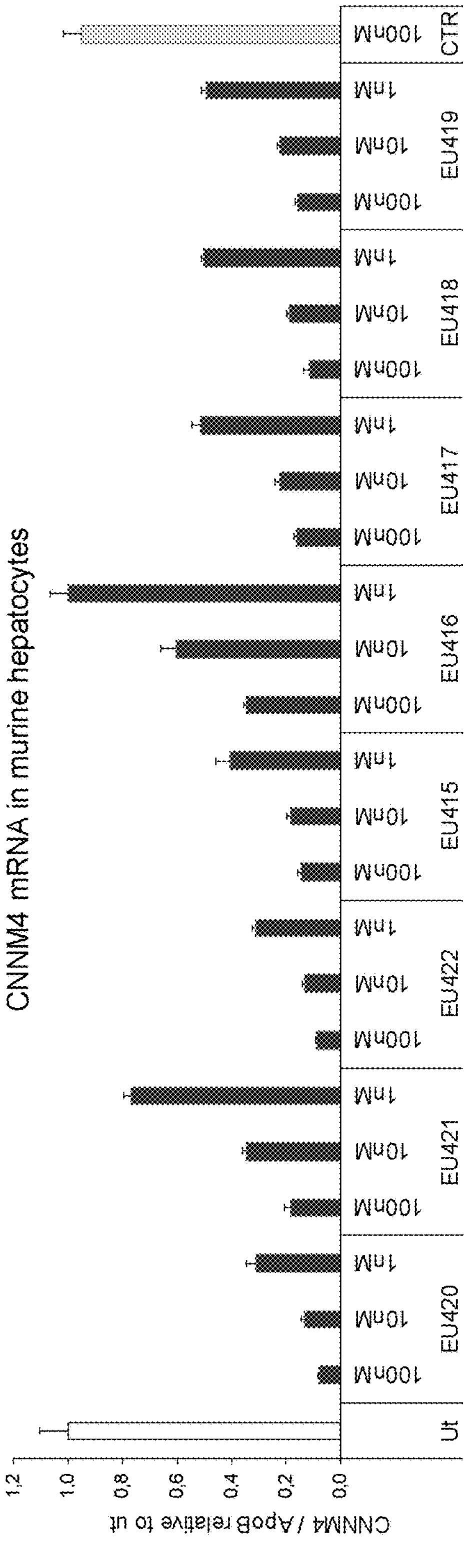
FIG. 17. Inhibition of CNNM4 gene expression in primary murine hepatocytes by receptor mediated uptake of CNNM4 siRNA conjugates.

Primary mouse hepatocytes were seeded in a 96-well plate at a density of 25 000 cells per well in plating medium and incubated with CNNM4 siRNA conjugates EU415 to EU422, in concentrations of 100 nM, 10 nM and 1 nM as shown in FIG. 17, or they were incubated with non-targeting control conjugates (Ctr) at 100 nM (Ctr is EU423). The following day, cells were lysed for RNA extraction and CNNM4 and ApoB mRNA levels were determined by Taqman qRT-PCR. Values obtained for CNNM4 mRNA were normalized to values generated for the housekeeping gene ApoB and related to mean of untreated sample (ut) set at 1-fold target gene expression. Each bar represents mean+/−SD from three biological replicates. siRNA conjugates used in this study are listed in Table 2. Results are shown in FIG. 17.

Example 12

Dose-dependent inhibition of CNNM4 target gene expression in the liver by CNNM4 siRNA conjugates.

The example shows reduction of CNNM4 mRNA levels in the liver of wild-type mice two weeks after single dosing of EU403, EU404, EU408, EU412 and EU114 by subcutaneous injection.

Figure 18:
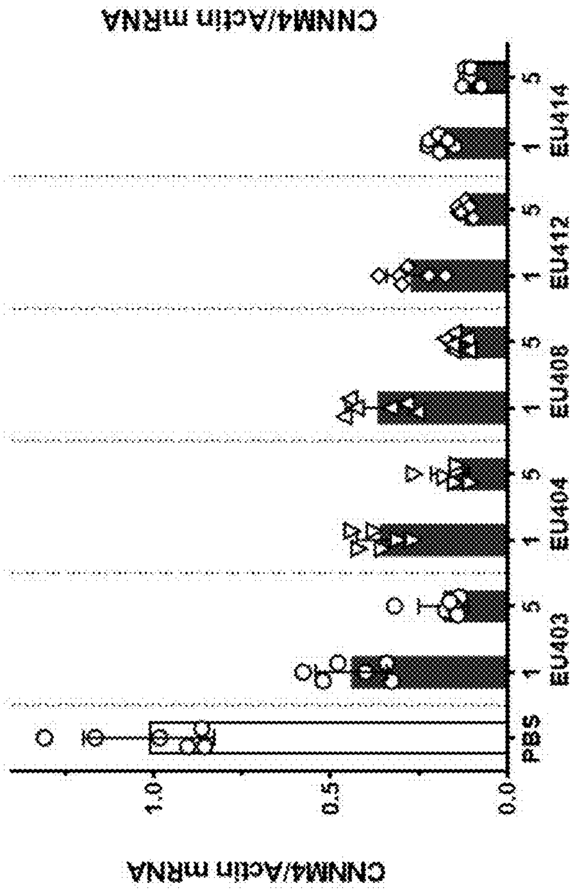
FIG. 18. Dose-dependent inhibition of CNNM4 target gene expression in the liver by CNNM4 siRNA conjugates.

Five- to seven-week old male C57BL/6 mice were treated with a single dose of 1 or 5 mg siRNA conjugate per kg body weight by subcutaneous injection. Control groups received a subcutaneous injection with the vehicle PBS. Two weeks after the treatment, liver samples were collected from all mice and snap frozen. RNA was extracted from liver samples and CNNM4 and Actin mRNA levels were determined by Taqman qRT-PCR. Values obtained for CNNM4 mRNA were normalized to values generated for the housekeeping gene Actin and related to mean of untreated sample (ut) set at 1-fold target gene expression. Each bar represents mean value from 6 animals+/−SD.

siRNA conjugates used in this study are listed in Table 2. The reduction of CNNM4 mRNA in mouse liver after treatment with siRNA conjugates is shown in FIG. 18.

Example 13

Dose-dependent inhibition of CNNM4 target gene expression in the liver by CNNM4 siRNA conjugates.

The example shows reduction of CNNM4 mRNA levels in the liver of wild-type mice two weeks after single dosing of EU418, EU420 and EU422 by subcutaneous injection.

Figure 19:
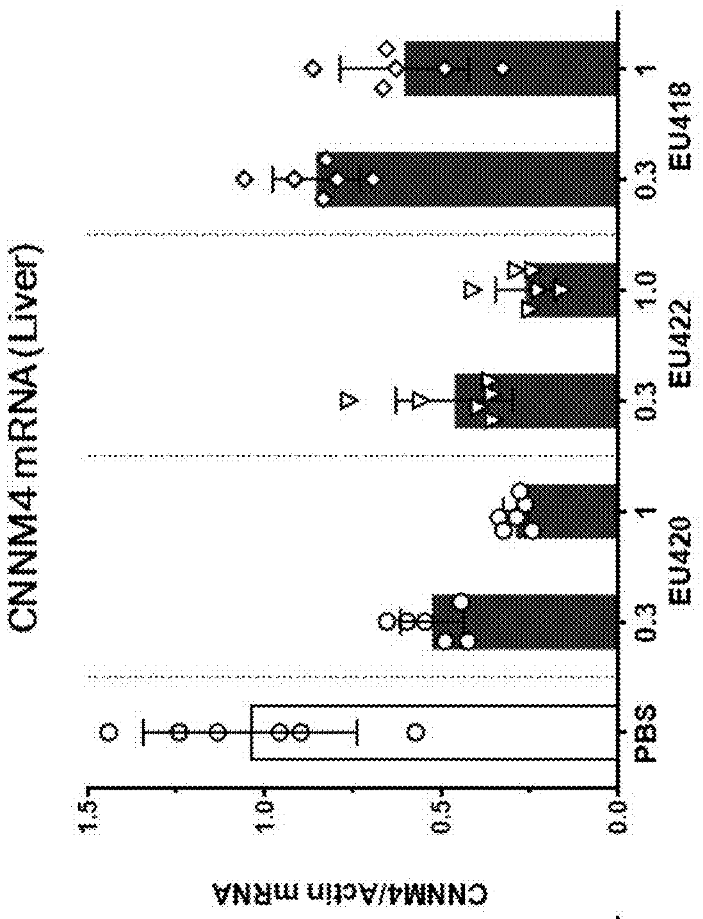
FIG. 19. Dose-dependent inhibition of CNNM4 target gene expression in the liver by CNNM4 siRNA conjugates.

Five- to seven-week old male C57BL/6 mice were treated with a single dose of 0.3 or 1 mg siRNA conjugate per kg body weight by subcutaneous injection. Control groups received a subcutaneous injection with the vehicle PBS. Two weeks after the treatment, liver samples were collected from all mice and snap frozen. RNA was extracted from liver samples and CNNM4 and Actin mRNA levels were determined by Taqman qRT-PCR. Values obtained for CNNM4 mRNA were normalized to values generated for the housekeeping gene Actin and related to mean of untreated sample (ut) set at 1-fold target gene expression. Each bar represents mean value from 6 animals+/−SD.

siRNA conjugates used in this study are listed in Table 2. The reduction of CNNM4 mRNA in mouse liver after treatment with siRNA conjugates is shown in FIG. 19.

Example 14

Long-lasting inhibition of CNNM4 target gene expression in the liver by CNNM4 siRNA conjugates.

The example shows reduction of CNNM4 mRNA levels in the liver of wild-type mice five weeks after a single dosing of EU418, EU420 and EU422 by subcutaneous injection.

Figure 20:
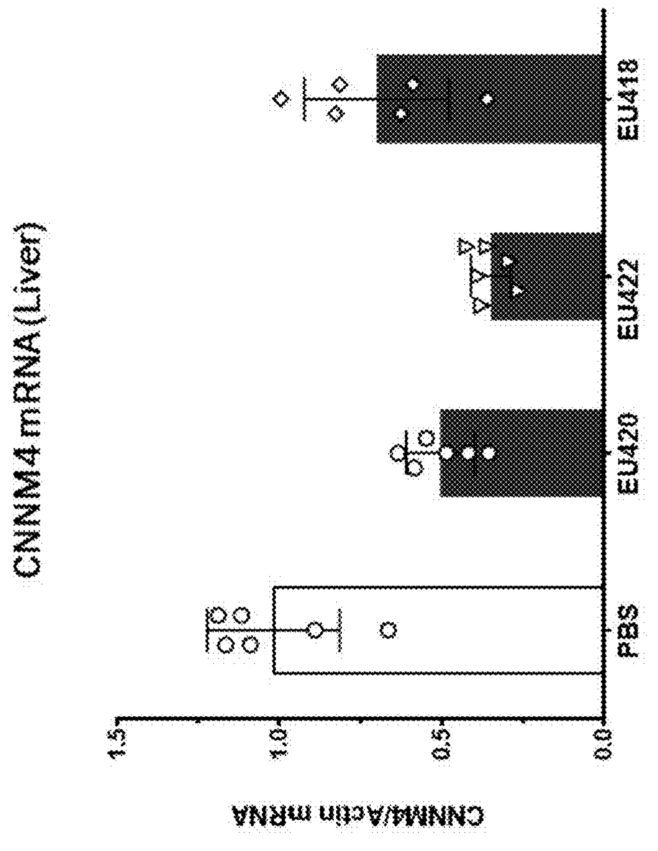
FIG. 20. Long-lasting inhibition of CNNM4 target gene expression in the liver by CNNM4 siRNA conjugates.

Five- to seven-week old male C57BL/6 mice were treated with a single dose of 1 mg siRNA conjugate per kg body weight by subcutaneous injection. Control groups received a subcutaneous injection with the vehicle PBS. Five weeks after the treatment, liver samples were collected from all mice and snap frozen. RNA was extracted from liver samples and CNNM4 and Actin mRNA levels were determined by Taqman qRT-PCR. Values obtained for CNNM4 mRNA were normalized to values generated for the housekeeping gene Actin and related to mean of PBS treated cohort (PBS) set at 1-fold target gene expression. Each bar represents mean value from 6 animals+/−SD.

siRNA conjugates used in this study are listed in Table 2. The reduction of CNNM4 mRNA in mouse liver after treatment with siRNA conjugates is shown in FIG. 20.

Example 15

Inhibition of CNNM4 expression in rodent a NASH model treated with CNNM4 siRNA conjugates.

The example shows reduction of CNNM4 mRNA levels in mice with NASH after treatment with a CNNM4 siRNA conjugate. The NASH phenotype was induced by feeding the mice with a diet devoid of choline and with 0.1% methionine for six weeks.

Figure 21:
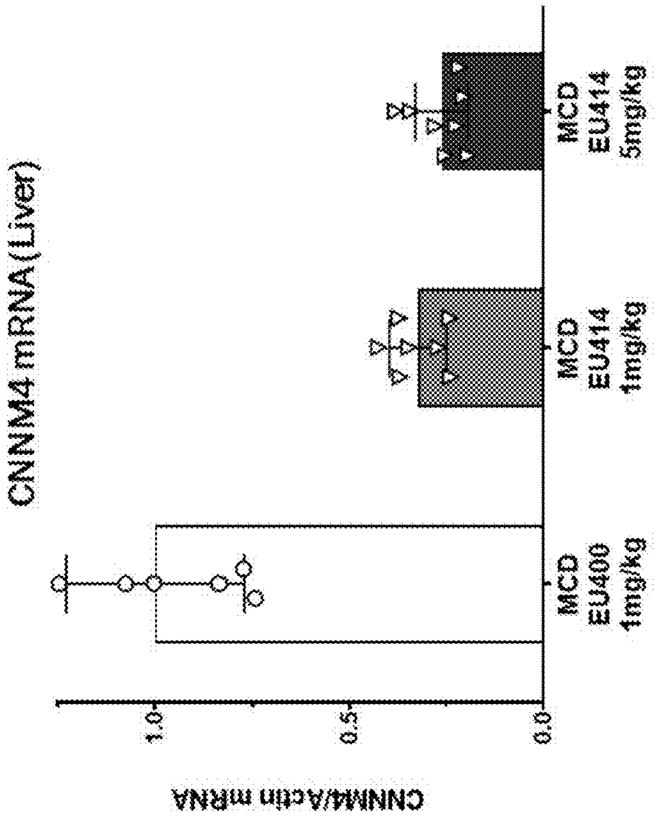
FIG. 21. Inhibition of CNNM4 expression in rodent a NASH model treated with CNNM4 siRNA conjugates.

Three-month old male C57BL/6 mice were maintained on a diet deficient in choline with 0.1% methionine (0.1% MCDD) (A02082006i, Research Diets, Inc., New Jersey, USA) for six weeks. After three weeks of 0.1% MCDD, mice were treated with 1 mg or 5 mg siRNA per kg body weight of CNNM4 siRNA conjugate (EU414). Control groups received 1 mg/kg non-targeting siRNA conjugate (EU400). Mice were then maintained on 0.1% MCDD for another three weeks and liver samples were subsequently collected from all mice and snap frozen. RNA was extracted from liver samples and CNNM4 and Actin mRNA levels were determined by Taqman qRT-PCR. Values obtained for CNNM4 mRNA were normalized to values generated for the housekeeping gene Actin and related to mean of EU400 treated cohort set at 1-fold target gene expression. Each bar represents mean value from 6-8 animals+/−SD.

siRNA conjugates used in this study are listed in Table 2. The reduction of CNNM4 mRNA in the liver of murine NASH models three weeks after treatment with CNNM4 siRNA conjugate is shown in FIG. 21.

Example 16

Treatment with CNNM4 siRNA conjugates reduces lipid accumulation in hepatocytes.

The example shows that lipid accumulation in hepatocytes is induced by oleic acid supplementation or by culturing the cells in methionine and choline deficient medium. Lipid accumulation is attenuated by treatment with CNNM4 siRNA conjugates.

Freshly isolated murine hepatocytes were seeded on coated cover slides in multi-well plates. Upon attachment, cells were incubated for 6 hours with 10 or 100 nM of EU403, EU404, EU408, EU412 or EU414. On the following day, the untreated cells (ut) were maintained in control medium (MEM/Gibco) for another 24 hours. The treated cells were cultured in the presence of 400 μM oleic acid (Sigma) or incubated with methionine- and choline-deficient DMEM/F12 medium (custom-made, Gibco) for 24 hours. Cells were then fixed in 4% paraformaldehyde solution. Lipid accumulation in hepatocytes was determined by staining of lipid bodies using boron-dipyromethene (BODIPY 493/503, Molecular Probes, Thermo Fisher Scientific). Images were acquired by fluorescence microscopy and BODIPY staining was quantified by ImageJ software.

Figure 22:
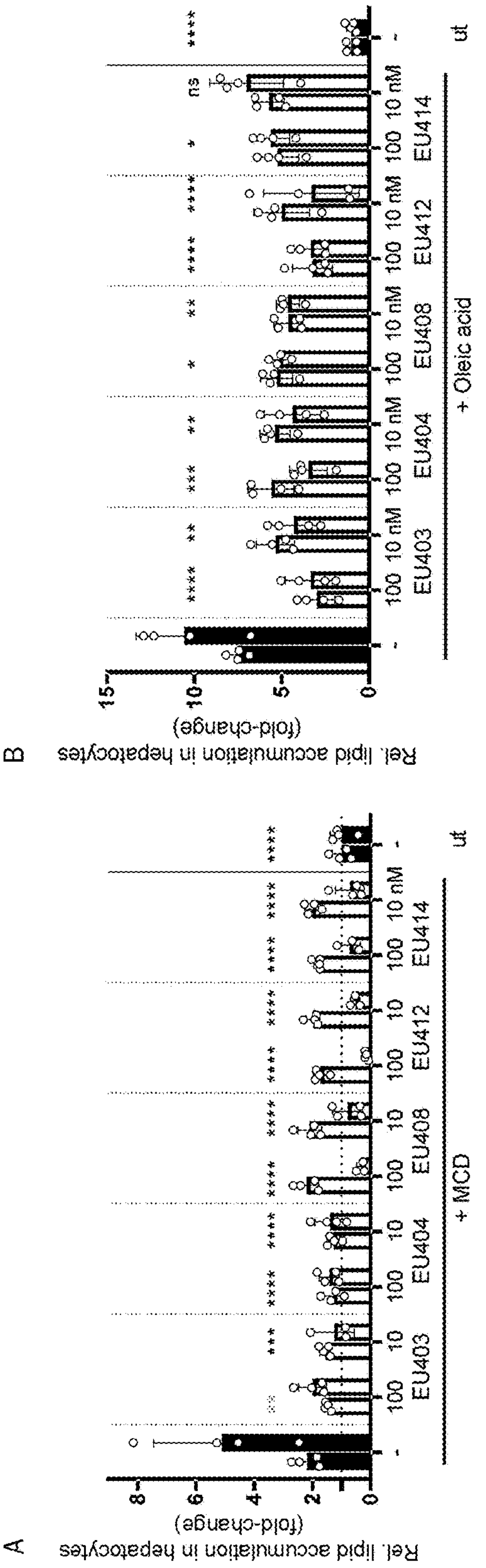
FIG. 22. Treatment with CNNM4 siRNA conjugates reduces lipid accumulation in hepatocytes.

Two independent experiments were carried out, each in quadruplicates. Values were normalized to mean values of untreated samples set at 1-fold. Each bar represents mean+/−SD. siRNA conjugates used in this study are listed in Table 2. The effect of CNNM4 siRNA treatment on lipid accumulation in methionine- and choline-deficient medium is shown in FIG. 22A. The effect of CNNM4 siRNA treatment on lipid accumulation induced by oleic acid is shown in FIG. 22B. Statistics: 2-way ANOVA with Dunnett's post-hoc test against respective oleic acid and MCD control group on log-transformed values. *p≤0.05; p≤0.01; *p≤001; ****p≤0.0001. There are no significant inter-experimental differences.

Example 17

Treatment with CNNM4 siRNA conjugates reduces mitochondrial reactive oxygen species (ROS) production in hepatocytes.

The example shows that mitochondrial ROS induced by oleic acid supplementation or by culturing cells in methionine- and choline-deficient medium is reduced by treatment with CNNM4 siRNA molecules.

Freshly prepared murine hepatocytes were seeded in multi-well plates. Upon attachment, cells were incubated for 6 hours with 1 nM, 10 or 100 nM of EU404 or EU414. On the following day, the untreated cells (ut) were maintained in control medium (MEM/Gibco) for another 24 hours. The treated cells were cultured in the presence of 400 μM oleic acid (Sigma) or incubated with methionine- and choline-deficient DMEM/F12 medium (custom-made, Gibco BRL) for 24 hours. Mitochondrial ROS production in hepatocytes was assessed using MitoSOX Red mitochondrial superoxide indicator (Invitrogen, USA). The cells were loaded with 2 μM MitoSOX Red for 10 min at 37° C. in a $CO_2$ incubator. The cells were then washed three times with PBS. Fluorescence was measured at 510 nm (excitation) and 595 (emission) using a plate reader SpectraMax M2 (bioNova, USA).

Figure 23:
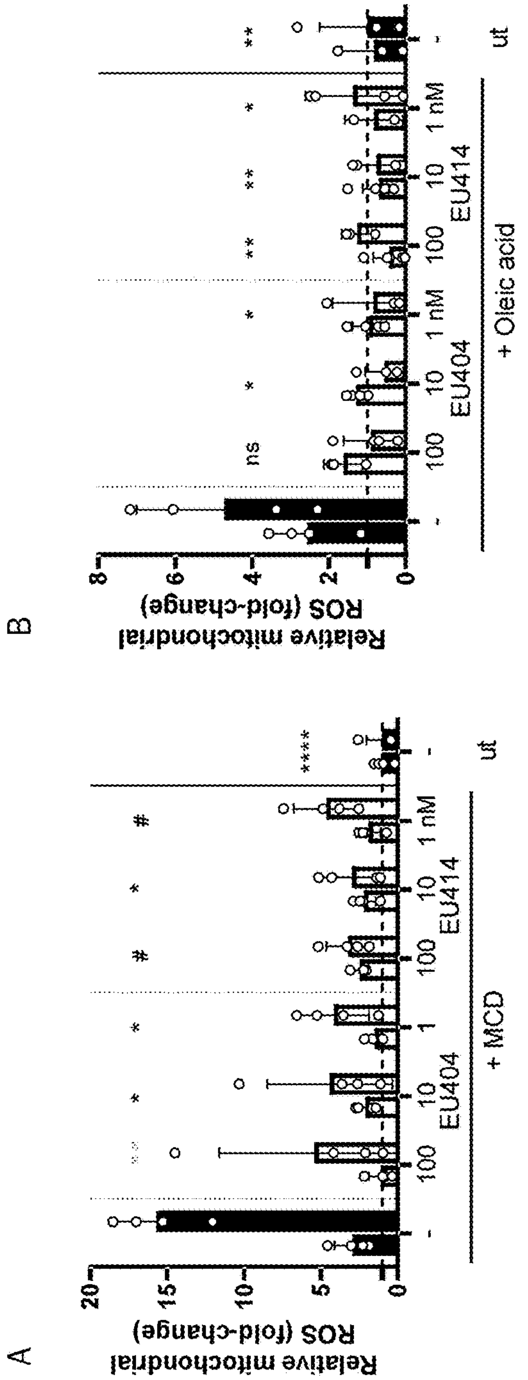
FIG. 23. Treatment with CNNM4 siRNA conjugates reduces mitochondrial reactive oxygen species (ROS) production in hepatocytes.

Two independent experiments were each carried out in quadruplicates. Values were normalized to mean values of untreated samples set at 1-fold. Each bar represents mean+/−SD. siRNA conjugates used in this study are listed in Table 2. The effect of CNNM4 siRNA treatment on mitochondrial ROS production in methionine- and choline-deficient medium is shown in FIG. 23A. The effect of CNNM4 siRNA treatment on ROS production induced by oleic acid is shown in FIG. 23B. Statistics: 2-way ANOVA with Dunnett's post-hoc test against respective oleic acid and MCD control group on log-transformed values. *$p \leq 0.05$; $p \leq 0.01$;*$p \leq 001$; ***$p \leq 0.0001$; # indicates significant inter-experimental differences ($p \leq 0.0001$).

Example 18

Treatment of rodent NASH model with CNNM4 siRNA conjugates reduces development of NASH.

The example shows that treatment with a CNNM4 siRNA conjugate reduces lipid accumulation, reactive oxygen species (ROS) and fibrosis in a rodent NASH model. The NASH phenotype was induced by feeding the mice with a diet devoid of choline and with 0.1% methionine for six weeks.

Figure 24:
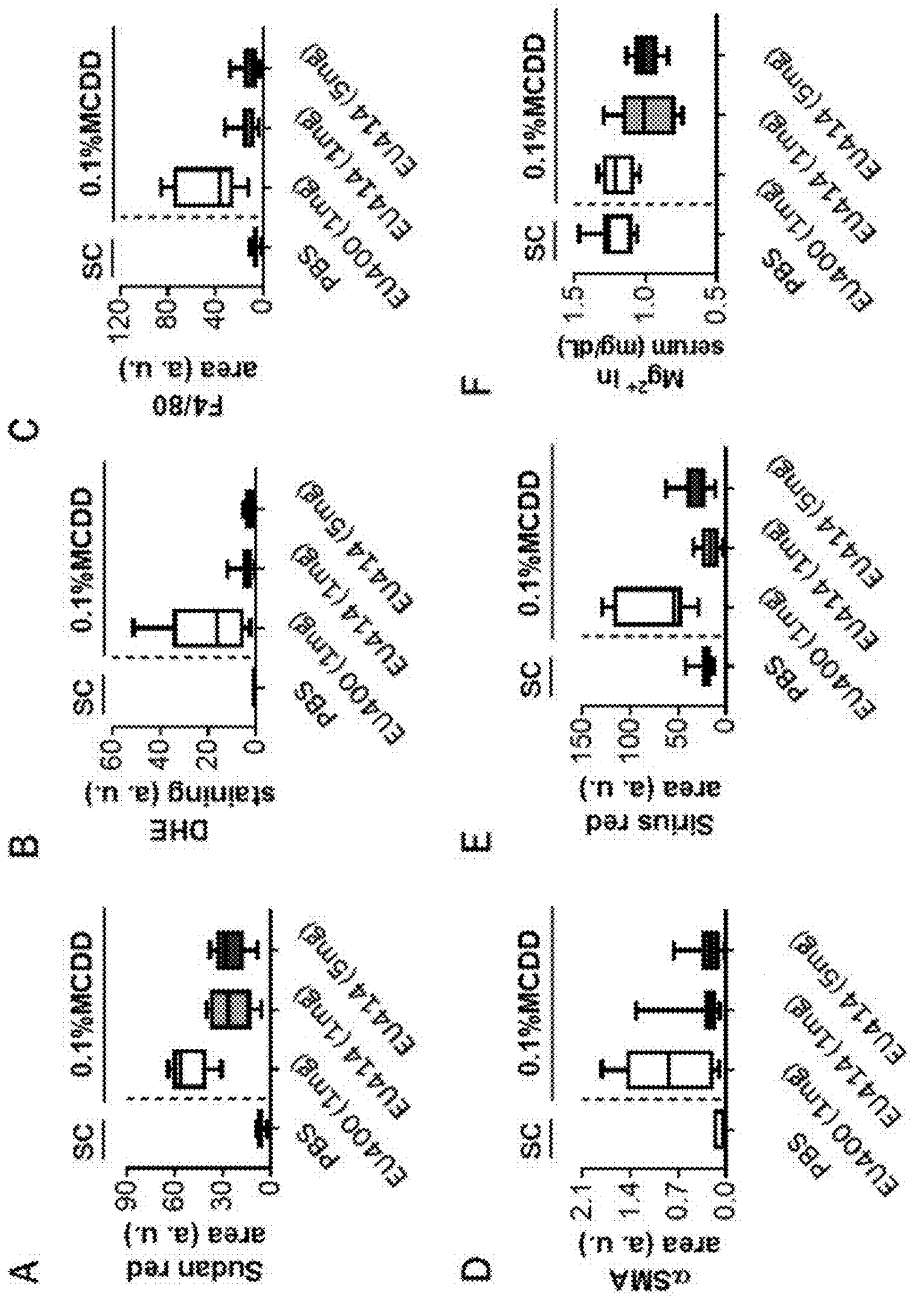
FIG. 24. Treatment of rodent NASH model with CNNM4 siRNA conjugates reduces development of NASH.

Three-month old male C57BL/6 mice were maintained on a diet deficient in choline with 0.1% methionine (0.1% MCDD) (A02082006i, Research Diets, Inc., New Jersey, USA) for six weeks or fed a standard chow (SC). After three weeks of 0.1% MCDD, mice were treated with 1 mg or 5 mg CNNM4 siRNA conjugate (EU414) per body weight. Control groups fed with 0.1% MCD received 1 mg/kg non-targeting siRNA conjugate (EU400). Control mice fed with normal chow (SC) received the vehicle PBS at the same time point (three weeks). Mice were subsequently maintained on 0.1% MCDD or standard chow (SC) for another three weeks as indicated in FIG. 24. Liver samples were collected from all mice at the end of the study and cryopreserved by embedding in optical coherence tomography cryocompound (OCT) or fixed with formalin and embedded in paraffin for preparation of sections. Lipid bodies and reactive oxygen species (ROS) were detected in cryosections by staining with Sudan red and Dihydroxyetidium (DHE), respectively. Liver fibrosis was assessed in paraffine sections by staining of the smooth muscle cell marker alpha smooth muscle actin (αSMA) by immunohistochemistry, as well as by detection of collagen fibers by Sirius red staining. Macrophages were detected by immunohistochemistry, by F4/80 staining of paraffin-embedded liver sections. Blood samples were collected from all animals at the six-week time point for serum preparation. Serum $Mg^{2+}$ levels were then determined using the QuantiCrom™ Magnesium Assay Kit (BioAssay Systems, USA).

siRNA conjugates used in this study are listed in Table 2. The reduction of liver steatosis by CNNM4 siRNA treatment in the 0.1% MCDD NASH model is shown in FIG. 24A. FIG. 24B shows reduction of reactive oxygen species by CNNM4 siRNA treatment. FIG. 24C shows the reduction of macrophage infiltration (F4/80 positive cells) in the liver by CNNM4 siRNA treatment. FIGS. 24D and 24E show the reduction in liver fibrosis by CNNM4 siRNA treatment in the same NASH model. These figures show quantifications of stained area percentages from each individual staining calculated using FIJI (https://imagej.net/Fiji.) in box and whisker plots with 5-95% percentile. n=5-7. (a.u.=arbitrary units). FIG. 24F shows reduction of serum $Mg^{2+}$ levels in 0.1% MCDD NASH model by treatment with EU414.

Example 19

CNNM4 siRNA conjugates protect hepatocytes from apoptosis and cell death induced by acetaminophen (APAP).

The example shows that inhibition of CNNM4 mRNA levels in primary hepatocytes with protects these cells from cell death induced by acetaminophen challenge.

Figure 25:
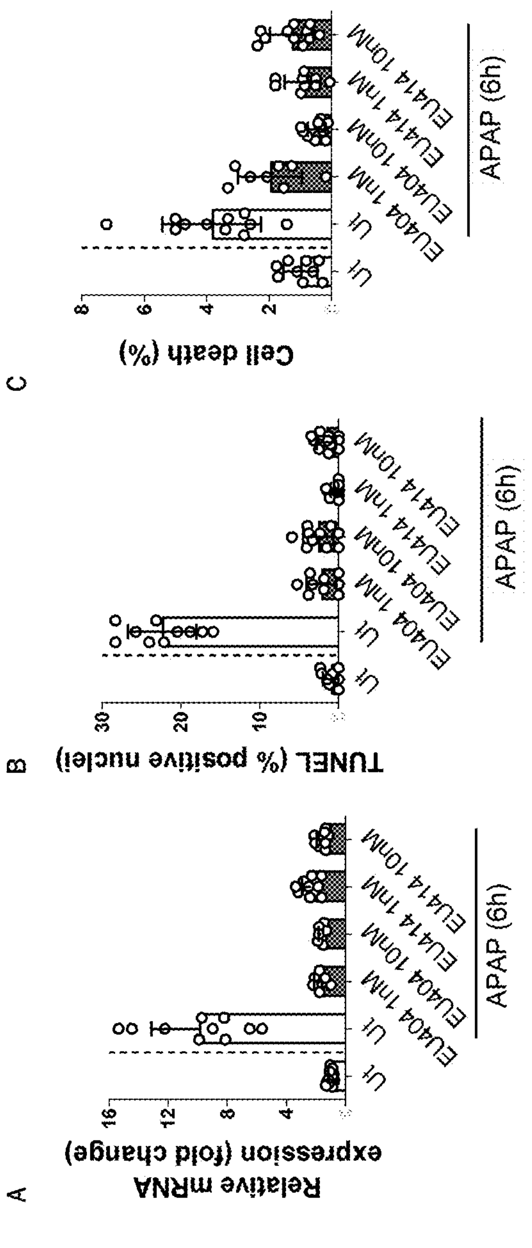
FIG. 25. CNNM4 siRNA conjugates protect hepatocytes from apoptosis and cell death induced by acetaminophen (APAP).

Freshly prepared murine hepatocytes were seeded in multi-well plates. Upon attachment, cells were incubated for 6 hours with 1 nM and 10 nM of EU404 or EU414 or left untreated. Thereafter, cells were cultured in serum-free culture medium (MEM) for 13 to 14 hours. Subsequently, they remained untreated (Ut) or 10 mM acetaminophen was added to the medium (APAP). 6 hours later, cells were stained by Tunel assay or Trypan Blue staining to determine the proportion of cells that were necrotic (Tunel positive) or had undergone cell death (Trypan Blue positive).

siRNA conjugates used in this study are listed in Table 2. The reduction of CNNM4 expression by EU414 and EU404 is shown in FIG. 25A. The reduction of Tunel positive cells (necrosis marker) and Tripan Blue positive cells (cell death marker) by CNNM4 siRNA treatment after exposure to Acetaminophen is shown in FIGS. 25A and 25B, respectively.

Example 20

Reduction of CNNM4 mRNA level in human Huh-7 cells by transfection of CNNM4 siRNAs.

In vitro test shows reduction of CNNM4 mRNA levels in human Huh-7 cells by transfection of CNNM4 siRNA molecules.

Figure 26:
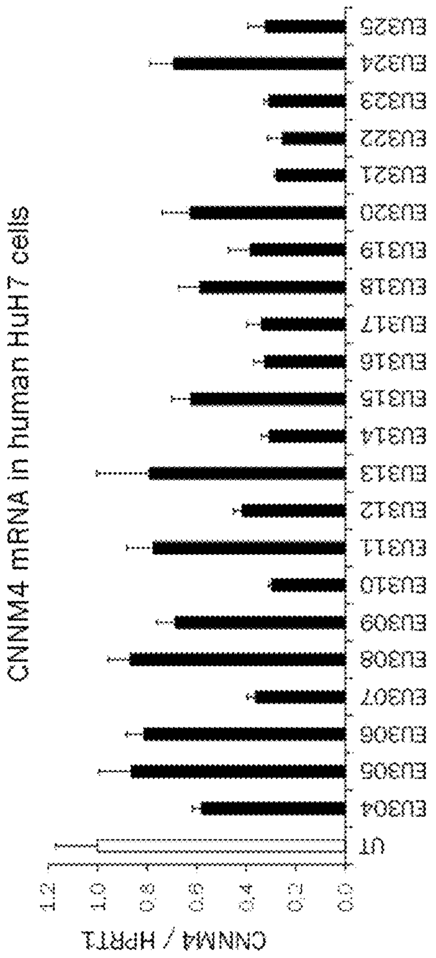
FIG. 26. Reduction of human CNNM4 mRNA level in human Huh-7 cells by transfection of CNNM4 siRNAs.

Huh7 cells were seeded in 96 well plates at a density of 20 000 cells per well and transfected with 0.5 nM siRNA and RNAiMAX at a final concentration of 1 μl/ml culture medium. The following day, cells were lysed for RNA extraction and CNNM4 and HPRT1 mRNA levels were determined by Taqman qRT-PCR. Values obtained for CNNM4 mRNA were normalized to values generated for the house keeping gene HRPT1 and related to mean of untreated sample (ut) set at 1-fold target gene expression. Each bar represents mean+/−SD from three biological replicates. siRNA duplexes used in this study are listed in Table 2. Results are shown in FIG. 26.

Example 21

Dose-dependent reduction of CNNM4 mRNA level in human Huh-7 cells by transfection of CNNM4 siRNAs.

In vitro test shows reduction of CNNM4 mRNA levels in human Huh-7 cells by transfection of different CNNM4 siRNA molecules in a dose range of 10 nM to 0.01 nM.

Figure 27:
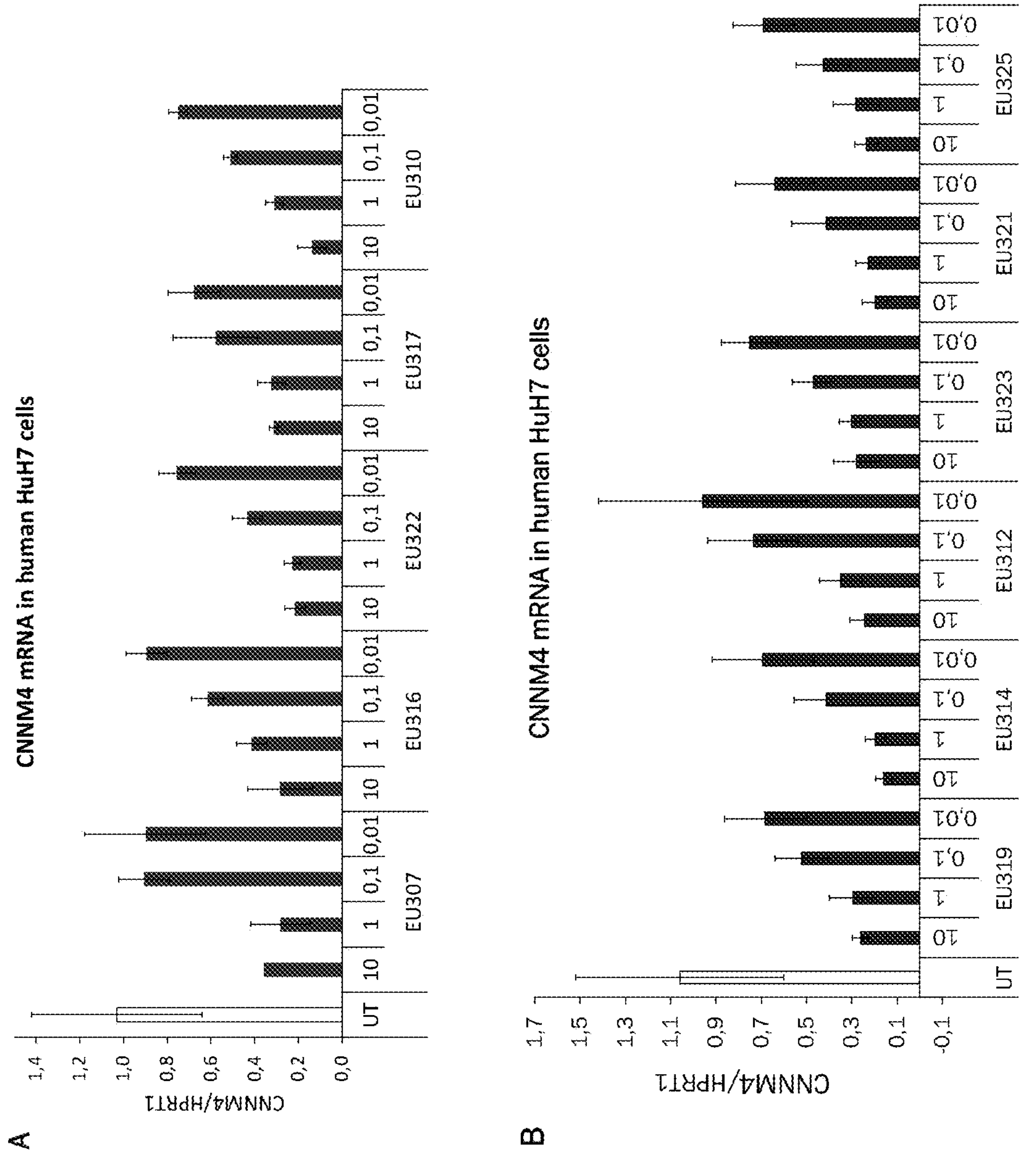
FIG. 27. Dose-dependent reduction of CNNM4 mRNA level in human Huh-7 cells by transfection of CNNM4 siRNAs.

Huh-7 cells were seeded in the 96 well plate at a density of 20 000 cells per well and transfected with 10 nM, 1 nM, 0.1 nM, 0.01 nM siRNA and RNAiMAX at a final concentration of 1 μl/ml culture medium. The following day cells were lysed for RNA extraction and CNNM4 and HPRT1 mRNA levels were determined by Taqman qRT-PCR. Values obtained for CNNM4 mRNA were normalized to values generated for the house keeping gene HPRT1 and related to mean of untreated sample (ut) set at 1-fold target gene expression. Each bar represents mean+/−SD from three biological replicates. siRNA duplexes used in this study are listed in Table 2. Results are shown in FIGS. 27A and B.

Example 22

Inhibition of CNNM4 gene expression in primary human hepatocytes by receptor mediated uptake.

The example shows dose-dependent reduction of human CNNM4 mRNA levels by EU424 to EU433 in primary human hepatocytes by receptor mediated uptake.

Figure 28:
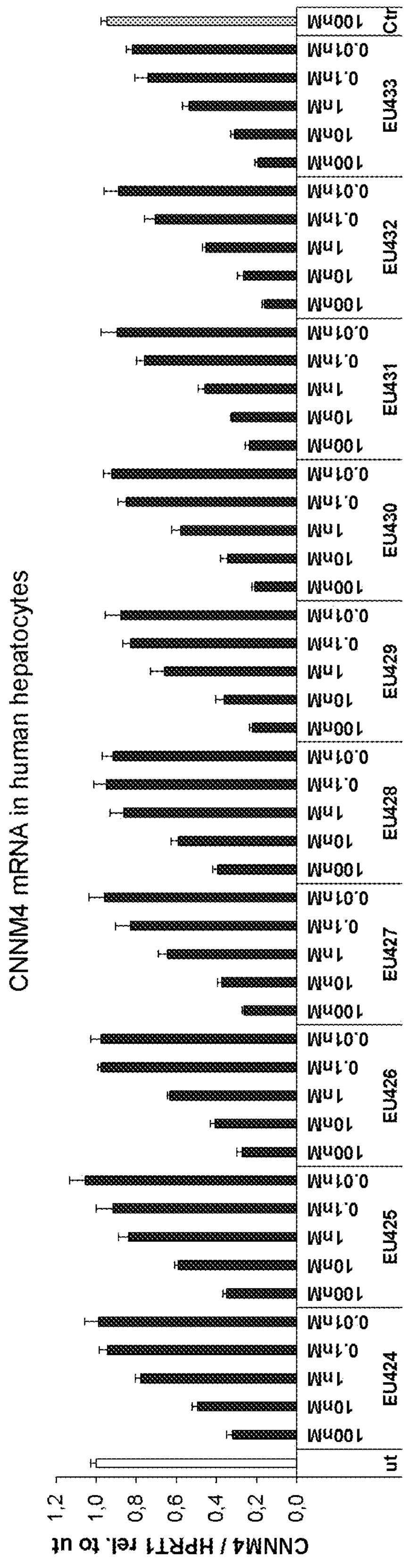
FIG. 28. Inhibition of CNNM4 gene expression in primary human hepatocytes by receptor mediated uptake.

Primary human hepatocytes (Life Technologies) were seeded in a 96 well plate at a density of 35 000 cells per well in plating medium and were subsequently incubated with CNNM4 siRNA conjugates EU424 to EU433 in concentrations of 100 nM, 10 nM, 1 nM, 0.1 nM or 0.01 nM or non-targeting control siRNA, EU423 (depicted as Ctr) as shown in FIG. 28. Values obtained for CNNM4 mRNA were normalized to values generated for the house keeping gene HPRT1 and related to mean of untreated sample (ut) set at 1-fold target gene expression. Each bar represents mean+/−SD from three biological replicates. siRNA conjugates used in this study are listed in Table 2. Results with EU424 to EU433 are shown in FIG. 28.

Example 23

Inhibition of CNNM4 gene expression in primary cynomolgus hepatocytes by receptor mediated uptake.

The example shows dose-dependent reduction of CNNM4 mRNA levels by EU429 to EU433 in primary cynomolgus hepatocytes by receptor mediated uptake.

Figure 29:
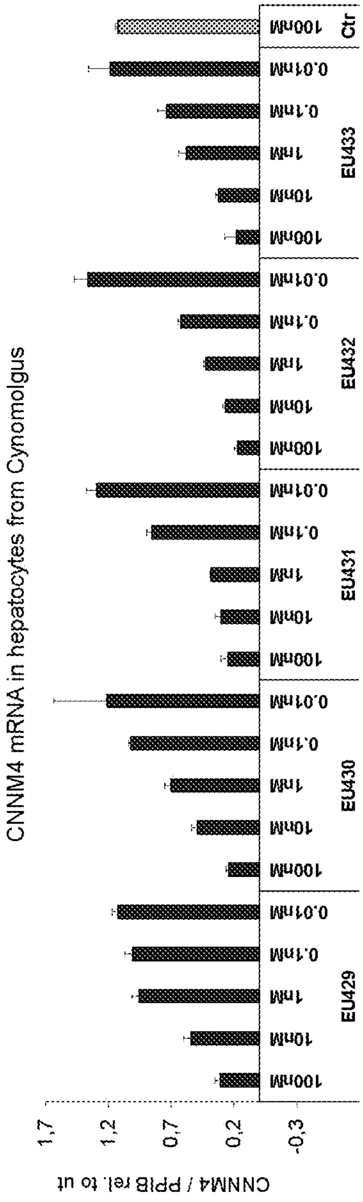
FIG. 29. Inhibition of CNNM4 gene expression in primary cynomolgus hepatocytes by receptor mediated uptake.

Primary hepatocytes were seeded in a 96 well plate at a density of 45 000 cells per well in plating medium and were subsequently incubated with CNNM4 siRNA conjugates EU429 to EU433 in concentrations of 100 nM, 10 nM, 1 nM, 0.1 or 0.01 nM or 100 nM non-targeting control siRNA, EU423 (depicted as Ctr) as shown in FIG. 29. Values obtained for CNNM4 mRNA were normalized to values generated for the house keeping gene PPIB and related to mean of untreated sample (ut) set at 1-fold target gene expression. Each bar represents mean+/−SD from three biological replicates. siRNA conjugates used in this study are listed in Table 2. Results with EU429 to 433 are shown in FIG. 29.

Example 24

Inhibition of CNNM4 gene expression in rodent model for NASH.

The example shows dose dependent reduction of CNNM4 mRNA levels by EU422 in a murine model for NASH.

Figure 30:
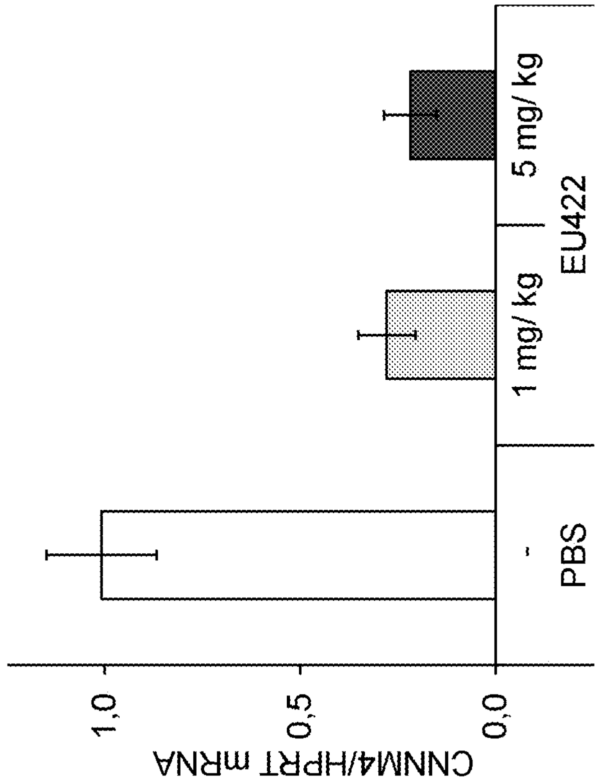
FIG. 30. Inhibition of CNNM4 gene expression in rodent model for NASH

5-week old C57BL/6 male mice were maintained on a DIO-NASH diet for about 32 weeks and randomized based on pre-liver biopsy fibrosis and steatosis score. Only animals with fibrosis score of ≥ 1 and steatosis score of ≥2 were included in the study. Animals were then maintained on DIO-NASH diet for another 16 weeks. At the 4 week, 8 week, and 12 week time points after the pre liver biopsy mice were treated with 1 mg/kg or 5 mg/kg EU422, respectively or with the vehicle PBS by subcutaneous injection. 4 weeks after the last treatment, liver samples were collected from all mice and snap frozen. RNA was extracted from liver samples and CNNM4 and HPRT mRNA levels were determined by Taqman qRT-PCR. Values obtained for CNNM4 mRNA were normalized to values generated for the house keeping gene HPRT and related to mean of untreated sample (ut) set at 1-fold target gene expression. Each bar represents mean value from 15 animals+/−SD.

siRNA conjugates used in this study are listed in Table 2. The reduction of CNNM4 mRNA in mouse liver after treatment with siRNA conjugates is shown in FIG. 30.

Summary Tables

TABLE 2

Summary duplex table

| Duplex | Single Strands |
|---|---|
| EU200 | EU200A<br>EU200B |
| EU201 | EU201A<br>EU201B |
| EU202 | EU202A<br>EU202B |
| EU203 | EU203A<br>EU203B |
| EU204 | EU204A<br>EU204B |
| EU205 | EU205A<br>EU205B |
| EU206 | EU206A<br>EU206B |
| EU207 | EU207A<br>EU207B |
| EU208 | EU208A<br>EU208B |
| EU209 | EU209A<br>EU209B |
| EU210 | EU210A<br>EU210B |
| EU211 | EU211A<br>EU211B |
| EU212 | EU212A<br>EU212B |
| EU213 | EU213A<br>EU213B |
| EU214 | EU214A<br>EU214B |
| EU215 | EU215A<br>EU215B |
| EU216 | EU216A<br>EU216B |
| EU217 | EU217A<br>EU217B |
| EU218 | EU218A<br>EU218B |
| EU219 | EU219A<br>EU219B |
| EU220 | EU220A<br>EU220B |
| EU221 | EU221A<br>EU221B |
| EU222 | EU222A<br>EU222B |
| EU223 | EU223A<br>EU223B |
| EU224 | EU224A<br>EU224B |
| EU225 | EU225A<br>EU225B |
| EU226 | EU226A<br>EU226B |
| EU227 | EU227A<br>EU227B |
| EU228 | EU228A<br>EU228B |
| EU229 | EU229A<br>EU229B |
| EU230 | EU230A<br>EU230B |
| EU231 | EU231A<br>EU231B |
| EU232 | EU232A<br>EU232B |
| EU233 | EU233A<br>EU233B |
| EU234 | EU234A<br>EU234B |

TABLE 2-continued

| Summary duplex table | |
|---|---|
| Duplex | Single Strands |
| EU235 | EU235A<br>EU235B |
| EU236 | EU236A<br>EU236B |
| EU237 | EU237A<br>EU237B |
| EU238 | EU238A<br>EU238B |
| EU239 | EU239A<br>EU239B |
| EU240 | EU240A<br>EU240B |
| EU241 | EU241A<br>EU241B |
| EU242 | EU242A<br>EU242B |
| EU243 | EU243A<br>EU243B |
| EU244 | EU244A<br>EU244B |
| EU245 | EU245A<br>EU245B |
| EU246 | EU246A<br>EU246B |
| EU247 | EU247A<br>EU247B |
| EU248 | EU248A<br>EU248B |
| EU249 | EU249A<br>EU249B |
| EU250 | EU250A<br>EU250B |
| EU251 | EU251A<br>EU251B |
| EU252 | EU252A<br>EU252B |
| EU253 | EU253A<br>EU253B |
| EU254 | EU254A<br>EU254B |
| EU255 | EU255A<br>EU255B |
| EU256 | EU256A<br>EU256B |
| EU257 | EU257A<br>EU257B |
| EU258 | EU258A<br>EU258B |
| EU259 | EU259A<br>EU259B |
| EU260 | EU260A<br>EU260B |
| EU261 | EU261A<br>EU261B |
| EU262 | EU262A<br>EU262B |
| EU263 | EU263A<br>EU263B |
| EU264 | EU264A<br>EU264B |
| EU265 | EU265A<br>EU265B |
| EU266 | EU266A<br>EU266B |
| EU267 | EU267A<br>EU267B |
| EU268 | EU268A<br>EU268B |
| EU269 | EU269A<br>EU269B |
| EU270 | EU270A<br>EU270B |
| EU271 | EU271A<br>EU271B |

TABLE 2-continued

| Summary duplex table | |
|---|---|
| Duplex | Single Strands |
| EU272 | EU272A<br>EU272B |
| EU273 | EU273A<br>EU273B |
| EU274 | EU274A<br>EU274B |
| EU275 | EU275A<br>EU275B |
| EU276 | EU276A<br>EU276B |
| EU277 | EU277A<br>EU277B |
| EU278 | EU278A<br>EU278B |
| EU279 | EU279A<br>EU279B |
| EU280 | EU280A<br>EU280B |
| EU281 | EU281A<br>EU281B |
| EU282 | EU282A<br>EU282B |
| EU283 | EU283A<br>EU283B |
| EU284 | EU284A<br>EU284B |
| EU285 | EU285A<br>EU285B |
| EU286 | EU286A<br>EU286B |
| EU287 | EU287A<br>EU287B |
| EU288 | EU288A<br>EU288B |
| EU289 | EU289A<br>EU289B |
| EU290 | EU290A<br>EU290B |
| EU291 | EU291A<br>EU291B |
| EU292 | EU292A<br>EU292B |
| EU293 | EU293A<br>EU293B |
| EU294 | EU294A<br>EU294B |
| EU295 | EU295A<br>EU295B |
| EU296 | EU296A<br>EU296B |
| EU297 | EU297A<br>EU297B |
| EU298 | EU298A<br>EU298B |
| EU299 | EU299A<br>EU299B |
| EU300 | EU300A<br>EU300B |
| EU301 | EU301A<br>EU301B |
| EU302 | EU302A<br>EU302B |
| EU303 | EU303A<br>EU303B |
| EU400 | EU400A<br>EU400B |
| EU401 | EU401A<br>EU401B |
| EU402 | EU402A<br>EU402B |
| EU403 | EU403A<br>EU403B |
| EU404 | EU404A<br>EU404B |

TABLE 2-continued

| Summary duplex table | |
|---|---|
| Duplex | Single Strands |
| EU405 | EU405A |
| | EU405B |
| EU406 | EU406A |
| | EU406B |
| EU407 | EU407A |
| | EU407B |
| EU408 | EU408A |
| | EU408B |
| EU409 | EU409A |
| | EU409B |
| EU410 | EU410A |
| | EU410B |
| EU411 | EU411A |
| | EU411B |
| EU412 | EU412A |
| | EU412B |
| EU413 | EU413A |
| | EU413B |
| EU414 | EU414A |
| | EU414B |
| Mm n1 | Mm n1 A |
| | Mm n1 B |
| Mn n2 | Mm n2 A |
| | Mm n2 B |
| Mm n3 | Mm n3 A |
| | Mm n3 B |
| Mm n4 | Mm n4 A |
| | Mm n4 B |
| Mm n5 | Mm n5 A |
| | Mm n5 B |
| Mm n6 | Mm n6 A |
| | Mn n6 B |
| Hs n1 | Hs n1 A |
| | Hs n1 B |
| Hs n2 | Hs n2 A |
| | Hs n2 B |
| Hs n3 | Hs n3 A |
| | Hs n3 B |
| Hs n4 | Hs n4 A |
| | Hs n4 B |
| Hs n5 | Hs n5 A |
| | Hs n5 B |
| Hs n6 | Hs n6 A |
| | Hs n6 B |
| Hs n7 | Hs n7 A |
| | Hs n7 B |
| Mm n7 | Mm n7 A |
| | Mm n7 B |
| Hs n7o | Hs n7 Ao |
| | Hs n7 Bo |
| Mm n7o | Mm n7 Ao |
| | Mm n7 Bo |
| EU415 | EU404A |
| | EU415B |
| EU416 | EU416A |
| | EU415B |
| EU417 | EU302A |
| | EU415B |
| EU418 | EU418A |
| | EU418B |
| EU419 | EU418A |
| | EU419B |
| EU420 | EU414A |
| | EU420B |
| EU421 | EU277A |
| | EU420B |
| EU422 | EU422A |
| | EU422B |

TABLE 2-continued

| Summary duplex table | |
|---|---|
| Duplex | Single Strands |
| EU423 | EU423A |
| | EU423B |
| EU304 | EU304A |
| | EU304B |
| EU305 | EU305A |
| | EU305B |
| EU306 | EU306A |
| | EU306B |
| EU307 | EU307A |
| | EU307B |
| EU308 | EU308A |
| | EU308B |
| EU309 | EU309A |
| | EU309B |
| EU310 | EU310A |
| | EU310B |
| EU311 | EU311A |
| | EU311B |
| EU312 | EU312A |
| | EU312B |
| EU313 | EU313A |
| | EU313B |
| EU314 | EU314A |
| | EU314B |
| EU315 | EU315A |
| | EU315B |
| EU316 | EU316A |
| | EU316B |
| EU317 | EU317A |
| | EU317B |
| EU318 | EU318A |
| | EU318B |
| EU319 | EU319A |
| | EU319B |
| EU320 | EU320A |
| | EU320B |
| EU321 | EU321A |
| | EU321B |
| EU322 | EU322A |
| | EU322B |
| EU323 | EU323A |
| | EU323B |
| EU324 | EU324A |
| | EU324B |
| EU325 | EU325A |
| | EU325B |
| EU424 | EU424A |
| | EU424B |
| EU425 | EU425A |
| | EU425B |
| EU426 | EU426A |
| | EU426B |
| EU427 | EU427A |
| | EU427B |
| EU428 | EU428A |
| | EU428B |
| EU429 | EU429A |
| | EU424B |
| EU430 | EU430A |
| | EU425B |
| EU431 | EU431A |
| | EU426B |
| EU432 | EU432A |
| | EU427B |
| EU433 | EU433A |
| | EU428B |

TABLE 3
| Summary abbreviations table | |
|---|---|
| Abbreviation | Meaning |
| mA, mU, mC, mG | 2'-O-Methyl RNA nucleotides |
| 2'-OMe | 2'-O-Methyl modification |
| fA, fU, fC, fG | 2' deoxy-2'-F RNA nucleotides |
| 2'-F | 2'-fluoro modification |
| (ps) | phosphorothioate |
| (ps2) | phosphorodithioate |
| (vp) | Vinyl-(E)-phosphonate |
| (vp)-mU | 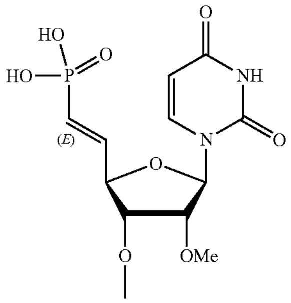 |
| (vp)-mU-phos | 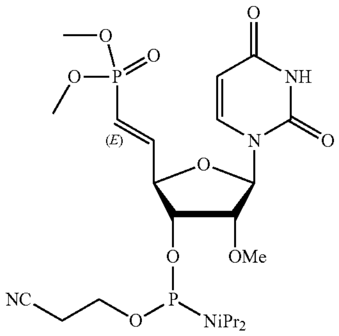 |
| ivA, ivC, ivU, ivG | inverted RNA (3'-3') nucleotides |
| ST23 | 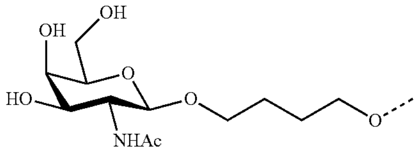 |
| ST23-phos | 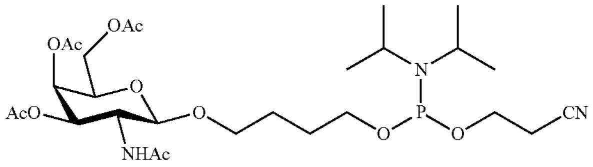 |
| ST43 (or C6XLT) | 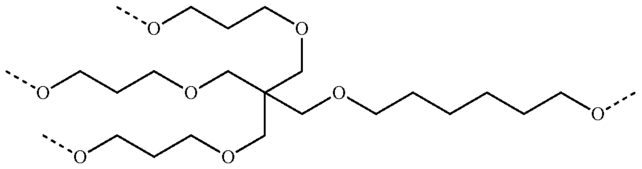 |
| ST43-phos (or C6XLT-phos) | 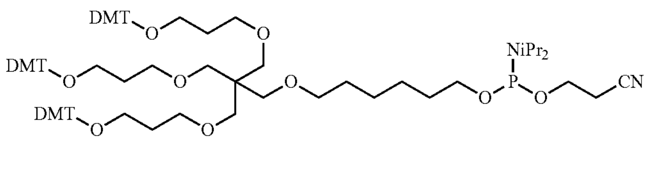 |

TABLE 3-continued
| Summary abbreviations table | |
|---|---|
| Abbreviation | Meaning |
| Ser(GN) (when at the end of a chain, one of the O --- is OH) | 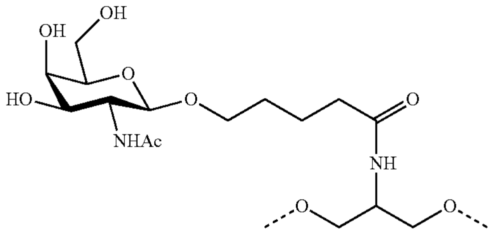 |
| [ST23(ps)]3 ST43(ps) | 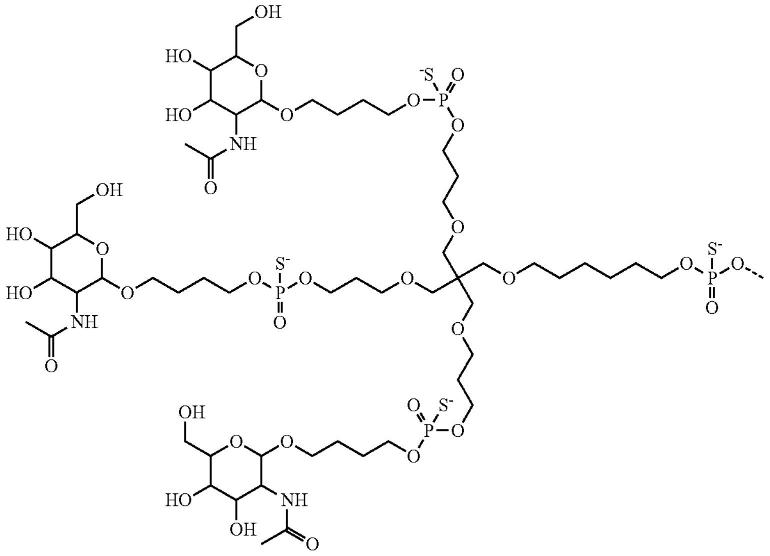 |
| [ST23]3 ST43 | 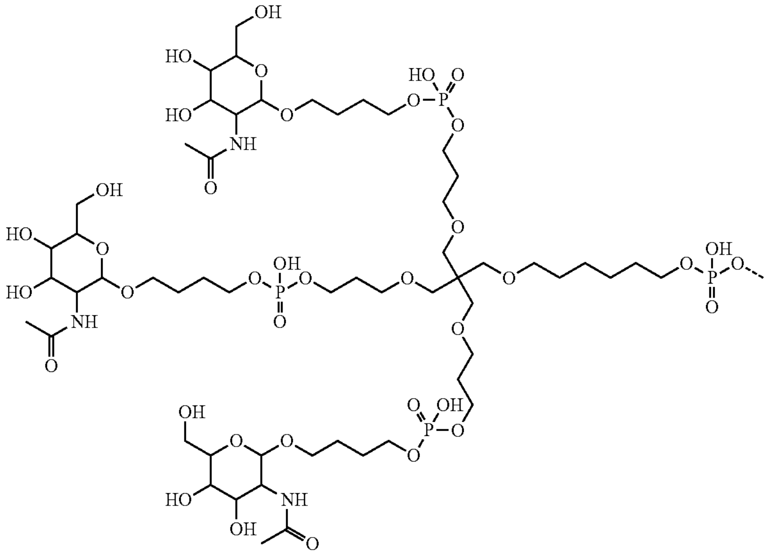 |

TABLE 3-continued

| Summary abbreviations table | |
|---|---|
| Abbreviation | Meaning |
| [ST23(ps)]3 ST41(ps) | 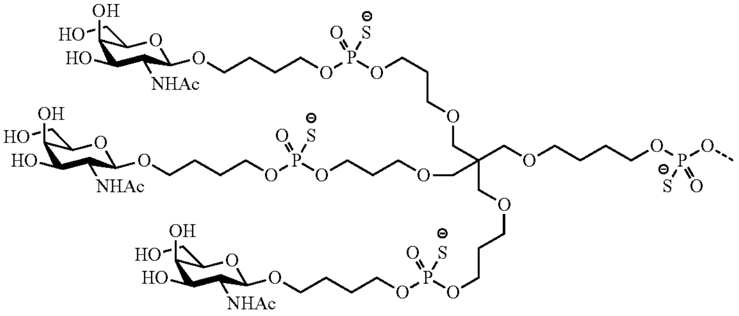 |
| [ST23]3 ST41 | 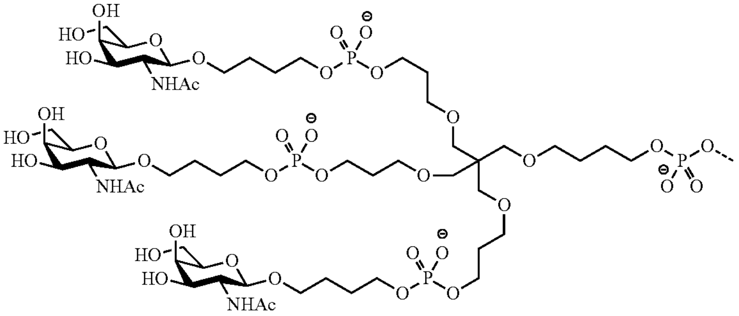 |

The abbreviations as shown in the above abbreviation table may be used herein. The list of abbreviations may not be exhaustive and further abbreviations and their meaning may be found throughout this document.

TABLE 4

Summary sequence table

| SEQ ID NO: | Name (A = 1$^{st}$ strand; B = 2$^{nd}$ strand) | Sequence 5'-3' | Unmodified sequence 5'-3' counterpart |
|---|---|---|---|
| 1 | EU200A | mU(ps)fC(ps)mGfAmAfGmUfAmUfUmCfCmGfCmGfUmA(ps)fC(ps)mG | UCGAAGUAUUCCGCGUACG |
| 2 | EU200B | mC(ps)mG(ps)mUmAmCmGfCfGfGmAmAmUmAmCmUmUmC(ps)mG(ps)mA | CGUACGCGGAAUACUUCGA |
| 3 | EU201A | mC(ps)fC(ps)mUfAmGfGmAfUmCfAmCfGmCfUmCfUmG(ps)fC(ps)mU | CCUAGGAUCACGCUCUGCU |
| 4 | EU201B | mA(ps)mG(ps)mCmAmGmAfGfCfGmUmGmAmUmCmCmUmA(ps)mG(ps)mG | AGCAGAGCGUGAUCCUAGG |
| 5 | EU202A | mG(ps)fA(ps)mCfUmUfGmUfUmGfCmAfGmCfUmCfGmC(ps)fC(ps)mA | GACUUGUUGCAGCUCGCCA |
| 6 | EU202B | mU(ps)mG(ps)mGmCmGmAfGfCfUmGmCmAmAmCmAmAmG(ps)mU(ps)mC | UGGCGAGCUGCAACAAGUC |
| 7 | EU203A | mC(ps)fA(ps)mCfGmAfCmUfUmGfUmUfGmCfAmGfCmU(ps)fC(ps)mG | CACGACUUGUUGCAGCUCG |
| 8 | EU203B | mC(ps)mG(ps)mAmGmCmUfGfCfAmAmCmAmAmGmUmCmG(ps)mU(ps)mG | CGAGCUGCAACAAGUCGUG |
| 9 | EU204A | mG(ps)fA(ps)mCfAmCfGmAfAmGfAmUfGmAfUmGfCmC(ps)fA(ps)mU | GACACGAAGAUGAUGCCAU |
| 10 | EU204B | mA(ps)mU(ps)mGmGmCmAfUfCfAmUmCmUmUmCmGmUmG(ps)mU(ps)mC | AUGGCAUCAUCUUCGUGUC |
| 11 | EU205A | mC(ps)fG(ps)mGfUmGfAmAfGmGfAmGfAmUfCmAfGmG(ps)fU(ps)mU | CGGUGAAGGAGAUCAGGUU |
| 12 | EU205B | mA(ps)mA(ps)mCmCmUmGfAfUfCmUmCmCmUmUmCmAmC(ps)mC(ps)mG | AACCUGAUCUCCUUCACCG |
| 13 | EU206A | mC(ps)fU(ps)mCfAmCfGmUfUmGfAmCfCmAfGmCfUmG(ps)fC(ps)mU | CUCACGUUGACCAGCUGCU |
| 14 | EU206B | mA(ps)mG(ps)mCmAmGmCfUfGfGmUmCmAmAmCmGmUmG(ps)mA(ps)mG | AGCAGCUGGUCAACGUGAG |
| 15 | EU207A | mG(ps)fG(ps)mCfUmCfCmUfCmCfAmCfCmAfUmGfAmA(ps)fG(ps)mA | GGCUCCUCCACCAUGAAGA |

TABLE 4-continued

Summary sequence table

| SEQ ID NO: | Name (A = 1st strand; B = 2nd strand) | Sequence 5'-3' | Unmodified sequence 5'-3' counterpart |
|---|---|---|---|
| 16 | EU207B | mU(ps)mC(ps)mUmUmCmAfUfGfGmUmGmGmAmGmGmAmG(ps)mC(ps)mC | UCUUCAUGGUGGAGGAGCC |
| 17 | EU208A | mG(ps)fA(ps)mAfAmAfUmAfUmGfCmCfCmGfAmCfAmG(ps)fC(ps)mA | GAAAAUAUGCCCGACAGCA |
| 18 | EU208B | mU(ps)mG(ps)mCmUmGmUfCfGfGmGmCmAmUmAmUmUmU(ps)mU(ps)mC | UGCUGUCGGGCAUAUUUUC |
| 19 | EU209A | mG(ps)fA(ps)mCfCmCfGmAfUmGfAmGfGmUfUmGfUmC(ps)fU(ps)mA | GACCCGAUGAGGUUGUCUA |
| 20 | EU209B | mU(ps)mA(ps)mGmAmCmAfAfCfCmUmCmAmUmCmGmGmG(ps)mU(ps)mC | UAGACAACCUCAUCGGGUC |
| 21 | EU210A | mG(ps)fG(ps)mAfCmCfCmGfAmUfGmAfGmGfUmUfGmU(ps)fC(ps)mU | GGACCCGAUGAGGUUGUCU |
| 22 | EU210B | mA(ps)mG(ps)mAmCmAmAfCfCfUmCmAmUmCmGmGmGmU(ps)mC(ps)mC | AGACAACCUCAUCGGGUCC |
| 23 | EU211A | mG(ps)fU(ps)mAfAmAfCmAfGmUfGmCfGmAfAmUfCmU(ps)fC(ps)mC | GUAAACAGUGCGAAUCUCC |
| 24 | EU211B | mG(ps)mG(ps)mAmGmAmUfUfCfGmCmAmCmUmGmUmUmU(ps)mA(ps)mC | GGAGAUUCGCACUGUUUAC |
| 25 | EU212A | mG(ps)fU(ps)mUfGmUfAmAfAmCfAmGfUmGfCmGfAmA(ps)fU(ps)mC | GUUGUAAACAGUGCGAAUC |
| 26 | EU212B | mG(ps)mA(ps)mUmUmCmGfCfAfCmUmGmUmUmUmAmCmA(ps)mA(ps)mC | GAUUCGCACUGUUUACAAC |
| 27 | EU213A | mC(ps)fA(ps)mUfUmAfUmAfGmGfGmCfUmCfUmGfUmC(ps)fA(ps)mC | CAUUAUAGGGCUCUGUCAC |
| 28 | EU213B | mG(ps)mU(ps)mGmAmCmAfGfAfGmCmCmCmUmAmUmAmA(ps)mU(ps)mG | GUGACAGAGCCCUAUAAUG |
| 29 | EU214A | mG(ps)fU(ps)mCfAmUfUmAfUmAfGmGfGmCfUmCfCmG(ps)fU(ps)mC | GUCAUUAUAGGGCUCCGUC |
| 30 | EU214B | mG(ps)mA(ps)mCmGmGmAfGfCfCmCmUmAmUmAmAmUmG(ps)mA(ps)mC | GACGGAGCCCUAUAAUGAC |
| 31 | EU215A | mG(ps)fA(ps)mUfCmAfUmAfUmUfGmAfGmCfUmCfCmU(ps)fC(ps)mU | GAUCAUAUUGAGCUCCUCU |
| 32 | EU215B | mA(ps)mG(ps)mAmGmGmAfGfCfUmCmAmAmUmAmUmGmA(ps)mU(ps)mC | AGAGGAGCUCAAUAUGAUC |
| 33 | EU216A | mG(ps)fC(ps)mUfGmGfGmUfCmAfUmGfAmUfAmUfCmC(ps)fU(ps)mC | GCUGGGUCAUGAUAUCCUC |
| 34 | EU216B | mG(ps)mA(ps)mGmGmAmUfAfUfCmAmUmGmAmCmCmCmA(ps)mG(ps)mC | GAGGAUAUCAUGACCCAGC |
| 35 | EU217A | mC(ps)fU(ps)mGfCmGfGmAfUmCfAmUfGmAfAmGfCmA(ps)fG(ps)mU | CUGCGGAUCAUGAAGCAGU |
| 36 | EU217B | mA(ps)mC(ps)mUmGmCmUfUfCfAmUmGmAmUmCmCmGmC(ps)mA(ps)mG | ACUGCUUCAUGAUCCGCAG |
| 37 | EU218A | mG(ps)fG(ps)mAfGmAfUmUfUmUfCmAfCmUfUmUfGmA(ps)fG(ps)mC | GGAGAUUUUCACUUUGAGC |
| 38 | EU218B | mG(ps)mC(ps)mUmCmAmAfAfGfUmGmAmAmAmAmUmCmU(ps)mC(ps)mC | GCUCAAAGUGAAAAUCUCC |
| 39 | EU219A | mC(ps)fU(ps)mUfAmUfUmUfCmGfGmGfUmGfUmAfCmA(ps)fG(ps)mG | CUUAUUUCGGGUGUACAGG |
| 40 | EU219B | mC(ps)mC(ps)mUmGmUmAfCfAfCmCmCmGmAmAmAmUmA(ps)mA(ps)mG | CCUGUACACCCGAAAUAAG |
| 41 | EU220A | mG(ps)fC(ps)mGfCmCfCmGfUmCfUmCfAmAfAmCfUmU(ps)fC(ps)mA | GCGCCCGUCUCAAACUUCA |
| 42 | EU220B | mU(ps)mG(ps)mAmAmGmUfUfUfGmAmGmAmCmGmGmGmC(ps)mG(ps)mC | UGAAGUUUGAGACGGGCGC |
| 43 | EU221A | mC(ps)fU(ps)mUfAmAfCmCfCmUfGmUfCmUfUmCfCmC(ps)fU(ps)mU | CUUAACCCUGUCUUCCCUU |
| 44 | EU221B | mA(ps)mA(ps)mGmGmGmAfAfGfAmCmAmGmGmGmUmUmA(ps)mA(ps)mG | AAGGGAAGACAGGGUUAAG |
| 45 | EU222A | mC(ps)fA(ps)mGfUmUfCmCfAmGfGmGfUmAfUmGfGmC(ps)fU(ps)mC | CAGUUCCAGGGUAUGGCUC |
| 46 | EU222B | mG(ps)mA(ps)mGmCmCmAfUfAfCmCmCmUmGmGmAmAmC(ps)mU(ps)mG | GAGCCAUACCCUGGAACUG |
| 47 | EU223A | mC(ps)fC(ps)mGfAmGfAmGfUmCfAmAfAmCfUmCfAmU(ps)fA(ps)mA | CCGAGAGUCAAACUCAUAA |
| 48 | EU223B | mU(ps)mU(ps)mAmUmGmAfGfUfUmUmGmAmCmUmCmUmC(ps)mG(ps)mG | UUAUGAGUUUGACUCUCGG |
| 49 | EU224A | mG(ps)fU(ps)mCfAmUfAmAfCmAfAmCfAmAfAmAfCmU(ps)fC(ps)mC | GUCAUAACAACAAAACUCC |
| 50 | EU224B | mG(ps)mG(ps)mAmGmUmUfUfUfGmUmUmGmUmUmAmUmG(ps)mA(ps)mC | GGAGUUUUGUUGUUAUGAC |
| 51 | EU225A | mC(ps)fC(ps)mAfUmAfUmAfUmCfGmUfUmUfAmGfCmA(ps)fA(ps)mA | CCAUAUAUCGUUUAGCAAA |

TABLE 4-continued

Summary sequence table

| SEQ ID NO: | Name (A = 1st strand; B = 2nd strand) | Sequence 5'-3' | Unmodified sequence 5'-3' counterpart |
|---|---|---|---|
| 52 | EU225B | mU(ps)mU(ps)mUmGmCmUfAfAfAmCmGmAmUmAmUmAmU(ps)mG(ps)mG | UUUGCUAAACGAUAUAUGG |
| 53 | EU226A | mA(ps)fG(ps)mAfUmGfAmUfGmCfCmAfUmCfCmGfGmG(ps)fU(ps)mU | AGAUGAUGCCAUCCGGGUU |
| 54 | EU226B | mA(ps)mA(ps)mCmCmCmGfGfAfUmGmGmCmAmUmCmAmU(ps)mC(ps)mU | AACCCGGAUGGCAUCAUCU |
| 55 | EU227A | mA(ps)fC(ps)mGfAmAfGmAfUmGfAmUfGmCfCmAfUmC(ps)fC(ps)mG | ACGAAGAUGAUGCCAUCCG |
| 56 | EU227B | mC(ps)mG(ps)mGmAmUmGfGfCfAmUmCmAmUmCmUmUmC(ps)mG(ps)mU | CGGAUGGCAUCAUCUUCGU |
| 57 | EU228A | mU(ps)fC(ps)mGfGmAfCmAfCmGfAmAfGmAfUmGfAmU(ps)fG(ps)mC | UCGGACACGAAGAUGAUGC |
| 58 | EU228B | mG(ps)mC(ps)mAmUmCmAfUfCfUmUmCmGmUmGmUmCmC(ps)mG(ps)mA | GCAUCAUCUUCGUGUCCGA |
| 59 | EU229A | mA(ps)fA(ps)mGfUmUfCmAfCmCfGmUfGmCfUmGfCmC(ps)fC(ps)mU | AAGUUCACCGUGCUGCCCU |
| 60 | EU229B | mA(ps)mG(ps)mGmGmCmAfGfCfAmCmGmGmUmGmAmAmC(ps)mU(ps)mU | AGGGCAGCACGGUGAACUU |
| 61 | EU230A | mU(ps)fC(ps)mGfGmUfGmAfAmGfGmAfGmAfUmCfAmG(ps)fG(ps)mU | UCGGUGAAGGAGAUCAGGU |
| 62 | EU230B | mA(ps)mC(ps)mCmUmGmAfUfCfUmCmCmUmUmCmAmCmC(ps)mG(ps)mA | ACCUGAUCUCCUUCACCGA |
| 63 | EU231A | mA(ps)fC(ps)mCfUmCfGmGfUmGfAmAfGmGfAmGfAmU(ps)fC(ps)mA | ACCUCGGUGAAGGAGAUCA |
| 64 | EU231B | mU(ps)mG(ps)mAmUmCmUfCfCfUmUmCmAmCmCmGmAmG(ps)mG(ps)mU | UGAUCUCCUUCACCGAGGU |
| 65 | EU232A | mA(ps)fG(ps)mGfAmAfCmUfUmGfGmUfAmAfUmCfAmC(ps)fC(ps)mA | AGGAACUUGGUAAUCACCA |
| 66 | EU232B | mU(ps)mG(ps)mGmUmGmAfUfUfAmCmCmAmAmGmUmUmC(ps)mC(ps)mU | UGGUGAUUACCAAGUUCCU |
| 67 | EU233A | mU(ps)fA(ps)mCfAmGfCmUfUmCfAmUfGmCfUmCfUmC(ps)fG(ps)mC | UACAGCUUCAUGCUCUCGC |
| 68 | EU233B | mG(ps)mC(ps)mGmAmGmAfGfCfAmUmGmAmAmGmCmUmG(ps)mU(ps)mA | GCGAGAGCAUGAAGCUGUA |
| 69 | EU234A | mA(ps)fU(ps)mGfAmAfGmAfGmCfAmGfUmGfAmGfUmCf(ps)C(ps)mU | AUGAAGAGCAGUGAGUCCU |
| 70 | EU234B | mA(ps)mG(ps)mGmAmCmUfCfAfCmUmGmCmUmCmUmUmC(ps)mA(ps)mU | AGGACUCACUGCUCUUCAU |
| 71 | EU235A | mA(ps)fG(ps)mGfUmAfGmUfUmGfCmCfCmUfUmGfCmG(ps)fC(ps)mC | AGGUAGUUGCCCUUGCGCC |
| 72 | EU235B | mG(ps)mG(ps)mCmGmCmAfAfGfGmGmCmAmAmCmUmAmC(ps)mC(ps)mU | GGCGCAAGGGCAACUACCU |
| 73 | EU236A | mU(ps)fG(ps)mUfGmAfGmGfGmAfGmGfUmGfUmUfGmA(ps)fC(ps)mC | UGUGAGGGAGGUGUUGACC |
| 74 | EU236B | mG(ps)mG(ps)mUmCmAmAfCfAfCmCmUmCmCmCmUmCmA(ps)mC(ps)mA | GGUCAACACCUCCCUCACA |
| 75 | EU237A | mA(ps)fU(ps)mUfGmUfGmAfGmGfGmAfGmGfUmGfUmU(ps)fG(ps)mA | AUUGUGAGGGAGGUGUUGA |
| 76 | EU237B | mU(ps)mC(ps)mAmAmCmAfCfCfUmCmCmCmUmCmAmCmA(ps)mA(ps)mU | UCAACACCUCCCUCACAAU |
| 77 | EU238A | mU(ps)fC(ps)mUfAmGfAmAfGmGfAmUfUmGfUmGfAmG(ps)fG(ps)mG | UCUAGAAGGAUUGUGAGGG |
| 78 | EU238B | mC(ps)mC(ps)mCmUmCmAfCfAfAmUmCmCmUmUmCmUmA(ps)mG(ps)mA | CCCUCACAAUCCUUCUAGA |
| 79 | EU239A | mU(ps)fU(ps)mGfUmCfUmAfGmAfAmGfGmAfUmUfGmU(ps)fG(ps)mA | UUGUCUAGAAGGAUUGUGA |
| 80 | EU239B | mU(ps)mC(ps)mAmCmAmAfUfCfCmUmUmCmUmAmGmAmC(ps)mA(ps)mA | UCACAAUCCUUCUAGACAA |
| 81 | EU240A | mU(ps)fG(ps)mAfGmGfUmUfGmUfCmUfAmGfAmAfGmG(ps)fA(ps)mU | UGAGGUUGUCUAGAAGGAU |
| 82 | EU240B | mA(ps)mU(ps)mCmCmUmUfCfUfAmGmAmCmAmAmCmCmU(ps)mC(ps)mA | AUCCUUCUAGACAACCUCA |
| 83 | EU241A | mA(ps)fU(ps)mCfUmCfCmCfCmAfAmAfGmAfUmGfAmC(ps)fA(ps)mA | AUCUCCCCAAAGAUGACAA |
| 84 | EU241B | mU(ps)mU(ps)mGmUmCmAfUfCfUmUmUmGmGmGmGmAmG(ps)mA(ps)mU | UUGUCAUCUUUGGGGAGAU |
| 85 | EU242A | mA(ps)fG(ps)mAfAmCfAmAfUmAfGmUfGmUfUmGfGmC(ps)fA(ps)mC | AGAACAAUAGUGUUGGCAC |
| 86 | EU242B | mG(ps)mU(ps)mGmCmCmAfAfCfAmCmUmAmUmUmGmUmU(ps)mC(ps)mU | GUGCCAACACUAUUGUUCU |
| 87 | EU243A | mA(ps)fG(ps)mCfAmUfAmAfAmGfAmAfUmUfUmGfGmU(ps)fG(ps)mA | AGCAUAAAGAAUUUGGUGA |

TABLE 4-continued

Summary sequence table

| SEQ ID NO: | Name (A = $1^{st}$ strand; B = $2^{nd}$ strand) | Sequence 5'-3' | Unmodified sequence 5'-3' counterpart |
|---|---|---|---|
| 88 | EU243B | mU(ps)mC(ps)mAmCmCmAfAfAfUmUmCmUmUmUmAmUmG(ps)mC(ps)mU | UCACCAAAUUCUUUAUGCU |
| 89 | EU244A | mU(ps)fU(ps)mGfUmAfAmAfCmAfGmUfGmCfGmAfAmU(ps)fC(ps)mU | UUGUAAACAGUGCGAAUCU |
| 90 | EU244B | mA(ps)mG(ps)mAmUmUmCfGfCfAmCmUmGmUmUmUmAmC(ps)mA(ps)mA | AGAUUCGCACUGUUUACAA |
| 91 | EU245A | mA(ps)fC(ps)mAfGmUfUmUfUmGfGmUfCmCfUmUfAmG(ps)fU(ps)mU | ACAGUUUUGGUCCUUAGUU |
| 92 | EU245B | mA(ps)mA(ps)mCmUmAmAfGfGfAmCmCmAmAmAmAmCmU(ps)mG(ps)mU | AACUAAGGACCAAAACUGU |
| 93 | EU246A | mA(ps)fU(ps)mAfUmCfCmUfCmUfAmCfAmGfUmUfUmU(ps)fG(ps)mG | AUAUCCUCUACAGUUUUGG |
| 94 | EU246B | mC(ps)mC(ps)mAmAmAmAfCfUfGmUmAmGmAmGmGmAmU(ps)mA(ps)mU | CCAAAACUGUAGAGGAUAU |
| 95 | EU247A | mA(ps)fU(ps)mAfUmCfUmAfCmAfAmUfAmUfUmGfGmA(ps)fC(ps)mU | AUAUCUACAAUAUUGGACU |
| 96 | EU247B | mA(ps)mG(ps)mUmCmCmAfAfUfAmUmUmGmUmAmGmAmU(ps)mA(ps)mU | AGUCCAAUAUUGUAGAUAU |
| 97 | EU248A | mA(ps)fA(ps)mUfAmUfCmUfAmCfAmAfUmAfUmUfGmG(ps)fA(ps)mC | AAUAUCUACAAUAUUGGAC |
| 98 | EU248B | mG(ps)mU(ps)mCmCmAmAfUfAfUmUmGmUmAmGmAmUmA(ps)mU(ps)mU | GUCCAAUAUUGUAGAUAUU |
| 99 | EU249A | mU(ps)fU(ps)mGfAmCfGmUfAmGfAmGfAmAfUmAfUmC(ps)fU(ps)mA | UUGACGUAGAGAAUAUCUA |
| 100 | EU249B | mU(ps)mA(ps)mGmAmUmAfUfUfCmUmCmUmAmCmGmUmC(ps)mA(ps)mA | UAGAUAUUCUCUACGUCAA |
| 101 | EU250A | mA(ps)fA(ps)mGfUmCfUmUfUmGfAmCfGmUfAmGfAmG(ps)fA(ps)mA | AAGUCUUUGACGUAGAGAA |
| 102 | EU250B | mU(ps)mU(ps)mCmUmCmUfAfCfGmUmCmAmAmAmGmAmC(ps)mU(ps)mU | UUCUCUACGUCAAAGACUU |
| 103 | EU251A | mU(ps)fA(ps)mGfAmAfGmCfGmAfGmUfGmAfUmAfGmU(ps)fC(ps)mU | UAGAAGCGAGUGAUAGUCU |
| 104 | EU251B | mA(ps)mG(ps)mAmCmUmAfUfCfAmCmUmCmGmCmUmUmC(ps)mU(ps)mA | AGACUAUCACUCGCUUCUA |
| 105 | EU252A | mU(ps)fU(ps)mGfAmAfGmGfCmAfGmAfGmAfAmGfUmC(ps)fA(ps)mC | UUGAAGGCAGAGAAGUCAC |
| 106 | EU252B | mG(ps)mU(ps)mGmAmCmUfUfCfUmCmUmGmCmCmUmUmC(ps)mA(ps)mA | GUGACUUCUCUGCCUUCAA |
| 107 | EU253A | mU(ps)fU(ps)mUfCmAfCmUfUmUfGmAfGmCfUmCfAmU(ps)fU(ps)mG | UUUCACUUUGAGCUCAUUG |
| 108 | EU253B | mC(ps)mA(ps)mAmUmGmAfGfCfUmCmAmAmAmGmUmGmA(ps)mA(ps)mA | CAAUGAGCUCAAAGUGAAA |
| 109 | EU254A | mA(ps)fA(ps)mCfUmGfGmUfUmGfCmUfGmCfUmGfCmC(ps)fU(ps)mG | AACUGGUUGCUGCUGCCUG |
| 110 | EU254B | mC(ps)mA(ps)mGmGmCmAfGfCfAmGmCmAmAmCmCmAmG(ps)mU(ps)mU | CAGGCAGCAGCAACCAGUU |
| 111 | EU255A | mU(ps)fU(ps)mGfAmGfAmAfGmAfGmUfUmGfUmGfGmU(ps)fC(ps)mU | UUGAGAAGAGUUGUGGUCU |
| 112 | EU255B | mA(ps)mG(ps)mAmCmCmAfCfAfAmCmUmCmUmUmCmUmC(ps)mA(ps)mA | AGACCACAACUCUUCUCAA |
| 113 | EU256A | mU(ps)fU(ps)mCfAmUfGmUfGmGfGmCfCmCfAmCfUmG(ps)fG(ps)mG | UUCAUGUGGGCCCACUGGG |
| 114 | EU256B | mC(ps)mC(ps)mCmAmGmUfGfGfGmCmCmCmAmCmAmUmG(ps)mA(ps)mA | CCCAGUGGGCCCACAUGAA |
| 115 | EU257A | mU(ps)fC(ps)mUfUmCfAmUfGmUfGmGfGmCfCmCfAmC(ps)fU(ps)mG | UCUUCAUGUGGGCCCACUG |
| 116 | EU257B | mC(ps)mA(ps)mGmUmGmGfGfCfCmCmAmCmAmUmGmAmA(ps)mG(ps)mA | CAGUGGGCCCACAUGAAGA |
| 117 | EU258A | mU(ps)fG(ps)mGfAmCfUmAfAmCfAmGfGmUfUmCfCmC(ps)fU(ps)mC | UGGACUAACAGGUUCCCUC |
| 118 | EU258B | mG(ps)mA(ps)mGmGmGmAfAfCfCmUmGmUmUmAmGmUmC(ps)mC(ps)mA | GAGGGAACCUGUUAGUCCA |
| 119 | EU259A | mU(ps)fU(ps)mCfCmUfUmAfAmCfCmCfUmGfUmCfUmU(ps)fC(ps)mC | UUCCUUAACCCUGUCUUCC |
| 120 | EU259B | mG(ps)mG(ps)mAmAmGmAfCfAfGmGmGmUmUmAmAmGmG(ps)mA(ps)mA | GGAAGACAGGGUUAAGGAA |
| 121 | EU260A | mA(ps)fG(ps)mUfUmCfCmUfUmAfAmCfCmCfUmGfUmC(ps)fU(ps)mU | AGUUCCUUAACCCUGUCUU |
| 122 | EU260B | mA(ps)mA(ps)mGmAmCmAfGfGfGmUmUmAmAmGmGmAmA(ps)mC(ps)mU | AAGACAGGGUUAAGGAACU |
| 123 | EU261A | mA(ps)fU(ps)mAfAmAfGmUfUmCfCmUfUmAfAmCfCmC(ps)fU(ps)mG | AUAAAGUUCCUUAACCCUG |

TABLE 4-continued

Summary sequence table

| SEQ ID NO: | Name (A = 1st strand; B = 2nd strand) | Sequence 5'-3' | Unmodified sequence 5'-3' counterpart |
|---|---|---|---|
| 124 | EU261B | mC(ps)mA(ps)mGmGmGmUfUfAfAmGmGmAmAmCmUmUmU(ps)mA(ps)mU | CAGGGUUAAGGAACUUUAU |
| 125 | EU262A | mA(ps)fA(ps)mAfUmAfAmAfGmUfUmCfCmUfUmAfAmC(ps)fC(ps)mC | AAAUAAAGUUCCUUAACCC |
| 126 | EU262B | mG(ps)mG(ps)mGmUmUmAfAfGfGmAmAmCmUmUmUmAmU(ps)mU(ps)mU | GGGUUAAGGAACUUUAUUU |
| 127 | EU263A | mU(ps)fA(ps)mCfAmUfAmAfAmGfUmUfCmCfUmUfAmA(ps)fC(ps)mC | UACAUAAAGUUCCUUAACC |
| 128 | EU263B | mG(ps)mG(ps)mUmUmAmAfGfGfAmAmCmUmUmUmAmUmG(ps)mU(ps)mA | GGUUAAGGAACUUUAUGUA |
| 129 | EU264A | mA(ps)fU(ps)mUfAmUfCmAfUmGfUmCfCmCfUmGfAmU(ps)fC(ps)mA | AUUAUCAUGUCCCUGAUCA |
| 130 | EU264B | mU(ps)mG(ps)mAmUmCmAfGfGfGmAmCmAmUmGmAmUmA(ps)mA(ps)mU | UGAUCAGGGACAUGAUAAU |
| 131 | EU265A | mA(ps)fU(ps)mAfAmAfGmAfAmCfCmUfGmCfUmUfCmC(ps)fG(ps)mU | AUAAAGAACCUGCUUCCGU |
| 132 | EU265B | mA(ps)mC(ps)mGmGmAmAfGfCfAmGmGmUmUmCmUmUmU(ps)mA(ps)mU | ACGGAAGCAGGUUCUUUAU |
| 133 | EU266A | mA(ps)fC(ps)mUfAmAfCmUfUmCfAmGfCmAfAmGfGmG(ps)fC(ps)mA | ACUAACUUCAGCAAGGGCA |
| 134 | EU266B | mU(ps)mG(ps)mCmCmCmUfUfGfCmUmGmAmAmGmUmUmA(ps)mG(ps)mU | UGCCCUUGCUGAAGUUAGU |
| 135 | EU267A | mU(ps)fG(ps)mGfUmGfCmAfAmGfAmCfAmAfUmCfCmC(ps)fU(ps)mG | UGGUGCAAGACAAUCCCUG |
| 136 | EU267B | mC(ps)mA(ps)mGmGmGmAfUfUfGmUmCmUmUmGmCmAmC(ps)mC(ps)mA | CAGGGAUUGUCUUGCACCA |
| 137 | EU268A | mA(ps)fU(ps)mAfAmAfUmAfGmGfAmGfUmCfAmUfCmU(ps)fG(ps)mC | AUAAAUAGGAGUCAUCUGC |
| 138 | EU268B | mG(ps)mC(ps)mAmGmAmUfGfAfCmUmCmCmUmAmUmUmU(ps)mA(ps)mU | GCAGAUGACUCCUAUUUAU |
| 139 | EU269A | mU(ps)fU(ps)mGfGmAfAmAfUmAfAmUfGmAfUmGfAmC(ps)fC(ps)mC | UUGGAAAUAAUGAUGACCC |
| 140 | EU269B | mG(ps)mG(ps)mGmUmCmAfUfCfAmUmUmAmUmUmUmCmC(ps)mA(ps)mA | GGGUCAUCAUUAUUUCCAA |
| 141 | EU270A | mA(ps)fA(ps)mAfCmUfCmAfUmAfAmCfAmAfUmGfCmC(ps)fA(ps)mA | AAACUCAUAACAAUGCCAA |
| 142 | EU270B | mU(ps)mU(ps)mGmGmCmAfUfUfGmUmUmAmUmGmAmGmU(ps)mU(ps)mU | UUGGCAUUGUUAUGAGUUU |
| 143 | EU271A | mA(ps)fU(ps)mUfAmUfCmAfUmUfGmUfUmUfUmGfUmG(ps)fA(ps)mC | AUUAUCAUUGUUUUGUGAC |
| 144 | EU271B | mG(ps)mU(ps)mCmAmCmAfAfAfAmCmAmAmUmGmAmUmA(ps)mA(ps)mU | GUCACAAAACAAUGAUAAU |
| 145 | EU272A | mU(ps)fU(ps)mGfUmUfUmAfGmCfAmAfAmUfAmUfUmA(ps)fU(ps)mC | UUGUUUAGCAAAUAUUAUC |
| 146 | EU272B | mG(ps)mA(ps)mUmAmAmUfAfUfUmUmGmCmUmAmAmAmC(ps)mA(ps)mA | GAUAAUAUUUGCUAAACAA |
| 147 | EU273A | mU(ps)fC(ps)mCfCmCfGmAfGmAfGmUfCmAfAmAfCmU(ps)fC(ps)mA | UCCCCGAGAGUCAAACUCA |
| 148 | EU273B | mU(ps)mG(ps)mAmGmUmUfUfGfAmCmUmCmUmCmGmGmG(ps)mG(ps)mA | UGAGUUUGACUCUCGGGGA |
| 149 | EU274A | mA(ps)fA(ps)mCfUmCfCmCfCmGfAmGfAmGfUmCfAmA(ps)fA(ps)mC | AACUCCCCGAGAGUCAAAC |
| 150 | EU274B | mG(ps)mU(ps)mUmUmGmAfCfUfCmUmCmGmGmGmGmAmG(ps)mU(ps)mU | GUUUGACUCUCGGGGAGUU |
| 151 | EU275A | mA(ps)fA(ps)mCfAmAfCmAfAmAfAmCfUmCfCmCfCmG(ps)fA(ps)mG | AACAACAAAACUCCCCGAG |
| 152 | EU275B | mC(ps)mU(ps)mCmGmGmGfGfAfGmUmUmUmUmGmUmUmG(ps)mU(ps)mU | CUCGGGGAGUUUUGUUGUU |
| 153 | EU276A | mA(ps)fU(ps)mAfAmCfAmAfCmAfAmAfAmCfUmCfCmC(ps)fC(ps)mG | AUAACAACAAAACUCCCCG |
| 154 | EU276B | mC(ps)mG(ps)mGmGmGmAfGfUfUmUmUmGmUmUmGmUmU(ps)mA(ps)mU | CGGGGAGUUUUGUUGUUAU |
| 155 | EU277A | mU(ps)fG(ps)mAfCmAfAmAfAmGfAmCfAmCfAmAfGmA(ps)fG(ps)mU | UGACAAAAGACACAAGAGU |
| 156 | EU277B | mA(ps)mC(ps)mUmCmUmUfGfUfGmUmCmUmUmUmUmGmU(ps)mC(ps)mA | ACUCUUGUGUCUUUUGUCA |
| 157 | EU278A | mU(ps)fU(ps)mGfUmUfUmUfGmUfGmAfCmAfAmAfAmG(ps)fA(ps)mC | UUGUUUUGUGACAAAAGAC |
| 158 | EU278B | mG(ps)mU(ps)mCmUmUmUfUfGfUmCmAmCmAmAmAmAmC(ps)mA(ps)mA | GUCUUUUGUCACAAAACAA |
| 159 | EU279A | mU(ps)fC(ps)mUfAmGfGmAfUmCfAmCfGmCfUmCfUmG(ps)fC(ps)mU | UCUAGGAUCACGCUCUGCU |

TABLE 4-continued

Summary sequence table

| SEQ ID NO: | Name (A = 1st strand; B = 2nd strand) | Sequence 5'-3' | Unmodified sequence 5'-3' counterpart |
|---|---|---|---|
| 160 | EU279B | mA(ps)mG(ps)mCmAmGmAfGfCfGmUmGmAmUmCmCmUmA(ps)mG(ps)mA | AGCAGAGCGUGAUCCUAGA |
| 161 | EU280A | mU(ps)fA(ps)mCfUmUfGmUfUmGfCmAfGmCfUmCfGmC(ps)fC(ps)mA | UACUUGUUGCAGCUCGCCA |
| 162 | EU280B | mU(ps)mG(ps)mGmCmGmAfGfCfUmGmCmAmAmCmAmAmG(ps)mU(ps)mA | UGGCGAGCUGCAACAAGUA |
| 163 | EU281A | mU(ps)fA(ps)mCfGmAfCmUfUmGfUmUfGmCfAmGfCmU(ps)fC(ps)mG | UACGACUUGUUGCAGCUCG |
| 164 | EU281B | mC(ps)mG(ps)mAmGmCmUfGfCfAmAmCmAmAmGmUmCmG(ps)mU(ps)mA | CGAGCUGCAACAAGUCGUA |
| 165 | EU282A | mU(ps)fA(ps)mCfAmCfGmAfAmGfAmUfGmAfUmGfCmC(ps)fA(ps)mU | UACACGAAGAUGAUGCCAU |
| 166 | EU282B | mA(ps)mU(ps)mGmGmCmAfUfCfAmUmCmUmUmCmGmUmG(ps)mU(ps)mA | AUGGCAUCAUCUUCGUGUA |
| 167 | EU283A | mU(ps)fG(ps)mGfUmGfAmAfGmGfAmGfAmUfCmAfGmG(ps)fU(ps)mU | UGGUGAAGGAGAUCAGGUU |
| 168 | EU283B | mA(ps)mA(ps)mCmCmUmGfAfUfCmUmCmCmUmUmCmAmC(ps)mC(ps)mA | AACCUGAUCUCCUUCACCA |
| 169 | EU284A | mU(ps)fU(ps)mCfAmCfGmUfUmGfAmCfCmAfGmCfUmG(ps)fC(ps)mU | UUCACGUUGACCAGCUGCU |
| 170 | EU284B | mA(ps)mG(ps)mCmAmGmCfUfGfGmUmCmAmAmCmGmUmG(ps)mA(ps)mA | AGCAGCUGGUCAACGUGAA |
| 171 | EU285A | mU(ps)fG(ps)mCfUmCfCmUfCmCfAmCfCmAfUmGfAmA(ps)fG(ps)mA | UGCUCCUCCACCAUGAAGA |
| 172 | EU285B | mU(ps)mC(ps)mUmUmCmAfUfGfGmUmGmGmAmGmGmAmG(ps)mC(ps)mA | UCUUCAUGGUGGAGGAGCA |
| 173 | EU286A | mU(ps)fA(ps)mAfAmAfUmAfUmGfCmCfCmGfAmCfAmG(ps)fC(ps)mA | UAAAAUAUGCCCGACAGCA |
| 174 | EU286B | mU(ps)mG(ps)mCmUmGmUfCfGfGmGmCmAmUmAmUmUmU(ps)mU(ps)mA | UGCUGUCGGGCAUAUUUUA |
| 175 | EU287A | mU(ps)fA(ps)mCfCmCfGmAfUmGfAmGfGmUfUmGfUmC(ps)fU(ps)mA | UACCCGAUGAGGUUGUCUA |
| 176 | EU287B | mU(ps)mA(ps)mGmAmCmAfAfCfCmUmCmAmUmCmGmGmG(ps)mU(ps)mA | UAGACAACCUCAUCGGGUA |
| 177 | EU288A | mU(ps)fG(ps)mAfCmCfCmGfAmUfGmAfGmGfUmUfGmU(ps)fC(ps)mU | UGACCCGAUGAGGUUGUCU |
| 178 | EU288B | mA(ps)mG(ps)mAmCmAmAfCfCfUmCmAmUmCmGmGmGmU(ps)mC(ps)mA | AGACAACCUCAUCGGGUCA |
| 179 | EU289A | mU(ps)fU(ps)mAfAmAfCmAfGmUfGmCfGmAfAmUfCmU(ps)fC(ps)mC | UUAAACAGUGCGAAUCUCC |
| 180 | EU289B | mG(ps)mG(ps)mAmGmAmUfUfCfGmCmAmCmUmGmUmUmU(ps)mA(ps)mA | GGAGAUUCGCACUGUUUAA |
| 181 | EU290A | mU(ps)fU(ps)mUfGmUfAmAfAmCfAmGfUmGfCmGfAmA(ps)fU(ps)mC | UUUGUAAACAGUGCGAAUC |
| 182 | EU290B | mG(ps)mA(ps)mUmUmCmGfCfAfCmUmGmUmUmUmAmCmA(ps)mA(ps)mA | GAUUCGCACUGUUUACAAA |
| 183 | EU291A | mU(ps)fA(ps)mUfUmAfUmAfGmGfGmCfUmCfUmGfUmC(ps)fA(ps)mC | UAUUAUAGGGCUCUGUCAC |
| 184 | EU291B | mG(ps)mU(ps)mGmAmCmAfGfAfGmCmCmCmUmAmUmAmA(ps)mU(ps)mA | GUGACAGAGCCCUAUAAUA |
| 185 | EU292A | mU(ps)fU(ps)mCfAmUfUmAfUmAfGmGfGmCfUmCfCmG(ps)fU(ps)mC | UUCAUUAUAGGGCUCCGUC |
| 186 | EU292B | mG(ps)mA(ps)mCmGmGmAfGfCfCmCmUmAmUmAmAmUmG(ps)mA(ps)mA | GACGGAGCCCUAUAAUGAA |
| 187 | EU293A | mU(ps)fA(ps)mUfCmAfUmAfUmUfGmAfGmCfUmCfCmU(ps)fC(ps)mU | UAUCAUAUUGAGCUCCUCU |
| 188 | EU293B | mA(ps)mG(ps)mAmGmGmAfGfCfUmCmAmAmUmAmUmGmA(ps)mU(ps)mA | AGAGGAGCUCAAUAUGAUA |
| 189 | EU294A | mU(ps)fC(ps)mUfGmGfGmUfCmAfUmGfAmUfAmUfCmC(ps)fU(ps)mC | UCUGGGUCAUGAUAUCCUC |
| 190 | EU294B | mG(ps)mA(ps)mGmGmAmUfAfUfCmAmUmGmAmCmCmCmA(ps)mG(ps)mA | GAGGAUAUCAUGACCCAGA |
| 191 | EU295A | mU(ps)fU(ps)mGfCmGfGmAfUmCfAmUfGmAfAmGfCmA(ps)fG(ps)mU | UUGCGGAUCAUGAAGCAGU |
| 192 | EU295B | mA(ps)mC(ps)mUmGmCmUfUfCfAmUmGmAmUmCmCmGmC(ps)mA(ps)mA | ACUGCUUCAUGAUCCGCAA |
| 193 | EU296A | mU(ps)fG(ps)mAfGmAfUmUfUmUfCmAfCmUfUmUfGmA(ps)fG(ps)mC | UGAGAUUUUCACUUUGAGC |
| 194 | EU296B | mG(ps)mC(ps)mUmCmAmAfAfGfUmGmAmAmAmAmUmCmU(ps)mC(ps)mA | GCUCAAAGUGAAAAUCUCA |
| 195 | EU297A | mU(ps)fU(ps)mUfAmUfUmUfCmGfGmGfUmGfUmAfCmA(ps)fG(ps)mG | UUUAUUUCGGGUGUACAGG |

TABLE 4-continued

Summary sequence table

| SEQ ID NO: | Name (A = 1st strand; B = 2nd strand) | Sequence 5'-3' | Unmodified sequence 5'-3' counterpart |
|---|---|---|---|
| 196 | EU297B | mC(ps)mC(ps)mUmGmUmAfCfAfCmCmCmGmAmAmAmUmA(ps)mA(ps)mA | CCUGUACACCCGAAAUAAA |
| 197 | EU298A | mU(ps)fC(ps)mGfCmCfCmGfUmCfUmCfAmAfAmCfUmU(ps)fC(ps)mA | UCGCCCGUCUCAAACUUCA |
| 198 | EU298B | mU(ps)mG(ps)mAmAmGmUfUfUfGmAmGmAmCmGmGmGmC(ps)mG(ps)mA | UGAAGUUUGAGACGGGCGA |
| 199 | EU299A | mU(ps)fU(ps)mUfAmAfCmCfCmUfGmUfCmUfUmCfCmC(ps)fU(ps)mU | UUUAACCCUGUCUUCCCUU |
| 200 | EU299B | mA(ps)mA(ps)mGmGmGmAfAfGfAmCmAmGmGmGmUmUmA(ps)mA(ps)mA | AAGGGAAGACAGGGUUAAA |
| 201 | EU300A | mU(ps)fA(ps)mGfUmUfCmCfAmGfGmGfUmAfUmGfGmC(ps)fU(ps)mC | UAGUUCCAGGGUAUGGCUC |
| 202 | EU300B | mG(ps)mA(ps)mGmCmCmAfUfAfCmCmCmUmGmGmAmAmC(ps)mU(ps)mA | GAGCCAUACCCUGGAACUA |
| 203 | EU301A | mU(ps)fC(ps)mGfAmGfAmGfUmCfAmAfAmCfUmCfAmU(ps)fA(ps)mA | UCGAGAGUCAAACUCAUAA |
| 204 | EU301B | mU(ps)mU(ps)mAmUmGmAfGfUfUmUmGmAmCmUmCmUmC(ps)mG(ps)mA | UUAUGAGUUUGACUCUCGA |
| 205 | EU302A | mU(ps)fU(ps)mCfAmUfAmAfCmAfAmCfAmAfAmAfCmU(ps)fC(ps)mC | UUCAUAACAACAAAACUCC |
| 206 | EU302B | mG(ps)mG(ps)mAmGmUmUfUfUfGmUmUmGmUmUmAmUmG(ps)mA(ps)mA | GGAGUUUUGUUGUUAUGAA |
| 207 | EU303A | mU(ps)fC(ps)mAfUmAfUmAfUmCfGmUfUmUfAmGfCmA(ps)fA(ps)mA | UCAUAUAUCGUUUAGCAAA |
| 208 | EU303B | mU(ps)mU(ps)mUmGmCmUfAfAfAmCmGmAmUmAmUmAmU(ps)mG(ps)mA | UUUGCUAAACGAUAUAUGA |
| 209 | EU400A | mU(ps)fC(ps)mGfAmAfGmUfAmUfUmCfCmGfCmGfUmA(ps)fC(ps)mG | UCGAAGUAUUCCGCGUACG |
| 210 | EU400B | [ST23(ps)]3ST43(ps)mCmGmUmAmCmGfCfGfGmAmAmUmAmCmUmUmC(ps)mG(ps)mA | CGUACGCGGAAUACUUCGA |
| 211 | EU401A | (vp)mUfAmCfGmAfCmUfUmGfUmUfGmCfAmGfCmU(ps)fC(ps)mG | UACGACUUGUUGCAGCUCG |
| 212 | EU401B | [ST23(ps)]3ST43(ps)mCmGmAmGmCmUfGfCfAmAmCmAmAmGmUmCmG(ps)mU(ps)mG | CGAGCUGCAACAAGUCGUG |
| 213 | EU402A | (vp)mUfGmAfGmAfUmUfUmUfCmAfCmUfUmUfGmA(ps)fG(ps)mC | UGAGAUUUUCACUUUGAGC |
| 214 | EU402B | [ST23(ps)]3ST43(ps)mGmCmUmCmAmAfAfGfUmGmAmAmAmAmUmCmU(ps)mC(ps)mC | GCUCAAAGUGAAAAUCUCC |
| 215 | EU403A | (vp)mUfCmGfAmGfAmGfUmCfAmAfAmCfUmCfAmU(ps)fA(ps)mA | UCGAGAGUCAAACUCAUAA |
| 216 | EU403B | [ST23(ps)]3ST43(ps)mUmUmAmUmGmAfGfUfUmUmGmAmCmUmCmUmC(ps)mG(ps)mG | UUAUGAGUUUGACUCUCGG |
| 217 | EU404A | (vp)mUfUmCfAmUfAmAfCmAfAmCfAmAfAmAfCmU(ps)fC(ps)mC | UUCAUAACAACAAAACUCC |
| 218 | EU404B | [ST23(ps)]3ST43(ps)mGmGmAmGmUmUfUfUfGmUmUmGmUmUmAmUmG(ps)mA(ps)mC | GGAGUUUUGUUGUUAUGAC |
| 219 | EU405A | (vp)mUfCmGfGmAfCmAfCmGfAmAfGmAfUmGfAmU(ps)fG(ps)mC | UCGGACACGAAGAUGAUGC |
| 220 | EU405B | [ST23(ps)]3ST43(ps)mGmCmAmUmCmAfUfCfUmUmCmGmUmGmUmCmC(ps)mG(ps)mA | GCAUCAUCUUCGUGUCCGA |
| 221 | EU406A | (vp)mUfUmAfUmCfUmAfCmAfAmUfAmUfUmGfGmA(ps)fC(ps)mU | UUAUCUACAAUAUUGGACU |
| 222 | EU406B | [ST23(ps)]3ST43(ps)mAmGmUmCmCmAfAfUfAmUmUmGmUmAmGmAmU(ps)mA(ps)mU | AGUCCAAUAUUGUAGAUAU |
| 223 | EU407A | (vp)mUfAmUfAmUfCmUfAmCfAmAfUmAfUmUfGmG(ps)fA(ps)mC | UAUAUCUACAAUAUUGGAC |
| 224 | EU407B | [ST23(ps)]3ST43(ps)mGmUmCmCmAmAfUfAfUmUmGmUmAmGmAmUmA(ps)mU(ps)mU | GUCCAAUAUUGUAGAUAUU |
| 225 | EU408A | (vp)mUfAmGfAmAfGmCfGmAfGmUfGmAfUmAfGmU(ps)fC(ps)mU | UAGAAGCGAGUGAUAGUCU |
| 226 | EU408B | [ST23(ps)]3ST43(ps)mAmGmAmCmUmAfUfCfAmCmUmCmGmCmUmUmC(ps)mU(ps)mA | AGACUAUCACUCGCUUCUA |
| 227 | EU409A | (vp)mUfGmGfAmCfUmAfAmCfAmGfGmUfUmCfCmC(ps)fU(ps)mC | UGGACUAACAGGUUCCCUC |
| 228 | EU409B | [ST23(ps)]3ST43(ps)mGmAmGmGmGmAfAfCfCmUmGmUmUmAmGmUmC(ps)mC(ps)mA | GAGGGAACCUGUUAGUCCA |
| 229 | EU410A | (vp)mUfUmAfAmAfGmUfUmCfCmUfUmAfAmCfCmC(ps)fU(ps)mG | UUAAAGUUCCUUAACCCUG |
| 230 | EU410B | [ST23(ps)]3ST43(ps)mCmAmGmGmGmUfUfAfAmGmGmAmAmCmUmUmU(ps)mA(ps)mU | CAGGGUUAAGGAACUUUAU |
| 231 | EU411A | (vp)mUfAmCfAmUfAmAfAmGfUmUfCmCfUmUfAmA(ps)fC(ps)mC | UACAUAAAGUUCCUUAACC |

TABLE 4-continued

Summary sequence table

| SEQ ID NO: | Name (A = 1st strand; B = 2nd strand) | Sequence 5'-3' | Unmodified sequence 5'-3' counterpart |
|---|---|---|---|
| 232 | EU411B | [ST23(ps)]3ST43(ps)mGmGmUmUmAmAfGfGfAmAmCmUmUmUmAmUmG(ps)mU(ps)mA | GGUUAAGGAACUUUAUGUA |
| 233 | EU412A | (vp)mUfUmUfAmUfCmAfUmUfGmUfUmUfUmGfUmG(ps)fA(ps)mC | UUUAUCAUUGUUUUGUGAC |
| 234 | EU412B | [ST23(ps)]3ST43(ps)mGmUmCmAmCmAfAfAfAmCmAmAmUmGmAmUmA(ps)mA(ps)mU | GUCACAAAACAAUGAUAAU |
| 235 | EU413A | (vp)mUfUmAfAmCfAmAfCmAfAmAfAmCfUmCfCmC(ps)fC(ps)mG | UUAACAACAAAACUCCCCG |
| 236 | EU413B | [ST23(ps)]3ST43(ps)mCmGmGmGmGmAfGfUfUmUmUmGmUmUmGmUmU(ps)mA(ps)mU | CGGGGAGUUUUGUUGUUAU |
| 237 | EU414A | (vp)mUfGmAfCmAfAmAfAmGfAmCfAmCfAmAfGmA(ps)fG(ps)mU | UGACAAAAGACACAAGAGU |
| 238 | EU414B | [ST23(ps)]3ST43(ps)mAmCmUmCmUmUfGfUfGmUmCmUmUmUmUmGmU(ps)mC(ps)mA | ACUCUUGUGUCUUUUGUCA |
| 239 | EU201Aun | CCUAGGAUCACGCUCUGCU | CCUAGGAUCACGCUCUGCU |
| 240 | EU201Bun | AGCAGAGCGUGAUCCUAGG | AGCAGAGCGUGAUCCUAGG |
| 241 | EU202Aun | GACUUGUUGCAGCUCGCCA | GACUUGUUGCAGCUCGCCA |
| 242 | EU202Bun | UGGCGAGCUGCAACAAGUC | UGGCGAGCUGCAACAAGUC |
| 243 | EU203Aun | CACGACUUGUUGCAGCUCG | CACGACUUGUUGCAGCUCG |
| 244 | EU203Bun | CGAGCUGCAACAAGUCGUG | CGAGCUGCAACAAGUCGUG |
| 245 | EU204Aun | GACACGAAGAUGAUGCCAU | GACACGAAGAUGAUGCCAU |
| 246 | EU204Bun | AUGGCAUCAUCUUCGUGUC | AUGGCAUCAUCUUCGUGUC |
| 247 | EU205Aun | CGGUGAAGGAGAUCAGGUU | CGGUGAAGGAGAUCAGGUU |
| 248 | EU205Bun | AACCUGAUCUCCUUCACCG | AACCUGAUCUCCUUCACCG |
| 249 | EU209Aun | GACCCGAUGAGGUUGUCUA | GACCCGAUGAGGUUGUCUA |
| 250 | EU209Bun | UAGACAACCUCAUCGGGUC | UAGACAACCUCAUCGGGUC |
| 251 | EU210Aun | GGACCCGAUGAGGUUGUCU | GGACCCGAUGAGGUUGUCU |
| 252 | EU210Bun | AGACAACCUCAUCGGGUCC | AGACAACCUCAUCGGGUCC |
| 253 | EU211Aun | GUAAACAGUGCGAAUCUCC | GUAAACAGUGCGAAUCUCC |
| 254 | EU211Bun | GGAGAUUCGCACUGUUUAC | GGAGAUUCGCACUGUUUAC |
| 255 | EU212Aun | GUUGUAAACAGUGCGAAUC | GUUGUAAACAGUGCGAAUC |
| 256 | EU212Bun | GAUUCGCACUGUUUACAAC | GAUUCGCACUGUUUACAAC |
| 257 | EU213Aun | CAUUAUAGGGCUCUGUCAC | CAUUAUAGGGCUCUGUCAC |
| 258 | EU213Bun | GUGACAGAGCCCUAUAAUG | GUGACAGAGCCCUAUAAUG |
| 259 | EU214Aun | GUCAUUAUAGGGCUCCGUC | GUCAUUAUAGGGCUCCGUC |
| 260 | EU214Bun | GACGGAGCCCUAUAAUGAC | GACGGAGCCCUAUAAUGAC |
| 261 | EU215Aun | GAUCAUAUUGAGCUCCUCU | GAUCAUAUUGAGCUCCUCU |
| 262 | EU215Bun | AGAGGAGCUCAAUAUGAUC | AGAGGAGCUCAAUAUGAUC |
| 263 | EU216Aun | GCUGGGUCAUGAUAUCCUC | GCUGGGUCAUGAUAUCCUC |
| 264 | EU216Bun | GAGGAUAUCAUGACCCAGC | GAGGAUAUCAUGACCCAGC |
| 265 | EU217Aun | CUGCGGAUCAUGAAGCAGU | CUGCGGAUCAUGAAGCAGU |
| 266 | EU217Bun | ACUGCUUCAUGAUCCGCAG | ACUGCUUCAUGAUCCGCAG |
| 267 | EU218Aun | GGAGAUUUUCACUUUGAGC | GGAGAUUUUCACUUUGAGC |

TABLE 4-continued

Summary sequence table

| SEQ ID NO: | Name (A = 1st strand; B = 2nd strand) | Sequence 5'-3' | Unmodified sequence 5'-3' counterpart |
|---|---|---|---|
| 268 | EU218Bun | GCUCAAAGUGAAAAUCUCC | GCUCAAAGUGAAAAUCUCC |
| 269 | EU219Aun | CUUAUUUCGGGUGUACAGG | CUUAUUUCGGGUGUACAGG |
| 270 | EU219Bun | CCUGUACACCCGAAAUAAG | CCUGUACACCCGAAAUAAG |
| 271 | EU220Aun | GCGCCCGUCUCAAACUUCA | GCGCCCGUCUCAAACUUCA |
| 272 | EU220Bun | UGAAGUUUGAGACGGGCGC | UGAAGUUUGAGACGGGCGC |
| 273 | EU221Aun | CUUAACCCUGUCUUCCCUU | CUUAACCCUGUCUUCCCUU |
| 274 | EU221Bun | AAGGGAAGACAGGGUUAAG | AAGGGAAGACAGGGUUAAG |
| 275 | EU222Aun | CAGUUCCAGGGUAUGGCUC | CAGUUCCAGGGUAUGGCUC |
| 276 | EU222Bun | GAGCCAUACCCUGGAACUG | GAGCCAUACCCUGGAACUG |
| 277 | EU223Aun | CCGAGAGUCAAACUCAUAA | CCGAGAGUCAAACUCAUAA |
| 278 | EU223Bun | UUAUGAGUUUGACUCUCGG | UUAUGAGUUUGACUCUCGG |
| 279 | EU224Aun | GUCAUAACAACAAAACUCC | GUCAUAACAACAAAACUCC |
| 280 | EU224Bun | GGAGUUUUGUUGUUAUGAC | GGAGUUUUGUUGUUAUGAC |
| 281 | EU225Aun | CCAUAUAUCGUUUAGCAAA | CCAUAUAUCGUUUAGCAAA |
| 282 | EU225Bun | UUUGCUAAACGAUAUAUGG | UUUGCUAAACGAUAUAUGG |
| 283 | EU226Aun | AGAUGAUGCCAUCCGGGUU | AGAUGAUGCCAUCCGGGUU |
| 284 | EU226Bun | AACCCGGAUGGCAUCAUCU | AACCCGGAUGGCAUCAUCU |
| 285 | EU227Aun | ACGAAGAUGAUGCCAUCCG | ACGAAGAUGAUGCCAUCCG |
| 286 | EU227Bun | CGGAUGGCAUCAUCUUCGU | CGGAUGGCAUCAUCUUCGU |
| 287 | EU228Aun | UCGGACACGAAGAUGAUGC | UCGGACACGAAGAUGAUGC |
| 288 | EU228Bun | GCAUCAUCUUCGUGUCCGA | GCAUCAUCUUCGUGUCCGA |
| 289 | EU230Aun | UCGGUGAAGGAGAUCAGGU | UCGGUGAAGGAGAUCAGGU |
| 290 | EU230Bun | ACCUGAUCUCCUUCACCGA | ACCUGAUCUCCUUCACCGA |
| 291 | EU231Aun | ACCUCGGUGAAGGAGAUCA | ACCUCGGUGAAGGAGAUCA |
| 292 | EU231Bun | UGAUCUCCUUCACCGAGGU | UGAUCUCCUUCACCGAGGU |
| 293 | EU233Aun | UACAGCUUCAUGCUCUCGC | UACAGCUUCAUGCUCUCGC |
| 294 | EU233Bun | GCGAGAGCAUGAAGCUGUA | GCGAGAGCAUGAAGCUGUA |
| 295 | EU234Aun | AUGAAGAGCAGUGAGUCCU | AUGAAGAGCAGUGAGUCCU |
| 296 | EU234Bun | AGGACUCACUGCUCUUCAU | AGGACUCACUGCUCUUCAU |
| 297 | EU235Aun | AGGUAGUUGCCCUUGCGCC | AGGUAGUUGCCCUUGCGCC |
| 298 | EU235Bun | GGCGCAAGGGCAACUACCU | GGCGCAAGGGCAACUACCU |
| 299 | EU236Aun | UGUGAGGGAGGUGUUGACC | UGUGAGGGAGGUGUUGACC |
| 300 | EU236Bun | GGUCAACACCUCCCUCACA | GGUCAACACCUCCCUCACA |
| 301 | EU237Aun | AUUGUGAGGGAGGUGUUGA | AUUGUGAGGGAGGUGUUGA |
| 302 | EU237Bun | UCAACACCUCCCUCACAAU | UCAACACCUCCCUCACAAU |
| 303 | EU238Aun | UCUAGAAGGAUUGUGAGGG | UCUAGAAGGAUUGUGAGGG |

TABLE 4-continued

Summary sequence table

| SEQ ID NO: | Name (A = 1st strand; B = 2nd strand) | Sequence 5'-3' | Unmodified sequence 5'-3' counterpart |
|---|---|---|---|
| 304 | EU238Bun | CCCUCACAAUCCUUCUAGA | CCCUCACAAUCCUUCUAGA |
| 305 | EU239Aun | UUGUCUAGAAGGAUUGUGA | UUGUCUAGAAGGAUUGUGA |
| 306 | EU239Bun | UCACAAUCCUUCUAGACAA | UCACAAUCCUUCUAGACAA |
| 307 | EU240Aun | UGAGGUUGUCUAGAAGGAU | UGAGGUUGUCUAGAAGGAU |
| 308 | EU240Bun | AUCCUUCUAGACAACCUCA | AUCCUUCUAGACAACCUCA |
| 309 | EU241Aun | AUCUCCCCAAAGAUGACAA | AUCUCCCCAAAGAUGACAA |
| 310 | EU241Bun | UUGUCAUCUUUGGGGAGAU | UUGUCAUCUUUGGGGAGAU |
| 311 | EU243Aun | AGCAUAAAGAAUUUGGUGA | AGCAUAAAGAAUUUGGUGA |
| 312 | EU243Bun | UCACCAAAUUCUUUAUGCU | UCACCAAAUUCUUUAUGCU |
| 313 | EU245Aun | ACAGUUUUGGUCCUUAGUU | ACAGUUUUGGUCCUUAGUU |
| 314 | EU245Bun | AACUAAGGACCAAAACUGU | AACUAAGGACCAAAACUGU |
| 315 | EU246Aun | AUAUCCUCUACAGUUUUGG | AUAUCCUCUACAGUUUUGG |
| 316 | EU246Bun | CCAAAACUGUAGAGGAUAU | CCAAAACUGUAGAGGAUAU |
| 317 | EU247Aun | AUAUCUACAAUAUUGGACU | AUAUCUACAAUAUUGGACU |
| 318 | EU247Bun | AGUCCAAUAUUGUAGAUAU | AGUCCAAUAUUGUAGAUAU |
| 319 | EU248Aun | AAUAUCUACAAUAUUGGAC | AAUAUCUACAAUAUUGGAC |
| 320 | EU248Bun | GUCCAAUAUUGUAGAUAUU | GUCCAAUAUUGUAGAUAUU |
| 321 | EU249Aun | UUGACGUAGAGAAUAUCUA | UUGACGUAGAGAAUAUCUA |
| 322 | EU249Bun | UAGAUAUUCUCUACGUCAA | UAGAUAUUCUCUACGUCAA |
| 323 | EU250Aun | AAGUCUUUGACGUAGAGAA | AAGUCUUUGACGUAGAGAA |
| 324 | EU250Bun | UUCUCUACGUCAAAGACUU | UUCUCUACGUCAAAGACUU |
| 325 | EU251Aun | UAGAAGCGAGUGAUAGUCU | UAGAAGCGAGUGAUAGUCU |
| 326 | EU251Bun | AGACUAUCACUCGCUUCUA | AGACUAUCACUCGCUUCUA |
| 327 | EU252Aun | UUGAAGGCAGAGAAGUCAC | UUGAAGGCAGAGAAGUCAC |
| 328 | EU252Bun | GUGACUUCUCUGCCUUCAA | GUGACUUCUCUGCCUUCAA |
| 329 | EU253Aun | UUUCACUUUGAGCUCAUUG | UUUCACUUUGAGCUCAUUG |
| 330 | EU253Bun | CAAUGAGCUCAAAGUGAAA | CAAUGAGCUCAAAGUGAAA |
| 331 | EU254Aun | AACUGGUUGCUGCUGCCUG | AACUGGUUGCUGCUGCCUG |
| 332 | EU254Bun | CAGGCAGCAGCAACCAGUU | CAGGCAGCAGCAACCAGUU |
| 333 | EU255Aun | UUGAGAAGAGUUGUGGUCU | UUGAGAAGAGUUGUGGUCU |
| 334 | EU255Bun | AGACCACAACUCUUCUCAA | AGACCACAACUCUUCUCAA |
| 335 | EU256Aun | UUCAUGUGGGCCCACUGGG | UUCAUGUGGGCCCACUGGG |
| 336 | EU256Bun | CCCAGUGGGCCCACAUGAA | CCCAGUGGGCCCACAUGAA |
| 337 | EU257Aun | UCUUCAUGUGGGCCCACUG | UCUUCAUGUGGGCCCACUG |
| 338 | EU257Bun | CAGUGGGCCCACAUGAAGA | CAGUGGGCCCACAUGAAGA |
| 339 | EU258Aun | UGGACUAACAGGUUCCCUC | UGGACUAACAGGUUCCCUC |

TABLE 4-continued

Summary sequence table

| SEQ ID NO: | Name (A = 1st strand; B = 2nd strand) | Sequence 5'-3' | Unmodified sequence 5'-3' counterpart |
|---|---|---|---|
| 340 | EU258Bun | GAGGGAACCUGUUAGUCCA | GAGGGAACCUGUUAGUCCA |
| 341 | EU259Aun | UUCCUUAACCCUGUCUUCC | UUCCUUAACCCUGUCUUCC |
| 342 | EU259Bun | GGAAGACAGGGUUAAGGAA | GGAAGACAGGGUUAAGGAA |
| 343 | EU260Aun | AGUUCCUUAACCCUGUCUU | AGUUCCUUAACCCUGUCUU |
| 344 | EU260Bun | AAGACAGGGUUAAGGAACU | AAGACAGGGUUAAGGAACU |
| 345 | EU261Aun | AUAAAGUUCCUUAACCCUG | AUAAAGUUCCUUAACCCUG |
| 346 | EU261Bun | CAGGGUUAAGGAACUUUAU | CAGGGUUAAGGAACUUUAU |
| 347 | EU262Aun | AAAUAAAGUUCCUUAACCC | AAAUAAAGUUCCUUAACCC |
| 348 | EU262Bun | GGGUUAAGGAACUUUAUUU | GGGUUAAGGAACUUUAUUU |
| 349 | EU263Aun | UACAUAAAGUUCCUUAACC | UACAUAAAGUUCCUUAACC |
| 350 | EU263Bun | GGUUAAGGAACUUUAUGUA | GGUUAAGGAACUUUAUGUA |
| 351 | EU264Aun | AUUAUCAUGUCCCUGAUCA | AUUAUCAUGUCCCUGAUCA |
| 352 | EU264Bun | UGAUCAGGGACAUGAUAAU | UGAUCAGGGACAUGAUAAU |
| 353 | EU265Aun | AUAAAGAACCUGCUUCCGU | AUAAAGAACCUGCUUCCGU |
| 354 | EU265Bun | ACGGAAGCAGGUUCUUUAU | ACGGAAGCAGGUUCUUUAU |
| 355 | EU266Aun | ACUAACUUCAGCAAGGGCA | ACUAACUUCAGCAAGGGCA |
| 356 | EU266Bun | UGCCCUUGCUGAAGUUAGU | UGCCCUUGCUGAAGUUAGU |
| 357 | EU267Aun | UGGUGCAAGACAAUCCCUG | UGGUGCAAGACAAUCCCUG |
| 358 | EU267Bun | CAGGGAUUGUCUUGCACCA | CAGGGAUUGUCUUGCACCA |
| 359 | EU269Aun | UUGGAAAUAAUGAUGACCC | UUGGAAAUAAUGAUGACCC |
| 360 | EU269Bun | GGGUCAUCAUUAUUUCCAA | GGGUCAUCAUUAUUUCCAA |
| 361 | EU271Aun | AUUAUCAUUGUUUUGUGAC | AUUAUCAUUGUUUUGUGAC |
| 362 | EU271Bun | GUCACAAAACAAUGAUAAU | GUCACAAAACAAUGAUAAU |
| 363 | EU273Aun | UCCCCGAGAGUCAAACUCA | UCCCCGAGAGUCAAACUCA |
| 364 | EU273Bun | UGAGUUUGACUCUCGGGGA | UGAGUUUGACUCUCGGGGA |
| 365 | EU274Aun | AACUCCCCGAGAGUCAAAC | AACUCCCCGAGAGUCAAAC |
| 366 | EU274Bun | GUUUGACUCUCGGGGAGUU | GUUUGACUCUCGGGGAGUU |
| 367 | EU275Aun | AACAACAAAACUCCCCGAG | AACAACAAAACUCCCCGAG |
| 368 | EU275Bun | CUCGGGGAGUUUUGUUGUU | CUCGGGGAGUUUUGUUGUU |
| 369 | EU276Aun | AUAACAACAAAACUCCCCG | AUAACAACAAAACUCCCCG |
| 370 | EU276Bun | CGGGGAGUUUUGUUGUUAU | CGGGGAGUUUUGUUGUUAU |
| 371 | EU277Aun | UGACAAAAGACACAAGAGU | UGACAAAAGACACAAGAGU |
| 372 | EU277Bun | ACUCUUGUGUCUUUUGUCA | ACUCUUGUGUCUUUUGUCA |
| 373 | EU279Aun | UCUAGGAUCACGCUCUGCU | UCUAGGAUCACGCUCUGCU |
| 374 | EU279Bun | AGCAGAGCGUGAUCCUAGA | AGCAGAGCGUGAUCCUAGA |
| 375 | EU280Aun | UACUUGUUGCAGCUCGCCA | UACUUGUUGCAGCUCGCCA |

TABLE 4-continued

Summary sequence table

| SEQ ID NO: | Name (A = $1^{st}$ strand; B = $2^{nd}$ strand) | Sequence 5'-3' | Unmodified sequence 5'-3' counterpart |
|---|---|---|---|
| 376 | EU280Bun | UGGCGAGCUGCAACAAGUA | UGGCGAGCUGCAACAAGUA |
| 377 | EU281Aun | UACGACUUGUUGCAGCUCG | UACGACUUGUUGCAGCUCG |
| 378 | EU281Bun | CGAGCUGCAACAAGUCGUA | CGAGCUGCAACAAGUCGUA |
| 379 | EU282Aun | UACACGAAGAUGAUGCCAU | UACACGAAGAUGAUGCCAU |
| 380 | EU282Bun | AUGGCAUCAUCUUCGUGUA | AUGGCAUCAUCUUCGUGUA |
| 381 | EU283Aun | UGGUGAAGGAGAUCAGGUU | UGGUGAAGGAGAUCAGGUU |
| 382 | EU283Bun | AACCUGAUCUCCUUCACCA | AACCUGAUCUCCUUCACCA |
| 383 | EU284Aun | UUCACGUUGACCAGCUGCU | UUCACGUUGACCAGCUGCU |
| 384 | EU284Bun | AGCAGCUGGUCAACGUGAA | AGCAGCUGGUCAACGUGAA |
| 385 | EU287Aun | UACCCGAUGAGGUUGUCUA | UACCCGAUGAGGUUGUCUA |
| 386 | EU287Bun | UAGACAACCUCAUCGGGUA | UAGACAACCUCAUCGGGUA |
| 387 | EU289Aun | UUAAACAGUGCGAAUCUCC | UUAAACAGUGCGAAUCUCC |
| 388 | EU289Bun | GGAGAUUCGCACUGUUUAA | GGAGAUUCGCACUGUUUAA |
| 389 | EU290Aun | UUUGUAAACAGUGCGAAUC | UUUGUAAACAGUGCGAAUC |
| 390 | EU290Bun | GAUUCGCACUGUUUACAAA | GAUUCGCACUGUUUACAAA |
| 391 | EU291Aun | UAUUAUAGGGCUCUGUCAC | UAUUAUAGGGCUCUGUCAC |
| 392 | EU291Bun | GUGACAGAGCCCUAUAAUA | GUGACAGAGCCCUAUAAUA |
| 393 | EU292Aun | UUCAUUAUAGGGCUCCGUC | UUCAUUAUAGGGCUCCGUC |
| 394 | EU292Bun | GACGGAGCCCUAUAAUGAA | GACGGAGCCCUAUAAUGAA |
| 395 | EU293Aun | UAUCAUAUUGAGCUCCUCU | UAUCAUAUUGAGCUCCUCU |
| 396 | EU293Bun | AGAGGAGCUCAAUAUGAUA | AGAGGAGCUCAAUAUGAUA |
| 397 | EU294Aun | UCUGGGUCAUGAUAUCCUC | UCUGGGUCAUGAUAUCCUC |
| 398 | EU294Bun | GAGGAUAUCAUGACCCAGA | GAGGAUAUCAUGACCCAGA |
| 399 | EU295Aun | UUGCGGAUCAUGAAGCAGU | UUGCGGAUCAUGAAGCAGU |
| 400 | EU295Bun | ACUGCUUCAUGAUCCGCAA | ACUGCUUCAUGAUCCGCAA |
| 401 | EU296Aun | UGAGAUUUUCACUUUGAGC | UGAGAUUUUCACUUUGAGC |
| 402 | EU296Bun | GCUCAAAGUGAAAAUCUCA | GCUCAAAGUGAAAAUCUCA |
| 403 | EU297Aun | UUUAUUUCGGGUGUACAGG | UUUAUUUCGGGUGUACAGG |
| 404 | EU297Bun | CCUGUACACCCGAAAUAAA | CCUGUACACCCGAAAUAAA |
| 405 | EU298Aun | UCGCCCGUCUCAAACUUCA | UCGCCCGUCUCAAACUUCA |
| 406 | EU298Bun | UGAAGUUUGAGACGGGCGA | UGAAGUUUGAGACGGGCGA |
| 407 | EU299Aun | UUUAACCCUGUCUUCCCUU | UUUAACCCUGUCUUCCCUU |
| 408 | EU299Bun | AAGGGAAGACAGGGUUAAA | AAGGGAAGACAGGGUUAAA |
| 409 | EU300Aun | UAGUUCCAGGGUAUGGCUC | UAGUUCCAGGGUAUGGCUC |
| 410 | EU300Bun | GAGCCAUACCCUGGAACUA | GAGCCAUACCCUGGAACUA |
| 411 | EU301Aun | UCGAGAGUCAAACUCAUAA | UCGAGAGUCAAACUCAUAA |

TABLE 4-continued

| Summary sequence table | | | |
|---|---|---|---|
| SEQ ID NO: | Name (A = 1st strand; B = 2nd strand) | Sequence 5'-3' | Unmodified sequence 5'-3' counterpart |
| 412 | EU301Bun | UUAUGAGUUUGACUCUCGA | UUAUGAGUUUGACUCUCGA |
| 413 | EU302Aun | UUCAUAACAACAAAACUCC | UUCAUAACAACAAAACUCC |
| 414 | EU302Bun | GGAGUUUUGUUGUUAUGAA | GGAGUUUUGUUGUUAUGAA |
| 415 | EU303Aun | UCAUAUAUCGUUUAGCAAA | UCAUAUAUCGUUUAGCAAA |
| 416 | EU303Bun | UUUGCUAAACGAUAUAUGA | UUUGCUAAACGAUAUAUGA |
| 417 | EU406Aun | UUAUCUACAAUAUUGGACU | UUAUCUACAAUAUUGGACU |
| 418 | EU407Aun | UAUAUCUACAAUAUUGGAC | UAUAUCUACAAUAUUGGAC |
| 419 | EU410Aun | UUAAAGUUCCUUAACCCUG | UUAAAGUUCCUUAACCCUG |
| 420 | EU412Aun | UUUAUCAUUGUUUUGUGAC | UUUAUCAUUGUUUUGUGAC |
| 421 | EU413Aun | UUAACAACAAAACUCCCCG | UUAACAACAAAACUCCCCG |
| 422 | Mm n1 A | GAACUGAGAAGGAGAGAAA | GAACUGAGAAGGAGAGAAA |
| 423 | Mm n1 B | UUUCUCUCCUUCUCAGUUC | UUUCUCUCCUUCUCAGUUC |
| 424 | Mm n2 A | GGGAGAAGCUGAUGGAGAU | GGGAGAAGCUGAUGGAGAU |
| 425 | Mm n2 B | AUCUCCAUCAGCUUCUCCC | AUCUCCAUCAGCUUCUCCC |
| 426 | Mm n3 A | CAAUGAACUCAAAGUGAAA | CAAUGAACUCAAAGUGAAA |
| 427 | Mm n3 B | UUUCACUUUGAGUUCAUUG | UUUCACUUUGAGUUCAUUG |
| 428 | Mm n4 A | CGGGAGAAGCUGAUGGAGA | CGGGAGAAGCUGAUGGAGA |
| 429 | Mm n4 B | UCUCCAUCAGCUUCUCCCG | UCUCCAUCAGCUUCUCCCG |
| 430 | Mm n5 A | UGGUGAAGGAGGAGUUAAA | UGGUGAAGGAGGAGUUAAA |
| 431 | Mm n5 B | UUUAACUCCUCCUUCACCA | UUUAACUCCUCCUUCACCA |
| 432 | Mm n6 A | GUGAAGGAGGAGUUAAAUA | GUGAAGGAGGAGUUAAAUA |
| 433 | Mn n6 B | UAUUUAACUCCUCCUUCAC | UAUUUAACUCCUCCUUCAC |
| 434 | Hs n1 A | GAUUGUAGCUGUUAAGAAA | GAUUGUAGCUGUUAAGAAA |
| 435 | Hs n1 B | UUUCUUAACAGCUACAAUC | UUUCUUAACAGCUACAAUC |
| 436 | Hs n2 A | AGGCAGAGCUCAAGGGAGA | AGGCAGAGCUCAAGGGAGA |
| 437 | Hs n2 B | UCUCCCUUGAGCUCUGCCU | UCUCCCUUGAGCUCUGCCU |
| 438 | Hs n3 A | GAUUGUAGCUGUUAAGAAA | GAUUGUAGCUGUUAAGAAA |
| 439 | Hs n3 B | UUUCUUAACAGCUACAAUC | UUUCUUAACAGCUACAAUC |
| 440 | Hs n4 A | CGAUGGAGAUUUAGAGUAU | CGAUGGAGAUUUAGAGUAU |
| 441 | Hs n4 B | AUACUCUAAAUCUCCAUCG | AUACUCUAAAUCUCCAUCG |
| 442 | Hs n5 A | GCUGAUGAGUGCAAAGAAA | GCUGAUGAGUGCAAAGAAA |
| 443 | Hs n5 B | UUUCUUUGCACUCAUCAGC | UUUCUUUGCACUCAUCAGC |
| 444 | Hs n6 A | CCUCAAAGCUCAAGGCACA | CCUCAAAGCUCAAGGCACA |
| 445 | Hs n6 B | UGUGCCUUGAGCUUUGAGG | UGUGCCUUGAGCUUUGAGG |
| 446 | Hs n7 A | UCCAUUAUCUCCGACAUGG | UCCAUUAUCUCCGACAUGG |
| 447 | Hs n7 B | CCAUGUCGGAGAUAAUGGA | CCAUGUCGGAGAUAAUGGA |

TABLE 4-continued

| Summary sequence table | | | |
|---|---|---|---|
| SEQ ID NO: | Name (A = 1st strand; B = 2nd strand) | Sequence 5'-3' | Unmodified sequence 5'-3' counterpart |
| 448 | Hs n7 Ao | UCCAUUAUCUCCGACAUGGTG | UCCAUUAUCUCCGACAUGGTG |
| 449 | Hs n7 Bo | CCAUGUCGGAGAUAAUGGATT | CCAUGUCGGAGAUAAUGGATT |
| 450 | Mm n7 A | UUUGGUGAGAACAAUAGUG | UUUGGUGAGAACAAUAGUG |
| 451 | Mm n7 B | CACUAUUGUUCUCACCAAA | CACUAUUGUUCUCACCAAA |
| 452 | Mm n7 Ao | UUUGGUGAGAACAAUAGUG | UUUGGUGAGAACAAUAGUGTT |
| 453 | Mm n7 Bo | CACUAUUGUUCUCACCAAA | CACUAUUGUUCUCACCAAATT |
| 454 | CNNM4 shRNA | UCUCUGCCUUCAAGGAUGCGGACAAUGAG | UCUCUGCCUUCAAGGAUGCGGACAAUGAG |
| 455 | EU415B | [ST23(ps)]3ST41(ps)mGmGmAmGmUmUfUfUfGmUmUmGmUmUmAmUmG(ps)mA(ps)mC | GGAGUUUUGUUGUUAUGAC |
| 456 | EU416A | mG(ps)fU(ps)mCfAmUfAmAfCmAfAmCfAmAfAmAfCmU(ps)fC(ps)mC | GUCAUAACAACAAAACUCC |
| 457 | EU418A | (vp)mUfUmCfAmUfAmAfCmAfAmCfAmAfAmAfCmUfC(ps2)mC | UUCAUAACAACAAAACUCC |
| 458 | EU418B | [ST23]3ST41mG(ps2)mGmAmGmUmUfUfUfGmUmUmGmUmUmAmUmGmA(ps2)mC | GGAGUUUUGUUGUUAUGAC |
| 459 | EU419B | [ST23]3ST41mG(ps2)mGmAmGmUmUfUfUfGmUmUmGmUmUmAmUmGmA(ps2)mA | GGAGUUUUGUUGUUAUGAA |
| 460 | EU420B | [ST23(ps)]3ST41(ps)mAmCmUmCmUmUfGfUfGmUmCmUmUmUmUmGmU(ps)mC(ps)mA | ACUCUUGUGUCUUUUGUCA |
| 461 | EU422A | (vp)mUfGmAfCmAfAmAfAmGfAmCfAmCfAmAfGmAfG(ps2)mU | UGACAAAAGACACAAGAGU |
| 462 | EU422B | [ST23]3ST41mA(ps2)mCmUmCmUmUfGfUfGmUmCmUmUmUmUmGmUmC(ps2)mA | ACUCUUGUGUCUUUUGUCA |
| 463 | EU423A | mU(ps)fC(ps)mGfAmAfGmUfAmUfUmCfCmGfCmGfUmA(ps)fC(ps)mG | UCGAAGUAUUCCGCGUACG |
| 464 | EU423B | [ST23(ps)]3ST41(ps)fCmGfUmAfCmGfCmGfGmAfAmUfAmCfUmUfC(ps)mG(ps)fA | CGUACGCGGAAUACUUCGA |
| 465 | EU304A | mU(ps)fC(ps)mCfUmUfGmUfCmCfGmUfCmCfAmCfUmU(ps)fC(ps)mA | UCCUUGUCCGUCCACUUCA |
| 466 | EU304B | mU(ps)mG(ps)mAmAmGmUfGfGfAmCmGmGmAmCmAmAmG(ps)mG(ps)mA | UGAAGUGGACGGACAAGGA |
| 467 | EU305A | mC(ps)fA(ps)mAfUmCfUmUfGmCfGmGfGmCfAmUfAmG(ps)fC(ps)mG | CAAUCUUGCGGGCAUAGCG |
| 468 | EU305B | mC(ps)mG(ps)mCmUmAmUfGfCfCmCmGmCmAmAmGmAmU(ps)mU(ps)mG | CGCUAUGCCCGCAAGAUUG |
| 469 | EU306A | mU(ps)fA(ps)mAfAmCfAmGfUmGfCmGfAmAfUmCfUmC(ps)fC(ps)mU | UAAACAGUGCGAAUCUCCU |
| 470 | EU306B | mA(ps)mG(ps)mGmAmGmAfUfUfCmGmCmAmCmUmGmUmU(ps)mU(ps)mA | AGGAGAUUCGCACUGUUUA |
| 471 | EU307A | mA(ps)fU(ps)mCfAmUfAmUfUmGfAmGfCmUfCmCfUmC(ps)fU(ps)mU | AUCAUAUUGAGCUCCUCUU |
| 472 | EU307B | mA(ps)mA(ps)mGmAmGmGfAfGfCmUmCmAmAmUmAmUmG(ps)mA(ps)mU | AAGAGGAGCUCAAUAUGAU |
| 473 | EU308A | mU(ps)fU(ps)mGfUmUfCmUfUmCfUmCfAmGfAmCfAmC(ps)fC(ps)mC | UUGUUCUUCUCAGACACCC |
| 474 | EU308B | mG(ps)mG(ps)mGmUmGmUfCfUfGmAmGmAmAmGmAmAmC(ps)mA(ps)mA | GGGUGUCUGAGAAGAACAA |
| 475 | EU309A | mG(ps)fA(ps)mGfAmUfUmUfUmCfAmCfUmUfUmGfAmG(ps)fC(ps)mU | GAGAUUUUCACUUUGAGCU |
| 476 | EU309B | mA(ps)mG(ps)mCmUmCmAfAfAfGmUmGmAmAmAmAmUmC(ps)mU(ps)mC | AGCUCAAAGUGAAAAUCUC |
| 477 | EU310A | mA(ps)fA(ps)mUfGmAfCmAfUmCfUmGfGmGfUmAfCmU(ps)fU(ps)mG | AAUGACAUCUGGGUACUUG |
| 478 | EU310B | mC(ps)mA(ps)mAmGmUmAfCfCfCmAmGmAmUmGmUmCmA(ps)mU(ps)mU | CAAGUACCCAGAUGUCAUU |
| 479 | EU311A | mU(ps)fU(ps)mAfUmUfUmCfGmGfGmUfGmUfAmCfAmG(ps)fG(ps)mU | UUAUUUCGGGUGUACAGGU |
| 480 | EU311B | mA(ps)mC(ps)mCmUmGmUfAfCfAmCmCmCmGmAmAmAmU(ps)mA(ps)mA | ACCUGUACACCCGAAAUAA |

TABLE 4-continued

Summary sequence table

| SEQ ID NO: | Name (A = 1st strand; B = 2nd strand) | Sequence 5'-3' | Unmodified sequence 5'-3' counterpart |
|---|---|---|---|
| 481 | EU312A | mU(ps)fU(ps)mGfAmUfGmUfAmCfUmGfCmAfAmGfUmC(ps)fC(ps)mA | UUGAUGUACUGCAAGUCCA |
| 482 | EU312B | mU(ps)mG(ps)mGmAmCmUfUfGfCmAmGmUmAmCmAmUmC(ps)mA(ps)mA | UGGACUUGCAGUACAUCAA |
| 483 | EU313A | mG(ps)fA(ps)mCfUmUfCmUfCmGfGmCfCmAfAmGfUmU(ps)fC(ps)mU | GACUUCUCGGCCAAGUUCU |
| 484 | EU313B | mA(ps)mG(ps)mAmAmCmUfUfGfGmCmCmGmAmGmAmAmG(ps)mU(ps)mC | AGAACUUGGCCGAGAAGUC |
| 485 | EU314A | mA(ps)fA(ps)mCfAmGfGmUfUmCfCmCfUmCfUmCfUmU(ps)fC(ps)mA | AACAGGUUCCCUCUCUUCA |
| 486 | EU314B | mU(ps)mG(ps)mAmAmGmAfGfAfGmGmGmAmAmCmCmUmG(ps)mU(ps)mU | UGAAGAGAGGGAACCUGUU |
| 487 | EU315A | mA(ps)fC(ps)mAfUmAfAmAfGmAfAmCfCmUfGmCfUmU(ps)fC(ps)mC | ACAUAAAGAACCUGCUUCC |
| 488 | EU315B | mG(ps)mG(ps)mAmAmGmCfAfGfGmUmUmCmUmUmUmAmU(ps)mG(ps)mU | GGAAGCAGGUUCUUUAUGU |
| 489 | EU316A | mU(ps)fA(ps)mCfUmAfCmUfAmAfCmUfUmCfAmGfCmA(ps)fA(ps)mG | UACUACUAACUUCAGCAAG |
| 490 | EU316B | mC(ps)mU(ps)mUmGmCmUfGfAfAmGmUmUmAmGmUmAmG(ps)mU(ps)mA | CUUGCUGAAGUUAGUAGUA |
| 491 | EU317A | mA(ps)fG(ps)mUfAmCfUmAfCmUfAmAfCmUfUmCfAmG(ps)fC(ps)mA | AGUACUACUAACUUCAGCA |
| 492 | EU317B | mU(ps)mG(ps)mCmUmGmAfAfGfUmUmAmGmUmAmGmUmA(ps)mC(ps)mU | UGCUGAAGUUAGUAGUACU |
| 493 | EU318A | mA(ps)fG(ps)mUfUmCfUmAfUmGfGmCfUmAfGmGfAmG(ps)fA(ps)mC | AGUUCUAUGGCUAGGAGAC |
| 494 | EU318B | mG(ps)mU(ps)mCmUmCmCfUfAfGmCmCmAmUmAmGmAmA(ps)mC(ps)mU | GUCUCCUAGCCAUAGAACU |
| 495 | EU319A | mA(ps)fA(ps)mCfAmAfAmAfGmUfCmUfGmGfUmGfUmC(ps)fU(ps)mU | AACAAAAGUCUGGUGUCUU |
| 496 | EU319B | mA(ps)mA(ps)mGmAmCmAfCfCfAmGmAmCmUmUmUmUmG(ps)mU(ps)mU | AAGACACCAGACUUUUGUU |
| 497 | EU320A | mG(ps)fA(ps)mAfAmUfAmAfUmGfAmUfGmAfCmCfCmU(ps)fC(ps)mU | GAAAUAAUGAUGACCCUCU |
| 498 | EU320B | mA(ps)mG(ps)mAmGmGmGfUfCfAmUmCmAmUmUmAmUmU(ps)mU(ps)mc | AGAGGGUCAUCAUUAUUUC |
| 499 | EU321A | mA(ps)fA(ps)mAfAmUfAmAfAmUfAmCfGmGfCmGfGmC(ps)fU(ps)mG | AAAAUAAAUACGGCGGCUG |
| 500 | EU321B | mC(ps)mA(ps)mGmCmCmGfCfCfGmUmAmUmUmUmAmUmU(ps)mU(ps)mU | CAGCCGCCGUAUUUAUUUU |
| 501 | EU322A | mA(ps)fU(ps)mGfCmAfAmAfAmUfAmAfAmUfAmCfGmG(ps)fC(ps)mG | AUGCAAAAUAAAUACGGCG |
| 502 | EU322B | mC(ps)mG(ps)mCmCmGmUfAfUfUmUmAmUmUmUmUmGmC(ps)mA(ps)mU | CGCCGUAUUUAUUUUGCAU |
| 503 | EU323A | mA(ps)fG(ps)mUfCmAfAmAfCmUfCmAfUmAfAmCfGmC(ps)fC(ps)mA | AGUCAAACUCAUAACGCCA |
| 504 | EU323B | mU(ps)mG(ps)mGmCmGmUfUfAfUmGmAmGmUmUmUmGmA(ps)mC(ps)mU | UGGCGUUAUGAGUUUGACU |
| 505 | EU324A | mC(ps)fA(ps)mUfAmAfCmAfAmCfAmAfAmAfCmUfCmC(ps)fC(ps)mC | CAUAACAACAAAACUCCCC |
| 506 | EU324B | mG(ps)mG(ps)mGmGmAmGfUfUfUmUmGmUmUmGmUmUmA(ps)mU(ps)mG | GGGGAGUUUUGUUGUUAUG |
| 507 | EU325A | mA(ps)fG(ps)mUfCmAfUmAfAmCfAmAfCmAfAmAfAmC(ps)fU(ps)mC | AGUCAUAACAACAAAACUC |
| 508 | EU325B | mG(ps)mA(ps)mGmUmUmUfUfGfUmUmGmUmUmAmUmGmA(ps)mC(ps)mU | GAGUUUUGUUGUUAUGACU |
| 509 | EU424A | mA(ps)fA(ps)mUfGmAfCmAfUmCfUmGfGmGfUmAfCmU(ps)fU(ps)mG | AAUGACAUCUGGGUACUUG |
| 510 | EU424B | [ST23(ps)]3ST41(ps)mCmAmAmGmUmAfCfCfCmAmGmAmUmGmUmCmA(ps)mU(ps)mU | CAAGUACCCAGAUGUCAUU |
| 511 | EU425A | mA(ps)fA(ps)mCfAmGfGmUfUmCfCmCfUmCfUmCfUmU(ps)fC(ps)mA | AACAGGUUCCCUCUCUUCA |
| 512 | EU425B | [ST23(ps)]3ST41(ps)mUmGmAmAmGmAfGfAfGmGmGmAmAmCmCmUmG(ps)mU(ps)mU | UGAAGAGAGGGAACCUGUU |
| 513 | EU426A | mA(ps)fA(ps)mAfAmUfAmAfAmUfAmCfGmGfCmGfGmC(ps)fU(ps)mG | AAAAUAAAUACGGCGGCUG |
| 514 | EU426B | [ST23(ps)]3ST41(ps)mCmAmGmCmCmGfCfCfGmUmAmUmUmUmAmUmU(ps)mU(ps)mU | CAGCCGCCGUAUUUAUUUU |
| 515 | EU427A | mA(ps)fU(ps)mGfCmAfAmAfAmUfAmAfAmUfAmCfGmG(ps)fC(ps)mG | AUGCAAAAUAAAUACGGCG |
| 516 | EU427B | [ST23(ps)]3ST41(ps)mCmGmCmCmGmUfAfUfUmUmAmUmUmUmUmGmC(ps)mA(ps)mU | CGCCGUAUUUAUUUUGCAU |

TABLE 4-continued

Summary sequence table

| SEQ ID NO: | Name (A = 1st strand; B = 2nd strand) | Sequence 5'-3' | Unmodified sequence 5'-3' counterpart |
|---|---|---|---|
| 517 | EU428A | mA(ps)fG(ps)mUfCmAfUmAfAmCfAmAfCmAfAmAfAmC(ps)fU(ps)mC | AGUCAUAACAACAAAACUC |
| 518 | EU428B | [ST23(ps)]3ST41(ps)mGmAmGmUmUmUfUfGfUmUmGmUmUmAmUmGmA(ps)mC(ps)mU | GAGUUUUGUUGUUAUGACU |
| 519 | EU429A | (vp)mUfAmUfGmAfCmAfUmCfUmGfGmGfUmAfCmU(ps)fU(ps)mG | UAUGACAUCUGGGUACUUG |
| 520 | EU430A | (vp)mUfAmCfAmGfGmUfUmCfCmCfUmCfUmCfUmU(ps)fC(ps)mA | UACAGGUUCCCUCUCUUCA |
| 521 | EU431A | (vp)mUfAmAfAmUfAmAfAmUfAmCfGmGfCmGfGmC(ps)fU(ps)mG | UAAAUAAAUACGGCGGCUG |
| 522 | EU432A | (vp)mUfUmGfCmAfAmAfAmUfAmAfAmUfAmCfGmG(ps)fC(ps)mG | UUGCAAAAUAAAUACGGCG |
| 523 | EU433A | (vp)mUfGmUfCmAfUmAfAmCfAmAfCmAfAmAfAmC(ps)fU(ps)mC | UGUCAUAACAACAAAACUC |
| 524 | EU304Aun | UCCUUGUCCGUCCACUUCA | UCCUUGUCCGUCCACUUCA |
| 525 | EU304Bun | UGAAGUGGACGGACAAGGA | UGAAGUGGACGGACAAGGA |
| 526 | EU307Aun | AUCAUAUUGAGCUCCUCUU | AUCAUAUUGAGCUCCUCUU |
| 527 | EU307Bun | AAGAGGAGCUCAAUAUGAU | AAGAGGAGCUCAAUAUGAU |
| 528 | EU310Aun | AAUGACAUCUGGGUACUUG | AAUGACAUCUGGGUACUUG |
| 529 | EU310Bun | CAAGUACCCAGAUGUCAUU | CAAGUACCCAGAUGUCAUU |
| 530 | EU312Aun | UUGAUGUACUGCAAGUCCA | UUGAUGUACUGCAAGUCCA |
| 531 | EU312Bun | UGGACUUGCAGUACAUCAA | UGGACUUGCAGUACAUCAA |
| 532 | EU314Aun | AACAGGUUCCCUCUCUUCA | AACAGGUUCCCUCUCUUCA |
| 533 | EU314Bun | UGAAGAGAGGGAACCUGUU | UGAAGAGAGGGAACCUGUU |
| 534 | EU316Aun | UACUACUAACUUCAGCAAG | UACUACUAACUUCAGCAAG |
| 535 | EU316Bun | CUUGCUGAAGUUAGUAGUA | CUUGCUGAAGUUAGUAGUA |
| 536 | EU317Aun | AGUACUACUAACUUCAGCA | AGUACUACUAACUUCAGCA |
| 537 | EU317Bun | UGCUGAAGUUAGUAGUACU | UGCUGAAGUUAGUAGUACU |
| 538 | EU319Aun | AACAAAAGUCUGGUGUCUU | AACAAAAGUCUGGUGUCUU |
| 539 | EU319Bun | AAGACACCAGACUUUUGUU | AAGACACCAGACUUUUGUU |
| 540 | EU321Aun | AAAAUAAAUACGGCGGCUG | AAAAUAAAUACGGCGGCUG |
| 541 | EU321Bun | CAGCCGCCGUAUUUAUUUU | CAGCCGCCGUAUUUAUUUU |
| 542 | EU322Aun | AUGCAAAAUAAAUACGGCG | AUGCAAAAUAAAUACGGCG |
| 543 | EU322Bun | CGCCGUAUUUAUUUUGCAU | CGCCGUAUUUAUUUUGCAU |
| 544 | EU323Aun | AGUCAAACUCAUAACGCCA | AGUCAAACUCAUAACGCCA |
| 545 | EU323Bun | UGGCGUUAUGAGUUUGACU | UGGCGUUAUGAGUUUGACU |
| 546 | EU325Aun | AGUCAUAACAACAAAACUC | AGUCAUAACAACAAAACUC |
| 547 | EU325Bun | GAGUUUUGUUGUUAUGACU | GAGUUUUGUUGUUAUGACU |
| 548 | EU429Aun | UAUGACAUCUGGGUACUUG | UAUGACAUCUGGGUACUUG |
| 549 | EU430Aun | UACAGGUUCCCUCUCUUCA | UACAGGUUCCCUCUCUUCA |
| 550 | EU431Aun | UAAAUAAAUACGGCGGCUG | UAAAUAAAUACGGCGGCUG |
| 551 | EU432Aun | UUGCAAAAUAAAUACGGCG | UUGCAAAAUAAAUACGGCG |
| 552 | EU433Aun | UGUCAUAACAACAAAACUC | UGUCAUAACAACAAAACUC |

TABLE 4-continued

| SEQ ID NO: | Name (A = 1$^{st}$ strand; B = 2$^{nd}$ strand) | Sequence 5'-3' | Unmodified sequence 5'-3' counterpart |
|---|---|---|---|
| Summary sequence table | | | |
| 553 | EU420B without linker | mAmCmUmCmUmUfGfUfGmUmCmUmUmUmUmGmU(ps)mC(ps)mA | ACUCUUGUGUCUUUUGUCA |
| 554 | EU422B without linker | mA(ps2)mCmUmCmUmUfGfUfGmUmCmUmUmUmUmGmUmC(ps2)mA | ACUCUUGUGUCUUUUGUCA |

The invention claimed is:

1. A double-stranded nucleic acid for inhibiting expression of CNNM4, wherein the nucleic acid comprises a first strand and a second strand, wherein the first strand sequence comprises a sequence of at least 15 nucleotides differing by no more than 3 nucleotides from the sequence set forth by SEQ ID NO: 371.

2. The nucleic acid of claim 1, wherein the first strand and the second strand form a duplex region of from 17-25 nucleotides in length.

3. The nucleic acid of claim 1, wherein the nucleic acid mediates RNA interference.

4. The nucleic acid of claim 1, wherein at least one nucleotide of the first and/or second strand is a modified nucleotide.

5. The nucleic acid of claim 1, wherein at least nucleotides 2 and 14 of the first strand are modified by a first modification, the nucleotides being numbered consecutively starting with nucleotide number 1 at the 5' end of the first strand.

6. The nucleic acid of claim 1, wherein the first strand has a terminal 5' (E)-vinylphosphonate nucleotide at its 5' end.

7. The nucleic acid of claim 1, wherein the nucleic acid comprises a phosphorothioate linkage between the terminal two or three 3' nucleotides and/or 5' nucleotides of the first and/or the second strand.

8. The nucleic acid of claim 1, comprising a phosphorodithioate linkage between each of the two, three or four terminal nucleotides at the 3' end of the first strand and/or comprising a phosphorodithioate linkage between each of the two, three or four terminal nucleotides at the 3' end of the second strand and/or a phosphorodithioate linkage between each of the two, three or four terminal nucleotides at the 5' end of the second strand and comprising a linkage other than a phosphorodithioate linkage between the two, three or four terminal nucleotides at the 5' end of the first strand.

9. The nucleic acid of claim 1, wherein the nucleic acid is conjugated to a ligand.

10. The nucleic acid of claim 9, wherein the ligand comprises (i) one or more N-acetyl galactosamine (GalNAc) moieties or derivatives thereof, and (ii) a linker, wherein the linker conjugates the at least one GalNAc moiety or derivative thereof to the nucleic acid.

11. A composition comprising the nucleic acid of claim 1 and one or more of a solvent, a delivery vehicle, a physiologically acceptable excipient, a carrier, a salt, a diluent, a buffer, a preservative and/or a further therapeutic agent selected from the group comprising an oligonucleotide, a small molecule, a monoclonal antibody, a polyclonal antibody and a peptide.

12. A method of preventing or treating a disease, disorder or syndrome comprising administering a pharmaceutically effective amount of the nucleic acid of claim 1 to an individual in need of treatment.

13. The method of claim 12, wherein the disease, disorder or syndrome is a liver disease, a kidney disease or a lung disease.

14. The method of claim 12, wherein the disease is an acute or chronic disease associated with hypomagnesemia in the liver selected from the group consisting of non-alcoholic steatohepatitis (NASH), liver cirrhosis, hepatocellular carcinoma (HCC), drug-induced liver injury (DILI), non-alcoholic fatty liver disease (NAFLD), fatty liver, liver cancer, liver fibrosis, veno-occlusive liver disease, hepatic sinusoidal obstruction syndrome (SOS), steatosis, Budd-Chiari syndrome, viral hepatitis B, viral hepatitis C, alcoholic hepatitis, hepatic ischemia reperfusion injury, primary biliary cirrhosis (PBC), a chronic liver disease, an acute liver disease, cholangiocarcinoma (bile duct cancer), and alpha1 anti-trypsin deficiency.

15. The method of claim 14, wherein the liver disease is selected from the group consisting of non-alcoholic steatohepatitis (NASH), liver cirrhosis, hepatocellular carcinoma (HCC), drug-induced liver injury (DILI) and non-alcoholic fatty liver disease (NAFLD).

16. A method of preventing or treating a disease, disorder or syndrome comprising administering a pharmaceutically effective amount of the composition of claim 11 to an individual in need of treatment.

17. The method of claim 16, wherein the disease, disorder or syndrome is a liver disease, a kidney disease or a lung disease.

18. The method of claim 16, wherein the disease is an acute or chronic disease associated with hypomagnesemia in the liver selected from the group consisting of non-alcoholic steatohepatitis (NASH), liver cirrhosis, hepatocellular carcinoma (HCC), drug-induced liver injury (DILI), non-alcoholic fatty liver disease (NAFLD), fatty liver, liver cancer, liver fibrosis, veno-occlusive liver disease, hepatic sinusoidal obstruction syndrome (SOS), steatosis, Budd-Chiari syndrome, viral hepatitis B, viral hepatitis C, alcoholic hepatitis, hepatic ischemia reperfusion injury, primary biliary cirrhosis (PBC), a chronic liver disease, an acute liver disease, cholangiocarcinoma (bile duct cancer), and alpha1 anti-trypsin deficiency.

19. The method of claim 18, wherein the liver disease is selected from the group consisting of non-alcoholic steatohepatitis (NASH), liver cirrhosis, hepatocellular carcinoma (HCC), drug-induced liver injury (DILI) and non-alcoholic fatty liver disease (NAFLD).

20. The nucleic acid of claim 4, wherein the modified nucleotide is a 2'-F modified nucleotide.

21. A double-stranded nucleic acid for inhibiting expression of CNNM4, wherein the nucleic acid comprises a first strand and a second strand, wherein the first strand sequence comprises a sequence of at least 15 nucleotides differing by no more than 3 nucleotides from the sequence set forth by SEQ ID NO: 371 having the sequence mU(ps)fG(ps)mA-fCmAfAmAfAmGfAmCfAmCfAmAfGmA(ps)fG(ps)mU, wherein m is methyl, f is a fluoro group, (ps) is phosphorothioate.

* * * * *

SEQUENCE LISTING

<160> NUMBER OF SEQ ID NOS: 554

<210> SEQ ID NO 1
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 1
ucgaaguauu ccgcguacg 19

<210> SEQ ID NO 2
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 2
cguacgcgga auacuucga 19

<210> SEQ ID NO 3
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 3
ccuaggauca cgcucugcu 19

<210> SEQ ID NO 4
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 4
agcagagcgu gauccuagg 19

<210> SEQ ID NO 5
<211> LENGTH: 19
<212> TYPE: RNA

<213> ORGANISM: Artificial Sequence
<220> FEATURE:
<223> OTHER INFORMATION: siRNA strand - sequence modified as per summary
sequence table at the end of the description

<400> SEQUENCE: 5
gacuuguugc agcucgcca 19

<210> SEQ ID NO 6
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 6
uggcgagcug caacaaguc 19

<210> SEQ ID NO 7
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 7
cacgacuugu ugcagcucg 19

<210> SEQ ID NO 8
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 8
cgagcugcaa caagucgug 19

<210> SEQ ID NO 9
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 9
gacacgaaga ugaugccau 19

<210> SEQ ID NO 10
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 10
auggcaucau cuucguguc 19

<210> SEQ ID NO 11
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 11
cggugaagga gaucagguu 19

<210> SEQ ID NO 12
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 12
aaccugaucu ccuucaccg 19

<210> SEQ ID NO 13
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 13
cucacguuga ccagcugcu 19

<210> SEQ ID NO 14
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 14
agcagcuggu caacgugag 19

<210> SEQ ID NO 15
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 15
ggcuccucca ccaugaaga 19

<210> SEQ ID NO 16
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 16
ucuucauggu ggaggagcc 19

<210> SEQ ID NO 17
<211> LENGTH: 19
<212> TYPE: RNA
<213> ORGANISM: Artificial Sequence
<220> FEATURE:

```
<223> OTHER INFORMATION: siRNA strand - sequence modified as per summary
      sequence table at the end of the description

<400> SEQUENCE: 17

gaaaauaugc ccgacagca                                                19


<210> SEQ ID NO 18
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 18

ugcugucggg cauauuuuc                                                19


<210> SEQ ID NO 19
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 19

gacccgauga gguugucua                                                19


<210> SEQ ID NO 20
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 20

uagacaaccu caucggguc                                                19


<210> SEQ ID NO 21
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 21

ggacccgaug agguugucu                                                19


<210> SEQ ID NO 22
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 22

agacaaccuc aucgggucc                                                19


<210> SEQ ID NO 23
<211> LENGTH: 19
<212> TYPE: RNA
<213> ORGANISM: Artificial Sequence
<220> FEATURE:
<223> OTHER INFORMATION: siRNA strand - sequence modified as per summary
```

sequence table at the end of the description

<400> SEQUENCE: 23
guaaacagug cgaaucucc 19

<210> SEQ ID NO 24
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 24
ggagauucgc acuguuuac 19

<210> SEQ ID NO 25
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 25
guuguaaaca gugcgaauc 19

<210> SEQ ID NO 26
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 26
gauucgcacu guuuacaac 19

<210> SEQ ID NO 27
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 27
cauuauaggg cucugucac 19

<210> SEQ ID NO 28
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 28
gugacagagc ccuauaaug 19

<210> SEQ ID NO 29
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 29
gucauuauag ggcuccguc 19

<210> SEQ ID NO 30
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 30
gacggagccc uauaaugac 19

<210> SEQ ID NO 31
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 31
gaucauauug agcuccucu 19

<210> SEQ ID NO 32
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 32
agaggagcuc aauaugauc 19

<210> SEQ ID NO 33
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 33
gcugggucau gauauccuc 19

<210> SEQ ID NO 34
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 34
gaggauauca ugacccagc 19

<210> SEQ ID NO 35
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 35
cugcggauca ugaagcagu 19

<210> SEQ ID NO 36
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 36
acugcuucau gauccgcag 19

<210> SEQ ID NO 37
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 37
ggagauuuuc acuuugagc 19

<210> SEQ ID NO 38
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 38
gcucaaagug aaaaucucc 19

<210> SEQ ID NO 39
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 39
cuuauuucgg guguacagg 19

<210> SEQ ID NO 40
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 40
ccuguacacc cgaaauaag 19

<210> SEQ ID NO 41
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 41
gcgcccgucu caaacuuca 19

<210> SEQ ID NO 42
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 42
ugaaguuuga gacgggcgc 19

<210> SEQ ID NO 43
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 43
cuuaacccug ucuucccuu 19

<210> SEQ ID NO 44
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 44
aagggaagac aggguuaag 19

<210> SEQ ID NO 45
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 45
caguuccagg guauggcuc 19

<210> SEQ ID NO 46
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 46
gagccauacc cuggaacug 19

<210> SEQ ID NO 47
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 47
ccgagaguca aacucauaa 19

<210> SEQ ID NO 48
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 48
uuaugaguuu gacucucgg 19

<210> SEQ ID NO 49
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 49
gucauaacaa caaaacucc 19

<210> SEQ ID NO 50
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 50
ggaguuuugu uguuaugac 19

<210> SEQ ID NO 51
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 51
ccauauaucg uuuagcaaa 19

<210> SEQ ID NO 52
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 52
uuugcuaaac gauauaugg 19

<210> SEQ ID NO 53
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 53
agaugaugcc auccggguu 19

<210> SEQ ID NO 54
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 54
aacccggaug gcaucaucu 19

<210> SEQ ID NO 55
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 55
acgaagauga ugccauccg 19

<210> SEQ ID NO 56
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 56
cggauggcau caucuucgu 19

<210> SEQ ID NO 57
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 57
ucggacacga agaugaugc 19

<210> SEQ ID NO 58
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 58
gcaucaucuu cguguccga 19

<210> SEQ ID NO 59
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 59
aaguucaccg ugcugcccu 19

<210> SEQ ID NO 60
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 60
agggcagcac ggugaacuu 19

<210> SEQ ID NO 61
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 61
ucggugaagg agaucaggu 19

<210> SEQ ID NO 62
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 62
accugaucuc cuucaccga 19

<210> SEQ ID NO 63
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 63
accucgguga aggagauca 19

<210> SEQ ID NO 64
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 64
ugaucuccuu caccgaggu 19

<210> SEQ ID NO 65
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 65
aggaacuugg uaaucacca 19

-continued

```
<210> SEQ ID NO 66
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 66

uggugauuac caaguuccu                                               19


<210> SEQ ID NO 67
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 67

uacagcuuca ugcucucgc                                               19


<210> SEQ ID NO 68
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 68

gcgagagcau gaagcugua                                               19


<210> SEQ ID NO 69
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 69

augaagagca gugaguccu                                               19


<210> SEQ ID NO 70
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 70

aggacucacu gcucuucau                                               19


<210> SEQ ID NO 71
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 71

agguaguugc ccuugcgcc                                               19


<210> SEQ ID NO 72
```

<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 72
ggcgcaaggg caacuaccu 19

<210> SEQ ID NO 73
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 73
ugugagggag guguugacc 19

<210> SEQ ID NO 74
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 74
ggucaacacc ucccucaca 19

<210> SEQ ID NO 75
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 75
auugugaggg agguguuga 19

<210> SEQ ID NO 76
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 76
ucaacaccuc ccucacaau 19

<210> SEQ ID NO 77
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 77
ucuagaagga uugugaggg 19

<210> SEQ ID NO 78
<211> LENGTH: 19

<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 78
cccucacaau ccuucuaga 19

<210> SEQ ID NO 79
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 79
uugucuagaa ggauuguga 19

<210> SEQ ID NO 80
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 80
ucacaauccu ucuagacaa 19

<210> SEQ ID NO 81
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 81
ugagguuguc uagaaggau 19

<210> SEQ ID NO 82
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 82
auccuucuag acaaccuca 19

<210> SEQ ID NO 83
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 83
aucuccccaa agaugacaa 19

<210> SEQ ID NO 84
<211> LENGTH: 19
<212> TYPE: RNA

```
<213> ORGANISM: Artificial Sequence
<220> FEATURE:
<223> OTHER INFORMATION: siRNA strand - sequence modified as per summary
      sequence table at the end of the description

<400> SEQUENCE: 84

uugucaucuu uggggagau                                                19


<210> SEQ ID NO 85
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 85

agaacaauag uguuggcac                                                19


<210> SEQ ID NO 86
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 86

gugccaacac uauuguucu                                                19


<210> SEQ ID NO 87
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 87

agcauaaaga auuugguga                                                19


<210> SEQ ID NO 88
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 88

ucaccaaauu cuuuaugcu                                                19


<210> SEQ ID NO 89
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 89

uuguaaacag ugcgaaucu                                                19


<210> SEQ ID NO 90
<211> LENGTH: 19
<212> TYPE: RNA
<213> ORGANISM: Artificial Sequence
```

<220> FEATURE:
<223> OTHER INFORMATION: siRNA strand - sequence modified as per summary
sequence table at the end of the description

<400> SEQUENCE: 90
agauucgcac uguuuacaa 19

<210> SEQ ID NO 91
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 91
acaguuuugg uccuuaguu 19

<210> SEQ ID NO 92
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 92
aacuaaggac caaaacugu 19

<210> SEQ ID NO 93
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 93
auauccucua caguuuugg 19

<210> SEQ ID NO 94
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 94
ccaaaacugu agaggauau 19

<210> SEQ ID NO 95
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 95
auaucuacaa uauuggacu 19

<210> SEQ ID NO 96
<211> LENGTH: 19
<212> TYPE: RNA
<213> ORGANISM: Artificial Sequence
<220> FEATURE:

<223> OTHER INFORMATION: siRNA strand - sequence modified as per summary sequence table at the end of the description

<400> SEQUENCE: 96
aguccaauau uguagauau 19

<210> SEQ ID NO 97
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 97
aauaucuaca auauuggac 19

<210> SEQ ID NO 98
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 98
guccaauauu guagauauu 19

<210> SEQ ID NO 99
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 99
uugacguaga gaauaucua 19

<210> SEQ ID NO 100
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 100
uagauauucu cuacgucaa 19

<210> SEQ ID NO 101
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 101
aagucuuuga cguagagaa 19

<210> SEQ ID NO 102
<211> LENGTH: 19
<212> TYPE: RNA
<213> ORGANISM: Artificial Sequence
<220> FEATURE:
<223> OTHER INFORMATION: siRNA strand - sequence modified as per summary -continued sequence table at the end of the description

<400> SEQUENCE: 102
uucucuacgu caaagacuu 19

<210> SEQ ID NO 103
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 103
uagaagcgag ugauagucu 19

<210> SEQ ID NO 104
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 104
agacuaucac ucgcuucua 19

<210> SEQ ID NO 105
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 105
uugaaggcag agaagucac 19

<210> SEQ ID NO 106
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 106
gugacuucuc ugccuucaa 19

<210> SEQ ID NO 107
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 107
uuucacuuug agcucauug 19

<210> SEQ ID NO 108
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description -continued

<400> SEQUENCE: 108
caaugagcuc aaagugaaa 19

<210> SEQ ID NO 109
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 109
aacugguugc ugcugccug 19

<210> SEQ ID NO 110
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 110
caggcagcag caaccaguu 19

<210> SEQ ID NO 111
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 111
uugagaagag uuguggucu 19

<210> SEQ ID NO 112
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 112
agaccacaac ucuucucaa 19

<210> SEQ ID NO 113
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 113
uucauguggg cccacuggg 19

<210> SEQ ID NO 114
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 114
cccagugggc ccacaugaa 19

<210> SEQ ID NO 115
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 115
ucuucaugug ggcccacug 19

<210> SEQ ID NO 116
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 116
cagugggccc acaugaaga 19

<210> SEQ ID NO 117
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 117
uggacuaaca gguucccuc 19

<210> SEQ ID NO 118
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 118
gagggaaccu guuagucca 19

<210> SEQ ID NO 119
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 119
uuccuuaacc cugucuucc 19

<210> SEQ ID NO 120
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 120
ggaagacagg guuaaggaa 19

<210> SEQ ID NO 121
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 121
aguuccuuaa cccugucuu 19

<210> SEQ ID NO 122
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 122
aagacagggu uaaggaacu 19

<210> SEQ ID NO 123
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 123
auaaaguucc uuaacccug 19

<210> SEQ ID NO 124
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 124
caggguuaag gaacuuuau 19

<210> SEQ ID NO 125
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 125
aaauaaaguu ccuuaaccc 19

<210> SEQ ID NO 126
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 126
ggguuaagga acuuuauuu 19

<210> SEQ ID NO 127
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 127
uacauaaagu uccuuaacc 19

<210> SEQ ID NO 128
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 128
gguuaaggaa cuuuaugua 19

<210> SEQ ID NO 129
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 129
auuaucaugu cccugauca 19

<210> SEQ ID NO 130
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 130
ugaucaggga caugauaau 19

<210> SEQ ID NO 131
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 131
auaaagaacc ugcuuccgu 19

<210> SEQ ID NO 132
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 132
acggaagcag guucuuuau 19

<210> SEQ ID NO 133
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 133
acuaacuuca gcaagggca 19

<210> SEQ ID NO 134
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 134
ugcccuugcu gaaguuagu 19

<210> SEQ ID NO 135
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 135
uggugcaaga caaucccug 19

<210> SEQ ID NO 136
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 136
cagggauugu cuugcacca 19

<210> SEQ ID NO 137
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 137
auaaauagga gucaucugc 19

<210> SEQ ID NO 138
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 138
gcagaugacu ccuauuuau 19

```
<210> SEQ ID NO 139
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 139

uuggaaauaa ugaugaccc                                               19


<210> SEQ ID NO 140
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 140

gggucaucau uauuuccaa                                               19


<210> SEQ ID NO 141
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 141

aaacucauaa caaugccaa                                               19


<210> SEQ ID NO 142
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 142

uuggcauugu uaugaguuu                                               19


<210> SEQ ID NO 143
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 143

auuaucauug uuuugugac                                               19


<210> SEQ ID NO 144
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 144

gucacaaaac aaugauaau                                               19
```

```
<210> SEQ ID NO 145
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 145

uuguuuagca aauauuauc                                                19


<210> SEQ ID NO 146
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 146

gauaauauuu gcuaaacaa                                                19


<210> SEQ ID NO 147
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 147

uccccgagag ucaaacuca                                                19


<210> SEQ ID NO 148
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 148

ugaguuugac ucucgggga                                                19


<210> SEQ ID NO 149
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 149

aacuccccga gagucaaac                                                19


<210> SEQ ID NO 150
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 150

guuugacucu cggggaguu                                                19


<210> SEQ ID NO 151
```

<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 151
aacaacaaaa cuccccgag 19

<210> SEQ ID NO 152
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 152
cucggggagu uuuguuguu 19

<210> SEQ ID NO 153
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 153
auaacaacaa aacuccccg 19

<210> SEQ ID NO 154
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 154
cggggaguuu uguuguuau 19

<210> SEQ ID NO 155
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 155
ugacaaaaga cacaagagu 19

<210> SEQ ID NO 156
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 156
acucuugugu cuuuuguca 19

<210> SEQ ID NO 157
<211> LENGTH: 19

<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 157
uuguuuugug acaaaagac 19

<210> SEQ ID NO 158
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 158
gucuuuuguc acaaaacaa 19

<210> SEQ ID NO 159
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 159
ucuaggauca cgcucugcu 19

<210> SEQ ID NO 160
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 160
agcagagcgu gauccuaga 19

<210> SEQ ID NO 161
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 161
uacuuguugc agcucgcca 19

<210> SEQ ID NO 162
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 162
uggcgagcug caacaagua 19

<210> SEQ ID NO 163
<211> LENGTH: 19
<212> TYPE: RNA

```
<213> ORGANISM: Artificial Sequence
<220> FEATURE:
<223> OTHER INFORMATION: siRNA strand - sequence modified as per summary
      sequence table at the end of the description

<400> SEQUENCE: 163

uacgacuugu ugcagcucg                                                19


<210> SEQ ID NO 164
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 164

cgagcugcaa caagucgua                                                19


<210> SEQ ID NO 165
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 165

uacacgaaga ugaugccau                                                19


<210> SEQ ID NO 166
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 166

auggcaucau cuucgugua                                                19


<210> SEQ ID NO 167
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 167

uggugaagga gaucagguu                                                19


<210> SEQ ID NO 168
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 168

aaccugaucu ccuucacca                                                19


<210> SEQ ID NO 169
<211> LENGTH: 19
<212> TYPE: RNA
<213> ORGANISM: Artificial Sequence
```

<220> FEATURE:
<223> OTHER INFORMATION: siRNA strand - sequence modified as per summary
sequence table at the end of the description

<400> SEQUENCE: 169
uucacguuga ccagcugcu 19

<210> SEQ ID NO 170
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 170
agcagcuggu caacgugaa 19

<210> SEQ ID NO 171
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 171
ugcuccucca ccaugaaga 19

<210> SEQ ID NO 172
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 172
ucuucauggu ggaggagca 19

<210> SEQ ID NO 173
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 173
uaaaauaugc ccgacagca 19

<210> SEQ ID NO 174
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 174
ugcugucggg cauauuuua 19

<210> SEQ ID NO 175
<211> LENGTH: 19
<212> TYPE: RNA
<213> ORGANISM: Artificial Sequence
<220> FEATURE:

<223> OTHER INFORMATION: siRNA strand - sequence modified as per summary
      sequence table at the end of the description

<400> SEQUENCE: 175
uacccgauga gguugucua                                                    19

<210> SEQ ID NO 176
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 176
uagacaaccu caucgggua                                                    19

<210> SEQ ID NO 177
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 177
ugacccgaug agguugucu                                                    19

<210> SEQ ID NO 178
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 178
agacaaccuc aucggguca                                                    19

<210> SEQ ID NO 179
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 179
uuaaacagug cgaaucucc                                                    19

<210> SEQ ID NO 180
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 180
ggagauucgc acuguuuaa                                                    19

<210> SEQ ID NO 181
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 181
uuuguaaaca gugcgaauc 19

<210> SEQ ID NO 182
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 182
gauucgcacu guuuacaaa 19

<210> SEQ ID NO 183
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 183
uauuauaggg cucugucac 19

<210> SEQ ID NO 184
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 184
gugacagagc ccuauaaua 19

<210> SEQ ID NO 185
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 185
uucauuauag ggcuccguc 19

<210> SEQ ID NO 186
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 186
gacggagccc uauaaugaa 19

<210> SEQ ID NO 187
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 187
uaucauauug agcuccucu 19

<210> SEQ ID NO 188
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 188
agaggagcuc aauaugaua 19

<210> SEQ ID NO 189
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 189
ucugggucau gauauccuc 19

<210> SEQ ID NO 190
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 190
gaggauauca ugacccaga 19

<210> SEQ ID NO 191
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 191
uugcggauca ugaagcagu 19

<210> SEQ ID NO 192
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 192
acugcuucau gauccgcaa 19

<210> SEQ ID NO 193
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 193
ugagauuuuc acuuugagc 19

<210> SEQ ID NO 194
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 194
gcucaaagug aaaaucuca 19

<210> SEQ ID NO 195
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 195
uuuauuucgg guguacagg 19

<210> SEQ ID NO 196
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 196
ccuguacacc cgaaauaaa 19

<210> SEQ ID NO 197
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 197
ucgcccgucu caaacuuca 19

<210> SEQ ID NO 198
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 198
ugaaguuuga gacgggcga 19

<210> SEQ ID NO 199
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 199
uuuaacccug ucuucccuu 19

<210> SEQ ID NO 200
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 200
aagggaagac aggguuaaa 19

<210> SEQ ID NO 201
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 201
uaguuccagg guauggcuc 19

<210> SEQ ID NO 202
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 202
gagccauacc cuggaacua 19

<210> SEQ ID NO 203
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 203
ucgagaguca aacucauaa 19

<210> SEQ ID NO 204
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 204
uuaugaguuu gacucucga 19

<210> SEQ ID NO 205
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 205
uucauaacaa caaaacucc 19

<210> SEQ ID NO 206
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 206
ggaguuuugu uguuaugaa 19

<210> SEQ ID NO 207
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 207
ucauauaucg uuuagcaaa 19

<210> SEQ ID NO 208
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 208
uuugcuaaac gauauauga 19

<210> SEQ ID NO 209
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 209
ucgaaguauu ccgcguacg 19

<210> SEQ ID NO 210
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 210
cguacgcgga auacuucga 19

<210> SEQ ID NO 211
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 211
uacgacuugu ugcagcucg 19

<210> SEQ ID NO 212
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 212
cgagcugcaa caagucgug 19

<210> SEQ ID NO 213
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 213
ugagauuuuc acuuugagc 19

<210> SEQ ID NO 214
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 214
gcucaaagug aaaaucucc 19

<210> SEQ ID NO 215
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 215
ucgagaguca aacucauaa 19

<210> SEQ ID NO 216
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 216
uuaugaguuu gacucucgg 19

<210> SEQ ID NO 217
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 217
uucauaacaa caaaacucc 19

<210> SEQ ID NO 218
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 218
ggaguuuugu uguuaugac 19

<210> SEQ ID NO 219
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 219
ucggacacga agaugaugc 19

<210> SEQ ID NO 220
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 220
gcaucaucuu cguguccga 19

<210> SEQ ID NO 221
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 221
uuaucuacaa uauuggacu 19

<210> SEQ ID NO 222
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 222
aguccaauau uguagauau 19

<210> SEQ ID NO 223
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 223
uauaucuaca auauuggac 19

<210> SEQ ID NO 224
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 224
guccaauauu guagauauu 19

<210> SEQ ID NO 225
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 225
uagaagcgag ugauagucu 19

<210> SEQ ID NO 226
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 226
agacuaucac ucgcuucua 19

<210> SEQ ID NO 227
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 227
uggacuaaca gguucccuc 19

<210> SEQ ID NO 228
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 228
gagggaaccu guuagucca 19

<210> SEQ ID NO 229
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 229
uuaaaguucc uuaacccug 19

<210> SEQ ID NO 230

<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 230
caggguuaag gaacuuuau 19

<210> SEQ ID NO 231
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 231
uacauaaagu uccuuaacc 19

<210> SEQ ID NO 232
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 232
gguuaaggaa cuuuaugua 19

<210> SEQ ID NO 233
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 233
uuuaucauug uuuugugac 19

<210> SEQ ID NO 234
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 234
gucacaaaac aaugauaau 19

<210> SEQ ID NO 235
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 235
uuaacaacaa aacuccccg 19

<210> SEQ ID NO 236
<211> LENGTH: 19

<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 236
cggggaguuu uguuguuau 19

<210> SEQ ID NO 237
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 237
ugacaaaaga cacaagagu 19

<210> SEQ ID NO 238
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 238
acucuugugu cuuuuguca 19

<210> SEQ ID NO 239
<211> LENGTH: 19
<212> TYPE: RNA
<213> ORGANISM: Artificial Sequence
<220> FEATURE:
<223> OTHER INFORMATION: siRNA strand

<400> SEQUENCE: 239
ccuaggauca cgcucugcu 19

<210> SEQ ID NO 240
<211> LENGTH: 19
<212> TYPE: RNA
<213> ORGANISM: Artificial Sequence
<220> FEATURE:
<223> OTHER INFORMATION: siRNA strand

<400> SEQUENCE: 240
agcagagcgu gauccuagg 19

<210> SEQ ID NO 241
<211> LENGTH: 19
<212> TYPE: RNA
<213> ORGANISM: Artificial Sequence
<220> FEATURE:
<223> OTHER INFORMATION: siRNA strand

<400> SEQUENCE: 241
gacuuguugc agcucgcca 19

<210> SEQ ID NO 242
<211> LENGTH: 19
<212> TYPE: RNA
<213> ORGANISM: Artificial Sequence
<220> FEATURE:
<223> OTHER INFORMATION: siRNA strand

<400> SEQUENCE: 242
uggcgagcug caacaaguc 19

<210> SEQ ID NO 243
<211> LENGTH: 19
<212> TYPE: RNA
<213> ORGANISM: Artificial Sequence
<220> FEATURE:
<223> OTHER INFORMATION: siRNA strand

<400> SEQUENCE: 243
cacgacuugu ugcagcucg 19

<210> SEQ ID NO 244
<211> LENGTH: 19
<212> TYPE: RNA
<213> ORGANISM: Artificial Sequence
<220> FEATURE:
<223> OTHER INFORMATION: siRNA strand

<400> SEQUENCE: 244
cgagcugcaa caagucgug 19

<210> SEQ ID NO 245
<211> LENGTH: 19
<212> TYPE: RNA
<213> ORGANISM: Artificial Sequence
<220> FEATURE:
<223> OTHER INFORMATION: siRNA strand

<400> SEQUENCE: 245
gacacgaaga ugaugccau 19

<210> SEQ ID NO 246
<211> LENGTH: 19
<212> TYPE: RNA
<213> ORGANISM: Artificial Sequence
<220> FEATURE:
<223> OTHER INFORMATION: siRNA strand

<400> SEQUENCE: 246
auggcaucau cuucguguc 19

<210> SEQ ID NO 247
<211> LENGTH: 19
<212> TYPE: RNA
<213> ORGANISM: Artificial Sequence
<220> FEATURE:
<223> OTHER INFORMATION: siRNA strand

<400> SEQUENCE: 247
cggugaagga gaucagguu 19

<210> SEQ ID NO 248
<211> LENGTH: 19
<212> TYPE: RNA
<213> ORGANISM: Artificial Sequence
<220> FEATURE:
<223> OTHER INFORMATION: siRNA strand

<400> SEQUENCE: 248
aaccugaucu ccuucaccg 19

<210> SEQ ID NO 249

<211> LENGTH: 19
<212> TYPE: RNA
<213> ORGANISM: Artificial Sequence
<220> FEATURE:
<223> OTHER INFORMATION: siRNA strand

<400> SEQUENCE: 249
gacccgauga gguugucua 19

<210> SEQ ID NO 250
<211> LENGTH: 19
<212> TYPE: RNA
<213> ORGANISM: Artificial Sequence
<220> FEATURE:
<223> OTHER INFORMATION: siRNA strand

<400> SEQUENCE: 250
uagacaaccu caucggguc 19

<210> SEQ ID NO 251
<211> LENGTH: 19
<212> TYPE: RNA
<213> ORGANISM: Artificial Sequence
<220> FEATURE:
<223> OTHER INFORMATION: siRNA strand

<400> SEQUENCE: 251
ggacccgaug agguugucu 19

<210> SEQ ID NO 252
<211> LENGTH: 19
<212> TYPE: RNA
<213> ORGANISM: Artificial Sequence
<220> FEATURE:
<223> OTHER INFORMATION: siRNA strand

<400> SEQUENCE: 252
agacaaccuc aucgggucc 19

<210> SEQ ID NO 253
<211> LENGTH: 19
<212> TYPE: RNA
<213> ORGANISM: Artificial Sequence
<220> FEATURE:
<223> OTHER INFORMATION: siRNA strand

<400> SEQUENCE: 253
guaaacagug cgaaucucc 19

<210> SEQ ID NO 254
<211> LENGTH: 19
<212> TYPE: RNA
<213> ORGANISM: Artificial Sequence
<220> FEATURE:
<223> OTHER INFORMATION: siRNA strand

<400> SEQUENCE: 254
ggagauucgc acuguuuac 19

<210> SEQ ID NO 255
<211> LENGTH: 19
<212> TYPE: RNA
<213> ORGANISM: Artificial Sequence
<220> FEATURE:
<223> OTHER INFORMATION: siRNA strand

<400> SEQUENCE: 255
guuguaaaca gugcgaauc 19

<210> SEQ ID NO 256
<211> LENGTH: 19
<212> TYPE: RNA
<213> ORGANISM: Artificial Sequence
<220> FEATURE:
<223> OTHER INFORMATION: siRNA strand

<400> SEQUENCE: 256
gauucgcacu guuuacaac 19

<210> SEQ ID NO 257
<211> LENGTH: 19
<212> TYPE: RNA
<213> ORGANISM: Artificial Sequence
<220> FEATURE:
<223> OTHER INFORMATION: siRNA strand

<400> SEQUENCE: 257
cauuauaggg cucugucac 19

<210> SEQ ID NO 258
<211> LENGTH: 19
<212> TYPE: RNA
<213> ORGANISM: Artificial Sequence
<220> FEATURE:
<223> OTHER INFORMATION: siRNA strand

<400> SEQUENCE: 258
gugacagagc ccuauaaug 19

<210> SEQ ID NO 259
<211> LENGTH: 19
<212> TYPE: RNA
<213> ORGANISM: Artificial Sequence
<220> FEATURE:
<223> OTHER INFORMATION: siRNA strand

<400> SEQUENCE: 259
gucauuauag ggcuccguc 19

<210> SEQ ID NO 260
<211> LENGTH: 19
<212> TYPE: RNA
<213> ORGANISM: Artificial Sequence
<220> FEATURE:
<223> OTHER INFORMATION: siRNA strand

<400> SEQUENCE: 260
gacggagccc uauaaugac 19

<210> SEQ ID NO 261
<211> LENGTH: 19
<212> TYPE: RNA
<213> ORGANISM: Artificial Sequence
<220> FEATURE:
<223> OTHER INFORMATION: siRNA strand

<400> SEQUENCE: 261
gaucauauug agcuccucu 19

<210> SEQ ID NO 262
<211> LENGTH: 19
<212> TYPE: RNA

<213> ORGANISM: Artificial Sequence
<220> FEATURE:
<223> OTHER INFORMATION: siRNA strand

<400> SEQUENCE: 262
agaggagcuc aauaugauc 19

<210> SEQ ID NO 263
<211> LENGTH: 19
<212> TYPE: RNA
<213> ORGANISM: Artificial Sequence
<220> FEATURE:
<223> OTHER INFORMATION: siRNA strand

<400> SEQUENCE: 263
gcugggucau gauauccuc 19

<210> SEQ ID NO 264
<211> LENGTH: 19
<212> TYPE: RNA
<213> ORGANISM: Artificial Sequence
<220> FEATURE:
<223> OTHER INFORMATION: siRNA strand

<400> SEQUENCE: 264
gaggauauca ugacccagc 19

<210> SEQ ID NO 265
<211> LENGTH: 19
<212> TYPE: RNA
<213> ORGANISM: Artificial Sequence
<220> FEATURE:
<223> OTHER INFORMATION: siRNA strand

<400> SEQUENCE: 265
cugcggauca ugaagcagu 19

<210> SEQ ID NO 266
<211> LENGTH: 19
<212> TYPE: RNA
<213> ORGANISM: Artificial Sequence
<220> FEATURE:
<223> OTHER INFORMATION: siRNA strand

<400> SEQUENCE: 266
acugcuucau gauccgcag 19

<210> SEQ ID NO 267
<211> LENGTH: 19
<212> TYPE: RNA
<213> ORGANISM: Artificial Sequence
<220> FEATURE:
<223> OTHER INFORMATION: siRNA strand

<400> SEQUENCE: 267
ggagauuuuc acuuugagc 19

<210> SEQ ID NO 268
<211> LENGTH: 19
<212> TYPE: RNA
<213> ORGANISM: Artificial Sequence
<220> FEATURE:
<223> OTHER INFORMATION: siRNA strand

<400> SEQUENCE: 268
gcucaaagug aaaaucucc 19

<210> SEQ ID NO 269
<211> LENGTH: 19
<212> TYPE: RNA
<213> ORGANISM: Artificial Sequence
<220> FEATURE:
<223> OTHER INFORMATION: siRNA strand

<400> SEQUENCE: 269
cuuauuucgg guguacagg 19

<210> SEQ ID NO 270
<211> LENGTH: 19
<212> TYPE: RNA
<213> ORGANISM: Artificial Sequence
<220> FEATURE:
<223> OTHER INFORMATION: siRNA strand

<400> SEQUENCE: 270
ccuguacacc cgaaauaag 19

<210> SEQ ID NO 271
<211> LENGTH: 19
<212> TYPE: RNA
<213> ORGANISM: Artificial Sequence
<220> FEATURE:
<223> OTHER INFORMATION: siRNA strand

<400> SEQUENCE: 271
gcgcccgucu caaacuuca 19

<210> SEQ ID NO 272
<211> LENGTH: 19
<212> TYPE: RNA
<213> ORGANISM: Artificial Sequence
<220> FEATURE:
<223> OTHER INFORMATION: siRNA strand

<400> SEQUENCE: 272
ugaaguuuga gacgggcgc 19

<210> SEQ ID NO 273
<211> LENGTH: 19
<212> TYPE: RNA
<213> ORGANISM: Artificial Sequence
<220> FEATURE:
<223> OTHER INFORMATION: siRNA strand

<400> SEQUENCE: 273
cuuaacccug ucuucccuu 19

<210> SEQ ID NO 274
<211> LENGTH: 19
<212> TYPE: RNA
<213> ORGANISM: Artificial Sequence
<220> FEATURE:
<223> OTHER INFORMATION: siRNA strand

<400> SEQUENCE: 274
aagggaagac aggguuaag 19

<210> SEQ ID NO 275
<211> LENGTH: 19
<212> TYPE: RNA
<213> ORGANISM: Artificial Sequence
<220> FEATURE:

<223> OTHER INFORMATION: siRNA strand

<400> SEQUENCE: 275
caguuccagg guauggcuc 19

<210> SEQ ID NO 276
<211> LENGTH: 19
<212> TYPE: RNA
<213> ORGANISM: Artificial Sequence
<220> FEATURE:
<223> OTHER INFORMATION: siRNA strand

<400> SEQUENCE: 276
gagccauacc cuggaacug 19

<210> SEQ ID NO 277
<211> LENGTH: 19
<212> TYPE: RNA
<213> ORGANISM: Artificial Sequence
<220> FEATURE:
<223> OTHER INFORMATION: siRNA strand

<400> SEQUENCE: 277
ccgagaguca aacucauaa 19

<210> SEQ ID NO 278
<211> LENGTH: 19
<212> TYPE: RNA
<213> ORGANISM: Artificial Sequence
<220> FEATURE:
<223> OTHER INFORMATION: siRNA strand

<400> SEQUENCE: 278
uuaugaguuu gacucucgg 19

<210> SEQ ID NO 279
<211> LENGTH: 19
<212> TYPE: RNA
<213> ORGANISM: Artificial Sequence
<220> FEATURE:
<223> OTHER INFORMATION: siRNA strand

<400> SEQUENCE: 279
gucauaacaa caaaacucc 19

<210> SEQ ID NO 280
<211> LENGTH: 19
<212> TYPE: RNA
<213> ORGANISM: Artificial Sequence
<220> FEATURE:
<223> OTHER INFORMATION: siRNA strand

<400> SEQUENCE: 280
ggaguuuugu uguuaugac 19

<210> SEQ ID NO 281
<211> LENGTH: 19
<212> TYPE: RNA
<213> ORGANISM: Artificial Sequence
<220> FEATURE:
<223> OTHER INFORMATION: siRNA strand

<400> SEQUENCE: 281
ccauauaucg uuuagcaaa 19

<210> SEQ ID NO 282
<211> LENGTH: 19
<212> TYPE: RNA
<213> ORGANISM: Artificial Sequence
<220> FEATURE:
<223> OTHER INFORMATION: siRNA strand

<400> SEQUENCE: 282
uuugcuaaac gauauaugg 19

<210> SEQ ID NO 283
<211> LENGTH: 19
<212> TYPE: RNA
<213> ORGANISM: Artificial Sequence
<220> FEATURE:
<223> OTHER INFORMATION: siRNA strand

<400> SEQUENCE: 283
agaugaugcc auccggguu 19

<210> SEQ ID NO 284
<211> LENGTH: 19
<212> TYPE: RNA
<213> ORGANISM: Artificial Sequence
<220> FEATURE:
<223> OTHER INFORMATION: siRNA strand

<400> SEQUENCE: 284
aacccggaug gcaucaucu 19

<210> SEQ ID NO 285
<211> LENGTH: 19
<212> TYPE: RNA
<213> ORGANISM: Artificial Sequence
<220> FEATURE:
<223> OTHER INFORMATION: siRNA strand

<400> SEQUENCE: 285
acgaagauga ugccauccg 19

<210> SEQ ID NO 286
<211> LENGTH: 19
<212> TYPE: RNA
<213> ORGANISM: Artificial Sequence
<220> FEATURE:
<223> OTHER INFORMATION: siRNA strand

<400> SEQUENCE: 286
cggauggcau caucuucgu 19

<210> SEQ ID NO 287
<211> LENGTH: 19
<212> TYPE: RNA
<213> ORGANISM: Artificial Sequence
<220> FEATURE:
<223> OTHER INFORMATION: siRNA strand

<400> SEQUENCE: 287
ucggacacga agaugaugc 19

<210> SEQ ID NO 288
<211> LENGTH: 19
<212> TYPE: RNA
<213> ORGANISM: Artificial Sequence
<220> FEATURE:
<223> OTHER INFORMATION: siRNA strand

<400> SEQUENCE: 288
gcaucaucuu cguguccga 19

<210> SEQ ID NO 289
<211> LENGTH: 19
<212> TYPE: RNA
<213> ORGANISM: Artificial Sequence
<220> FEATURE:
<223> OTHER INFORMATION: siRNA strand

<400> SEQUENCE: 289
ucggugaagg agaucaggu 19

<210> SEQ ID NO 290
<211> LENGTH: 19
<212> TYPE: RNA
<213> ORGANISM: Artificial Sequence
<220> FEATURE:
<223> OTHER INFORMATION: siRNA strand

<400> SEQUENCE: 290
accugaucuc cuucaccga 19

<210> SEQ ID NO 291
<211> LENGTH: 19
<212> TYPE: RNA
<213> ORGANISM: Artificial Sequence
<220> FEATURE:
<223> OTHER INFORMATION: siRNA strand

<400> SEQUENCE: 291
accucgguga aggagauca 19

<210> SEQ ID NO 292
<211> LENGTH: 19
<212> TYPE: RNA
<213> ORGANISM: Artificial Sequence
<220> FEATURE:
<223> OTHER INFORMATION: siRNA strand

<400> SEQUENCE: 292
ugaucuccuu caccgaggu 19

<210> SEQ ID NO 293
<211> LENGTH: 19
<212> TYPE: RNA
<213> ORGANISM: Artificial Sequence
<220> FEATURE:
<223> OTHER INFORMATION: siRNA strand

<400> SEQUENCE: 293
uacagcuuca ugcucucgc 19

<210> SEQ ID NO 294
<211> LENGTH: 19
<212> TYPE: RNA
<213> ORGANISM: Artificial Sequence
<220> FEATURE:
<223> OTHER INFORMATION: siRNA strand

<400> SEQUENCE: 294
gcgagagcau gaagcugua 19

<210> SEQ ID NO 295
<211> LENGTH: 19

<212> TYPE: RNA
<213> ORGANISM: Artificial Sequence
<220> FEATURE:
<223> OTHER INFORMATION: siRNA strand

<400> SEQUENCE: 295
augaagagca gugaguccu 19

<210> SEQ ID NO 296
<211> LENGTH: 19
<212> TYPE: RNA
<213> ORGANISM: Artificial Sequence
<220> FEATURE:
<223> OTHER INFORMATION: siRNA strand

<400> SEQUENCE: 296
aggacucacu gcucuucau 19

<210> SEQ ID NO 297
<211> LENGTH: 19
<212> TYPE: RNA
<213> ORGANISM: Artificial Sequence
<220> FEATURE:
<223> OTHER INFORMATION: siRNA strand

<400> SEQUENCE: 297
agguaguugc ccuugcgcc 19

<210> SEQ ID NO 298
<211> LENGTH: 19
<212> TYPE: RNA
<213> ORGANISM: Artificial Sequence
<220> FEATURE:
<223> OTHER INFORMATION: siRNA strand

<400> SEQUENCE: 298
ggcgcaaggg caacuaccu 19

<210> SEQ ID NO 299
<211> LENGTH: 19
<212> TYPE: RNA
<213> ORGANISM: Artificial Sequence
<220> FEATURE:
<223> OTHER INFORMATION: siRNA strand

<400> SEQUENCE: 299
ugugagggag guguugacc 19

<210> SEQ ID NO 300
<211> LENGTH: 19
<212> TYPE: RNA
<213> ORGANISM: Artificial Sequence
<220> FEATURE:
<223> OTHER INFORMATION: siRNA strand

<400> SEQUENCE: 300
ggucaacacc ucccucaca 19

<210> SEQ ID NO 301
<211> LENGTH: 19
<212> TYPE: RNA
<213> ORGANISM: Artificial Sequence
<220> FEATURE:
<223> OTHER INFORMATION: siRNA strand

<400> SEQUENCE: 301
auugugaggg agguguuga 19

<210> SEQ ID NO 302
<211> LENGTH: 19
<212> TYPE: RNA
<213> ORGANISM: Artificial Sequence
<220> FEATURE:
<223> OTHER INFORMATION: siRNA strand

<400> SEQUENCE: 302
ucaacaccuc ccucacaau 19

<210> SEQ ID NO 303
<211> LENGTH: 19
<212> TYPE: RNA
<213> ORGANISM: Artificial Sequence
<220> FEATURE:
<223> OTHER INFORMATION: siRNA strand

<400> SEQUENCE: 303
ucuagaagga uugugaggg 19

<210> SEQ ID NO 304
<211> LENGTH: 19
<212> TYPE: RNA
<213> ORGANISM: Artificial Sequence
<220> FEATURE:
<223> OTHER INFORMATION: siRNA strand

<400> SEQUENCE: 304
cccucacaau ccuucuaga 19

<210> SEQ ID NO 305
<211> LENGTH: 19
<212> TYPE: RNA
<213> ORGANISM: Artificial Sequence
<220> FEATURE:
<223> OTHER INFORMATION: siRNA strand

<400> SEQUENCE: 305
uugucuagaa ggauuguga 19

<210> SEQ ID NO 306
<211> LENGTH: 19
<212> TYPE: RNA
<213> ORGANISM: Artificial Sequence
<220> FEATURE:
<223> OTHER INFORMATION: siRNA strand

<400> SEQUENCE: 306
ucacaauccu ucuagacaa 19

<210> SEQ ID NO 307
<211> LENGTH: 19
<212> TYPE: RNA
<213> ORGANISM: Artificial Sequence
<220> FEATURE:
<223> OTHER INFORMATION: siRNA strand

<400> SEQUENCE: 307
ugagguuguc uagaaggau 19

<210> SEQ ID NO 308
<211> LENGTH: 19
<212> TYPE: RNA
<213> ORGANISM: Artificial Sequence
<220> FEATURE:
<223> OTHER INFORMATION: siRNA strand

<400> SEQUENCE: 308
auccuucuag acaaccuca 19

<210> SEQ ID NO 309
<211> LENGTH: 19
<212> TYPE: RNA
<213> ORGANISM: Artificial Sequence
<220> FEATURE:
<223> OTHER INFORMATION: siRNA strand

<400> SEQUENCE: 309
aucuccccaa agaugacaa 19

<210> SEQ ID NO 310
<211> LENGTH: 19
<212> TYPE: RNA
<213> ORGANISM: Artificial Sequence
<220> FEATURE:
<223> OTHER INFORMATION: siRNA strand

<400> SEQUENCE: 310
uugucaucuu uggggagau 19

<210> SEQ ID NO 311
<211> LENGTH: 19
<212> TYPE: RNA
<213> ORGANISM: Artificial Sequence
<220> FEATURE:
<223> OTHER INFORMATION: siRNA strand

<400> SEQUENCE: 311
agcauaaaga auuuggguga 19

<210> SEQ ID NO 312
<211> LENGTH: 19
<212> TYPE: RNA
<213> ORGANISM: Artificial Sequence
<220> FEATURE:
<223> OTHER INFORMATION: siRNA strand

<400> SEQUENCE: 312
ucaccaaauu cuuuaugcu 19

<210> SEQ ID NO 313
<211> LENGTH: 19
<212> TYPE: RNA
<213> ORGANISM: Artificial Sequence
<220> FEATURE:
<223> OTHER INFORMATION: siRNA strand

<400> SEQUENCE: 313
acaguuuugg uccuuaguu 19

<210> SEQ ID NO 314
<211> LENGTH: 19
<212> TYPE: RNA
<213> ORGANISM: Artificial Sequence
<220> FEATURE:
<223> OTHER INFORMATION: siRNA strand

<400> SEQUENCE: 314
aacuaaggac caaaacugu 19

<210> SEQ ID NO 315
<211> LENGTH: 19
<212> TYPE: RNA
<213> ORGANISM: Artificial Sequence
<220> FEATURE:
<223> OTHER INFORMATION: siRNA strand

<400> SEQUENCE: 315
auauccucua caguuuugg 19

<210> SEQ ID NO 316
<211> LENGTH: 19
<212> TYPE: RNA
<213> ORGANISM: Artificial Sequence
<220> FEATURE:
<223> OTHER INFORMATION: siRNA strand

<400> SEQUENCE: 316
ccaaaacugu agaggauau 19

<210> SEQ ID NO 317
<211> LENGTH: 19
<212> TYPE: RNA
<213> ORGANISM: Artificial Sequence
<220> FEATURE:
<223> OTHER INFORMATION: siRNA strand

<400> SEQUENCE: 317
auaucuacaa uauuggacu 19

<210> SEQ ID NO 318
<211> LENGTH: 19
<212> TYPE: RNA
<213> ORGANISM: Artificial Sequence
<220> FEATURE:
<223> OTHER INFORMATION: siRNA strand

<400> SEQUENCE: 318
aguccaauau uguagauau 19

<210> SEQ ID NO 319
<211> LENGTH: 19
<212> TYPE: RNA
<213> ORGANISM: Artificial Sequence
<220> FEATURE:
<223> OTHER INFORMATION: siRNA strand

<400> SEQUENCE: 319
aauaucuaca auauuggac 19

<210> SEQ ID NO 320
<211> LENGTH: 19
<212> TYPE: RNA
<213> ORGANISM: Artificial Sequence
<220> FEATURE:
<223> OTHER INFORMATION: siRNA strand

<400> SEQUENCE: 320
guccaauauu guagauauu 19

<210> SEQ ID NO 321
<211> LENGTH: 19
<212> TYPE: RNA
<213> ORGANISM: Artificial Sequence
<220> FEATURE:
<223> OTHER INFORMATION: siRNA strand

<400> SEQUENCE: 321
uugacguaga gaauaucua 19

<210> SEQ ID NO 322
<211> LENGTH: 19
<212> TYPE: RNA
<213> ORGANISM: Artificial Sequence
<220> FEATURE:
<223> OTHER INFORMATION: siRNA strand

<400> SEQUENCE: 322
uagauauucu cuacgucaa 19

<210> SEQ ID NO 323
<211> LENGTH: 19
<212> TYPE: RNA
<213> ORGANISM: Artificial Sequence
<220> FEATURE:
<223> OTHER INFORMATION: siRNA strand

<400> SEQUENCE: 323
aagucuuuga cguagagaa 19

<210> SEQ ID NO 324
<211> LENGTH: 19
<212> TYPE: RNA
<213> ORGANISM: Artificial Sequence
<220> FEATURE:
<223> OTHER INFORMATION: siRNA strand

<400> SEQUENCE: 324
uucucuacgu caaagacuu 19

<210> SEQ ID NO 325
<211> LENGTH: 19
<212> TYPE: RNA
<213> ORGANISM: Artificial Sequence
<220> FEATURE:
<223> OTHER INFORMATION: siRNA strand

<400> SEQUENCE: 325
uagaagcgag ugauagucu 19

<210> SEQ ID NO 326
<211> LENGTH: 19
<212> TYPE: RNA
<213> ORGANISM: Artificial Sequence
<220> FEATURE:
<223> OTHER INFORMATION: siRNA strand

<400> SEQUENCE: 326
agacuaucac ucgcuucua 19

<210> SEQ ID NO 327
<211> LENGTH: 19
<212> TYPE: RNA
<213> ORGANISM: Artificial Sequence
<220> FEATURE:
<223> OTHER INFORMATION: siRNA strand

<400> SEQUENCE: 327
uugaaggcag agaagucac 19

<210> SEQ ID NO 328

<211> LENGTH: 19
<212> TYPE: RNA
<213> ORGANISM: Artificial Sequence
<220> FEATURE:
<223> OTHER INFORMATION: siRNA strand

<400> SEQUENCE: 328
gugacuucuc ugccuucaa 19

<210> SEQ ID NO 329
<211> LENGTH: 19
<212> TYPE: RNA
<213> ORGANISM: Artificial Sequence
<220> FEATURE:
<223> OTHER INFORMATION: siRNA strand

<400> SEQUENCE: 329
uuucacuuug agcucauug 19

<210> SEQ ID NO 330
<211> LENGTH: 19
<212> TYPE: RNA
<213> ORGANISM: Artificial Sequence
<220> FEATURE:
<223> OTHER INFORMATION: siRNA strand

<400> SEQUENCE: 330
caaugagcuc aaagugaaa 19

<210> SEQ ID NO 331
<211> LENGTH: 19
<212> TYPE: RNA
<213> ORGANISM: Artificial Sequence
<220> FEATURE:
<223> OTHER INFORMATION: siRNA strand

<400> SEQUENCE: 331
aacugguugc ugcugccug 19

<210> SEQ ID NO 332
<211> LENGTH: 19
<212> TYPE: RNA
<213> ORGANISM: Artificial Sequence
<220> FEATURE:
<223> OTHER INFORMATION: siRNA strand

<400> SEQUENCE: 332
caggcagcag caaccaguu 19

<210> SEQ ID NO 333
<211> LENGTH: 19
<212> TYPE: RNA
<213> ORGANISM: Artificial Sequence
<220> FEATURE:
<223> OTHER INFORMATION: siRNA strand

<400> SEQUENCE: 333
uugagaagag uuguggucu 19

<210> SEQ ID NO 334
<211> LENGTH: 19
<212> TYPE: RNA
<213> ORGANISM: Artificial Sequence
<220> FEATURE:
<223> OTHER INFORMATION: siRNA strand

<400> SEQUENCE: 334
agaccacaac ucuucucaa 19

<210> SEQ ID NO 335
<211> LENGTH: 19
<212> TYPE: RNA
<213> ORGANISM: Artificial Sequence
<220> FEATURE:
<223> OTHER INFORMATION: siRNA strand

<400> SEQUENCE: 335
uucauguggg cccacuggg 19

<210> SEQ ID NO 336
<211> LENGTH: 19
<212> TYPE: RNA
<213> ORGANISM: Artificial Sequence
<220> FEATURE:
<223> OTHER INFORMATION: siRNA strand

<400> SEQUENCE: 336
cccagugggc ccacaugaa 19

<210> SEQ ID NO 337
<211> LENGTH: 19
<212> TYPE: RNA
<213> ORGANISM: Artificial Sequence
<220> FEATURE:
<223> OTHER INFORMATION: siRNA strand

<400> SEQUENCE: 337
ucuucaugug ggcccacug 19

<210> SEQ ID NO 338
<211> LENGTH: 19
<212> TYPE: RNA
<213> ORGANISM: Artificial Sequence
<220> FEATURE:
<223> OTHER INFORMATION: siRNA strand

<400> SEQUENCE: 338
cagugggccc acaugaaga 19

<210> SEQ ID NO 339
<211> LENGTH: 19
<212> TYPE: RNA
<213> ORGANISM: Artificial Sequence
<220> FEATURE:
<223> OTHER INFORMATION: siRNA strand

<400> SEQUENCE: 339
uggacuaaca gguucccuc 19

<210> SEQ ID NO 340
<211> LENGTH: 19
<212> TYPE: RNA
<213> ORGANISM: Artificial Sequence
<220> FEATURE:
<223> OTHER INFORMATION: siRNA strand

<400> SEQUENCE: 340
gagggaaccu guuagucca 19

<210> SEQ ID NO 341
<211> LENGTH: 19
<212> TYPE: RNA

<213> ORGANISM: Artificial Sequence
<220> FEATURE:
<223> OTHER INFORMATION: siRNA strand

<400> SEQUENCE: 341
uuccuuaacc cugucuucc 19

<210> SEQ ID NO 342
<211> LENGTH: 19
<212> TYPE: RNA
<213> ORGANISM: Artificial Sequence
<220> FEATURE:
<223> OTHER INFORMATION: siRNA strand

<400> SEQUENCE: 342
ggaagacagg guuaaggaa 19

<210> SEQ ID NO 343
<211> LENGTH: 19
<212> TYPE: RNA
<213> ORGANISM: Artificial Sequence
<220> FEATURE:
<223> OTHER INFORMATION: siRNA strand

<400> SEQUENCE: 343
aguuccuuaa cccugucuu 19

<210> SEQ ID NO 344
<211> LENGTH: 19
<212> TYPE: RNA
<213> ORGANISM: Artificial Sequence
<220> FEATURE:
<223> OTHER INFORMATION: siRNA strand

<400> SEQUENCE: 344
aagacagggu uaaggaacu 19

<210> SEQ ID NO 345
<211> LENGTH: 19
<212> TYPE: RNA
<213> ORGANISM: Artificial Sequence
<220> FEATURE:
<223> OTHER INFORMATION: siRNA strand

<400> SEQUENCE: 345
auaaaguucc uuaacccug 19

<210> SEQ ID NO 346
<211> LENGTH: 19
<212> TYPE: RNA
<213> ORGANISM: Artificial Sequence
<220> FEATURE:
<223> OTHER INFORMATION: siRNA strand

<400> SEQUENCE: 346
caggguuaag gaacuuuau 19

<210> SEQ ID NO 347
<211> LENGTH: 19
<212> TYPE: RNA
<213> ORGANISM: Artificial Sequence
<220> FEATURE:
<223> OTHER INFORMATION: siRNA strand

<400> SEQUENCE: 347
aaauaaaguu ccuuaaccc 19

<210> SEQ ID NO 348
<211> LENGTH: 19
<212> TYPE: RNA
<213> ORGANISM: Artificial Sequence
<220> FEATURE:
<223> OTHER INFORMATION: siRNA strand

<400> SEQUENCE: 348
ggguuaagga acuuuauuu 19

<210> SEQ ID NO 349
<211> LENGTH: 19
<212> TYPE: RNA
<213> ORGANISM: Artificial Sequence
<220> FEATURE:
<223> OTHER INFORMATION: siRNA strand

<400> SEQUENCE: 349
uacauaaagu uccuuaacc 19

<210> SEQ ID NO 350
<211> LENGTH: 19
<212> TYPE: RNA
<213> ORGANISM: Artificial Sequence
<220> FEATURE:
<223> OTHER INFORMATION: siRNA strand

<400> SEQUENCE: 350
gguuaaggaa cuuuaugua 19

<210> SEQ ID NO 351
<211> LENGTH: 19
<212> TYPE: RNA
<213> ORGANISM: Artificial Sequence
<220> FEATURE:
<223> OTHER INFORMATION: siRNA strand

<400> SEQUENCE: 351
auuaucaugu cccugauca 19

<210> SEQ ID NO 352
<211> LENGTH: 19
<212> TYPE: RNA
<213> ORGANISM: Artificial Sequence
<220> FEATURE:
<223> OTHER INFORMATION: siRNA strand

<400> SEQUENCE: 352
ugaucaggga caugauaau 19

<210> SEQ ID NO 353
<211> LENGTH: 19
<212> TYPE: RNA
<213> ORGANISM: Artificial Sequence
<220> FEATURE:
<223> OTHER INFORMATION: siRNA strand

<400> SEQUENCE: 353
auaaagaacc ugcuuccgu 19

<210> SEQ ID NO 354
<211> LENGTH: 19
<212> TYPE: RNA
<213> ORGANISM: Artificial Sequence
<220> FEATURE:

<223> OTHER INFORMATION: siRNA strand

<400> SEQUENCE: 354
acggaagcag guucuuuau 19

<210> SEQ ID NO 355
<211> LENGTH: 19
<212> TYPE: RNA
<213> ORGANISM: Artificial Sequence
<220> FEATURE:
<223> OTHER INFORMATION: siRNA strand

<400> SEQUENCE: 355
acuaacuuca gcaagggca 19

<210> SEQ ID NO 356
<211> LENGTH: 19
<212> TYPE: RNA
<213> ORGANISM: Artificial Sequence
<220> FEATURE:
<223> OTHER INFORMATION: siRNA strand

<400> SEQUENCE: 356
ugcccuugcu gaaguuagu 19

<210> SEQ ID NO 357
<211> LENGTH: 19
<212> TYPE: RNA
<213> ORGANISM: Artificial Sequence
<220> FEATURE:
<223> OTHER INFORMATION: siRNA strand

<400> SEQUENCE: 357
uggugcaaga caaucccug 19

<210> SEQ ID NO 358
<211> LENGTH: 19
<212> TYPE: RNA
<213> ORGANISM: Artificial Sequence
<220> FEATURE:
<223> OTHER INFORMATION: siRNA strand

<400> SEQUENCE: 358
cagggauugu cuugcacca 19

<210> SEQ ID NO 359
<211> LENGTH: 19
<212> TYPE: RNA
<213> ORGANISM: Artificial Sequence
<220> FEATURE:
<223> OTHER INFORMATION: siRNA strand

<400> SEQUENCE: 359
uuggaaauaa ugaugaccc 19

<210> SEQ ID NO 360
<211> LENGTH: 19
<212> TYPE: RNA
<213> ORGANISM: Artificial Sequence
<220> FEATURE:
<223> OTHER INFORMATION: siRNA strand

<400> SEQUENCE: 360
gggucaucau uauuuccaa 19

-continued

<210> SEQ ID NO 361
<211> LENGTH: 19
<212> TYPE: RNA
<213> ORGANISM: Artificial Sequence
<220> FEATURE:
<223> OTHER INFORMATION: siRNA strand

<400> SEQUENCE: 361
auuaucauug uuuugugac 19

<210> SEQ ID NO 362
<211> LENGTH: 19
<212> TYPE: RNA
<213> ORGANISM: Artificial Sequence
<220> FEATURE:
<223> OTHER INFORMATION: siRNA strand

<400> SEQUENCE: 362
gucacaaaac aaugauaau 19

<210> SEQ ID NO 363
<211> LENGTH: 19
<212> TYPE: RNA
<213> ORGANISM: Artificial Sequence
<220> FEATURE:
<223> OTHER INFORMATION: siRNA strand

<400> SEQUENCE: 363
uccccgagag ucaaacuca 19

<210> SEQ ID NO 364
<211> LENGTH: 19
<212> TYPE: RNA
<213> ORGANISM: Artificial Sequence
<220> FEATURE:
<223> OTHER INFORMATION: siRNA strand

<400> SEQUENCE: 364
ugaguuugac ucucgggga 19

<210> SEQ ID NO 365
<211> LENGTH: 19
<212> TYPE: RNA
<213> ORGANISM: Artificial Sequence
<220> FEATURE:
<223> OTHER INFORMATION: siRNA strand

<400> SEQUENCE: 365
aacuccccga gagucaaac 19

<210> SEQ ID NO 366
<211> LENGTH: 19
<212> TYPE: RNA
<213> ORGANISM: Artificial Sequence
<220> FEATURE:
<223> OTHER INFORMATION: siRNA strand

<400> SEQUENCE: 366
guuugacucu cggggaguu 19

<210> SEQ ID NO 367
<211> LENGTH: 19
<212> TYPE: RNA
<213> ORGANISM: Artificial Sequence
<220> FEATURE:
<223> OTHER INFORMATION: siRNA strand

<400> SEQUENCE: 367
aacaacaaaa cuccccgag 19

<210> SEQ ID NO 368
<211> LENGTH: 19
<212> TYPE: RNA
<213> ORGANISM: Artificial Sequence
<220> FEATURE:
<223> OTHER INFORMATION: siRNA strand

<400> SEQUENCE: 368
cucggggagu uuuguuguu 19

<210> SEQ ID NO 369
<211> LENGTH: 19
<212> TYPE: RNA
<213> ORGANISM: Artificial Sequence
<220> FEATURE:
<223> OTHER INFORMATION: siRNA strand

<400> SEQUENCE: 369
auaacaacaa aacuccccg 19

<210> SEQ ID NO 370
<211> LENGTH: 19
<212> TYPE: RNA
<213> ORGANISM: Artificial Sequence
<220> FEATURE:
<223> OTHER INFORMATION: siRNA strand

<400> SEQUENCE: 370
cggggaguuu uguuguuau 19

<210> SEQ ID NO 371
<211> LENGTH: 19
<212> TYPE: RNA
<213> ORGANISM: Artificial Sequence
<220> FEATURE:
<223> OTHER INFORMATION: siRNA strand

<400> SEQUENCE: 371
ugacaaaaga cacaagagu 19

<210> SEQ ID NO 372
<211> LENGTH: 19
<212> TYPE: RNA
<213> ORGANISM: Artificial Sequence
<220> FEATURE:
<223> OTHER INFORMATION: siRNA strand

<400> SEQUENCE: 372
acucuugugu cuuuuguca 19

<210> SEQ ID NO 373
<211> LENGTH: 19
<212> TYPE: RNA
<213> ORGANISM: Artificial Sequence
<220> FEATURE:
<223> OTHER INFORMATION: siRNA strand

<400> SEQUENCE: 373
ucuaggauca cgcucugcu 19

<210> SEQ ID NO 374
<211> LENGTH: 19

<212> TYPE: RNA
<213> ORGANISM: Artificial Sequence
<220> FEATURE:
<223> OTHER INFORMATION: siRNA strand

<400> SEQUENCE: 374
agcagagcgu gauccuaga 19

<210> SEQ ID NO 375
<211> LENGTH: 19
<212> TYPE: RNA
<213> ORGANISM: Artificial Sequence
<220> FEATURE:
<223> OTHER INFORMATION: siRNA strand

<400> SEQUENCE: 375
uacuuguugc agcucgcca 19

<210> SEQ ID NO 376
<211> LENGTH: 19
<212> TYPE: RNA
<213> ORGANISM: Artificial Sequence
<220> FEATURE:
<223> OTHER INFORMATION: siRNA strand

<400> SEQUENCE: 376
uggcgagcug caacaagua 19

<210> SEQ ID NO 377
<211> LENGTH: 19
<212> TYPE: RNA
<213> ORGANISM: Artificial Sequence
<220> FEATURE:
<223> OTHER INFORMATION: siRNA strand

<400> SEQUENCE: 377
uacgacuugu ugcagcucg 19

<210> SEQ ID NO 378
<211> LENGTH: 19
<212> TYPE: RNA
<213> ORGANISM: Artificial Sequence
<220> FEATURE:
<223> OTHER INFORMATION: siRNA strand

<400> SEQUENCE: 378
cgagcugcaa caagucgua 19

<210> SEQ ID NO 379
<211> LENGTH: 19
<212> TYPE: RNA
<213> ORGANISM: Artificial Sequence
<220> FEATURE:
<223> OTHER INFORMATION: siRNA strand

<400> SEQUENCE: 379
uacacgaaga ugaugccau 19

<210> SEQ ID NO 380
<211> LENGTH: 19
<212> TYPE: RNA
<213> ORGANISM: Artificial Sequence
<220> FEATURE:
<223> OTHER INFORMATION: siRNA strand

<400> SEQUENCE: 380
auggcaucau cuucgugua 19

<210> SEQ ID NO 381
<211> LENGTH: 19
<212> TYPE: RNA
<213> ORGANISM: Artificial Sequence
<220> FEATURE:
<223> OTHER INFORMATION: siRNA strand

<400> SEQUENCE: 381
uggugaagga gaucagguu 19

<210> SEQ ID NO 382
<211> LENGTH: 19
<212> TYPE: RNA
<213> ORGANISM: Artificial Sequence
<220> FEATURE:
<223> OTHER INFORMATION: siRNA strand

<400> SEQUENCE: 382
aaccugaucu ccuucacca 19

<210> SEQ ID NO 383
<211> LENGTH: 19
<212> TYPE: RNA
<213> ORGANISM: Artificial Sequence
<220> FEATURE:
<223> OTHER INFORMATION: siRNA strand

<400> SEQUENCE: 383
uucacguuga ccagcugcu 19

<210> SEQ ID NO 384
<211> LENGTH: 19
<212> TYPE: RNA
<213> ORGANISM: Artificial Sequence
<220> FEATURE:
<223> OTHER INFORMATION: siRNA strand

<400> SEQUENCE: 384
agcagcuggu caacgugaa 19

<210> SEQ ID NO 385
<211> LENGTH: 19
<212> TYPE: RNA
<213> ORGANISM: Artificial Sequence
<220> FEATURE:
<223> OTHER INFORMATION: siRNA strand

<400> SEQUENCE: 385
uacccgauga gguugucua 19

<210> SEQ ID NO 386
<211> LENGTH: 19
<212> TYPE: RNA
<213> ORGANISM: Artificial Sequence
<220> FEATURE:
<223> OTHER INFORMATION: siRNA strand

<400> SEQUENCE: 386
uagacaaccu caucgggua 19

<210> SEQ ID NO 387
<211> LENGTH: 19
<212> TYPE: RNA
<213> ORGANISM: Artificial Sequence
<220> FEATURE:
<223> OTHER INFORMATION: siRNA strand

<400> SEQUENCE: 387
uuaaacagug cgaaucucc 19

<210> SEQ ID NO 388
<211> LENGTH: 19
<212> TYPE: RNA
<213> ORGANISM: Artificial Sequence
<220> FEATURE:
<223> OTHER INFORMATION: siRNA strand

<400> SEQUENCE: 388
ggagauucgc acuguuuaa 19

<210> SEQ ID NO 389
<211> LENGTH: 19
<212> TYPE: RNA
<213> ORGANISM: Artificial Sequence
<220> FEATURE:
<223> OTHER INFORMATION: siRNA strand

<400> SEQUENCE: 389
uuuguaaaca gugcgaauc 19

<210> SEQ ID NO 390
<211> LENGTH: 19
<212> TYPE: RNA
<213> ORGANISM: Artificial Sequence
<220> FEATURE:
<223> OTHER INFORMATION: siRNA strand

<400> SEQUENCE: 390
gauucgcacu guuuacaaa 19

<210> SEQ ID NO 391
<211> LENGTH: 19
<212> TYPE: RNA
<213> ORGANISM: Artificial Sequence
<220> FEATURE:
<223> OTHER INFORMATION: siRNA strand

<400> SEQUENCE: 391
uauuauaggg cucugucac 19

<210> SEQ ID NO 392
<211> LENGTH: 19
<212> TYPE: RNA
<213> ORGANISM: Artificial Sequence
<220> FEATURE:
<223> OTHER INFORMATION: siRNA strand

<400> SEQUENCE: 392
gugacagagc ccuauaaua 19

<210> SEQ ID NO 393
<211> LENGTH: 19
<212> TYPE: RNA
<213> ORGANISM: Artificial Sequence
<220> FEATURE:
<223> OTHER INFORMATION: siRNA strand

<400> SEQUENCE: 393
uucauuauag ggcuccguc 19

<210> SEQ ID NO 394
<211> LENGTH: 19
<212> TYPE: RNA
<213> ORGANISM: Artificial Sequence
<220> FEATURE:
<223> OTHER INFORMATION: siRNA strand

<400> SEQUENCE: 394
gacggagccc uauaaugaa 19

<210> SEQ ID NO 395
<211> LENGTH: 19
<212> TYPE: RNA
<213> ORGANISM: Artificial Sequence
<220> FEATURE:
<223> OTHER INFORMATION: siRNA strand

<400> SEQUENCE: 395
uaucauauug agcuccucu 19

<210> SEQ ID NO 396
<211> LENGTH: 19
<212> TYPE: RNA
<213> ORGANISM: Artificial Sequence
<220> FEATURE:
<223> OTHER INFORMATION: siRNA strand

<400> SEQUENCE: 396
agaggagcuc aauaugaua 19

<210> SEQ ID NO 397
<211> LENGTH: 19
<212> TYPE: RNA
<213> ORGANISM: Artificial Sequence
<220> FEATURE:
<223> OTHER INFORMATION: siRNA strand

<400> SEQUENCE: 397
ucugggucau gauauccuc 19

<210> SEQ ID NO 398
<211> LENGTH: 19
<212> TYPE: RNA
<213> ORGANISM: Artificial Sequence
<220> FEATURE:
<223> OTHER INFORMATION: siRNA strand

<400> SEQUENCE: 398
gaggauauca ugacccaga 19

<210> SEQ ID NO 399
<211> LENGTH: 19
<212> TYPE: RNA
<213> ORGANISM: Artificial Sequence
<220> FEATURE:
<223> OTHER INFORMATION: siRNA strand

<400> SEQUENCE: 399
uugcggauca ugaagcagu 19

<210> SEQ ID NO 400
<211> LENGTH: 19
<212> TYPE: RNA
<213> ORGANISM: Artificial Sequence
<220> FEATURE:
<223> OTHER INFORMATION: siRNA strand

<400> SEQUENCE: 400
acugcuucau gauccgcaa 19

<210> SEQ ID NO 401
<211> LENGTH: 19
<212> TYPE: RNA
<213> ORGANISM: Artificial Sequence
<220> FEATURE:
<223> OTHER INFORMATION: siRNA strand

<400> SEQUENCE: 401
ugagauuuuc acuuugagc 19

<210> SEQ ID NO 402
<211> LENGTH: 19
<212> TYPE: RNA
<213> ORGANISM: Artificial Sequence
<220> FEATURE:
<223> OTHER INFORMATION: siRNA strand

<400> SEQUENCE: 402
gcucaaagug aaaaucuca 19

<210> SEQ ID NO 403
<211> LENGTH: 19
<212> TYPE: RNA
<213> ORGANISM: Artificial Sequence
<220> FEATURE:
<223> OTHER INFORMATION: siRNA strand

<400> SEQUENCE: 403
uuuauuucgg guguacagg 19

<210> SEQ ID NO 404
<211> LENGTH: 19
<212> TYPE: RNA
<213> ORGANISM: Artificial Sequence
<220> FEATURE:
<223> OTHER INFORMATION: siRNA strand

<400> SEQUENCE: 404
ccuguacacc cgaaauaaa 19

<210> SEQ ID NO 405
<211> LENGTH: 19
<212> TYPE: RNA
<213> ORGANISM: Artificial Sequence
<220> FEATURE:
<223> OTHER INFORMATION: siRNA strand

<400> SEQUENCE: 405
ucgcccgucu caaacuuca 19

<210> SEQ ID NO 406
<211> LENGTH: 19
<212> TYPE: RNA
<213> ORGANISM: Artificial Sequence
<220> FEATURE:
<223> OTHER INFORMATION: siRNA strand

<400> SEQUENCE: 406
ugaaguuuga gacgggcga 19

<210> SEQ ID NO 407

<211> LENGTH: 19
<212> TYPE: RNA
<213> ORGANISM: Artificial Sequence
<220> FEATURE:
<223> OTHER INFORMATION: siRNA strand

<400> SEQUENCE: 407
uuuaacccug ucuucccuu 19

<210> SEQ ID NO 408
<211> LENGTH: 19
<212> TYPE: RNA
<213> ORGANISM: Artificial Sequence
<220> FEATURE:
<223> OTHER INFORMATION: siRNA strand

<400> SEQUENCE: 408
aagggaagac aggguuaaa 19

<210> SEQ ID NO 409
<211> LENGTH: 19
<212> TYPE: RNA
<213> ORGANISM: Artificial Sequence
<220> FEATURE:
<223> OTHER INFORMATION: siRNA strand

<400> SEQUENCE: 409
uaguuccagg guauggcuc 19

<210> SEQ ID NO 410
<211> LENGTH: 19
<212> TYPE: RNA
<213> ORGANISM: Artificial Sequence
<220> FEATURE:
<223> OTHER INFORMATION: siRNA strand

<400> SEQUENCE: 410
gagccauacc cuggaacua 19

<210> SEQ ID NO 411
<211> LENGTH: 19
<212> TYPE: RNA
<213> ORGANISM: Artificial Sequence
<220> FEATURE:
<223> OTHER INFORMATION: siRNA strand

<400> SEQUENCE: 411
ucgagaguca aacucauaa 19

<210> SEQ ID NO 412
<211> LENGTH: 19
<212> TYPE: RNA
<213> ORGANISM: Artificial Sequence
<220> FEATURE:
<223> OTHER INFORMATION: siRNA strand

<400> SEQUENCE: 412
uuaugaguuu gacucucga 19

<210> SEQ ID NO 413
<211> LENGTH: 19
<212> TYPE: RNA
<213> ORGANISM: Artificial Sequence
<220> FEATURE:
<223> OTHER INFORMATION: siRNA strand

<400> SEQUENCE: 413
uucauaacaa caaaacucc 19

<210> SEQ ID NO 414
<211> LENGTH: 19
<212> TYPE: RNA
<213> ORGANISM: Artificial Sequence
<220> FEATURE:
<223> OTHER INFORMATION: siRNA strand

<400> SEQUENCE: 414
ggaguuuugu uguuaugaa 19

<210> SEQ ID NO 415
<211> LENGTH: 19
<212> TYPE: RNA
<213> ORGANISM: Artificial Sequence
<220> FEATURE:
<223> OTHER INFORMATION: siRNA strand

<400> SEQUENCE: 415
ucauauaucg uuuagcaaa 19

<210> SEQ ID NO 416
<211> LENGTH: 19
<212> TYPE: RNA
<213> ORGANISM: Artificial Sequence
<220> FEATURE:
<223> OTHER INFORMATION: siRNA strand

<400> SEQUENCE: 416
uuugcuaaac gauauauga 19

<210> SEQ ID NO 417
<211> LENGTH: 19
<212> TYPE: RNA
<213> ORGANISM: Artificial Sequence
<220> FEATURE:
<223> OTHER INFORMATION: siRNA strand

<400> SEQUENCE: 417
uuaucuacaa uauuggacu 19

<210> SEQ ID NO 418
<211> LENGTH: 19
<212> TYPE: RNA
<213> ORGANISM: Artificial Sequence
<220> FEATURE:
<223> OTHER INFORMATION: siRNA strand

<400> SEQUENCE: 418
uauaucuaca auauuggac 19

<210> SEQ ID NO 419
<211> LENGTH: 19
<212> TYPE: RNA
<213> ORGANISM: Artificial Sequence
<220> FEATURE:
<223> OTHER INFORMATION: siRNA strand

<400> SEQUENCE: 419
uuaaaguucc uuaacccug 19

<210> SEQ ID NO 420
<211> LENGTH: 19
<212> TYPE: RNA

<213> ORGANISM: Artificial Sequence
<220> FEATURE:
<223> OTHER INFORMATION: siRNA strand

<400> SEQUENCE: 420
uuuaucauug uuuugugac 19

<210> SEQ ID NO 421
<211> LENGTH: 19
<212> TYPE: RNA
<213> ORGANISM: Artificial Sequence
<220> FEATURE:
<223> OTHER INFORMATION: siRNA strand

<400> SEQUENCE: 421
uuaacaacaa aacuccccg 19

<210> SEQ ID NO 422
<211> LENGTH: 19
<212> TYPE: RNA
<213> ORGANISM: Artificial Sequence
<220> FEATURE:
<223> OTHER INFORMATION: siRNA strand

<400> SEQUENCE: 422
gaacugagaa ggagagaaa 19

<210> SEQ ID NO 423
<211> LENGTH: 19
<212> TYPE: RNA
<213> ORGANISM: Artificial Sequence
<220> FEATURE:
<223> OTHER INFORMATION: siRNA strand

<400> SEQUENCE: 423
uuucucuccu ucucaguuc 19

<210> SEQ ID NO 424
<211> LENGTH: 19
<212> TYPE: RNA
<213> ORGANISM: Artificial Sequence
<220> FEATURE:
<223> OTHER INFORMATION: siRNA strand

<400> SEQUENCE: 424
gggagaagcu gauggagau 19

<210> SEQ ID NO 425
<211> LENGTH: 19
<212> TYPE: RNA
<213> ORGANISM: Artificial Sequence
<220> FEATURE:
<223> OTHER INFORMATION: siRNA strand

<400> SEQUENCE: 425
aucuccauca gcuucuccc 19

<210> SEQ ID NO 426
<211> LENGTH: 19
<212> TYPE: RNA
<213> ORGANISM: Artificial Sequence
<220> FEATURE:
<223> OTHER INFORMATION: siRNA strand

<400> SEQUENCE: 426
caaugaacuc aaagugaaa 19

<210> SEQ ID NO 427
<211> LENGTH: 19
<212> TYPE: RNA
<213> ORGANISM: Artificial Sequence
<220> FEATURE:
<223> OTHER INFORMATION: siRNA strand

<400> SEQUENCE: 427
uuucacuuug aguucauug 19

<210> SEQ ID NO 428
<211> LENGTH: 19
<212> TYPE: RNA
<213> ORGANISM: Artificial Sequence
<220> FEATURE:
<223> OTHER INFORMATION: siRNA strand

<400> SEQUENCE: 428
cgggagaagc ugauggaga 19

<210> SEQ ID NO 429
<211> LENGTH: 19
<212> TYPE: RNA
<213> ORGANISM: Artificial Sequence
<220> FEATURE:
<223> OTHER INFORMATION: siRNA strand

<400> SEQUENCE: 429
ucuccaucag cuucucccg 19

<210> SEQ ID NO 430
<211> LENGTH: 19
<212> TYPE: RNA
<213> ORGANISM: Artificial Sequence
<220> FEATURE:
<223> OTHER INFORMATION: siRNA strand

<400> SEQUENCE: 430
uggugaagga ggaguuaaa 19

<210> SEQ ID NO 431
<211> LENGTH: 19
<212> TYPE: RNA
<213> ORGANISM: Artificial Sequence
<220> FEATURE:
<223> OTHER INFORMATION: siRNA strand

<400> SEQUENCE: 431
uuuaacuccu ccuucacca 19

<210> SEQ ID NO 432
<211> LENGTH: 19
<212> TYPE: RNA
<213> ORGANISM: Artificial Sequence
<220> FEATURE:
<223> OTHER INFORMATION: siRNA strand

<400> SEQUENCE: 432
gugaaggagg aguuaaaua 19

<210> SEQ ID NO 433
<211> LENGTH: 19
<212> TYPE: RNA
<213> ORGANISM: Artificial Sequence
<220> FEATURE:

<223> OTHER INFORMATION: siRNA strand

<400> SEQUENCE: 433
uauuuaacuc cuccuucac 19

<210> SEQ ID NO 434
<211> LENGTH: 19
<212> TYPE: RNA
<213> ORGANISM: Artificial Sequence
<220> FEATURE:
<223> OTHER INFORMATION: siRNA strand

<400> SEQUENCE: 434
gauuguagcu guuaagaaa 19

<210> SEQ ID NO 435
<211> LENGTH: 19
<212> TYPE: RNA
<213> ORGANISM: Artificial Sequence
<220> FEATURE:
<223> OTHER INFORMATION: siRNA strand

<400> SEQUENCE: 435
uuucuuaaca gcuacaauc 19

<210> SEQ ID NO 436
<211> LENGTH: 19
<212> TYPE: RNA
<213> ORGANISM: Artificial Sequence
<220> FEATURE:
<223> OTHER INFORMATION: siRNA strand

<400> SEQUENCE: 436
aggcagagcu caagggaga 19

<210> SEQ ID NO 437
<211> LENGTH: 19
<212> TYPE: RNA
<213> ORGANISM: Artificial Sequence
<220> FEATURE:
<223> OTHER INFORMATION: siRNA strand

<400> SEQUENCE: 437
ucucccuuga gcucugccu 19

<210> SEQ ID NO 438
<211> LENGTH: 19
<212> TYPE: RNA
<213> ORGANISM: Artificial Sequence
<220> FEATURE:
<223> OTHER INFORMATION: siRNA strand

<400> SEQUENCE: 438
gauuguagcu guuaagaaa 19

<210> SEQ ID NO 439
<211> LENGTH: 19
<212> TYPE: RNA
<213> ORGANISM: Artificial Sequence
<220> FEATURE:
<223> OTHER INFORMATION: siRNA strand

<400> SEQUENCE: 439
uuucuuaaca gcuacaauc 19

<210> SEQ ID NO 440
<211> LENGTH: 19
<212> TYPE: RNA
<213> ORGANISM: Artificial Sequence
<220> FEATURE:
<223> OTHER INFORMATION: siRNA strand

<400> SEQUENCE: 440
cgauggagau uuagaguau 19

<210> SEQ ID NO 441
<211> LENGTH: 19
<212> TYPE: RNA
<213> ORGANISM: Artificial Sequence
<220> FEATURE:
<223> OTHER INFORMATION: siRNA strand

<400> SEQUENCE: 441
auacucuaaa ucuccaucg 19

<210> SEQ ID NO 442
<211> LENGTH: 19
<212> TYPE: RNA
<213> ORGANISM: Artificial Sequence
<220> FEATURE:
<223> OTHER INFORMATION: siRNA strand

<400> SEQUENCE: 442
gcugaugagu gcaaagaaa 19

<210> SEQ ID NO 443
<211> LENGTH: 19
<212> TYPE: RNA
<213> ORGANISM: Artificial Sequence
<220> FEATURE:
<223> OTHER INFORMATION: siRNA strand

<400> SEQUENCE: 443
uuucuuugca cucaucagc 19

<210> SEQ ID NO 444
<211> LENGTH: 19
<212> TYPE: RNA
<213> ORGANISM: Artificial Sequence
<220> FEATURE:
<223> OTHER INFORMATION: siRNA strand

<400> SEQUENCE: 444
ccucaaagcu caaggcaca 19

<210> SEQ ID NO 445
<211> LENGTH: 19
<212> TYPE: RNA
<213> ORGANISM: Artificial Sequence
<220> FEATURE:
<223> OTHER INFORMATION: siRNA strand

<400> SEQUENCE: 445
ugugccuuga gcuuugagg 19

<210> SEQ ID NO 446
<211> LENGTH: 19
<212> TYPE: RNA
<213> ORGANISM: Artificial Sequence
<220> FEATURE:
<223> OTHER INFORMATION: siRNA strand

<400> SEQUENCE: 446
uccauuaucu ccgacaugg 19

<210> SEQ ID NO 447
<211> LENGTH: 19
<212> TYPE: RNA
<213> ORGANISM: Artificial Sequence
<220> FEATURE:
<223> OTHER INFORMATION: siRNA strand

<400> SEQUENCE: 447
ccaugucgga gauaaugga 19

<210> SEQ ID NO 448
<211> LENGTH: 21
<212> TYPE: DNA
<213> ORGANISM: Artificial Sequence
<220> FEATURE:
<223> OTHER INFORMATION: siRNA strand

<400> SEQUENCE: 448
uccauuaucu ccgacauggt g 21

<210> SEQ ID NO 449
<211> LENGTH: 21
<212> TYPE: DNA
<213> ORGANISM: Artificial Sequence
<220> FEATURE:
<223> OTHER INFORMATION: siRNA strand

<400> SEQUENCE: 449
ccaugucgga gauaauggat t 21

<210> SEQ ID NO 450
<211> LENGTH: 19
<212> TYPE: RNA
<213> ORGANISM: Artificial Sequence
<220> FEATURE:
<223> OTHER INFORMATION: siRNA strand

<400> SEQUENCE: 450
uuuggugaga acaauagug 19

<210> SEQ ID NO 451
<211> LENGTH: 19
<212> TYPE: RNA
<213> ORGANISM: Artificial Sequence
<220> FEATURE:
<223> OTHER INFORMATION: siRNA strand

<400> SEQUENCE: 451
cacuauuguu cucaccaaa 19

<210> SEQ ID NO 452
<211> LENGTH: 21
<212> TYPE: DNA
<213> ORGANISM: Artificial Sequence
<220> FEATURE:
<223> OTHER INFORMATION: siRNA strand

<400> SEQUENCE: 452
uuuggugaga acaauagugt t 21

<210> SEQ ID NO 453
<211> LENGTH: 21

-continued

<212> TYPE: DNA
<213> ORGANISM: Artificial Sequence
<220> FEATURE:
<223> OTHER INFORMATION: siRNA strand

<400> SEQUENCE: 453
cacuauuguu cucaccaaat t 21

<210> SEQ ID NO 454
<211> LENGTH: 29
<212> TYPE: RNA
<213> ORGANISM: Artificial Sequence
<220> FEATURE:
<223> OTHER INFORMATION: shRNA

<400> SEQUENCE: 454
ucucugccuu caaggaugcg gacaaugag 29

<210> SEQ ID NO 455
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 455
ggaguuuugu uguuaugac 19

<210> SEQ ID NO 456
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 456
gucauaacaa caaaacucc 19

<210> SEQ ID NO 457
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 457
uucauaacaa caaaacucc 19

<210> SEQ ID NO 458
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 458
ggaguuuugu uguuaugac 19

<210> SEQ ID NO 459
<211> LENGTH: 19
<212> TYPE: RNA
<213> ORGANISM: Artificial Sequence
<220> FEATURE:

<223> OTHER INFORMATION: siRNA strand - sequence modified as per summary sequence table at the end of the description

<400> SEQUENCE: 459
ggaguuuugu uguuaugaa 19

<210> SEQ ID NO 460
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 460
acucuugugu cuuuuguca 19

<210> SEQ ID NO 461
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 461
ugacaaaaga cacaagagu 19

<210> SEQ ID NO 462
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 462
acucuugugu cuuuuguca 19

<210> SEQ ID NO 463
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 463
ucgaaguauu ccgcguacg 19

<210> SEQ ID NO 464
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 464
cguacgcgga auacuucga 19

<210> SEQ ID NO 465
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 465
uccuuguccg uccacuuca 19

<210> SEQ ID NO 466
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 466
ugaaguggac ggacaagga 19

<210> SEQ ID NO 467
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 467
caaucuugcg ggcauagcg 19

<210> SEQ ID NO 468
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 468
cgcuaugccc gcaagauug 19

<210> SEQ ID NO 469
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 469
uaaacagugc gaaucuccu 19

<210> SEQ ID NO 470
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 470
aggagauucg cacuguuua 19

<210> SEQ ID NO 471
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 471
aucauauuga gcuccucuu 19

<210> SEQ ID NO 472
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 472
aagaggagcu caauaugau 19

<210> SEQ ID NO 473
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 473
uuguucuucu cagacaccc 19

<210> SEQ ID NO 474
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 474
gggugucuga gaagaacaa 19

<210> SEQ ID NO 475
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 475
gagauuuuca cuuugagcu 19

<210> SEQ ID NO 476
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 476
agcucaaagu gaaaaucuc 19

<210> SEQ ID NO 477
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description -continued

<400> SEQUENCE: 477
aaugacaucu ggguacuug 19

<210> SEQ ID NO 478
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 478
caaguaccca gaugucauu 19

<210> SEQ ID NO 479
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 479
uuauuucggg uguacaggu 19

<210> SEQ ID NO 480
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 480
accuguacac ccgaaauaa 19

<210> SEQ ID NO 481
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 481
uugauguacu gcaagucca 19

<210> SEQ ID NO 482
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 482
uggacuugca guacaucaa 19

<210> SEQ ID NO 483
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 483
gacuucucgg ccaaguucu 19

<210> SEQ ID NO 484
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 484
agaacuuggc cgagaaguc 19

<210> SEQ ID NO 485
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 485
aacagguucc cucucuuca 19

<210> SEQ ID NO 486
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 486
ugaagagagg gaaccuguu 19

<210> SEQ ID NO 487
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 487
acauaaagaa ccugcuucc 19

<210> SEQ ID NO 488
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 488
ggaagcaggu ucuuuaugu 19

<210> SEQ ID NO 489
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 489
uacuacuaac uucagcaag 19

<210> SEQ ID NO 490
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 490
cuugcugaag uuaguagua 19

<210> SEQ ID NO 491
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 491
aguacuacua acuucagca 19

<210> SEQ ID NO 492
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 492
ugcugaaguu aguaguacu 19

<210> SEQ ID NO 493
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 493
aguucuaugg cuaggagac 19

<210> SEQ ID NO 494
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 494
gucuccuagc cauagaacu 19

<210> SEQ ID NO 495
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 495
aacaaaaguc uggugucuu 19

<210> SEQ ID NO 496
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 496
aagacaccag acuuuuguu 19

<210> SEQ ID NO 497
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 497
gaaauaauga ugacccucu 19

<210> SEQ ID NO 498
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 498
agagggucau cauuauuuc 19

<210> SEQ ID NO 499
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 499
aaaauaaaua cggcggcug 19

<210> SEQ ID NO 500
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 500
cagccgccgu auuuauuuu 19

<210> SEQ ID NO 501
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 501
augcaaaaua aauacggcg 19

-continued

<210> SEQ ID NO 502
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 502
cgccguauuu auuuugcau 19

<210> SEQ ID NO 503
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 503
agucaaacuc auaacgcca 19

<210> SEQ ID NO 504
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 504
uggcguuaug aguuugacu 19

<210> SEQ ID NO 505
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 505
cauaacaaca aaacucccc 19

<210> SEQ ID NO 506
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 506
ggggaguuuu guuguuaug 19

<210> SEQ ID NO 507
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 507
agucauaaca acaaaacuc 19

<210> SEQ ID NO 508
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 508
gaguuuuguu guuaugacu 19

<210> SEQ ID NO 509
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 509
aaugacaucu ggguacuug 19

<210> SEQ ID NO 510
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 510
caaguaccca gaugucauu 19

<210> SEQ ID NO 511
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 511
aacagguucc cucucuuca 19

<210> SEQ ID NO 512
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 512
ugaagagagg gaaccuguu 19

<210> SEQ ID NO 513
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 513
aaaauaaaua cggcggcug 19

<210> SEQ ID NO 514

<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 514
cagccgccgu auuuauuuu 19

<210> SEQ ID NO 515
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 515
augcaaaaua aauacggcg 19

<210> SEQ ID NO 516
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 516
cgccguauuu auuuugcau 19

<210> SEQ ID NO 517
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 517
agucauaaca acaaaacuc 19

<210> SEQ ID NO 518
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 518
gaguuuuguu guuaugacu 19

<210> SEQ ID NO 519
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 519
uaugacaucu ggguacuug 19

<210> SEQ ID NO 520
<211> LENGTH: 19

<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 520
uacagguucc cucucuuca 19

<210> SEQ ID NO 521
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 521
uaaauaaaua cggcggcug 19

<210> SEQ ID NO 522
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 522
uugcaaaaua aauacggcg 19

<210> SEQ ID NO 523
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 523
ugucauaaca acaaaacuc 19

<210> SEQ ID NO 524
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 524
uccuuguccg uccacuuca 19

<210> SEQ ID NO 525
<211> LENGTH: 19
<212> TYPE: RNA
<213> ORGANISM: Artificial Sequence
<220> FEATURE:
<223> OTHER INFORMATION: siRNA strand - sequence modified as per summary
sequence table at the end of the description

<400> SEQUENCE: 525
ugaaguggac ggacaagga 19

<210> SEQ ID NO 526
<211> LENGTH: 19
<212> TYPE: RNA

<213> ORGANISM: Artificial Sequence
<220> FEATURE:
<223> OTHER INFORMATION: siRNA strand

<400> SEQUENCE: 526
aucauauuga gcuccucuu 19

<210> SEQ ID NO 527
<211> LENGTH: 19
<212> TYPE: RNA
<213> ORGANISM: Artificial Sequence
<220> FEATURE:
<223> OTHER INFORMATION: siRNA strand

<400> SEQUENCE: 527
aagaggagcu caauaugau 19

<210> SEQ ID NO 528
<211> LENGTH: 19
<212> TYPE: RNA
<213> ORGANISM: Artificial Sequence
<220> FEATURE:
<223> OTHER INFORMATION: siRNA strand

<400> SEQUENCE: 528
aaugacaucu ggguacuug 19

<210> SEQ ID NO 529
<211> LENGTH: 19
<212> TYPE: RNA
<213> ORGANISM: Artificial Sequence
<220> FEATURE:
<223> OTHER INFORMATION: siRNA strand

<400> SEQUENCE: 529
caaguaccca gaugucauu 19

<210> SEQ ID NO 530
<211> LENGTH: 19
<212> TYPE: RNA
<213> ORGANISM: Artificial Sequence
<220> FEATURE:
<223> OTHER INFORMATION: siRNA strand

<400> SEQUENCE: 530
uugauguacu gcaagucca 19

<210> SEQ ID NO 531
<211> LENGTH: 19
<212> TYPE: RNA
<213> ORGANISM: Artificial Sequence
<220> FEATURE:
<223> OTHER INFORMATION: siRNA strand

<400> SEQUENCE: 531
uggacuugca guacaucaa 19

<210> SEQ ID NO 532
<211> LENGTH: 19
<212> TYPE: RNA
<213> ORGANISM: Artificial Sequence
<220> FEATURE:
<223> OTHER INFORMATION: siRNA strand

<400> SEQUENCE: 532
aacagguucc cucucuuca 19

<210> SEQ ID NO 533
<211> LENGTH: 19
<212> TYPE: RNA
<213> ORGANISM: Artificial Sequence
<220> FEATURE:
<223> OTHER INFORMATION: siRNA strand

<400> SEQUENCE: 533
ugaagagagg gaaccuguu 19

<210> SEQ ID NO 534
<211> LENGTH: 19
<212> TYPE: RNA
<213> ORGANISM: Artificial Sequence
<220> FEATURE:
<223> OTHER INFORMATION: siRNA strand

<400> SEQUENCE: 534
uacuacuaac uucagcaag 19

<210> SEQ ID NO 535
<211> LENGTH: 19
<212> TYPE: RNA
<213> ORGANISM: Artificial Sequence
<220> FEATURE:
<223> OTHER INFORMATION: siRNA strand

<400> SEQUENCE: 535
cuugcugaag uuaguagua 19

<210> SEQ ID NO 536
<211> LENGTH: 19
<212> TYPE: RNA
<213> ORGANISM: Artificial Sequence
<220> FEATURE:
<223> OTHER INFORMATION: siRNA strand

<400> SEQUENCE: 536
aguacuacua acuucagca 19

<210> SEQ ID NO 537
<211> LENGTH: 19
<212> TYPE: RNA
<213> ORGANISM: Artificial Sequence
<220> FEATURE:
<223> OTHER INFORMATION: siRNA strand

<400> SEQUENCE: 537
ugcugaaguu aguaguacu 19

<210> SEQ ID NO 538
<211> LENGTH: 19
<212> TYPE: RNA
<213> ORGANISM: Artificial Sequence
<220> FEATURE:
<223> OTHER INFORMATION: siRNA strand

<400> SEQUENCE: 538
aacaaaaguc uggugucuu 19

<210> SEQ ID NO 539
<211> LENGTH: 19
<212> TYPE: RNA
<213> ORGANISM: Artificial Sequence
<220> FEATURE:

<223> OTHER INFORMATION: siRNA strand

<400> SEQUENCE: 539
aagacaccag acuuuuguu 19

<210> SEQ ID NO 540
<211> LENGTH: 19
<212> TYPE: RNA
<213> ORGANISM: Artificial Sequence
<220> FEATURE:
<223> OTHER INFORMATION: siRNA strand

<400> SEQUENCE: 540
aaaauaaaua cggcggcug 19

<210> SEQ ID NO 541
<211> LENGTH: 19
<212> TYPE: RNA
<213> ORGANISM: Artificial Sequence
<220> FEATURE:
<223> OTHER INFORMATION: siRNA strand

<400> SEQUENCE: 541
cagccgccgu auuuauuuu 19

<210> SEQ ID NO 542
<211> LENGTH: 19
<212> TYPE: RNA
<213> ORGANISM: Artificial Sequence
<220> FEATURE:
<223> OTHER INFORMATION: siRNA strand

<400> SEQUENCE: 542
augcaaaaua aauacggcg 19

<210> SEQ ID NO 543
<211> LENGTH: 19
<212> TYPE: RNA
<213> ORGANISM: Artificial Sequence
<220> FEATURE:
<223> OTHER INFORMATION: siRNA strand

<400> SEQUENCE: 543
cgccguauuu auuuugcau 19

<210> SEQ ID NO 544
<211> LENGTH: 19
<212> TYPE: RNA
<213> ORGANISM: Artificial Sequence
<220> FEATURE:
<223> OTHER INFORMATION: siRNA strand

<400> SEQUENCE: 544
agucaaacuc auaacgcca 19

<210> SEQ ID NO 545
<211> LENGTH: 19
<212> TYPE: RNA
<213> ORGANISM: Artificial Sequence
<220> FEATURE:
<223> OTHER INFORMATION: siRNA strand

<400> SEQUENCE: 545
uggcguuaug aguuugacu 19

<210> SEQ ID NO 546
<211> LENGTH: 19
<212> TYPE: RNA
<213> ORGANISM: Artificial Sequence
<220> FEATURE:
<223> OTHER INFORMATION: siRNA strand

<400> SEQUENCE: 546
agucauaaca acaaaacuc 19

<210> SEQ ID NO 547
<211> LENGTH: 19
<212> TYPE: RNA
<213> ORGANISM: Artificial Sequence
<220> FEATURE:
<223> OTHER INFORMATION: siRNA strand

<400> SEQUENCE: 547
gaguuuuguu guuaugacu 19

<210> SEQ ID NO 548
<211> LENGTH: 19
<212> TYPE: RNA
<213> ORGANISM: Artificial Sequence
<220> FEATURE:
<223> OTHER INFORMATION: siRNA strand

<400> SEQUENCE: 548
uaugacaucu ggguacuug 19

<210> SEQ ID NO 549
<211> LENGTH: 19
<212> TYPE: RNA
<213> ORGANISM: Artificial Sequence
<220> FEATURE:
<223> OTHER INFORMATION: siRNA strand

<400> SEQUENCE: 549
uacagguucc cucucuuca 19

<210> SEQ ID NO 550
<211> LENGTH: 19
<212> TYPE: RNA
<213> ORGANISM: Artificial Sequence
<220> FEATURE:
<223> OTHER INFORMATION: siRNA strand

<400> SEQUENCE: 550
uaaauaaaua cggcggcug 19

<210> SEQ ID NO 551
<211> LENGTH: 19
<212> TYPE: RNA
<213> ORGANISM: Artificial Sequence
<220> FEATURE:
<223> OTHER INFORMATION: siRNA strand

<400> SEQUENCE: 551
uugcaaaaua aauacggcg 19

<210> SEQ ID NO 552
<211> LENGTH: 19
<212> TYPE: RNA
<213> ORGANISM: Artificial Sequence
<220> FEATURE:
<223> OTHER INFORMATION: siRNA strand -continued

```
<400> SEQUENCE: 552

ugucauaaca acaaaacuc                                                  19


<210> SEQ ID NO 553
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 553

acucuugugu cuuuuguca                                                  19


<210> SEQ ID NO 554
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 554

acucuugugu cuuuuguca                                                  19
```